United States Patent
Leabman

(10) Patent No.: US 11,523,777 B2
(45) Date of Patent: Dec. 13, 2022

(54) SYSTEMS FOR RADIO WAVE BASED HEALTH MONITORING THAT INCLUDE AN ALIGNMENT FEATURE

(71) Applicant: MOVANO INC., San Ramon, CA (US)

(72) Inventor: Michael A. Leabman, San Ramon, CA (US)

(73) Assignee: Movano Inc., Pleasanton, CA (US)

( * ) Notice: Subject to any disclaimer, the term of this patent is extended or adjusted under 35 U.S.C. 154(b) by 576 days.

(21) Appl. No.: 16/683,020

(22) Filed: Nov. 13, 2019

(65) Prior Publication Data

US 2020/0187816 A1    Jun. 18, 2020

Related U.S. Application Data

(60) Provisional application No. 62/781,523, filed on Dec. 18, 2018, provisional application No. 62/894,741, (Continued)

(51) Int. Cl.
*A61B 5/05* (2021.01)
*A61B 5/00* (2006.01)
(Continued)

(52) U.S. Cl.
CPC ............ *A61B 5/6824* (2013.01); *A45C 11/00* (2013.01); *A61B 5/0004* (2013.01);
(Continued)

(58) Field of Classification Search
CPC ....... A61B 5/05; A61B 5/0004; A61B 5/0022; A61B 5/0024; A61B 5/021;
(Continued)

(56) References Cited

U.S. PATENT DOCUMENTS

| 5,642,733 A | 7/1997 | Archibald et al. |
| 6,128,276 A | 10/2000 | Agee |

(Continued)

FOREIGN PATENT DOCUMENTS

| CN | 106539568 A | 3/2017 |
| WO | 2010131029 A1 | 11/2010 |
| WO | 2017111623 A1 | 6/2017 |

OTHER PUBLICATIONS

American Diabetes Association, "Economic Costs of Diabetes in the U.S. in 2017", https://doi.org/10.2337/dci18-0007, Mar. 22, 2018, 12 pgs.

(Continued)

*Primary Examiner* — Kerri L McNally
*Assistant Examiner* — Thang D Tran
(74) *Attorney, Agent, or Firm* — Loza & Loza, LLP

(57) ABSTRACT

A device for monitoring a health parameter of a person is disclosed. The device includes a device body, a radio frequency (RF) front-end connected to the device body and including a semiconductor substrate and an antenna array including at least one transmit antenna configured to transmit radio waves below the skin surface of a person and a two-dimensional array of receive antennas configured to receive radio waves, the received radio waves including a reflected portion of the transmitted radio waves, wherein the semiconductor substrate includes circuits configured to generate signals in response to the received radio waves, and an alignment feature integrated into the device body and configured to align the antenna array with an object.

44 Claims, 82 Drawing Sheets

Related U.S. Application Data filed on Aug. 31, 2019, provisional application No. 62/912,582, filed on Oct. 8, 2019.

(51) Int. Cl.

| | | |
|---|---|---|
| *A61B 5/021* | (2006.01) | |
| *A61B 5/024* | (2006.01) | |
| *A61B 5/145* | (2006.01) | |
| *G01S 13/88* | (2006.01) | |
| *G01S 7/40* | (2006.01) | |
| *G06F 1/16* | (2006.01) | |
| *G06F 3/01* | (2006.01) | |
| *G06F 3/04812* | (2022.01) | |
| *G06F 3/16* | (2006.01) | |
| *H01Q 1/38* | (2006.01) | |
| *H01Q 21/06* | (2006.01) | |
| *A61B 5/022* | (2006.01) | |
| *G06F 17/14* | (2006.01) | |
| *H04B 7/06* | (2006.01) | |
| *H01Q 1/27* | (2006.01) | |
| *A45C 11/00* | (2006.01) | |
| *G01S 13/87* | (2006.01) | |
| *H04B 1/3888* | (2015.01) | |
| *A61B 8/08* | (2006.01) | |
| *G06N 20/00* | (2019.01) | |
| *A61B 5/0265* | (2006.01) | |
| *G01S 7/02* | (2006.01) | |

(52) U.S. Cl.
CPC .......... *A61B 5/0022* (2013.01); *A61B 5/0024* (2013.01); *A61B 5/021* (2013.01); *A61B 5/022* (2013.01); *A61B 5/02116* (2013.01); *A61B 5/02444* (2013.01); *A61B 5/14532* (2013.01); *A61B 5/489* (2013.01); *A61B 5/681* (2013.01); *A61B 5/683* (2013.01); *A61B 5/684* (2013.01); *A61B 5/6815* (2013.01); *A61B 5/6898* (2013.01); *A61B 5/7257* (2013.01); *A61B 5/7264* (2013.01); *A61B 5/742* (2013.01); *A61B 5/7405* (2013.01); *A61B 5/7455* (2013.01); *A61B 8/488* (2013.01); *G01S 7/4004* (2013.01); *G01S 7/4026* (2013.01); *G01S 13/87* (2013.01); *G01S 13/88* (2013.01); *G06F 1/163* (2013.01); *G06F 3/016* (2013.01); *G06F 3/04812* (2013.01); *G06F 3/167* (2013.01); *G06F 17/142* (2013.01); *H01Q 1/273* (2013.01); *H01Q 1/38* (2013.01); *H01Q 21/061* (2013.01); *H04B 1/3888* (2013.01); *H04B 7/0617* (2013.01); *A45C 2011/002* (2013.01); *A61B 5/0265* (2013.01); *A61B 5/05* (2013.01); *A61B 5/6833* (2013.01); *G01S 7/028* (2021.05); *G06N 20/00* (2019.01)

(58) Field of Classification Search
CPC . A61B 5/02116; A61B 5/022; A61B 5/02444; A61B 5/14532; A61B 5/489; A61B 5/681; A61B 5/6815; A61B 5/6824; A61B 5/684; A61B 5/6898; A61B 5/7257; A61B 5/7264; A61B 5/7405; A61B 5/742; A61B 5/7455; A61B 8/488; A61B 5/0265; A61B 5/6833; A45C 11/00; A45C 2011/002; G01S 7/4004; G01S 7/4026; G01S 13/87; G01S 13/88; G01S 7/028; G06F 1/163; G06F 3/016; G06F 3/04812; G06F 3/167; G06F 17/142; H01Q 1/273; H01Q 1/38; H01Q 21/061; H04B 1/3888; H04B 7/0617; G06N 20/00

USPC ........................................................ 600/407
See application file for complete search history.

(56) References Cited

U.S. PATENT DOCUMENTS

| | | | |
|---|---|---|---|
| 6,512,737 | B1 | 1/2003 | Agee |
| 6,579,311 | B1* | 6/2003 | Makower ............... A61B 17/11 |
| | | | 606/8 |
| 6,664,920 | B1 | 12/2003 | Mott et al. |
| 7,936,301 | B2 | 5/2011 | Niedzwiecki |
| 9,408,564 | B2 | 8/2016 | Porch et al. |
| 9,575,560 | B2 | 2/2017 | Poupyrev et al. |
| 10,092,207 | B1 | 10/2018 | Windmiller |
| 10,398,370 | B2 | 9/2019 | Boshra et al. |
| 10,478,099 | B2 | 11/2019 | Lor et al. |
| 2008/0169961 | A1 | 7/2008 | Steinway et al. |
| 2008/0319285 | A1 | 12/2008 | Hancock |
| 2009/0171182 | A1 | 7/2009 | Stafford |
| 2010/0177182 | A1* | 7/2010 | Kagenow ............... A61B 5/489 |
| | | | 348/E7.085 |
| 2010/0283700 | A1 | 11/2010 | Rajanish et al. |
| 2010/0324398 | A1 | 12/2010 | Tzyy-Ping |
| 2011/0221519 | A1 | 9/2011 | Katoh et al. |
| 2012/0007787 | A1* | 1/2012 | Schantz ..................... G01S 5/14 |
| | | | 343/788 |
| 2012/0150000 | A1 | 4/2012 | Al-Shamma'a et al. |
| 2012/0143029 | A1* | 6/2012 | Silverstein ........... A61B 8/0891 |
| | | | 600/374 |
| 2013/0297223 | A1* | 11/2013 | Fischer .................. G16B 45/00 |
| | | | 702/21 |
| 2014/0134959 | A1 | 5/2014 | Tasic et al. |
| 2014/0228680 | A1* | 8/2014 | Fukuda ............. A61M 25/0127 |
| | | | 600/424 |
| 2015/0263777 | A1* | 9/2015 | Fraden ................. H04B 1/3888 |
| | | | 455/575.8 |
| 2015/0313542 | A1* | 11/2015 | Goldberg ............. G04B 47/063 |
| | | | 368/282 |
| 2015/0351690 | A1* | 12/2015 | Toth ..................... A61B 5/6839 |
| | | | 600/391 |
| 2016/0041617 | A1 | 2/2016 | Poupyrev |
| 2016/0051171 | A1 | 2/2016 | Pikov et al. |
| 2016/0072933 | A1 | 3/2016 | Cox, II |
| 2016/0097716 | A1 | 4/2016 | Gulati et al. |
| 2016/0231236 | A1 | 8/2016 | Gulati et al. |
| 2016/0252607 | A1 | 9/2016 | Saboo et al. |
| 2016/0320852 | A1 | 11/2016 | Poupyrev |
| 2017/0023673 | A1 | 1/2017 | Mansour et al. |
| 2017/0055834 | A1* | 3/2017 | Thoen .................... A61B 5/002 |
| 2017/0156646 | A1 | 6/2017 | Gulati et al. |
| 2017/0164878 | A1* | 6/2017 | Connor .................. G09B 19/00 |
| 2017/0181645 | A1* | 6/2017 | Mahalingam .......... G16H 40/67 |
| 2017/0185284 | A1* | 6/2017 | Bhavaraju ............ A61B 5/7475 |
| 2017/0238835 | A1 | 8/2017 | Melamed |
| 2018/0046258 | A1 | 2/2018 | Poupyrev |
| 2018/0103906 | A1 | 4/2018 | Gandhi et al. |
| 2018/0120420 | A1 | 5/2018 | Mcmahon et al. |
| 2018/0133441 | A1 | 5/2018 | Kellerman ........ A61M 25/0127 |
| 2018/0196134 | A1 | 7/2018 | Safavi-Naeini et al. |
| 2018/0217252 | A1 | 8/2018 | Noujeim et al. |
| 2018/0303386 | A1 | 10/2018 | Hall et al. |
| 2018/0303417 | A1 | 10/2018 | Mensinger et al. |
| 2018/0306723 | A1 | 10/2018 | Ashrafi |
| 2018/0307314 | A1 | 10/2018 | Connor |
| 2018/0322351 | A1* | 11/2018 | Shaker .................... G06V 40/10 |
| 2018/0348341 | A1 | 12/2018 | Phelan et al. |
| 2019/0008422 | A1* | 1/2019 | Leath .................... A61B 5/0507 |
| 2019/0064342 | A1 | 2/2019 | Daisy et al. |
| 2019/0064344 | A1 | 2/2019 | Turner |
| 2019/0082532 | A1* | 3/2019 | Majidi .................... G06F 1/163 |
| 2019/0095602 | A1* | 3/2019 | Setlak .................... G06F 1/1686 |
| 2019/0097328 | A1 | 3/2019 | Yong et al. |
| 2019/0101870 | A1 | 4/2019 | Pandya et al. |
| 2019/0117068 | A1 | 4/2019 | Thomson et al. |
| 2019/0216393 | A1 | 7/2019 | Baheti et al. |
| 2019/0219368 | A1 | 7/2019 | Baheti et al. |
| 2019/0219687 | A1* | 7/2019 | Baheti ..................... G01S 7/415 |

(56) References Cited

U.S. PATENT DOCUMENTS

| | | | |
|---|---|---|---|
| 2019/0257933 A1 | 8/2019 | Nath et al. | |
| 2019/0290161 A1* | 9/2019 | Chase | A61B 5/7246 |
| 2019/0298265 A1 | 10/2019 | Keating et al. | |
| 2020/0099122 A1* | 3/2020 | Rogers | H01Q 9/0428 |
| 2020/0133398 A1 | 4/2020 | Williams et al. | |
| 2020/0155047 A1* | 5/2020 | Rogers | B01L 3/502715 |
| 2020/0202517 A1* | 6/2020 | Venkatesan | A61B 5/489 |
| 2020/0204004 A1* | 6/2020 | Jang | H02J 50/12 |
| 2021/0145352 A1* | 5/2021 | Rogers | A61B 5/7225 |

OTHER PUBLICATIONS

Bruen, Danielle et al. "Glucose Sensing for Diabetes Monitoring: Recent Developments", Sensors 2017, 21 pgs.

Cano-Garcia, Helena et al. "Millimeter-Wave Sensing of Diabetes-Relevant Glucose Concentration Changes in Pigs", J Infrared Milli Terahz Waves (2018) 39: pp. 761-772.

Cespedes, Fabiola Araujo, "RF Sensing System for Continous Blood Blucose Monitoring", Nov. 2017, 121 pgs.

Cheggoju, Shiva Prasad, "Development of Non-Invasive Glucos Sensor", A Thesis Presented to The Graduate Faculty of the University of Akron, May 2016, 80 pgs.

Droitcour, Amy Diane, "Non-Contact Measurement of Heat and Respiration Rates with a Single-Chip Microwave Doppler Radar", A Dissertation Submitted to the Department of Electrical Engineering and the Committee on Graduate Studies of Stanford University, Jun. 2006, 470 pgs.

Gia, Tuan Nguyen, "IoT-based continuous glucose monitoring system: A feasibility study", 8th International Conference on Ambient Systems, Networks and Technologies (ANT-2017), pp. 327-334.

Girão, P. Silva et al. "Microwave Doppler radar in unobtrusive health monitoring", Journal of Physics: Conference Series, file:///C:/Users/Mark%20Wilson/Downloads/Microwave_Doppler_radar_in_unobtrusive_health_moni.pdf, retrieved Oct. 22, 2018, 11 pgs.

Gonzales, Wilbert Villena, "The Progress of Glucose Monitoring—A Review of Invasive to Minimally and Non-Invasive Tehniques, Devices and Sensors", Sensors 2019, 45 pgs.

IHS, "Wearables and Glucose Monitoring" The New Frontier in Diabetes Management, file:///C:/Users/Mark%20Wilson/Downloads/wearables-and-glucose-monitoring%20(1).pdf, retrieved Jun. 19, 2020, 6 pgs.

Jain, Vipul et al. "A Single-Chip Dual-Band 22-29-GHz/77-81-GHz BiCMOS Transceiver for Automotive Radars", IEEE 2009, 17 pgs.

Klaric-Felic, Gordana et al. "Single-Chip Millimeter-Wave Radar", Article in Microwave Journal—Jan. 2015, 10 pgs.

Lien, Jaime, "Soli: Ubiquitous Gesture Sensing with Millimeter Wave Radar", ACM Trans, Graph, vol. 35, No. 4, Article 142, Jul. 2016, 19 pgs.

Mazlouman, Shahrzad Jalaliet al. Contact-less Monitoring of the Major Blood Vessels Supplying Head and Brain (Carotid Arteries), NSTI-Nanotech 2009, 4 pgs.

Nasr, Ismail et al. "A Highly Integrated 60 GHz 6-Channel transceiver with Antenna in Package for Smart Sensing and Short-Range Communications" IEEE Journal of Solid-State Circuits, vol. 51, No. 9, Sep. 2016, pp. 2066-2076.

Nahar, Sabikun, "Design and Implementation of a Stepped Frequency Continous Wave Radar System for Biomedical Applications", Masters Theses, University of Tennessee, Knoxville, 85 pgs.

Omer, Ala Eldin et al. "Blood Glucose Level Monitoring Using and FMCW Millimeter-Wave Radar Sensor", Remote Sensing, 2020, 25 pgs.

Omer, Ala Eldin et al. "Glucose Levels Detection Using mm-Wave Radar", SensorsLetters, vol. 2, No. 3, Sep. 2018, 5 pgs.

Ram, Suresh et al. "Compact Radar Form Factors Accelerate commercial Adoption", Microwaves & RF, Jul. 2016, 2 pgs.

Saha, Shimul et al. "A Glucose sensing System Based on Transmission Measurements at Millimetre Waves using Micro strip Patch Antennas", Scientific Reports, 11 pgs.

Shaker, George et al. "Non-Invasive Monitoring of Glucose Level Changes Utilizing a mm-Wave Radar System", International Journal of Mobile Human Computer Interaction, vol. 10, issue 3, Jul.-Sep. 2018, 20 pgs.

Siegel, Peter H. et al. "Millimeter-Wave Non-Invasive Monitoring of Glucose in Anesthetized Rats", International Conference on Infrared, Millimeter, and Terhaertz Waves, Tucson, AZ, Sep. 14-19, 2014, 2 pgs.

Smith, John L., "The Pursuit of Noninvasive Glucose: "Hunting the Deceitful Turkey", Sixth Edition"Revised and Expanded, 2018, 225 pgs.

Torp, Hans "Signal processing in Ultrasound Doppler and Color Flow Imaging", http://folk.ntnu.no/htorp/Undervisning/FlowMeas02/papers/EstBloodVel.pdf, retrieved Jun. 19, 2020, 22 pgs.

Yi, Xiang et al. "A 24/77 GHz Dual-Band Receiver for Automotive Radar Applications", vol. 7, 2019, pp. 48053-48059.

Yilmaz, Tuba et al. "Radio-Frequency and Microwave Techniques for Non-Invasive Measurement of Blood Glucose Levels", Diagnosis 2019, 34 pgs.

Nahar, Sabikun, "Design and Implementation of a Stepped Frequency Continous Wave Radar System for Biomedical Applications", Masters Theses, University of Tennessee, Knoxville, Aug. 2018, 85 pgs.

Saha, Shimul et al. "A Glucose sensing System Based on Transmission Measurements at Millimetre Waves using Micro strip Patch Antennas", Scientific Reports 7:6855, Jul. 31, 2017, 11 pgs.

* cited by examiner

IMPULSE

CHIRP

STEPPED

BLOOD FLOW

| | |
|---|---|
| Time (absolute) | variable (controlled) |
| TX/RX frequency | variable (controlled) |
| TX1 – state (active/inactive (e.g., PA on/off)) | variable (controlled) |
| TX2 – state (active/inactive (e.g., PA on/off)) | variable (controlled) |
| RX1 – state (active/inactive) | variable (controlled) |
| RX1 – detected amplitude | variable (detected) |
| RX1 – detected phase | variable (detected) |
| RX2 – state (active/inactive) | variable (controlled) |
| RX2 – detected amplitude | variable (detected) |
| RX2 – detected phase | variable (detected) |
| RX3 – state (active/inactive) | variable (controlled) |
| RX3 – detected amplitude | variable (detected) |
| RX3 – detected phase | variable (detected) |
| RX4 – state (active/inactive) | variable (controlled) |
| RX4 – detected amplitude | variable (detected) |
| RX4 – detected phase | variable (detected) |
| TX1 – antenna 2D position | fixed |
| TX1 – antenna orientation (polarization) | fixed |
| TX2 – antenna 2D position | fixed |
| TX2 – antenna orientation (polarization) | fixed |
| RX1 – antenna 2D position | fixed |
| RX1 – antenna orientation (polarization) | fixed |
| RX2 – antenna 2D position | fixed |
| RX2 – antenna orientation (polarization) | fixed |
| RX3 – antenna 2D position | fixed |
| RX3 – antenna orientation (polarization) | fixed |
| RX4 – antenna 2D position | fixed |
| RX4 – antenna orientation (polarization) | fixed |

FIG. 23

| | |
|---|---|
| Time (absolute) | t1 |
| TX/RX frequency | X GHz |
| TX1 – state (active/inactive (e.g., PA on/off)) | active |
| TX2 – state (active/inactive (e.g., PA on/off)) | inactive |
| RX1 – state (active/inactive) | active |
| RX1 – detected amplitude | amp1 |
| RX1 – detected phase | ph1 |
| RX2 – state (active/inactive) | inactive |
| RX2 – detected amplitude | n/a |
| RX2 – detected phase | n/a |
| RX3 – state (active/inactive) | inactive |
| RX3 – detected amplitude | n/a |
| RX3 – detected phase | n/a |
| RX4 – state (active/inactive) | active |
| RX4 – detected amplitude | amp4 |
| RX4 – detected phase | ph4 |
| TX1 – antenna 2D position | left |
| TX1 – antenna orientation (polarization) | vertical |
| TX2 – antenna 2D position | right |
| TX2 – antenna orientation (polarization) | horizontal |
| RX1 – antenna 2D position | upper-left |
| RX1 – antenna orientation (polarization) | vertical |
| RX2 – antenna 2D position | upper-right |
| RX2 – antenna orientation (polarization) | horizontal |
| RX3 – antenna 2D position | lower-left |
| RX3 – antenna orientation (polarization) | horizontal |
| RX4 – antenna 2D position | lower-right |
| RX4 – antenna orientation (polarization) | vertical |

FIG. 24

| Time (absolute) | t1 |
|---|---|
| TX/RX frequency | X GHz |
| RX1 – detected amplitude | variable |
| RX1 – detected phase | variable |
| RX2 – detected amplitude | variable |
| RX2 – detected phase | variable |
| RX3 – detected amplitude | variable |
| RX3 – detected phase | variable |
| RX4 – detected amplitude | variable |
| RX4 – detected phase | variable |

FIG. 26

| | |
|---|---|
| Time (absolute) | t1 |
| Known Glucose level | Z mg/dL |
| TX/RX frequency | X GHz |
| RX1 – detected amplitude | variable |
| RX1 – detected phase | variable |
| RX2 – detected amplitude | variable |
| RX2 – detected phase | variable |
| RX3 – detected amplitude | variable |
| RX3 – detected phase | variable |
| RX4 – detected amplitude | variable |
| RX4 – detected phase | variable |

FIG. 29

| | |
|---|---|
| Time (absolute) | t1 |
| Glucose level | Z1 |
| TX/RX frequency | X GHz |
| RX1 – detected amplitude | amp1 |
| RX1 – detected phase | ph1-t1 |
| RX2 – detected amplitude | amp2-t1 |
| RX2 – detected phase | ph2-t1 |
| RX3 – detected amplitude | amp3-t1 |
| RX3 – detected phase | ph3-t1 |
| RX4 – detected amplitude | amp4-t1 |
| RX4 – detected phase | ph4-t1 |

FIG. 30A

| | |
|---|---|
| Time (absolute) | t2 |
| Glucose level | Z2 |
| TX/RX frequency | X GHz + $\Delta f$ |
| RX1 – detected amplitude | amp1-t2 |
| RX1 – detected phase | ph1-t2 |
| RX2 – detected amplitude | amp2-t2 |
| RX2 – detected phase | ph2-t2 |
| RX3 – detected amplitude | amp3-t2 |
| RX3 – detected phase | ph3-t2 |
| RX4 – detected amplitude | amp4-t2 |
| RX4 – detected phase | ph4-t2 |

FIG. 30B

| | |
|---|---|
| Time (absolute) | t3 |
| Glucose level | Z3 |
| TX/RX frequency | X GHz + $2\Delta f$ |
| RX1 – detected amplitude | amp1-t3 |
| RX1 – detected phase | ph1-t3 |
| RX2 – detected amplitude | amp2-t3 |
| RX2 – detected phase | ph2-t3 |
| RX3 – detected amplitude | amp3-t3 |
| RX3 – detected phase | ph3-t3 |
| RX4 – detected amplitude | amp4-t3 |
| RX4 – detected phase | ph4-t3 |

FIG. 30C

| | |
|---|---|
| Time (absolute) | tn |
| Glucose level | Zn |
| TX/RX frequency | X GHz + $(n-1)\Delta f$ |
| RX1 – detected amplitude | amp1-tn |
| RX1 – detected phase | ph1-tn |
| RX2 – detected amplitude | amp2-tn |
| RX2 – detected phase | ph2-tn |
| RX3 – detected amplitude | amp3-tn |
| RX3 – detected phase | ph3-tn |
| RX4 – detected amplitude | amp4-tn |
| RX4 – detected phase | ph4-tn |

FIG. 30D

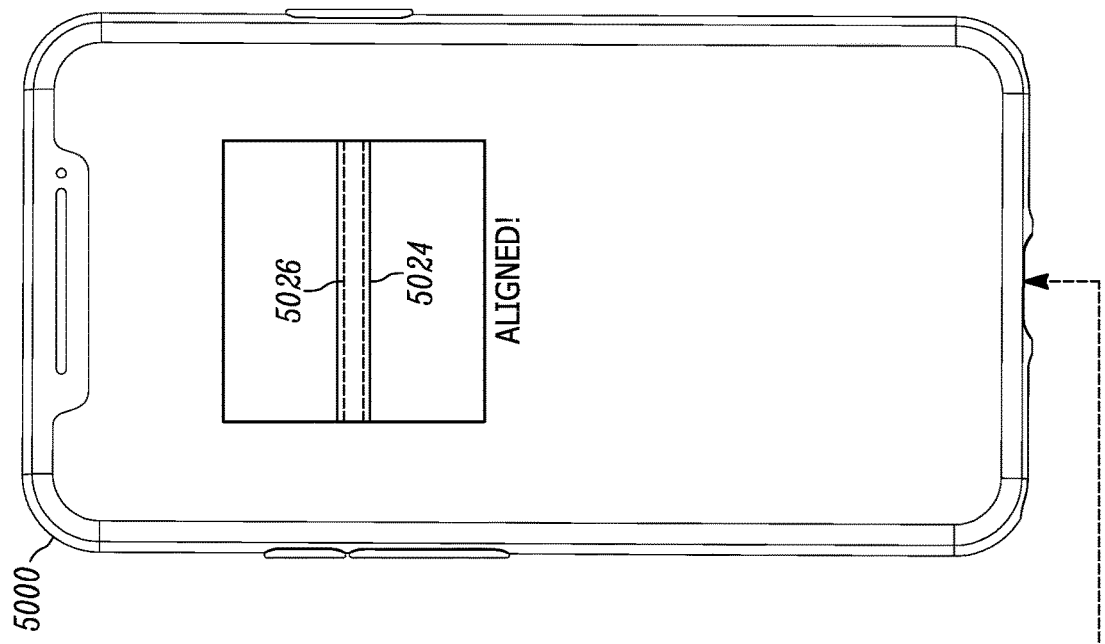
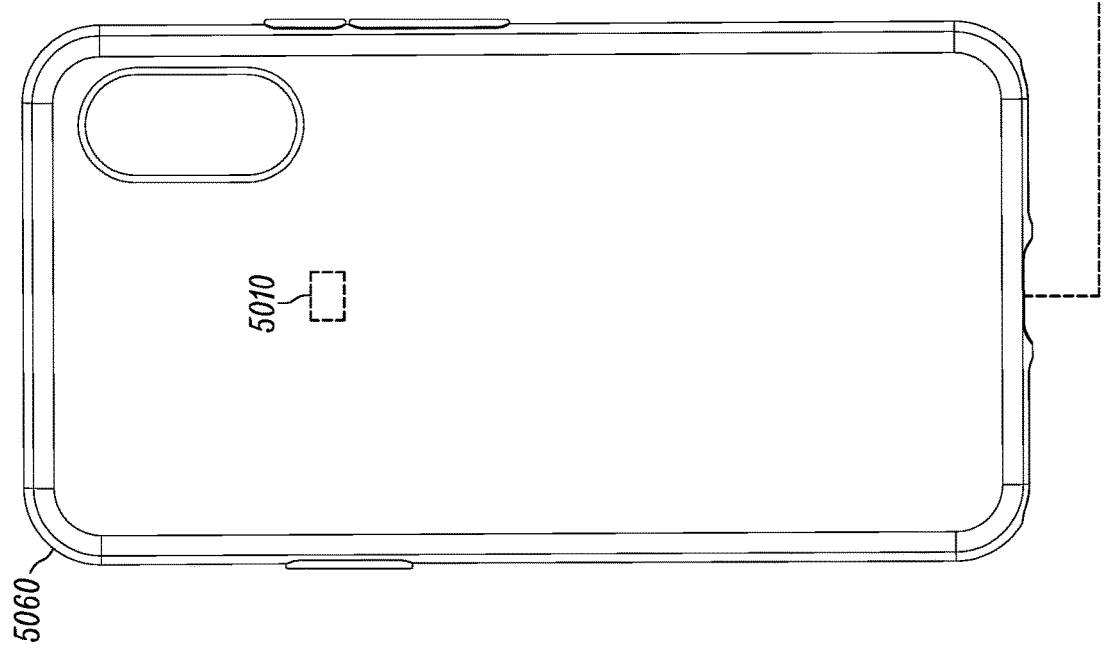
FIG. 50A

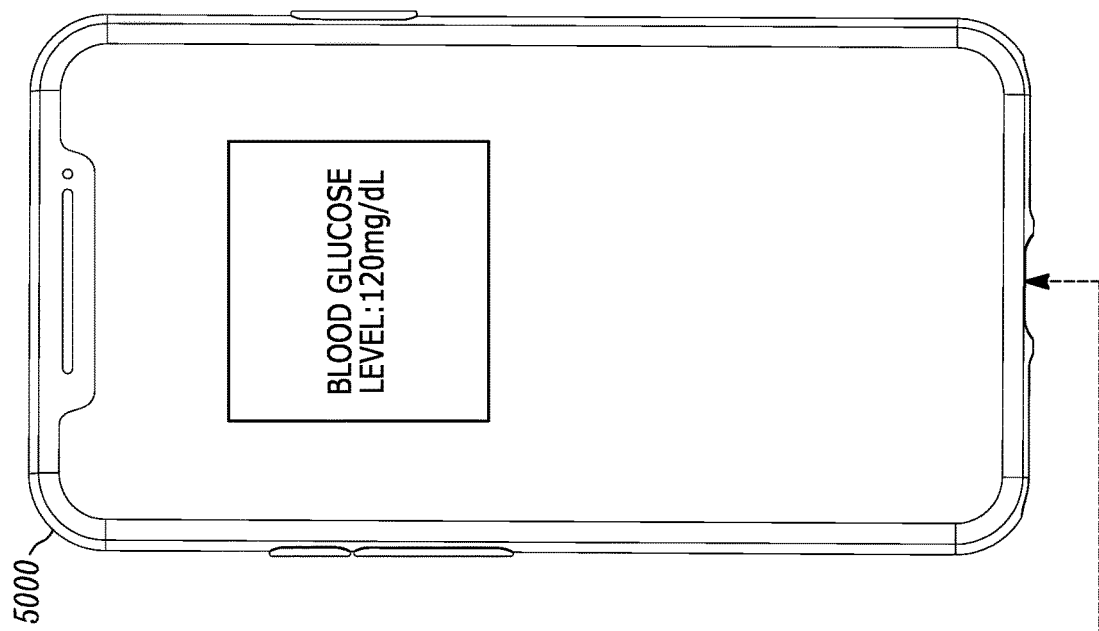
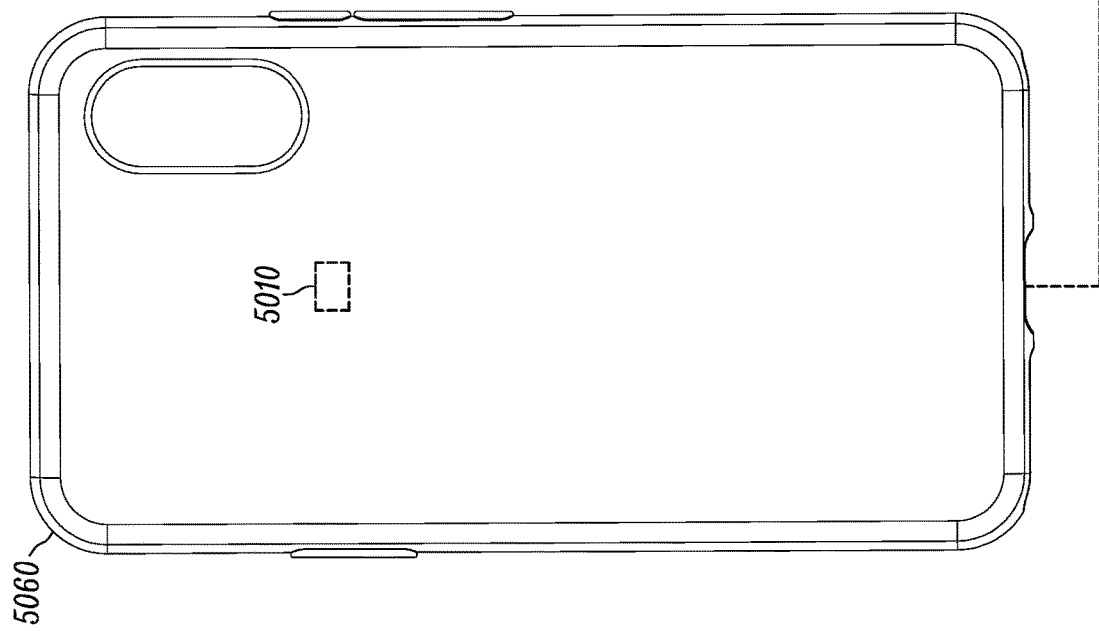
FIG. 50B

SYSTEMS FOR RADIO WAVE BASED HEALTH MONITORING THAT INCLUDE AN ALIGNMENT FEATURE

BACKGROUND

Diabetes is a medical disorder in which a person's blood glucose level, also known as blood sugar level, is elevated over an extended period of time. If left untreated, diabetes can lead to severe medical complications such as cardiovascular disease, kidney disease, stroke, foot ulcers, and eye damage. It has been estimated that the total cost of diabetes in the U.S. in 2017 was $327 billion, American Diabetes Association, "Economic Costs of Diabetes in the U.S. in 2017," published online on Mar. 22, 2018.

Diabetes is typically caused by either the pancreas not producing enough insulin, referred to as "Type 1" diabetes, or because the cells of the person do not properly respond to insulin that is produced, referred to as "Type 2" diabetes. Managing diabetes may involve monitoring a person's blood glucose level and administering insulin when the person's blood glucose level is too high to bring the blood glucose level down to a desired level. A person may need to measure their blood glucose level up to ten times a day depending on many factors, including the severity of the diabetes and the person's medical history. Billions of dollars are spent each year on equipment and supplies used to monitor blood glucose levels.

SUMMARY

A device for monitoring a health parameter of a person is disclosed. The device includes a device body, a radio frequency (RF) front-end connected to the device body and including a semiconductor substrate and an antenna array including at least one transmit antenna configured to transmit radio waves below the skin surface of a person and a two-dimensional array of receive antennas configured to receive radio waves, the received radio waves including a reflected portion of the transmitted radio waves, wherein the semiconductor substrate includes circuits configured to generate signals in response to the received radio waves, and an alignment feature integrated into the device body and configured to align the antenna array with an object.

Other aspects in accordance with the invention will become apparent from the following detailed description, taken in conjunction with the accompanying drawings, illustrated by way of example of the principles of the invention.

BRIEF DESCRIPTION OF THE DRAWINGS

FIG. 23 is a table of parameters related to stepped frequency scanning in a system such as the above-described system.

FIG. 24 is a table of parameters similar to the table of FIG. 23 in which examples are associated with each parameter for a given step in a stepped frequency scanning operation in order to give some context to the table.

FIG. 26 is a table of raw data that is generated during stepped frequency scanning.

FIG. 29 is an example of a table of a raw data record generated during stepped frequency scanning that is used to generate the training data.

FIGS. 30A-30D are tables of at least portions of raw data records that are generated during a learning process that spans the time of t1-tn, where n corresponds to the number of time intervals, T, in the stepped frequency scanning.

FIG. 50A illustrates alignment information being communicated from the removable smartphone case to the smartphone.

FIG. 50B illustrates health parameter information being communicated from the removable smartphone case to the smartphone.

Throughout the description, similar reference numbers may be used to identify similar elements.

DETAILED DESCRIPTION

Figure 1A:
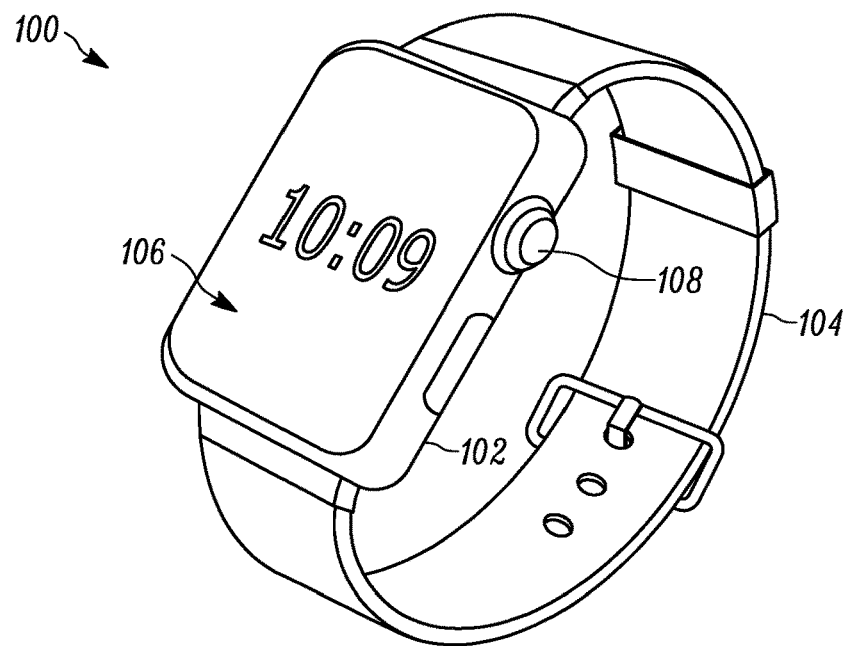
FIGS. 1A and 1B are perspective views of a smartwatch.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment", "an embodiment", or similar language means that a particular feature, structure, or characteristic described in connection with the indicated embodiment is included in at least one embodiment of the present invention. Thus, the phrases "in one embodiment", "in an embodiment", and similar language throughout this specification may, but do not necessarily, all refer to the same embodiment.

Traditional blood glucose level monitoring is accomplished by pricking a finger to draw blood and measuring the blood glucose level with a blood glucose meter, or "glucometer." Continuous glucose monitoring can be accomplished by applying a continuous glucose monitor (CGM) to an area on the body such as the torso. The continuous glucose monitor utilizes a needle that is continuously embedded through the skin to obtain access to blood.

Although blood glucose meters and continuous glucose monitors work well to monitor blood glucose levels, both techniques are invasive in nature in that they require physical penetration of the skin by a sharp object.

Various non-invasive techniques for monitoring blood glucose levels have been explored. Example techniques for monitoring blood glucose levels include techniques based on infrared (IR) spectroscopy, near infrared (NIR) spectroscopy, mid infrared (MIR) spectroscopy, photoacoustic spectroscopy, fluorescence spectroscopy, Raman spectroscopy, optical coherence tomography (OCT), and microwave sensing, Ruochong Zhang et al., "Noninvasive Electromagnetic Wave Sensing of Glucose," Oct. 1, 2018.

In the category of microwave sensing, millimeter range radio waves have been identified as useful for monitoring blood glucose levels. An example of using millimeter range radio waves to monitor blood glucose levels is described by Peter H. Siegel et al., "Millimeter-Wave Non-Invasive Monitoring of Glucose in Anesthetized Rats," 2014 International Conference on Infrared, Millimeter, and Terahertz Waves, Tucson, Ariz., Sep. 14-19, 2014. Here, Siegel et al. describes using the Ka band (27-40 GHz) to measure blood glucose levels through the ear of a lab rat.

Another example of using millimeter range radio waves to monitor blood glucose levels is described by George Shaker et al., "Non-Invasive Monitoring of Glucose Level Changes Utilizing a mm-Wave Radar System," International Journal of Mobile Human Computer Interaction, Volume 10, Issue 3, July-September 2018. Here, Shaker et al. utilizes a millimeter range sensing system referred to as "Soli," (see Jaime Lien et. al., "Soli: Ubiquitous Gesture Sensing with Millimeter Wave Radar," ACM Trans. Graph. 35, 4 Article 142, July 2016) to monitor blood glucose levels. Shaker et al. utilizes radio waves in the 57-64 GHz frequency range to monitor blood glucose levels. Although the Soli sensor system includes transmit (TX) and receive (RX) antennas on the same integrated circuit (IC) device (i.e., the same "chip") and thus in the same plane, Shaker et al. concludes that for blood glucose monitoring, a radar sensing system configuration would ideally have its antennas placed on opposite sides of the sample under test to be able to effectively monitor blood glucose levels. When the transmit (TX) and receive (RX) antennas were on the same side of the sample under test, Shaker et al. was not able to find any discernible trend in the magnitude or phase of the sensor signals.

Another example of using millimeter range radio waves to monitor blood glucose levels is described by Shimul Saha et al., "A Glucose Sensing System Based on Transmission Measurements at Millimeter Waves using Micro strip Patch Antennas," Scientific Reports, published online Jul. 31, 2017. Here, Saha et al. notes that millimeter wave spectroscopy in reflection mode has been used for non-invasive glucose sensing through human skin, but concludes that signals from reflection mode detection yield information that is insufficient for tracking the relevant changes in blood glucose levels. Saha et al. investigates radio waves in the range of 20-100 GHz for monitoring blood glucose levels and concludes that an optimal sensing frequency is in the range of 40-80 GHz.

Although blood glucose level monitoring using millimeter range radio waves has been shown to be technically feasible, implementation of practical monitoring methods and systems has yet to be realized. For example, a practical realization of a monitoring system may include a monitoring system that can be integrated into a wearable device, such as a smartwatch.

In accordance with an embodiment of the invention, methods and systems for monitoring the blood glucose level of a person using millimeter range radio waves involve transmitting millimeter range radio waves below the skin surface, receiving a reflected portion of the radio waves on multiple receive antennas, isolating a signal from a particular location in response to the received radio waves, and outputting a signal that corresponds to a blood glucose level in the person in response to the isolated signals. In an embodiment, beamforming is used in the receive process to isolate radio waves that are reflected from a specific location (e.g., onto a specific blood vessel) to provide a high-quality signal that corresponds to blood glucose levels in the specific blood vessel. In another embodiment, Doppler effect processing can be used to isolate radio waves that are reflected from a specific location (e.g., reflected from a specific blood vessel) to provide a high-quality signal that corresponds to blood glucose levels in the specific blood vessel. Analog and/or digital signal processing techniques can be used to implement beamforming and/or Doppler effect processing and digital signal processing of the received signals can be used to dynamically adjust (or "focus") a received beam onto the desired location. In still another embodiment, beamforming and Doppler effect processing can be used together to isolate radio waves that are reflected from a specific location (e.g., reflected from a specific blood vessel) to provide a high-quality signal that corresponds to blood glucose levels in the specific blood vessel.

As described above, Siegal et al., Shaker et al., and Saha et al., utilize radio waves in the range of about 27-80 GHz, commonly around 60 GHz, to monitor blood glucose levels. Saha et al. discloses that a frequency of around 60 GHz is desirable for glucose detection using electromagnetic transmission data and notes that for increasingly higher frequencies, the losses are prohibitively high for the signal-to-noise ratio (SNR) to exceed the noise level of a sensing instrument such as a Vector Network Analyzer (VNA).

In contrast to conventional techniques, it has been discovered that using a higher frequency range, e.g., 122-126 GHz, to monitor blood glucose levels can provide certain benefits that heretofore have not been recognized. For example, transmitting millimeter range radio waves in the frequency range of 122-126 GHz results in a shallower penetration depth within a human body than radio waves in the frequency range around 60 GHz for a similar transmission power. A shallower penetration depth can reduce undesirable reflections (e.g., reflections off of bone and dense tissue such as tendons, ligaments, and muscle), which can reduce the signal processing burden and improve the quality of the desired signal that is generated from the location of a blood vessel.

Additionally, transmitting millimeter range radio waves in the frequency range of 122-126 GHz enables higher resolution sensing than radio waves at around 60 GHz due to the shorter wavelengths, e.g., 2.46-2.38 mm for 122-126 GHz radio waves versus 5 mm for 60 GHz radio waves. Higher resolution sensing allows a receive beam to be focused more precisely (e.g., through beamforming and/or Doppler effect processing) onto a particular blood vessel, such as the basilic vein on the posterior of the wrist, which can also improve the quality of the desired signal.

Additionally, utilizing millimeter range radio waves in the frequency range of 122-126 GHz to monitor blood glucose levels enables the size of the corresponding transmit and receive antennas to be reduced in comparison to techniques that utilize radio waves in the frequency range of 20-80

GHz. For example, the size of antennas can be reduced by a factor of approximately two by using radio waves in the 122-126 GHz frequency range instead of radio waves in the 60 GHz frequency range, which can enable a smaller form factor for the antennas and for the overall sensor system. Additionally, the frequency range of 122-126 GHz is an unlicensed band of the industrial, scientific, and medical (ISM) radio bands as defined by the International Telecommunication Union (ITU) Radio Regulations. Thus, methods and systems for monitoring blood glucose levels that are implemented using a frequency range of 122-126 GHz do not require a license.

Figure 1B:
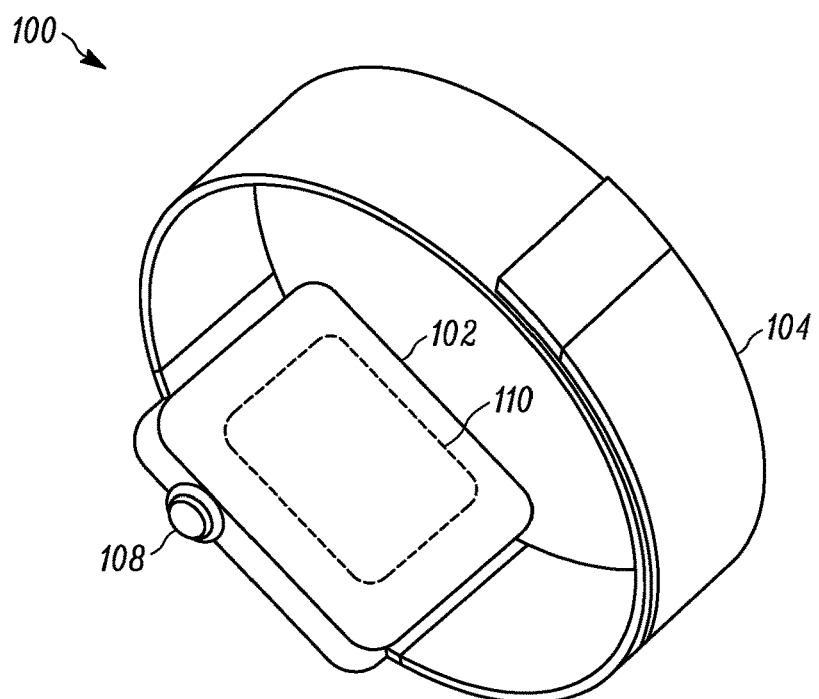

FIGS. 1A and 1B are perspective views of a smartwatch 100, which is a device that provides various computing functionality beyond simply giving the time. Smartwatches are well known in the field. The smartwatch includes a case 102 (also referred to as a "housing") and a strap 104 (e.g., an attachment device) and the strap is typically attached to the case by lugs (not shown). FIG. 1A is a top perspective view of the smartwatch that shows a front face 106 of the case and a crown 108 and FIG. 1B is a back perspective view of the smartwatch that shows a back plate of the case. FIG. 1B also includes a dashed line block 110 that represents a sensor system, such as a sensor system for health monitoring. The sensor system may be partially or fully embedded within the case. In some embodiments, the sensor system may include a sensor integrated circuit (IC) device or IC devices with transmit and/or receive antennas integrated therewith. In some embodiments, the back plate of the case may have openings that allow radio waves to pass more easily to and from smartwatch. In some embodiments, the back plate of the case may have areas of differing materials that create channels through which radio waves can pass more easily. For example, in an embodiment, the back plate of the case may be made primarily of metal with openings in the metal at locations that correspond to sensor antennas that are filled with a material (e.g., plastic or glass) that allows radio waves to pass to and from the smartwatch more easily than through the metal case.

Although a smartwatch is described as one device in which a millimeter range radio wave sensing system can be included, a millimeter range radio wave sensing system can be included in other sensing devices, including various types of wearable devices and/or devices that are not wearable but that are brought close to, or in contact with, the skin of a person only when health monitoring is desired. For example, a millimeter range radio wave sensing system can be incorporated into a smartphone. In an embodiment, a millimeter range radio wave sensing system can be included in a health and fitness tracking device that is worn on the wrist and tracks, among other things, a person's movements. In another embodiment, a millimeter range radio wave sensing system can be incorporated into a device such as dongle or cover (e.g., a protective cover that is placed over a smartphone for protection) that is paired (e.g., via a local data connection such as USB or BLUETOOTH) with a device such as a smartphone or smartwatch to implement health monitoring. For example, a dongle may include many of the components described below with reference to FIG. 6, while the paired device (e.g., the smartphone or smartwatch) includes a digital signal processing capability (e.g., through a Digital Signal Processor (DSP)) and instruction processing capability (e.g., through a Central Processing Unit (CPU)). In another example, a millimeter range sensing system may be incorporated into a device that is attached to the ear. In an embodiment, the sensing system could be attached to the lobe of the ear or have an attachment element that wraps around the ear or wraps around a portion of the ear.

Figure 2A:
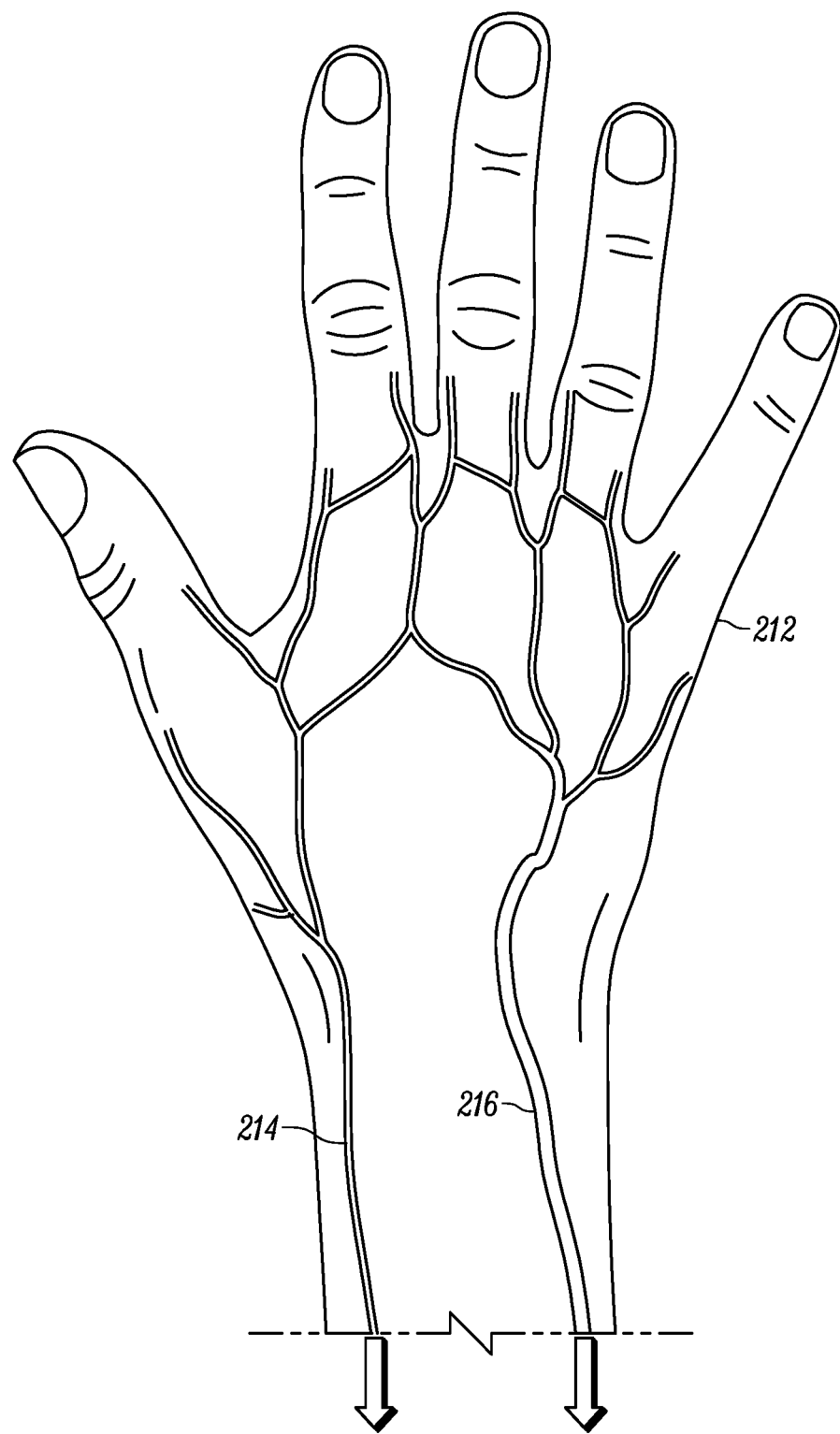
FIG. 2A depicts a posterior view of a right hand with the typical approximate location of the cephalic vein and the basilic vein overlaid/superimposed.
Figure 2B:
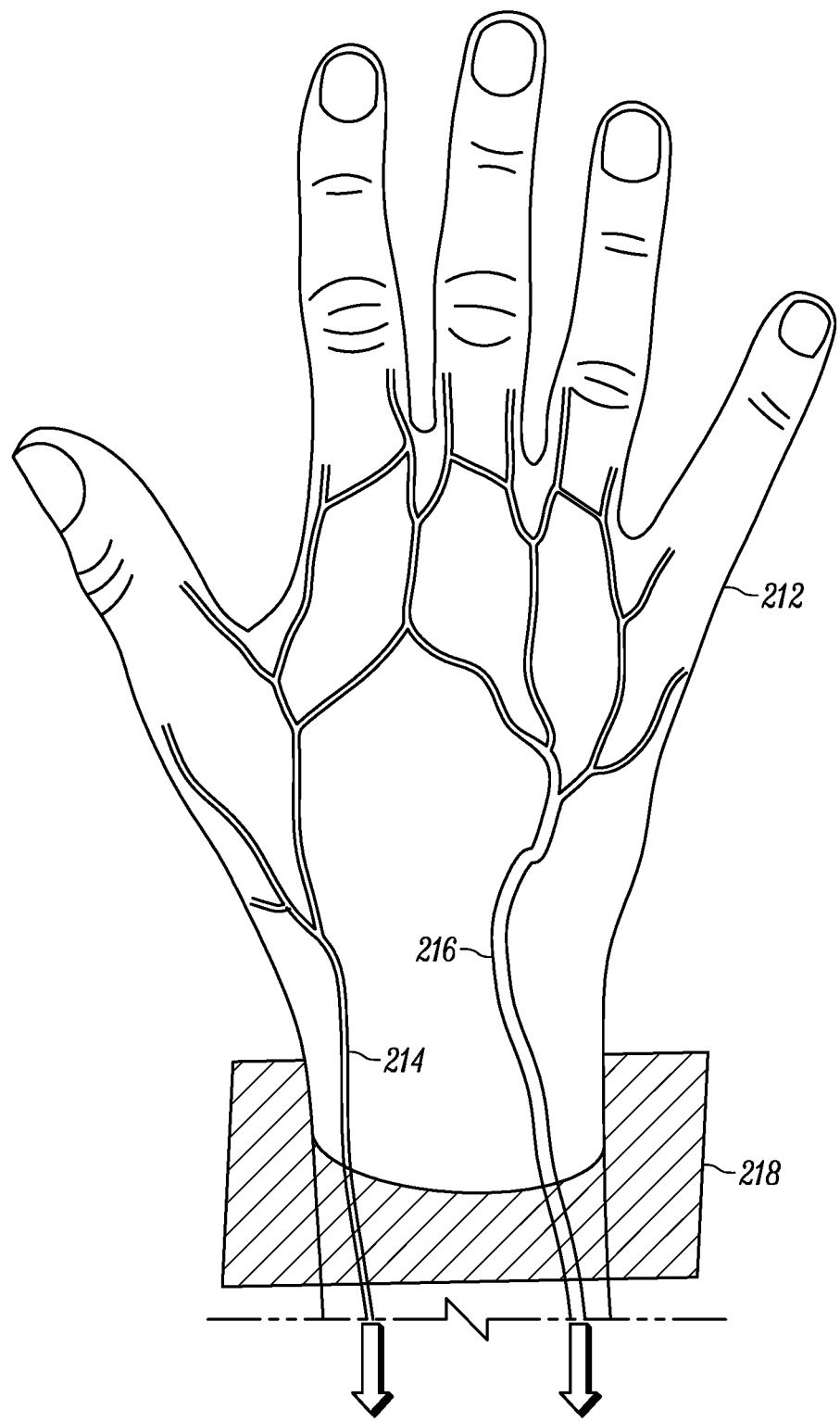
FIG. 2B depicts the location of a cross-section of the wrist from FIG. 2A.
Figure 2C:
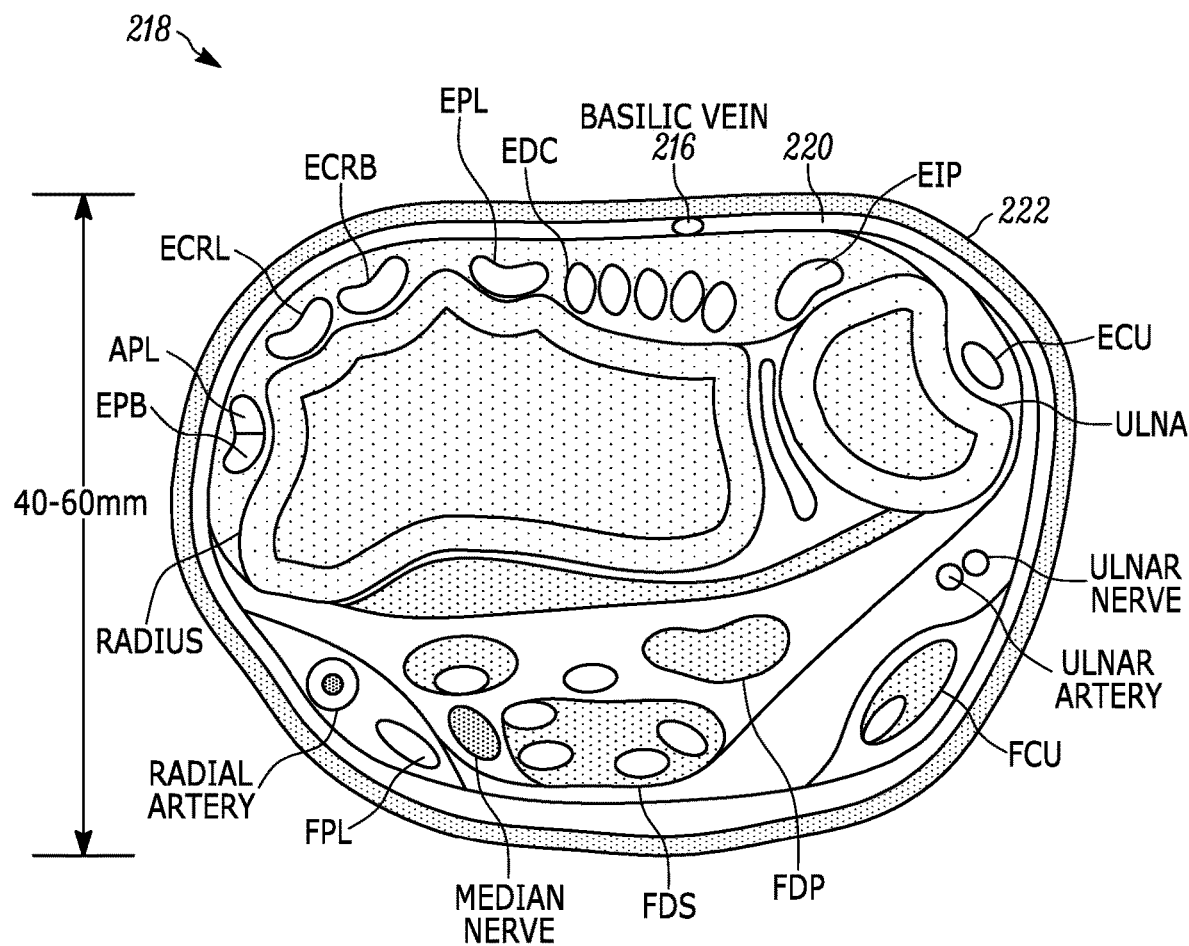
FIG. 2C depicts the cross-section of the wrist from the approximate location shown in FIG. 2B (as viewed in the direction from the elbow to the hand).

Wearable devices such as smartwatches and health and fitness trackers are often worn on the wrist similar to a traditional wristwatch. In order to monitor blood glucose levels using millimeter range radio waves, it has been discovered that the anatomy of the wrist is an important consideration. FIG. 2A depicts a posterior view of a right hand 212 with the typical approximate location of the cephalic vein 214 and the basilic vein 216 overlaid/superimposed. FIG. 2B depicts the location of a cross-section of the wrist 218 from FIG. 2A and FIG. 2C depicts the cross-section of the wrist 218 from the approximate location shown in FIG. 2B (as viewed in the direction from the elbow to the hand). In FIG. 2C, the cross-section is oriented on the page such that the posterior portion of the wrist is on the top and the anterior portion of the wrist is on the bottom. The depth dimension of a wrist is identified on the left side and typically ranges from 40-60 mm (based on a wrist circumference in the range of 140-190 mm). Anatomic features of the wrist shown in FIG. 2C include the abductor pollicis longus (APL), the extensor carpi radialis brevis (ECRB), the extensor carpi radialis longus (ECRL), the extensor carpi ulnaris (ECU), the extensor indicis proprius (EIP), the extensor pollicis brevis (EPB), the extensor pollicis longus (EPL), the flexor carpi ulnaris (FCU), the flexor digitorum superficialis (FDS), the flexor pollicis longus (FPL), the basilic vein 216, the radius, the ulna, the radial artery, the median nerve, the ulnar artery, and the ulnar nerve. FIG. 2C also depicts the approximate location of the basilic vein in subcutaneous tissue 220 below the skin 222. In some embodiments and as is disclosed below, the location of a blood vessel such as the basilic vein is of particular interest to monitoring blood glucose levels using millimeter range radio waves.

Figure 3:
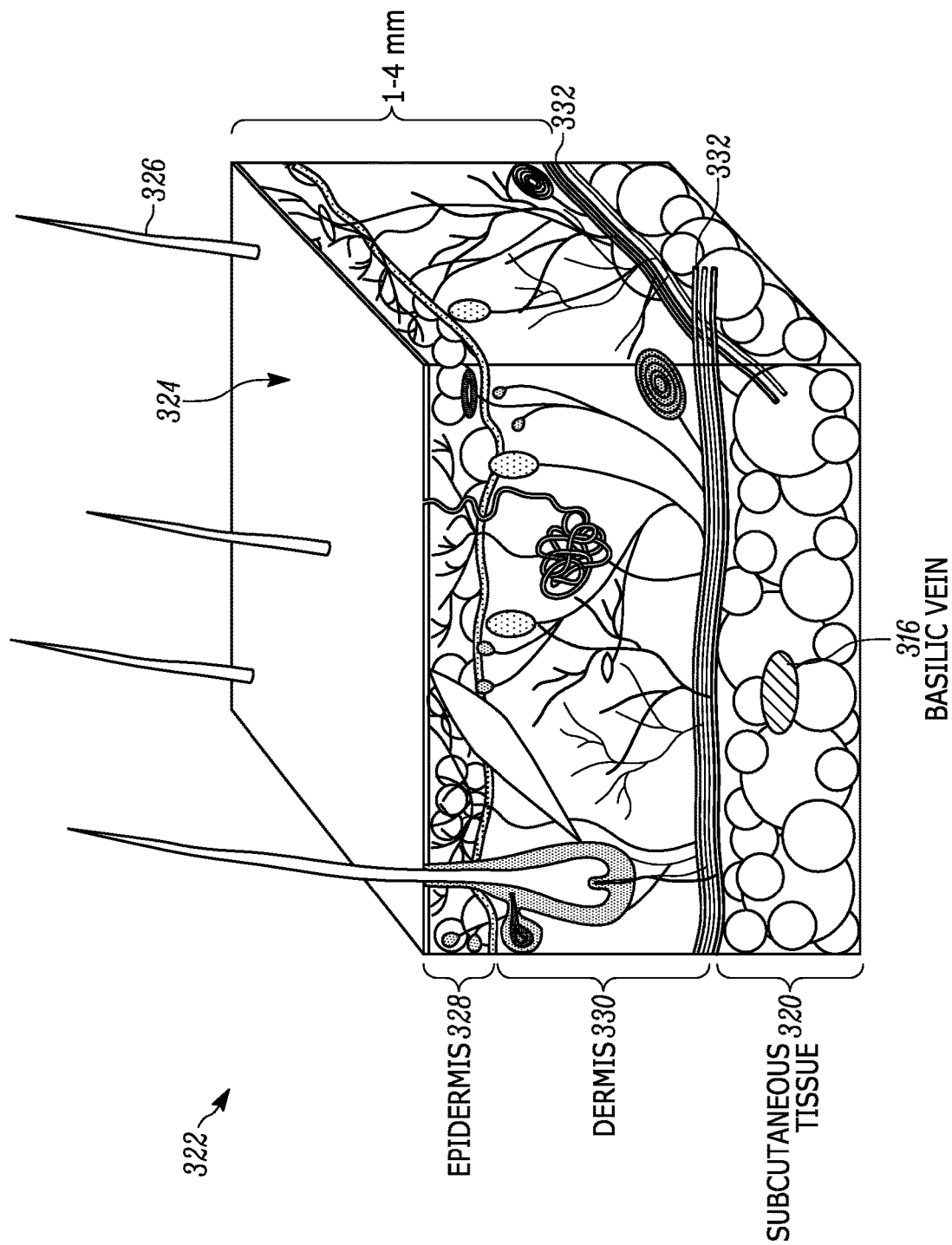
FIG. 3 is a perspective view of human skin that includes a skin surface, hairs, and the epidermis and dermis layers of the skin.

FIG. 3 is a perspective view of human skin 322 that includes a skin surface 324, hairs 326, and the epidermis 328 and dermis 330 layers of the skin. The skin is located on top of subcutaneous tissue 320. In an example, the thickness of human skin in the wrist area is around 1-4 mm and the thickness of the subcutaneous tissue may vary from 1-34 mm, although these thicknesses may vary based on many factors. As shown in FIG. 3, very small blood vessels 332 (e.g., capillaries having a diameter in the range of approximately 5-10 microns) are located around the interface between the dermis and the subcutaneous tissue while veins, such as the cephalic and basilic veins, are located in the subcutaneous tissue just below the skin. For example, the cephalic and basilic veins may have a diameter in the range of 1-4 mm and may be approximately 2-10 mm below the surface of the skin, although these diameters and depths may vary based on many factors. FIG. 3 depicts an example location of the basilic vein 316 in the area of the wrist.

Figure 4A:
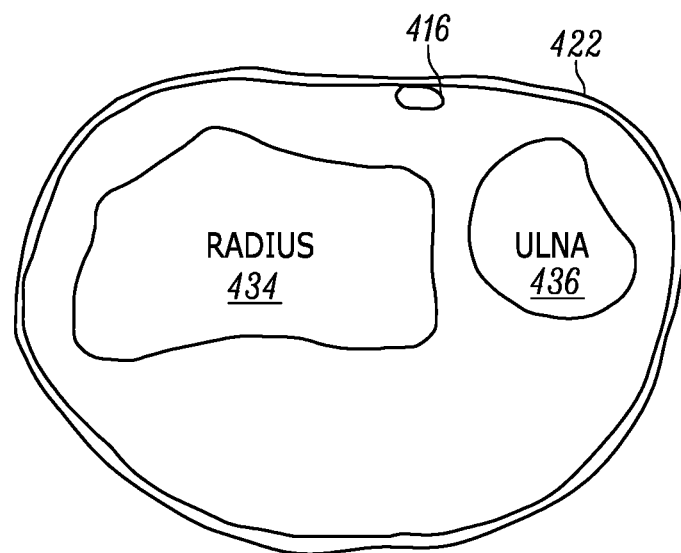
FIG. 4A depicts a simplified version of the cross-section of FIG. 2C, which shows the skin, the radius and ulna bones, and the basilic vein.
Figure 4B:
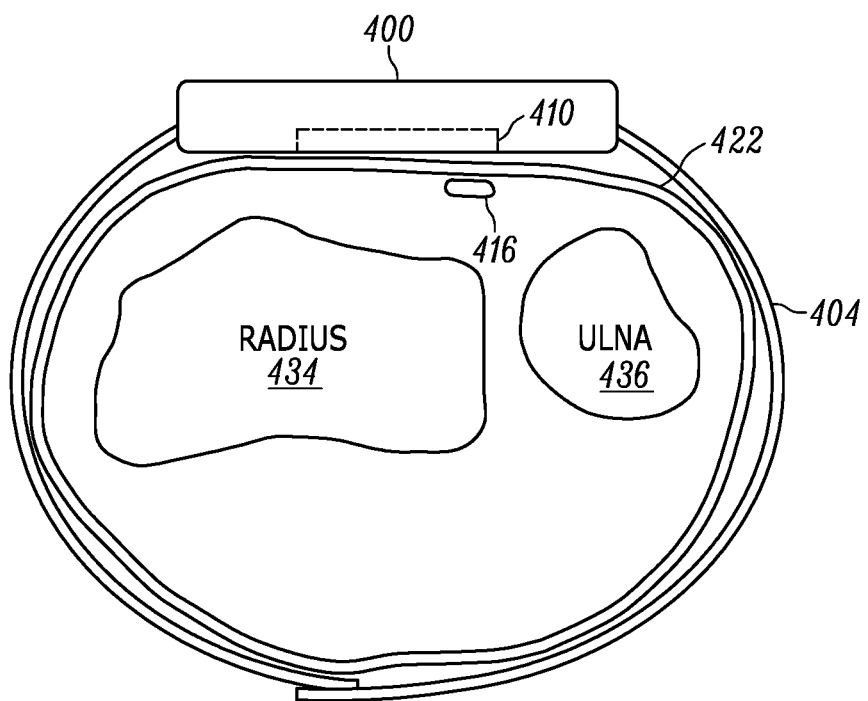
FIG. 4B depicts the wrist cross-section of FIG. 4A in a case where a smartwatch is attached to the wrist.

FIG. 4A depicts a simplified version of the cross-section of FIG. 2C, which shows the skin 422, the radius and ulna bones 434 and 436, and the basilic vein 416. FIG. 4B depicts the wrist cross-section of FIG. 4A in a case where a smartwatch 400, such as the smartwatch shown in FIGS. 1A and 1B, is attached to the wrist by a strap 404. FIG. 4B illustrates an example of the location of the smartwatch relative to the wrist and in particular relative to the basilic vein of the wrist. In the example of FIG. 4B, dashed line block 410 represents the approximate location of a sensor system and corresponds to the dashed line block 110 shown in FIG. 1B. The location of the smartwatch relative to the anatomy of the wrist, including the bones and a vein such as the basilic vein, is an important consideration in implementing blood glucose monitoring using millimeter range radio waves.

Figure 4C:
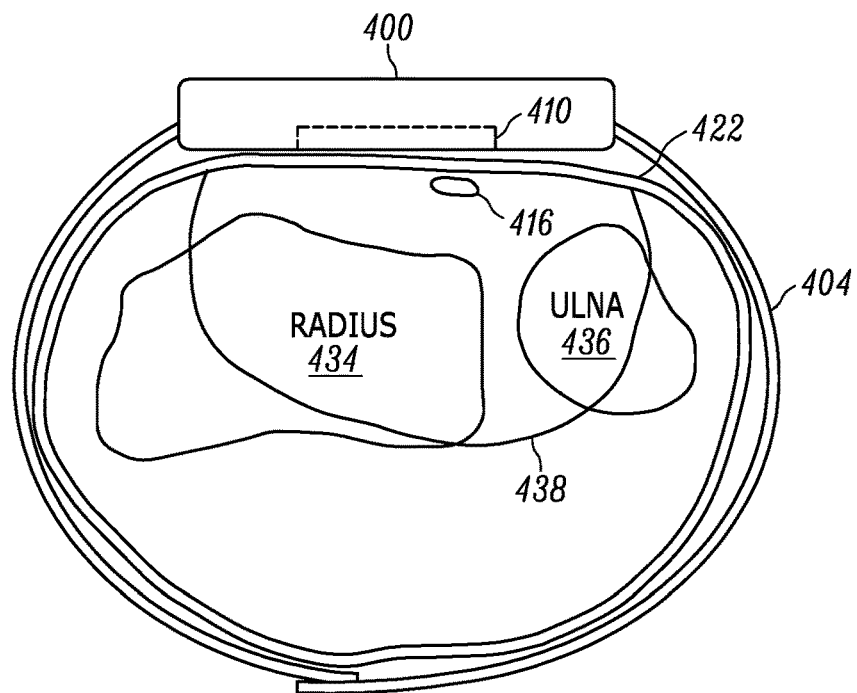
FIG. 4C illustrates, in two dimensions, an example of the penetration depth (which corresponds to a 3D illumination space) of radio waves transmitted from the sensor system of the smartwatch at a frequency of 60 GHz and a transmission power of 15 dBm.
Figure 4D:
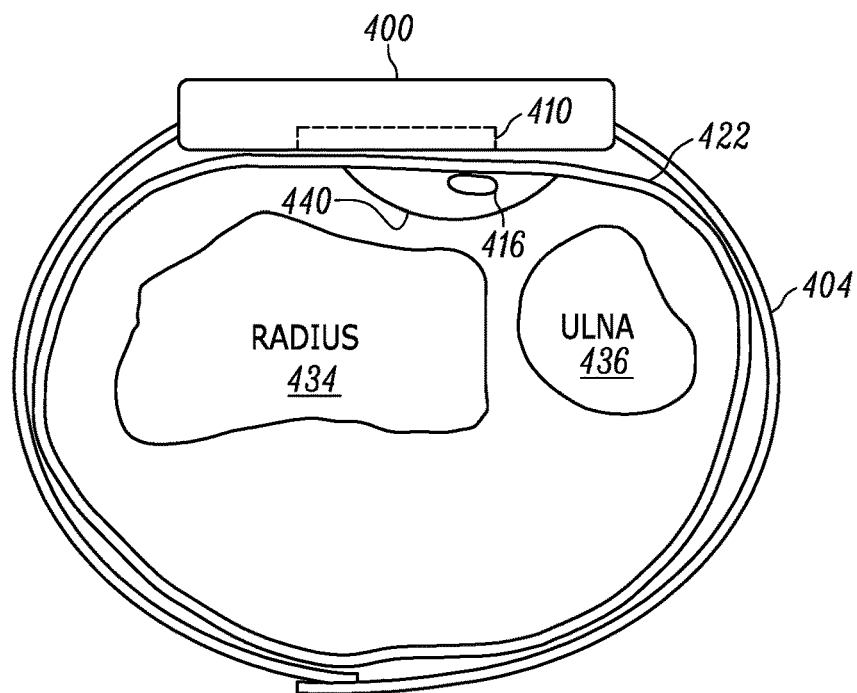
FIG. 4D illustrates, in two dimensions, an example of the penetration depth (which corresponds to a 3D illumination space) of radio waves transmitted from the sensor system of the smartwatch at a frequency of 122-126 GHz and transmit power of 15 dBm.

The magnitude of the reflected and received radio waves is a function of the power of the transmitted radio waves. With regard to the anatomy of the human body, it has been realized that radio waves transmitted at around 60 GHz at a particular transmission power level (e.g., 15 dBm) penetrate deeper (and thus illuminate a larger 3D space) into the human body than radio waves transmitted at 122-126 GHz at the same transmission power level (e.g., 15 dBm). FIG. 4C illustrates, in two dimensions, an example of the penetration depth (which corresponds to a 3D illumination space) of radio waves 438 transmitted from the sensor system of the smartwatch at a frequency of 60 GHz and a transmission power of 15 dBm. FIG. 4D illustrates, in two dimensions, an example of the penetration depth (which corresponds to a 3D illumination space) of radio waves 440 transmitted from the sensor system of the smartwatch at a frequency of 122-126 GHz and transmit power of 15 dBm, which is the same transmission power as used in the example of FIG. 4C. As illustrated by FIGS. 4C and 4D, for equivalent transmission powers (e.g., 15 dBm), radio waves 438 transmitted at 60 GHz penetrate deeper into the wrist (and thus have a corresponding larger illumination space) than radio waves 440 that are transmitted at 122-126 GHz. The deeper penetration depth of the 60 GHz radio waves results in more radio waves being reflected from anatomical features within the wrist. For example, a large quantity of radio waves will be reflected from the radius and ulna bones 434 and 436 in the wrist as well as from dense tissue such as tendons and ligaments that are located between the skin and the bones at the posterior of the wrist, see FIG. 2C, which shows tendons and ligaments that are located between the skin and the bones at the posterior of the wrist. Likewise the shallower penetration of the 122-126 GHz radio waves results in fewer radio waves being reflected from undesired anatomical features within the wrist (e.g., anatomical features other than the targeted blood vessel or vein). For example, a much smaller or negligible magnitude of radio waves will be reflected from the radius and ulna bones in the wrist as well as from dense tissue such as tendons and ligaments that are located between the skin and the bones at the posterior of the wrist.

It has been realized that the penetration depth (and corresponding 3D illumination space), is an important factor in the complexity of the signal processing that is performed to obtain an identifiable signal that corresponds to the blood glucose level in the wrist (e.g., in the basilic vein of the wrist). In order to accurately measure the blood glucose level in a vein such as the basilic vein, it is desirable to isolate reflections from the area of the vein from all of the other reflections that are detected (e.g., from reflections from the radius and ulna bones in the wrist as well as from dense tissue such as tendons and ligaments that are located between the skin and the bones at the posterior of the wrist). In an embodiment, radio waves are transmitted at an initial power such that the power of the radio waves has diminished by approximately one-half (e.g., ±10%) at a depth of 6 mm below the skin surface. Reflections can be isolated using various techniques including signal processing techniques that are used for beamforming, Doppler effect, and/or leakage mitigation. The larger quantity of reflections in the 60 GHz case will likely need more intensive signal processing to remove signals that correspond to unwanted reflections in order to obtain a signal of sufficient quality to monitor a blood parameter such as the blood glucose level in a person.

Figure 5:
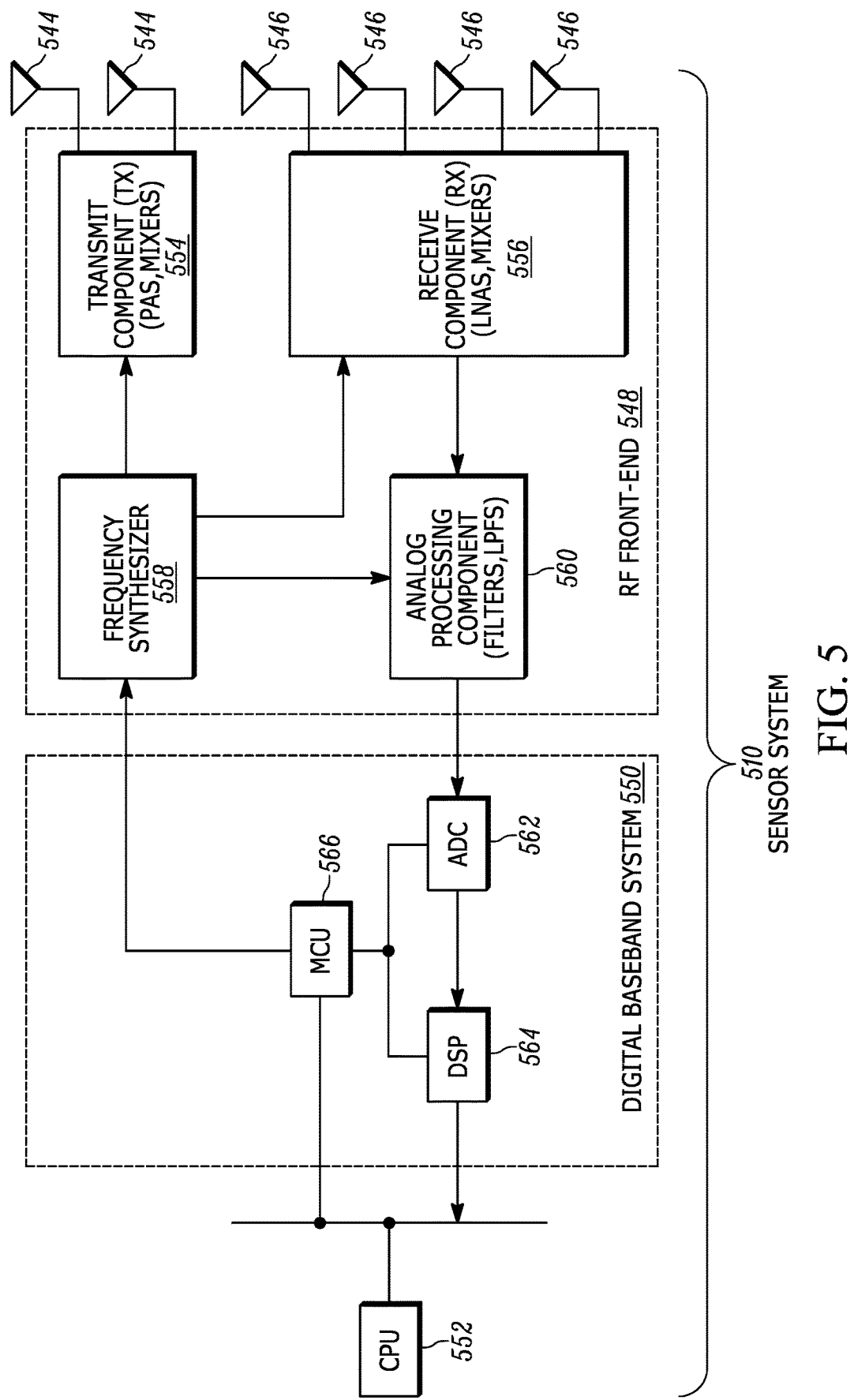
FIG. 5 depicts a functional block diagram of an embodiment of a sensor system that utilizes millimeter range radio waves to monitor a health parameter such as the blood glucose level in a person.

FIG. 5 depicts a functional block diagram of an embodiment of a sensor system 510 that utilizes millimeter range radio waves to monitor a health parameter such as the blood glucose level in a person. The sensor system includes transmit (TX) antennas 544, receive (RX) antennas 546, an RF front-end 548, a digital baseband system 550, and a CPU 552. The components of the sensor system may be integrated together in various ways. For example, some combination of components may be fabricated on the same semiconductor substrate and/or included in the same packaged IC device or a combination of packaged IC devices. As described above, in an embodiment, the sensor system is designed to transmit and receive radio waves in the range of 122-126 GHz.

In the embodiment of FIG. 5, the sensor system 510 includes two TX antennas 544 and four RX antennas 546. Although two TX and four RX antennas are used, there could be another number of antennas, e.g., one or more TX antennas and two or more RX antennas. In an embodiment, the antennas are configured to transmit and receive millimeter range radio waves. For example, the antennas are configured to transmit and receive radio waves in the 122-126 GHz frequency range, e.g., wavelengths in the range of 2.46-2.38 mm.

In the embodiment of FIG. 5, the RF front-end 548 includes a transmit (TX) component 554, a receive (RX) component 556, a frequency synthesizer 558, and an analogue processing component 560. The transmit component may include elements such as power amplifiers and mixers. The receive component may include elements such as low noise amplifiers (LNAs), variable gain amplifiers (VGAs), and mixers. The frequency synthesizer includes elements to generate electrical signals at frequencies that are used by the transmit and receive components. In an embodiment the frequency synthesizer may include elements such as a crystal oscillator, a phase-locked loop (PLL), a frequency doubler, and/or a combination thereof. The analogue processing component may include elements such as mixers and filters, e.g., low pass filters (LPFs). In an embodiment, components of the RF front-end are implemented in hardware as electronic circuits that are fabricated on the same semiconductor substrate.

The digital baseband system 550 includes an analog-to-digital converter (ADC) 562, a digital signal processor (DSP) 564, and a microcontroller unit (MCU) 566. Although the digital baseband system is shown as including certain elements, the digital baseband system may include some other configuration, including some other combination of elements. The digital baseband system is connected to the CPU 552 via a bus.

Figure 6:
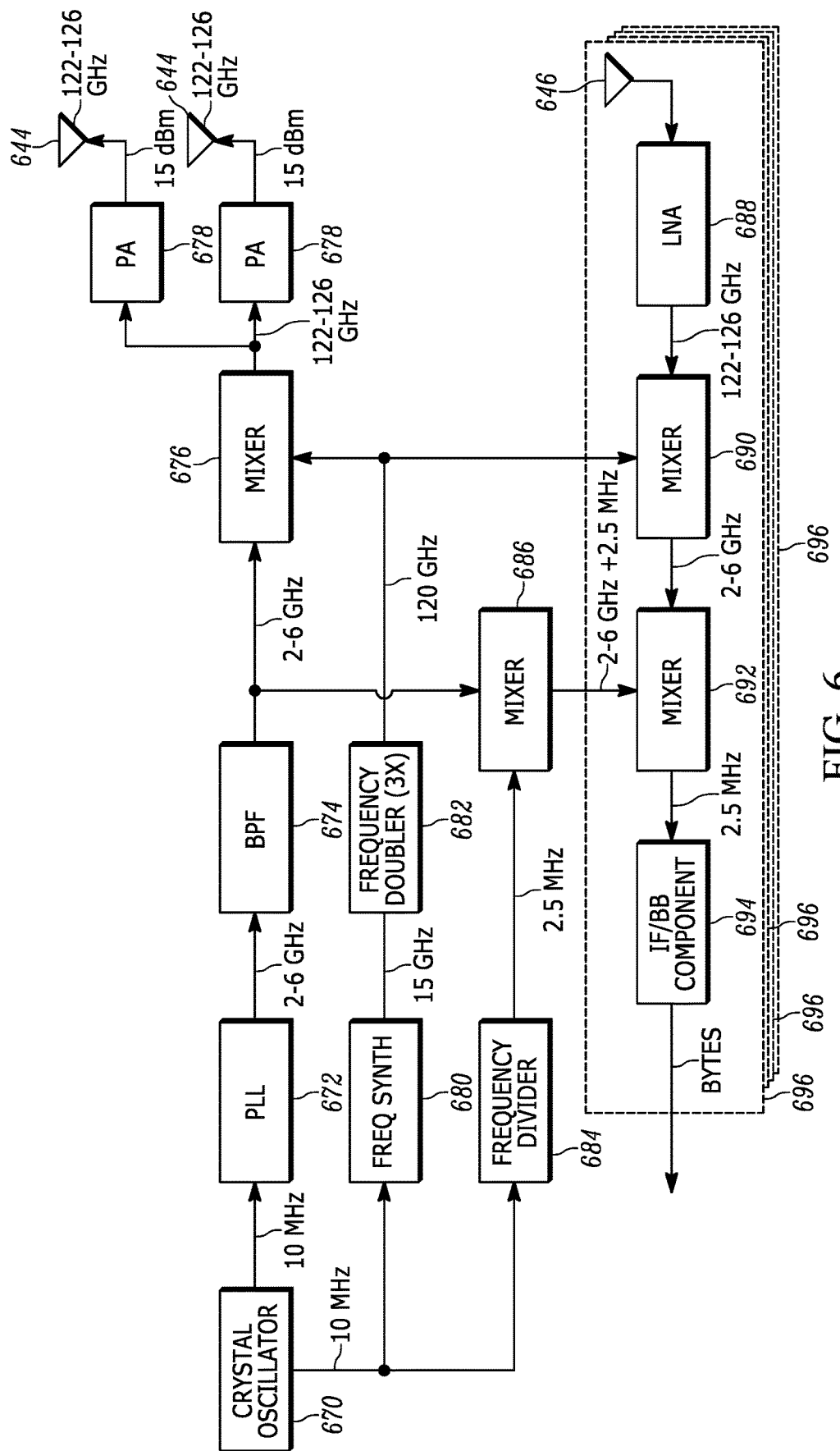
FIG. 6 depicts an expanded view of an embodiment of portions of the sensor system of FIG. 5, including elements of the RF front-end.

FIG. 6 depicts an expanded view of an embodiment of portions of the sensor system 510 of FIG. 5, including elements of the RF front-end. In the embodiment of FIG. 6, the elements include a crystal oscillator 670, a phase locked loop (PLL) 672, a bandpass filter (BPF) 674, a mixer 676, power amplifiers (PAs) 678, TX antennas 644, a frequency synthesizer 680, a frequency doubler 682, a frequency divider 684, a mixer 686, an RX antenna 646, a low noise amplifier (LNA) 688, a mixer 690, a mixer 692, and an Intermediate Frequency/Baseband (IF/BB) component 694. As illustrated in FIG. 6, the group of receive components identified within and dashed box 696 is repeated four times, e.g., once for each of four distinct RX antennas.

Operation of the system shown in FIG. 6 is described with reference to a transmit operation and with reference to a receive operation. The description of a transmit operation generally corresponds to a left-to-right progression in FIG. 6 and description of a receive operation generally corresponds to a right-to-left progression in FIG. 6. With regard to the transmit operation, the crystal oscillator 670 generates an analog signal at a frequency of 10 MHz. The 10 MHz signal is provided to the PLL 672, to the frequency synthesizer 680, and to the frequency divider 684. The PLL uses the 10 MHz signal to generate an analog signal that is in the 2-6 GHz frequency range. The 2-6 GHz signal is provided to the BPF 674, which filters the input signal and passes a signal in the 2-6 GHz range to the mixer 676. The 2-6 GHz signal is also provided to the mixer 686.

Dropping down in FIG. 6, the 10 MHz signal is used by the frequency synthesizer 680 to produce a 15 GHz signal. The 15 GHz signal is used by the frequency doubler 682 to generate a signal at 120 GHz. In an embodiment, the frequency doubler includes a series of three frequency doublers that each double the frequency, e.g., from 15 GHz to 30 GHz, and then from 30 GHz to 60 GHz, and then from 60 GHz to 120 GHz. The 120 GHz signal and the 2-6 GHz signal are provided to the mixer 676, which mixes the two signals to generate a signal at 122-126 GHz depending on the frequency of the 2-6 GHz signal. The 122-126 GHz signal output from the mixer 676 is provided to the power amplifiers 678, and RF signals in the 122-126 GHz range are output from the TX antennas 644. In an embodiment, the 122-126 GHz signals are output at 15 dBm (decibels (dB) with reference to 1 milliwatt (mW)). In an embodiment and as described below, the PLL is controlled to generate discrete frequency pulses between 2-6 GHz that are used for stepped frequency transmission.

The 10 MHz signal from the crystal oscillator 670 is also provided to the frequency divider 684, which divides the frequency down, e.g., from 10 MHz to 2.5 MHz via, for example, two divide by two operations, and provides an output signal at 2.5 MHz to the mixer 686. The mixer 686 also receives the 2-6 GHz signal from the BPF 674 and provides a signal at 2-6 GHz+2.5 MHz to the mixer 692 for receive signal processing.

With reference to a receive operation, electromagnetic (EM) energy is received at the RX antenna 646 and converted to electrical signals, e.g., voltage and current. For example, electromagnetic energy in the 122-126 GHz frequency band is converted to an electrical signal that corresponds in frequency (e.g., GHz), magnitude (e.g., power in dBm), and phase to the electromagnetic energy that is received at the RX antenna. The electrical signal is provided to the LNA 688. In an embodiment, the LNA amplifies signals in the 122-126 GHz frequency range and outputs an amplified 122-126 GHz signal. The amplified 122-126 GHz signal is provided to the mixer 690, which mixes the 120 GHz signal from the frequency doubler 682 with the received 122-126 GHz signal to generate a 2-6 GHz signal that corresponds to the electromagnetic energy that was received at the RX antenna. The 2-6 GHz signal is then mixed with the 2-6 GHz+2.5 MHz signal at mixer 692 to generate a 2.5 MHz signal that corresponds to the electromagnetic energy that was received at the RX antenna. For example, when a 122 GHz signal is being transmitted from the TX antennas and received at the RX antenna, the mixer 692 receives a 2 GHz signal that corresponds to the electromagnetic energy that was received at the antenna and a 2 GHz+2.5 MHz signal from the mixer 686. The mixer 692 mixes the 2 GHz signal that corresponds to the electromagnetic energy that was received at the RX antenna with the 2 GHz+2.5 MHz signal from the mixer 686 to generate a 2.5 MHz signal that corresponds to the electromagnetic energy that was received at the RX antenna. The 2.5 MHz signal that corresponds to the electromagnetic energy that was received at the RX antenna is provided to the IF/BB component 694 for analog-to-digital conversion. The above-described receive process can be implemented in parallel on each of the four receive paths 696. As is described below, the system described with reference to FIG. 6 can be used to generate various discrete frequencies that can be used to implement, for example, stepped frequency radar detection. As described above, multiple mixing operations are performed to implement a sensor system at such a high frequency, e.g., in the 122-126 GHz range. The multiple mixers and corresponding mixing operations implement a "compound mixing" architecture that enables use of such high frequencies.

Figure 7:
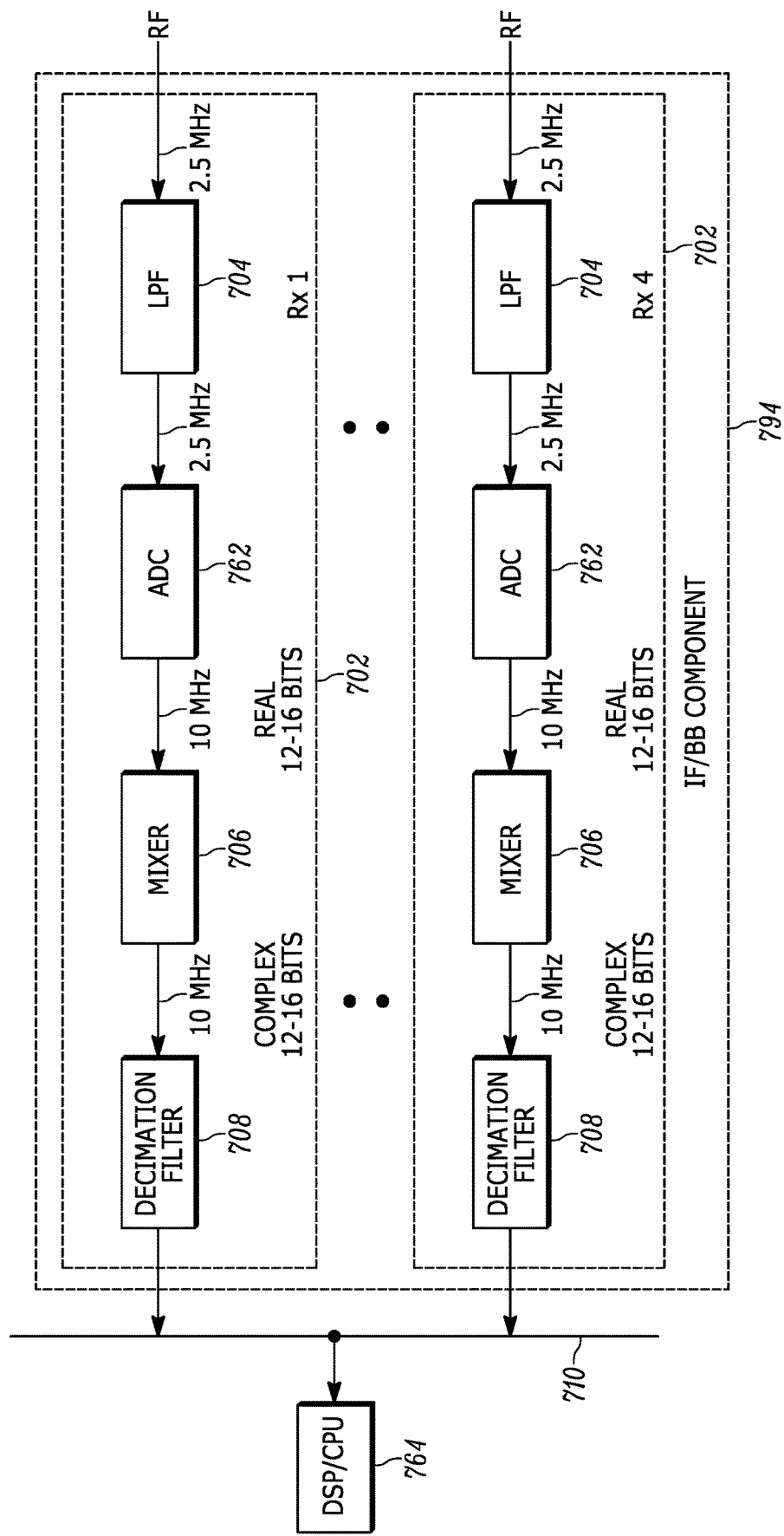
FIG. 7 depicts an embodiment of the IF/BB component shown in FIG. 6.

FIG. 7 depicts an embodiment of the IF/BB component 794 shown in FIG. 6. The IF/BB component of FIG. 7 includes similar signal paths 702 for each of the four receive paths/RX antennas and each signal path includes a low pass filter (LPF) 704, an analog-to-digital converter (ADC) 762, a mixer 706, and a decimation filter 708. The operation of receive path 1, RX1, is described.

As described above with reference to FIG. 6, the 2.5 MHz signal from mixer 692 (FIG. 6) is provided to the IF/BB component 694/794, in particular, to the LPF 704 of the IF/BB component 794. In an embodiment, the LPF filters the 2.5 MHz signal to remove the negative frequency spectrum and noise outside of the desired bandwidth. After passing through the LPF, the 2.5 MHz signal is provided to the ADC 762, which converts the 2.5 MHz signal (e.g., IF signal) to digital data at a sampling rate of 10 MHz (e.g., as 12-16 bits of "real" data). The mixer 706 multiplies the digital data with a complex vector to generate a digital signal (e.g., 12-16 bits of "complex" data), which is also sampled at 10 MHz. Although the signal is sampled at 10 MHz, other sampling rates are possible, e.g., 20 MHz. The digital data sampled at 10 MHz is provided to the decimation filter, which is used to reduce the amount of data by selectively discarding a portion of the sampled data. For example, the decimation filter reduces the amount of data by reducing the sampling rate and getting rid of a certain percentage of the samples, such that fewer samples are retained. The reduction in sample retention can be represented by a decimation factor, M, and may be, for example, about 10 or 100 depending on the application, where M equals the input sample rate divided by the output sample rate.

The output of the decimation filter 706 is digital data that is representative of the electromagnetic energy that was received at the corresponding RX antenna. In an embodiment, samples are output from the IF/BB component 794 at rate of 1 MHz (using a decimation factor of 10) or at a rate of 100 kHz (using a decimation factor of 100). The digital data is provided to a DSP and/or CPU 764 via a bus 710 for further processing. For example, the digital data is processed to isolate a signal from a particular location, e.g., to isolate signals that correspond to electromagnetic energy that was reflected by the blood in a vein of the person. In an embodiment, signal processing techniques are applied to implement beamforming, Doppler effect processing, and/or leakage mitigation to isolate a desired signal from other undesired signals.

In conventional RF systems, the analog-to-digital conversion process involves a high direct current (DC), such that the I ("real") and Q ("complex") components of the RF signal at DC are lost at the ADC. Using the system as described above with reference to FIGS. 5-7, the intermediate IF is not baseband, so I and Q can be obtained after analog-to-digital conversion and digital mixing as shown in FIG. 7.

In an embodiment, digital signal processing of the received signals may involve implementing Kalman filters to smooth out noisy data. In another embodiment, digital signal processing of the received signals may involve combining receive chains digitally. Other digital signal processing may be used to implement beamforming, Doppler effect processing, and ranging. Digital signal processing may be implemented in a DSP and/or in a CPU.

In an embodiment, certain components of the sensor system are integrated onto a single semiconductor substrate and/or onto a single packaged IC device (e.g., a packaged IC device that includes multiple different semiconductor substrates (e.g., different die) and antennas). For example, elements such as the components of the RF front-end 548, and/or components of the digital baseband system 550 (FIGS. 5-7) are integrated onto the same semiconductor substrate (e.g., the same die). In an embodiment, components of the sensor system are integrated onto a single semiconductor substrate that is approximately 5 mm×5 mm. In an embodiment, the TX antennas and RX antennas are attached to an outer surface of the semiconductor substrate and/or to an outer surface of an IC package and electrically connected to the circuits integrated into the semiconductor substrate. In an embodiment, the TX and RX antennas are attached to the outer surface of the IC package such that the TX and RX antenna attachments points are very close to the corresponding transmit and receive circuits such as the PAs and LNAs. In an embodiment, the semiconductor substrate and the packaged IC device includes outputs for outputting electrical signals to another components such as a DSP, a CPU, and or a bus. In some embodiments, the packaged IC device may include the DSP and/or CPU or the packaged IC device may include some DSP and/or CPU functionality.

Figure 8A:
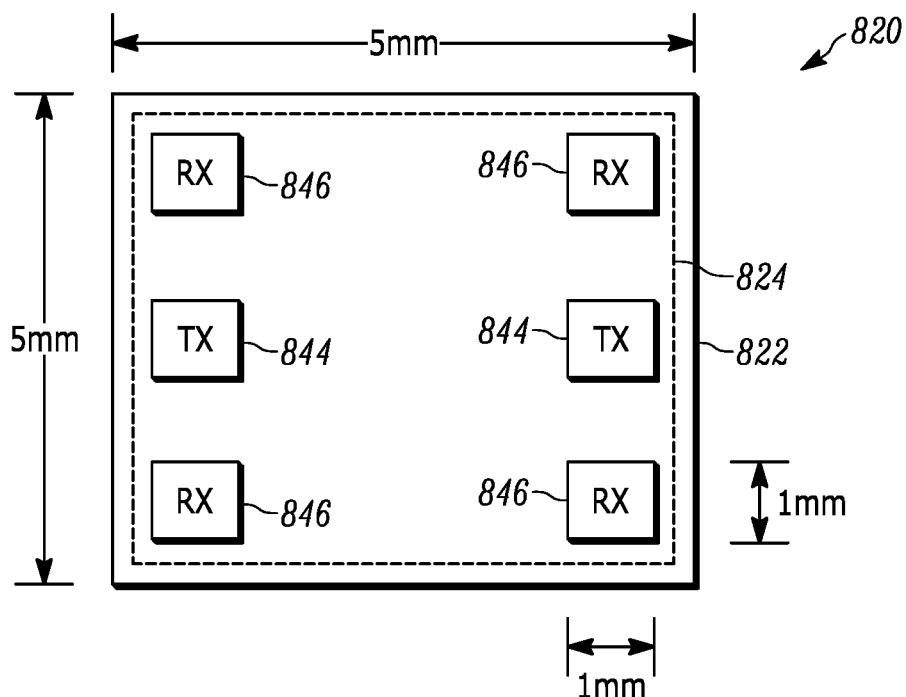
FIG. 8A depicts an example embodiment of a plan view of an IC device that includes two TX antennas and four antennas 846 as well as some of the components from the RF front-end and the digital baseband (not shown) as described above with regard to FIGS. 5-7.
Figure 8B:
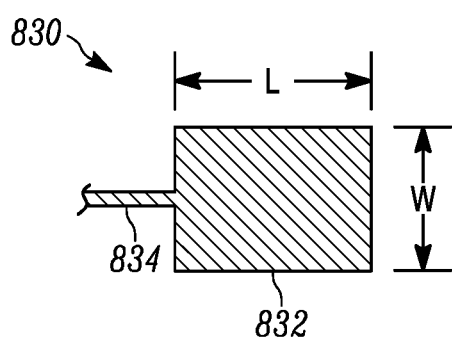
FIG. 8B depicts an embodiment of a microstrip patch antenna that can be used for the TX and/or RX antennas of the IC device of FIG. 8A.

FIG. 8A depicts an example embodiment of a plan view of an IC device 820 that includes two TX antennas 844 and four RX antennas 846 as well as some of the components from the RF front-end and the digital baseband (not shown) as described above with regard to FIGS. 5-7. In FIG. 8A, the outer footprint of the IC device represents a packaged IC device 822 and the inner footprint (as represented by the dashed box 824) represents a semiconductor substrate that includes circuits that are fabricated into the semiconductor substrate to conduct and process electrical signals that are transmitted by the TX antennas and/or received by the RX antennas. In the embodiment of FIG. 8A, the packaged IC device has dimensions of 5 mm×5 mm (e.g., referred to as the device "footprint") and the semiconductor substrate has a footprint that is slightly smaller than the footprint of the packaged IC device, e.g., the semiconductor substrate has dimensions of approximately 0.1-1 mm less than the packaged IC device on each side. Although not shown, in an example embodiment, the packaged IC device has a thickness of approximately 0.3-2 mm and the semiconductor substrate has a thickness in the range of about 0.1-0.7 mm. In an embodiment, the TX and RX antennas are designed for millimeter range radio waves, for example, radio waves of 122-126 GHz have wavelengths in the range of 2.46 to 2.38 mm. In FIG. 8A, the TX and RX antennas are depicted as square boxes of approximately 1 mm×1 mm and the antennas are all attached on the same planar surface of the IC device package. For example, the antennas are attached on the top surface of the IC package (e.g., on top of a ceramic package material) directly above the semiconductor substrate with conductive vias that electrically connect a conductive pad of the semiconductor substrate to a transmission line of the antenna. Although the TX and RX antennas may not be square, the boxes correspond to an approximate footprint of the TX and RX antennas. In an embodiment, the antennas are microstrip patch antennas and the dimensions of the antennas are a function of the wavelength of the radio waves. Other types of antennas such as dipole antennas are also possible. FIG. 8B depicts an embodiment of a microstrip patch antenna 830 that can be used for the TX and/or RX antennas 844 and 846 of the IC device of FIG. 8A. As shown in FIG. 8B, the microstrip patch antenna has a patch portion 832 (with dimensions length (L)×width (W)) and a microstrip transmission line 834. In some embodiments, microstrip patch antennas have length and width dimensions of one-half the wavelength of the target radio waves. Thus, microstrip patch antennas designed for radio waves of 122-126 GHz (e.g., wavelengths in the range of 2.46 to 2.38 mm), the patch antennas may have length and width dimensions of around 1.23-1.19 mm, but no more than 1.3 mm. It is noted that because antenna size is a function of wavelength, the footprint of the antennas shown in FIGS. 8A and 8B can be made to be around one-half the size of antennas designed for radio waves around 60 GHz (e.g., wavelength of approximately 5 mm). Additionally, the small antenna size of the antennas shown in FIGS. 8A and 8B makes it advantageous to attach all six of the antennas to the top surface of the package of the IC device within the footprint of the semiconductor substrate, which makes the packaged IC device more compact than known devices such as the "Soli" device. That is, attaching all of the TX and RX antennas within the footprint of the semiconductor substrate (or mostly within the footprint of the semiconductor substrate, e.g., greater than 90% within the footprint).

In an embodiment, the RX antennas form a phased antenna array and for the application of health monitoring it is desirable to have as much spatial separation as possible between the RX antennas to improve overall signal quality by obtaining unique signals from each RX antenna. For example, spatial separation of the RX antennas enables improved depth discrimination to isolate signals that correspond to reflections from blood in a vein from reflections from other anatomical features. Thus, as shown in FIG. 8A, the RX antennas 846 are located at the corners of the rectangular shaped IC device. For example, the RX antennas are located flush with the corners of the semiconductor substrate 824 and/or flush with the corners of the IC device package or within less than about 0.5 mm from the corners of the semiconductor substrate 824 and/or from the corners of the IC device package. Although the IC device shown in FIG. 8A has dimensions of 5 mm×5 mm, IC devices having smaller (e.g., approximately 3 mm×3 mm) or larger dimensions are possible. In an embodiment, the IC device has dimensions of no more than 7 mm×7 mm.

In the embodiment of FIG. 8A, the TX antennas 844 are located on opposite sides of the IC chip approximately in the middle between the two RX antennas 846 that are on the same side. As shown in FIG. 8A, the TX antenna on the left side of the IC device is vertically aligned with the two RX antennas on the left side of the IC device and the TX antenna on the right side of the IC device is vertically aligned with the two RX antennas on the right side of the IC device. Although one arrangement of the TX and RX antennas is shown in FIG. 8A, other arrangements are possible.

Figure 8C:
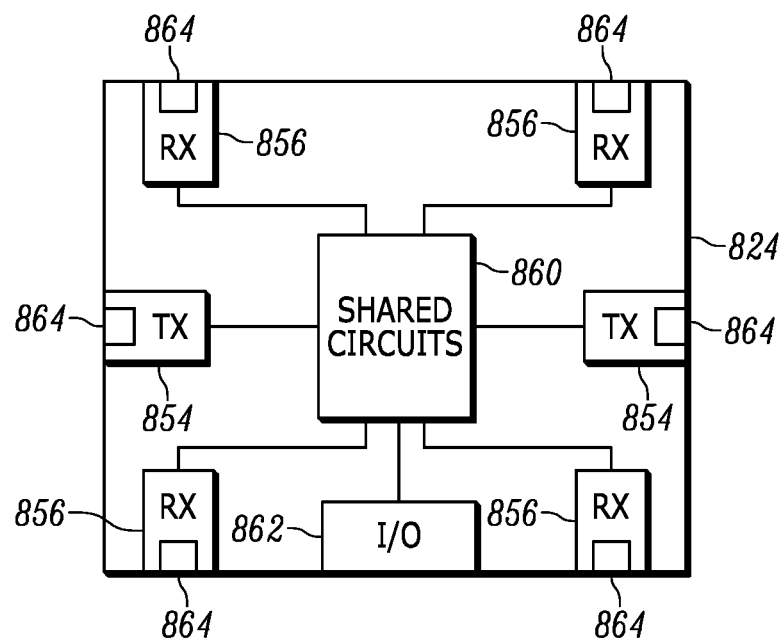
FIG. 8C depicts an example of the physical layout of circuit components on a semiconductor substrate, such as the semiconductor substrate (die) depicted in FIG. 8A.
Figure 8D:
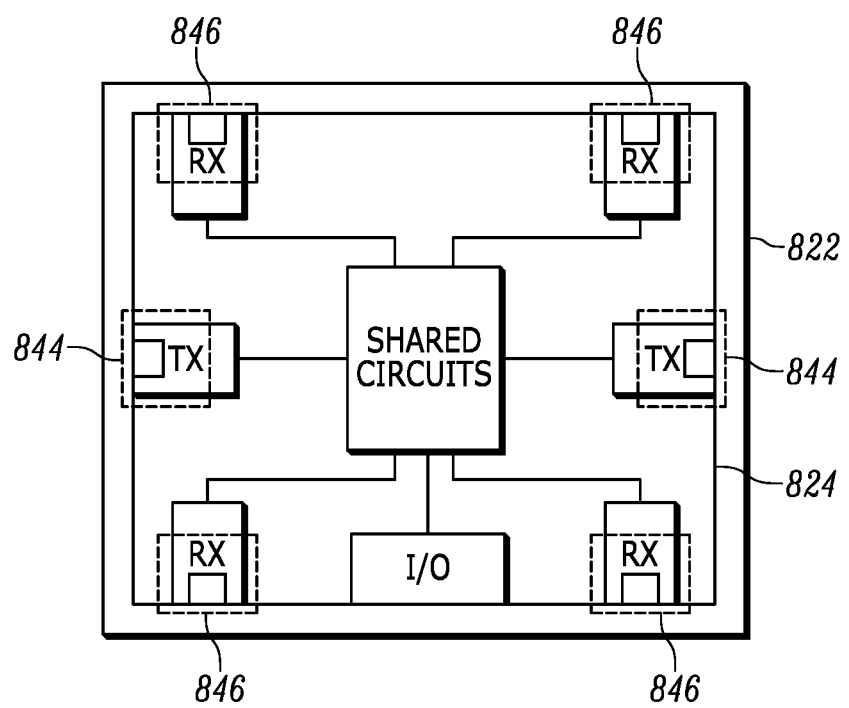
FIG. 8D depicts a packaged IC device similar to the packaged IC device shown in FIG. 8A superimposed over the semiconductor substrate shown in FIG. 8C.

At extremely high frequencies (e.g., 30-300 GHz) conductor losses can be very significant. Additionally, conductor losses at extremely high frequencies are known to be frequency-dependent, with higher frequencies exhibiting higher conductor losses. In many health monitoring applications, power, such as battery power, is a limited resource that must be conserved. Additionally, for reasons as described above such as limiting undesired reflections, low power transmissions may be desirable for health monitoring reasons. Because of the low power environment, conductor losses can severely impact performance of the sensor system. For example, significant conductor losses can occur between the antennas and the conductive pads of the semiconductor substrate, or "die," and between the conductive pads and the transmit/receive components in the die, e.g., the channel-specific circuits such as amplifiers, filters, mixers, etc. In order to reduce the impact of conductor losses in the sensor system, it is important to locate the antennas as close to the channel-specific transmit/receive components of the die as possible. In an embodiment, the transmit and receive components are strategically fabricated on the semiconductor substrate in locations that correspond to the desired locations of the antennas. Thus, when the TX and RX antennas are physically and electrically attached to the IC device, the TX and RX antennas are as close as possible to the transmit and receive components on the die, e.g., collocated such that a portion of the channel specific transmit/receive component overlaps from a plan view perspective a portion of the respective TX/RX antenna. FIG. 8C depicts an example of the physical layout of circuit components on a semiconductor substrate, such as the semiconductor substrate (die) depicted in FIG. 8A. In the embodiment of FIG. 8C, the die 824 includes two TX components 854, four RX components 856, shared circuits 860, and an input/output interface (I/O) 862. In the example of FIG. 8C, each TX component includes channel-specific circuits (not shown) such as amplifiers, each RX component includes channel-specific circuits (not shown) such as mixers, filters, and LNAs, and the shared circuits include, for example, a voltage control oscillator (VCO), a local oscillator (LO), frequency synthesizers, PLLs, BPFs, divider(s), mixers, ADCs, buffers, digital logic, a DSP, CPU, or some combination thereof that may be utilized in conjunction with the channel-specific TX and RX components. As shown in FIG. 8C, the transmit and receive components 854 and 856 each include an interface 864 (such as a conductive pad) that provides an electrical interface between the circuits on the die and a corresponding antenna. FIG. 8D depicts a packaged IC device 822 similar to the packaged IC device shown in FIG. 8A superimposed over the semiconductor substrate 824 shown in FIG. 8C. FIG. 8D illustrates the locations of the TX and RX antennas 844 and 846 relative to the transmit and receive components 854 and 856 of the die (from a plan view perspective). As illustrated in FIG. 8D, the TX and RX antennas 844 and 846 are located directly over the interfaces 864 of the corresponding transmit and receive components 854 and 856. In an embodiment in which the antennas are attached to a top surface of the package (which may be less than 0.5 mm thick), the antennas can be connected to the interface of the respective transmit/receive components by a distance that is a fraction of a millimeter. In an embodiment, a via that is perpendicular to the plane of the die connects the interface of the transmit/receive component to a transmission line of the antenna. More than one via may be used when the antenna has more than one transmission line. Such a collocated configuration enables the desired distribution of the TX and RX antennas to be maintained while effectively managing conductor losses in the system. Such a close proximity between antennas and channel-specific circuits of the die is extremely important at frequencies in the 122-126 GHz range and provides an improvement over sensor systems that include conductive traces of multiple millimeters between the antennas and the die.

Although the example of FIGS. 8A-8D shows the antennas within the footprint of the packaged IC device 822, in some other embodiments, the antennas may extend outside the footprint of the die and/or the packaged IC device while still being collocated with the corresponding transmit/receive components on the die. For example, the antennas may be dipole antennas that have portions of the antennas that extend outside the footprint of the die and/or the packaged IC device.

It has been realized that for the application of monitoring a health parameter such as the blood glucose level in the blood of a person, it is important that the TX antennas are able to illuminate at least one vein near the skin of the person. In order for a TX antenna to illuminate at least one vein near the skin of the person, it is desirable for at least one of the antennas to be spatially close to a vein. Because of variations in the locations of veins relative to the location of the monitoring system (e.g., a smartwatch), it has been found that a transverse configuration of the TX antennas relative to the expected location of a vein or veins provides desirable conditions for monitoring a health parameter such as the blood glucose level in the blood of a person. When the wearable device is worn on a portion of a limb such as the wrist, the TX antennas are distributed in a transverse configuration relative to the limb and relative to the expected location of a vein or veins that will be illuminated by the TX antennas.

Figure 9:
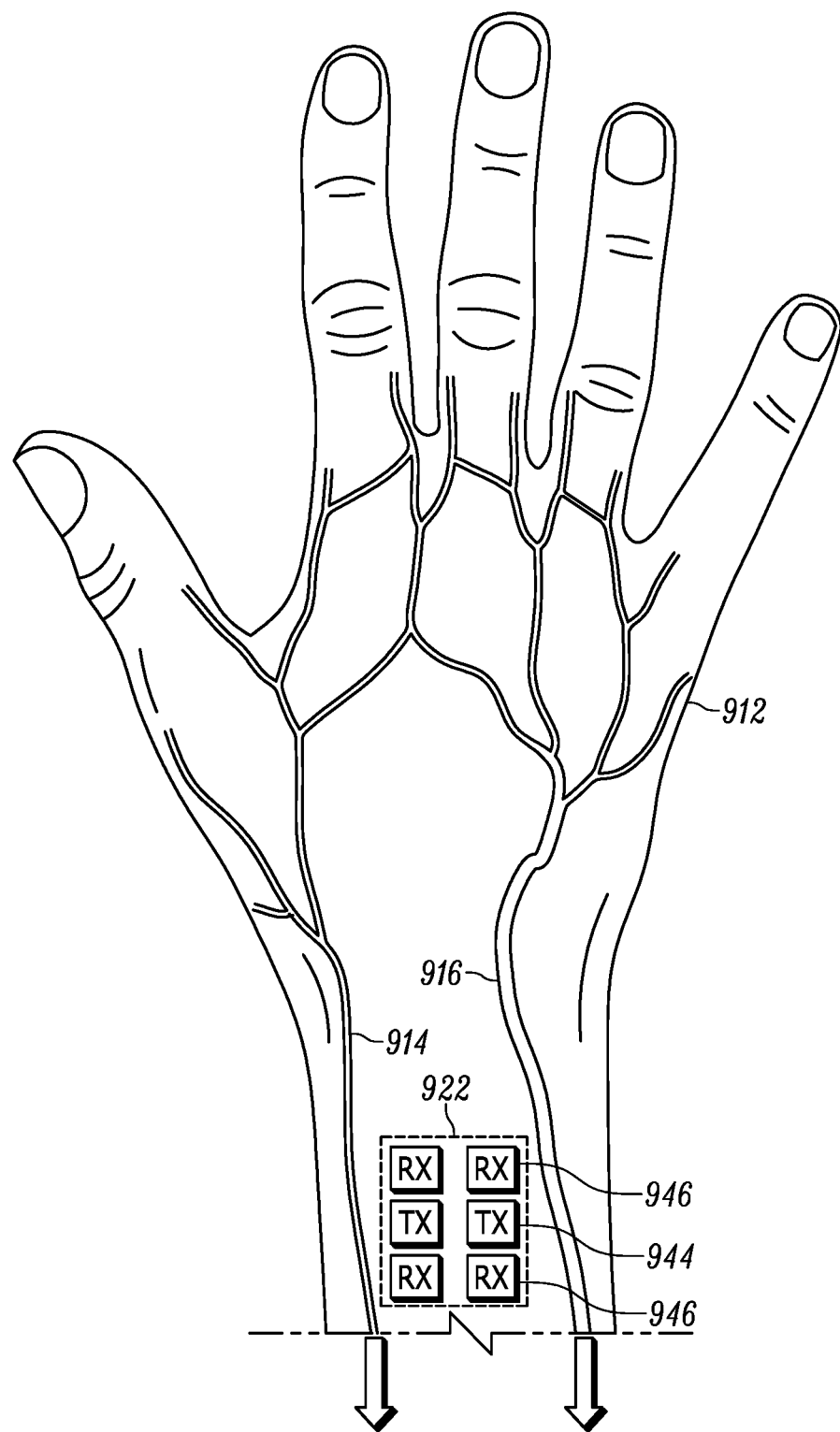
FIG. 9 depicts an IC device similar to that of FIG. 8A overlaid on the hand/wrist that is described above with reference to FIG. 2A-2C.

FIG. 9 depicts an IC device 922 similar to that of FIG. 8A overlaid on the hand/wrist 912 that is described above with reference to FIG. 2A-2C. The IC device is oriented with regard to the basilic and cephalic veins 914 and 916 such that the two TX antennas 944 are configured transverse to the basilic and cephalic veins. That is, the two TX antennas are distributed transversely relative to the orientation (e.g., the linear direction) of the vessel or vessels that will be monitored, such as the basilic and cephalic veins. For example, in a transverse configuration, a straight line that passes through the two TX antennas would be transverse to the vessel or vessels that will be monitored, such as the basilic and cephalic veins. In an embodiment in which the wearable device is worn on the wrist, the transverse configuration of the TX antennas is such that a line passing through both of the TX antennas is approximately orthogonal to the wrist and approximately orthogonal to the orientation of the vessel or vessels that will be monitored, such as the basilic and cephalic veins. For example, a line passing through both of the TX antennas and the orientation of the vessel or vessels that will be monitored, such as the basilic and cephalic veins, may be without about 20 degrees from orthogonal.

Figure 10:
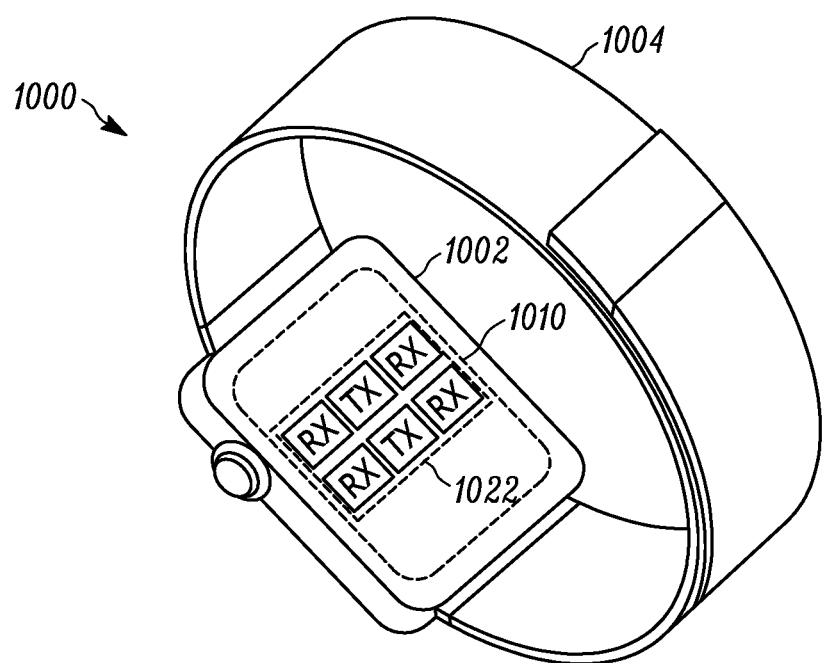
FIG. 10 depicts an IC device similar to that of FIG. 8A overlaid on the back of the smartwatch.

FIG. 10 depicts an IC device 1022 similar to that of FIG. 8A overlaid on the back of the case 1002 of the smartwatch 1000 described above with reference to FIGS. 1A and 1B. As shown in FIGS. 9 and 10, the two TX antennas are configured such that when the smartwatch is worn on the wrist, the two TX antennas are transverse to veins such as the basilic and cephalic veins that run parallel to the length of the arm and wrist.

Figure 11:
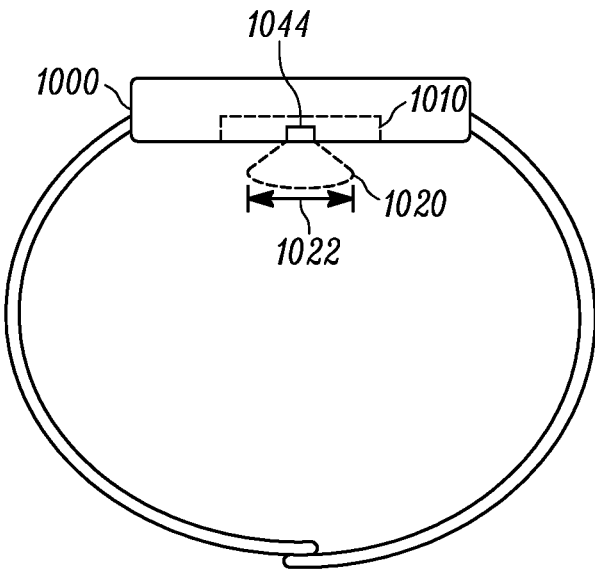
FIG. 11 depicts a side view of a sensor system in a case in which the two TX antennas are configured parallel to veins such as the basilic and cephalic veins of a person wearing the smartwatch.
Figure 12:
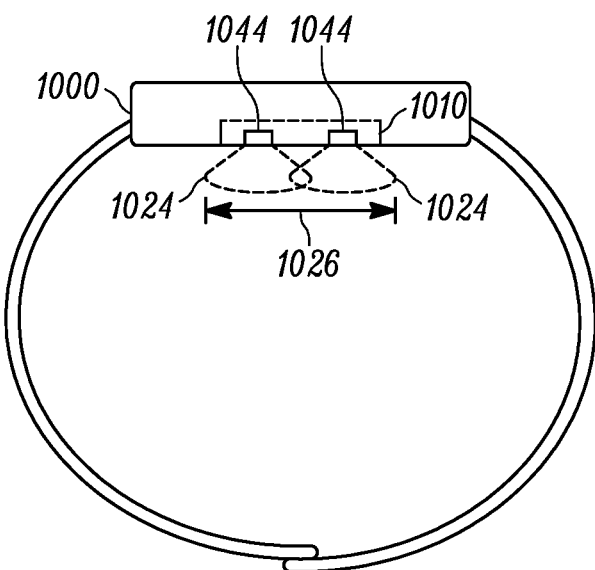
FIG. 12 depicts the same side view as shown in FIG. 11 in a case in which the two TX antennas are configured transverse to veins such as the basilic and cephalic veins of a person wearing the smartwatch.

FIGS. 11 and 12 are provided to illustrate the expanded illumination volume that can be achieved by a sensor system 1010 that includes a transverse TX antenna configuration. FIG. 11 depicts a side view of a sensor system in a case in which the two TX antennas 1044 are configured parallel to veins such as the basilic and cephalic veins of a person wearing the smartwatch 1000. In the view shown in FIG. 11, the two TX antennas are in-line with each other such that only one of the two TX antennas is visible from the side view. When the TX antennas transmit millimeter range radio waves, the electromagnetic energy may have a two-dimensional (2D) illumination pattern as illustrated by dashed line 1020. Given the two-dimensional pattern as illustrated in FIG. 11, the two TX antennas illuminate an area that has a maximum width in the transverse direction (transverse to veins that run parallel to the length of the arm and wrist and referred to herein as the transverse width) identified by arrow 1022. Although the illumination pattern is described and illustrated in two dimensions (2D), it should be understood that illumination actually covers a 3D space or volume.

FIG. 12 depicts the same side view as shown in FIG. 11 in a case in which the two TX antennas 1044 are configured transverse to veins such as the basilic and cephalic veins of a person wearing the smartwatch 1000. In the view shown in FIG. 12, the two TX antennas are spatially separated from each other such that both of the TX antennas are visible from the side view. When the TX antennas transmit millimeter range radio waves, the electromagnetic energy may have a 2D illumination pattern as illustrated by dashed lines 1024. Given the 2D elimination patterns of the two TX antennas, the two TX antennas combine to illuminate an area that has a width in the transverse direction (transverse width) identified by arrow 1026, which is wider than the transverse width for the TX antenna configuration shown in FIG. 11 (e.g., almost twice as wide). A wider illumination area improves the coverage area for the sensor system 1010 and increases the likelihood that the sensor system will illuminate a vein in the person wearing the smartwatch. An increased likelihood that a vein is illuminated can provide more reliable feedback from the feature of interest (e.g., blood in the vein) and thus more reliable monitoring results. Additionally, a wider illumination area can increase the power of the radio waves that illuminate a vein, resulting in an increase in the power of the electromagnetic energy that is reflected from the vein, which can improve the quality of the received signals.

It has been established that the amount of glucose in the blood (blood glucose level) affects the reflectivity of millimeter range radio waves. However, when millimeter range radio waves are applied to the human body (e.g., at or near the skin surface), electromagnetic energy is reflected from many objects including the skin itself, fibrous tissue such as muscle and tendons, and bones. In order to effectively monitor a health parameter such as the blood glucose level of a person, electrical signals that correspond to electromagnetic energy that is reflected from blood (e.g., from the blood in a vein) should be isolated from electrical signals that correspond to electromagnetic energy that is reflected from other objects such as the skin itself, fibrous tissue, and bone, as well as from electrical signals that correspond to electromagnetic energy that is emitted directly from the TX antennas (referred to herein as electromagnetic energy leakage or simply as "leakage") and received by an antenna without passing through the skin of the person.

Various techniques that can be implemented alone or in combination to isolate electrical signals that correspond to reflections from blood from other electrical signals that correspond to other reflections (such as reflections from bone and/or fibrous tissue such as muscle and tendons) and/or signals that correspond to leakage are described below. Such techniques relate to and/or involve, for example, transmission characteristics, beamforming, Doppler effect processing, leakage mitigation, and antenna design.

As is known in the field, radar detection involves transmitting electromagnetic energy and receiving reflected portions of the transmitted electromagnetic energy. Techniques for transmitting electromagnetic energy in radar systems include impulse, chirp, and stepped frequency techniques.

Figure 13A:
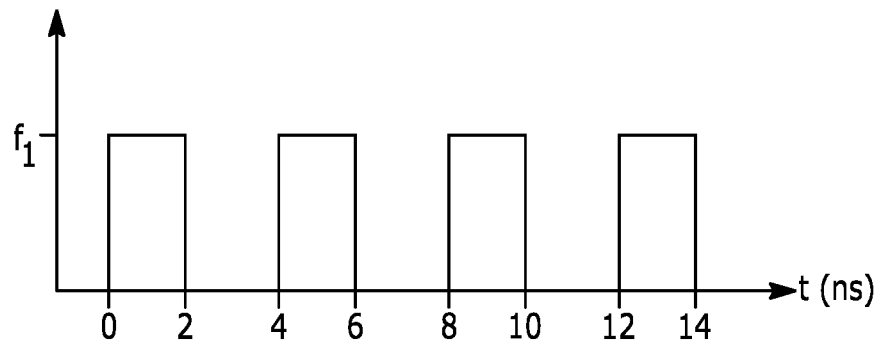
FIGS. 13A-13C depict frequency versus time graphs of impulse, chirp, and stepped frequency techniques for transmitting electromagnetic energy in a radar system.
Figure 13B:
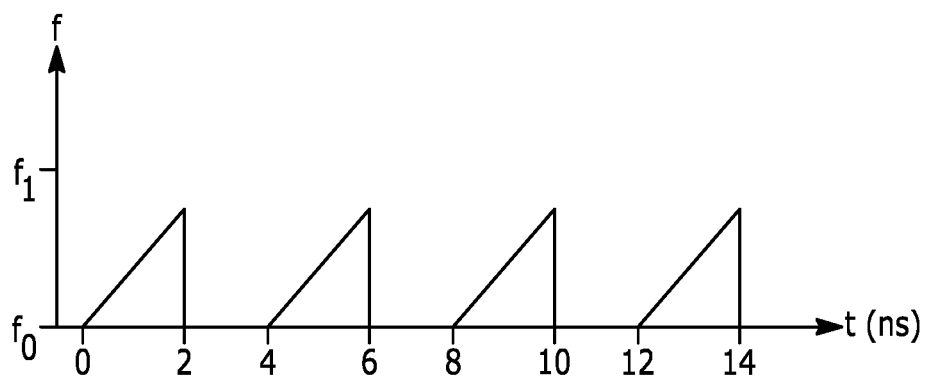
Figure 13C:
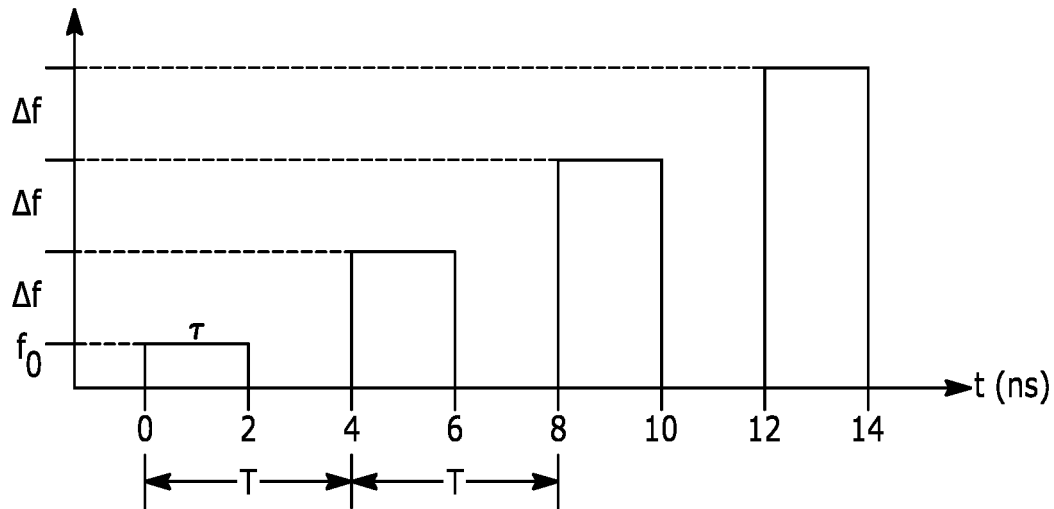

FIGS. 13A-13C depict frequency versus time graphs of impulse, chirp, and stepped frequency techniques for transmitting electromagnetic energy in a radar system. FIG. 13A depicts a radar transmission technique that involves transmitting pulses of electromagnetic energy at the same frequency for each pulse, referred to as "impulse" transmission. In the example of FIG. 13A, each pulse is at frequency, $f_1$, and lasts for a constant interval of approximately 2 ns. The pulses are each separated by approximately 2 ns.

FIG. 13B depicts a radar transmission technique that involves transmitting pulses of electromagnetic energy at an increasing frequency for each interval, referred to herein as "chirp" transmission. In the example of FIG. 13B, each chirp increases in frequency from frequency $f_0$ to $f_1$ over an interval of 2 ns and each chirp is separated by 2 ns. In other embodiments, the chirps may be separated by very short intervals (e.g., a fraction of a nanosecond) or no interval.

FIG. 13C depicts a radar transmission technique that involves transmitting pulses of electromagnetic energy at the same frequency during a particular pulse but at an increased frequency from pulse-to-pulse, referred to herein as a "stepped frequency" transmission or a stepped frequency pattern. In the example of FIG. 13C, each pulse has a constant frequency over the interval of the pulse (e.g., over 2 ns), but the frequency increases by an increment of $\Delta f$ from pulse-to-pulse. For example, the frequency of the first pulse is $f_0$, the frequency of the second pulse is $f_0 + \Delta f$, the frequency of the third pulse is $f_0 + 2\Delta f$, and the frequency of the fourth pulse is $f_0 + 3\Delta f$, and so on.

Figure 14:
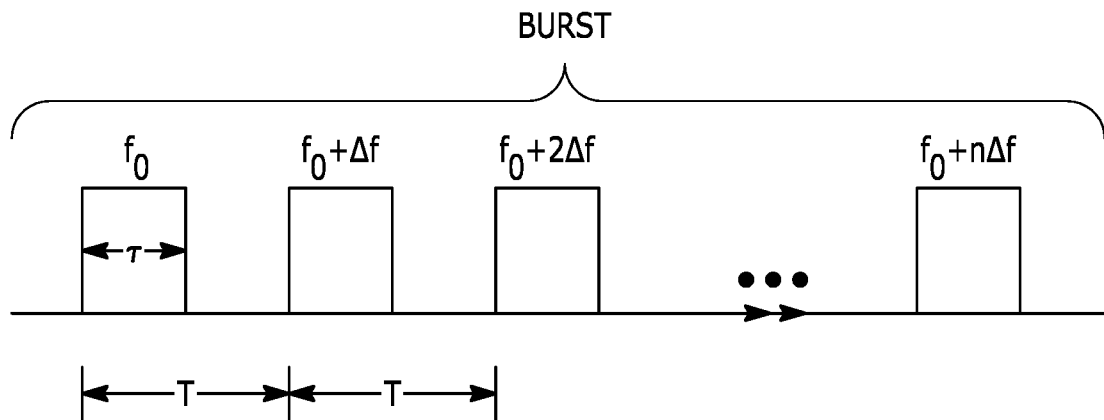
FIG. 14 depicts a burst of electromagnetic energy using stepped frequency transmission.

In an embodiment, the sensor system described herein is operated using stepped frequency transmission. Operation of the sensor system using stepped frequency transmission is described in more detail below. FIG. 14 depicts a burst of electromagnetic energy using stepped frequency transmission. The frequency of the pulses in the burst can be expressed as:

$$f_n = f_0 + n\Delta f$$

where $f_0$=starting carrier frequency, $\Delta f$=step size, T=pulse length (active, per frequency), T=repetition interval, n=1, . . . N, each burst consists of N pulses (frequencies) and a coherent processing interval (CPI)=N·T=1 full burst.

Using stepped frequency transmission enables relatively high range resolution. High range resolution can be advantageous when trying to monitor a health parameter such as the blood glucose level in a vein that may, for example, have a diameter in the range of 1-4 mm. For example, in order to effectively isolate a signal that corresponds to reflections of electromagnetic energy from the blood in a 1-4 mm diameter vein, it is desirable to have a high range resolution, which is provided by the 122-126 GHz frequency range.

Using stepped frequency transmission, range resolution can be expressed as:

$$\Delta R = c/2B$$

wherein c=speed of light, B=effective bandwidth. The range resolution can then be expressed as:

$$\Delta R = c/2N \cdot \Delta f$$

wherein B=N·$\Delta f$. Thus, range resolution does not depend on instantaneous bandwidth and the range resolution can be increased arbitrarily by increasing N·$\Delta f$.

Figure 15A:
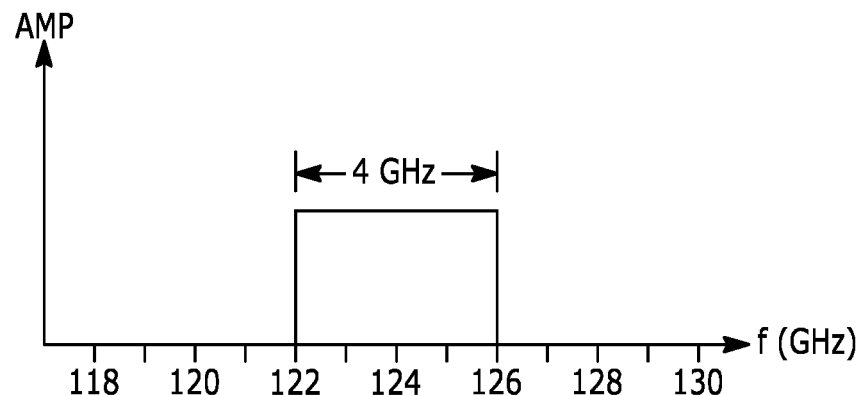
FIG. 15A depicts a graph of the transmission bandwidth, B, of transmitted electromagnetic energy in the frequency range of 122-126 GHz.
Figure 15B:
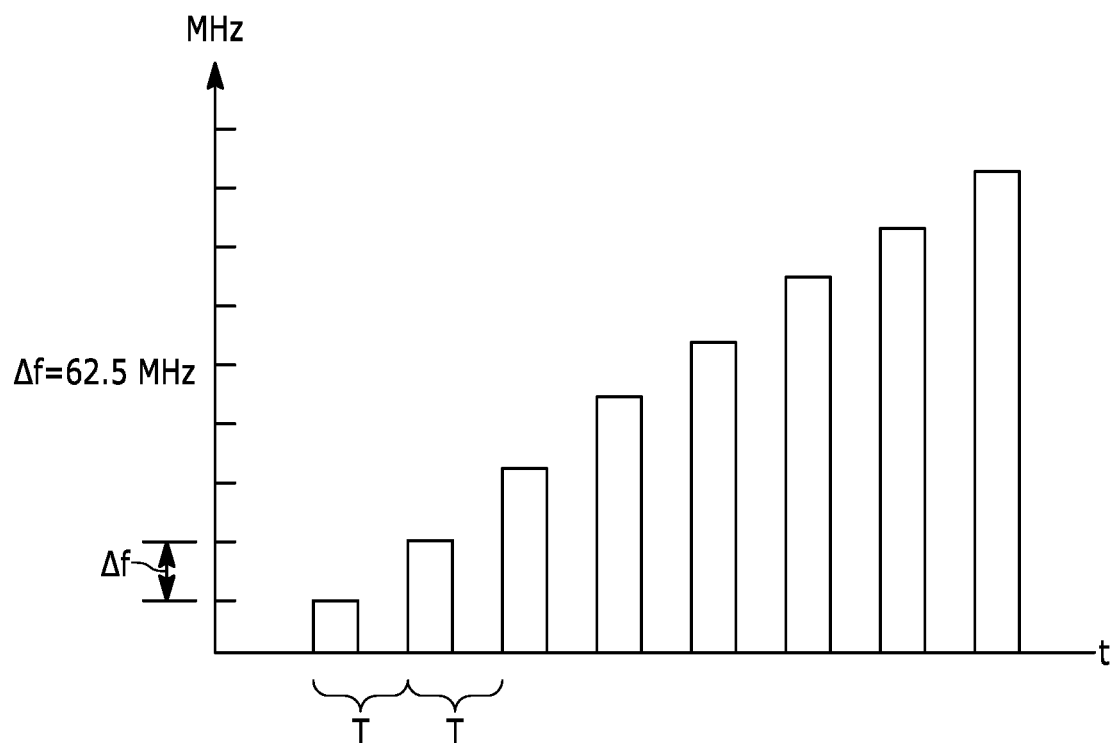
FIG. 15B depicts a graph of stepped frequency pulses that have a repetition interval, T, and a step size, Δf, of 62.5 MHz.

In an embodiment, the electromagnetic energy is transmitted from the TX antennas in the frequency range of approximately 122-126 GHz, which corresponds to a total bandwidth of approximately 4 GHz, e.g., B=4 GHz. FIG. 15A depicts a graph of the transmission bandwidth, B, of transmitted electromagnetic energy in the frequency range of 122-126 GHz. Within a 4 GHz bandwidth, from 122-126 GHz, discrete frequency pulses can be transmitted. For example, in an embodiment, the number of discrete frequencies that can be transmitted ranges from, for example, 64-256 discrete frequencies. In a case with 64 discrete frequency pulses and a repetition interval, T, over 4 GHz of bandwidth, the step size, $\Delta f$, is 62.5 MHz (e.g., 4 GHz of bandwidth divided by 64=62.5 MHz) and in a case with 256 discrete frequency pulses and a repetition interval, T, over 4 GHz of bandwidth, the step size, $\Delta f$, is 15.625 MHz (e.g., 4 GHz of bandwidth divided by 256=15.625 MHz). FIG. 15B depicts a graph of stepped frequency pulses that have a repetition interval, T, and a step size, $\Delta f$, of 62.5 MHz (e.g., 4 GHz of bandwidth divided by 64=62.5 MHz). As described above, an example sensor system has four RX antennas. Assuming a discrete frequency can be received on each RX antenna, degrees of freedom (DOF) of the sensor system in the receive operations can be expressed as: 4 RX antennas×64 discrete frequencies=256 DOF; and 4 RX antennas×256 discrete frequencies=1K DOF. The number of degrees of freedom (also referred to as "transmission frequency diversity") can provide signal diversity, which can be beneficial in an environment such as the anatomy of a person. For example, the different discrete frequencies may have different responses to the different anatomical features of the person. Thus, greater transmission frequency diversity can translate to greater signal diversity, and ultimately to more accurate health monitoring.

Figure 16A:
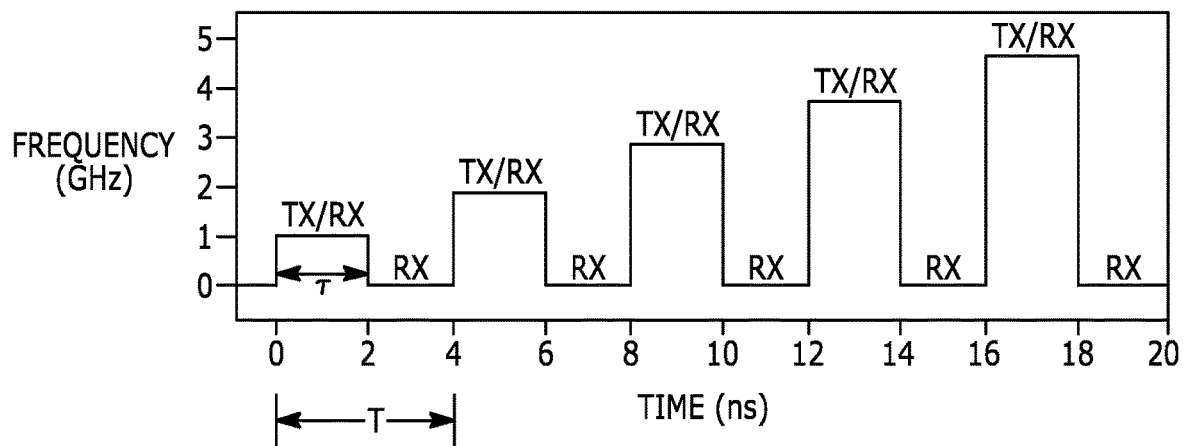
FIG. 16A depicts a frequency versus time graph of transmission pulses, with transmit (TX) interval and receive (RX) intervals identified relative to the pulses.
Figure 16B:
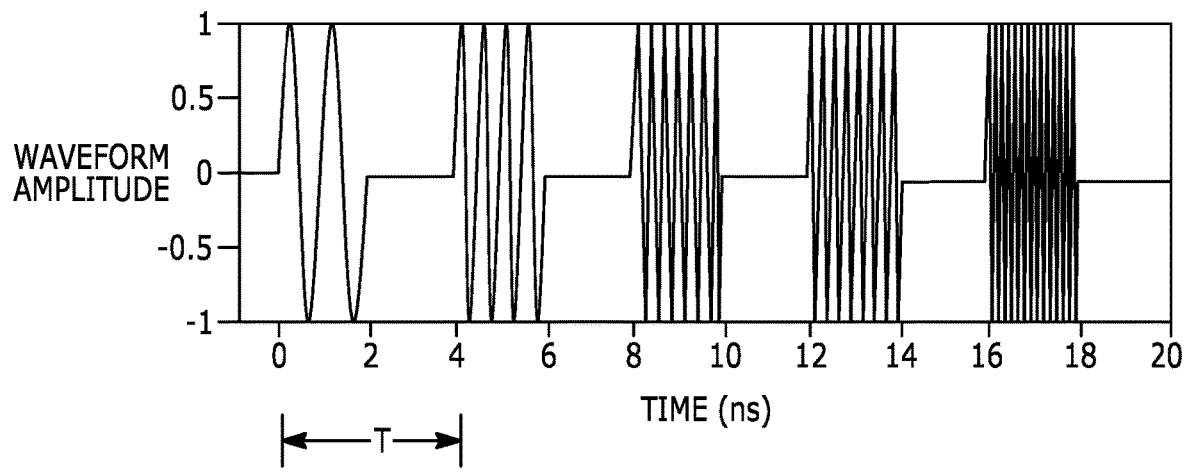
FIG. 16B depicts an amplitude versus time graph of the transmission waveforms that corresponds to FIG. 16A.

One feature of a stepped frequency transmission approach is that the sensor system receives reflected electromagnetic energy at basically the same frequency over the repetition interval, T. That is, as opposed to chirp transmission, the frequency of the pulse does not change over the interval of the pulse and therefore the received reflected electromagnetic energy is at the same frequency as the transmitted electromagnetic energy for the respective interval. FIG. 16A depicts a frequency versus time graph of transmission pulses, with transmit (TX) interval and receive (RX) intervals identified relative to the pulses. As illustrated in FIG. 16A, RX operations for the first pulse occur during the pulse length, $\tau$, of repetition interval, T, and during the interval between the next pulse. FIG. 16B depicts an amplitude versus time graph of the transmission waveforms that corresponds to FIG. 16A. As illustrated in FIG. 16B, the amplitude of the pulses is constant while the frequency increases by $\Delta f$ at each repetition interval, T.

In an embodiment, the power of the transmitted electromagnetic energy can be set to achieve a desired penetration depth and/or a desired illumination volume. In an embodiment, the transmission power from the TX antennas is about 15 dBm.

In an embodiment, electromagnetic energy can be transmitted from the TX antennas one TX antenna at a time (referred to herein as "transmit diversity"). For example, a signal is transmitted from a first one of the two TX antennas while the second one of the two TX antennas is idle and then a signal is transmitted from the second TX antenna while the first TX antenna is idle. Transmit diversity may reveal that illumination from one of the two TX antennas provides a higher quality signal than illumination from the other of the two TX antennas. This may be especially true when trying to illuminate a vein whose location may vary from person to person and/or from moment to moment (e.g., depending on the position of the wearable device relative to the vein). Thus, transmit diversity can provide sets of received signals that are independent of each other and may have different characteristics, e.g., signal power, SNR, etc.

Some theory related to operating the sensor system using a stepped frequency approach is described with reference to FIG. 17, which illustrates operations related to transmitting, receiving, and processing phases of the sensor system operation. With reference to the upper portion of FIG. 17, a time versus amplitude graph of a transmitted signal burst, similar to the graph of FIG. 16B, is shown. The graph represents the waveforms of five pulses of a burst at frequencies of $f_0$, $f_0+\Delta f$, $f_0+2\Delta f$, $f_0+3\Delta f$, and $f_0+4\Delta f$.

Figure 17:
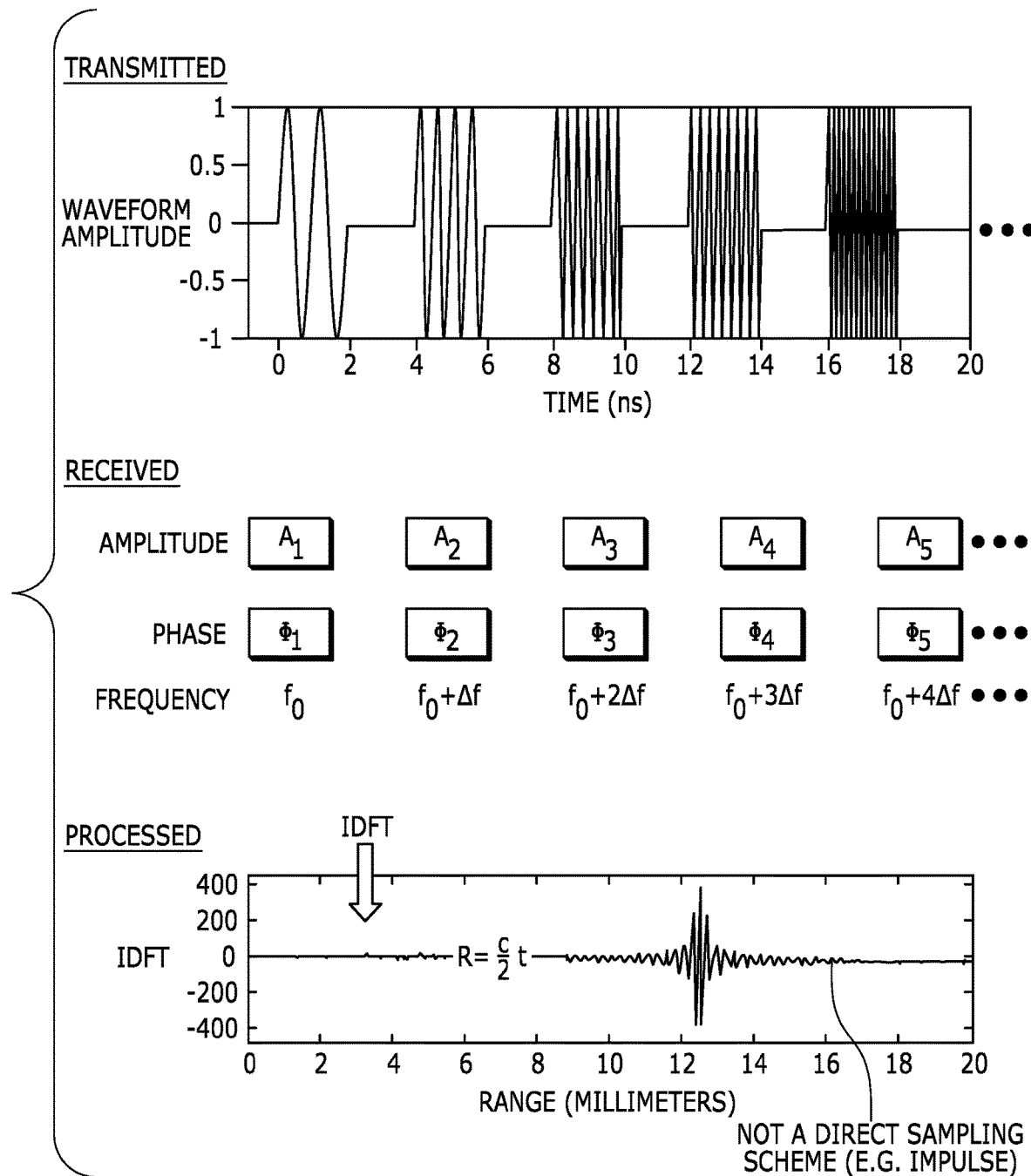
FIG. 17 illustrates operations related to transmitting, receiving, and processing phases of the sensor system operation.

The middle portion of FIG. 17 represents values of received signals that correspond to the amplitude, phase, and frequency of each pulse in the burst of four pulses. In an embodiment, received signals are placed in range bins such that there is one complex sample per range bin per frequency. Inverse Discrete Fourier Transforms (IDFTs) are then performed on a per-range bin basis to determine range information. The bottom portion of FIG. 17 illustrates an IDFT process that produces a signal that corresponds to the range of a particular object. For example, the range may correspond to a vein such as the basilic vein. In an embodiment, some portion of the signal processing is performed digitally by a DSP or CPU. Although one example of a signal processing scheme is described with reference to FIG. 17, other signal processing schemes may be implemented to isolate signals that correspond to reflections from blood in a vein (such as the basilic vein) from signals that correspond to reflections from other undesired anatomical features (such as tissue and bones) and from signals that correspond to leakage from the TX antennas.

Figure 18:
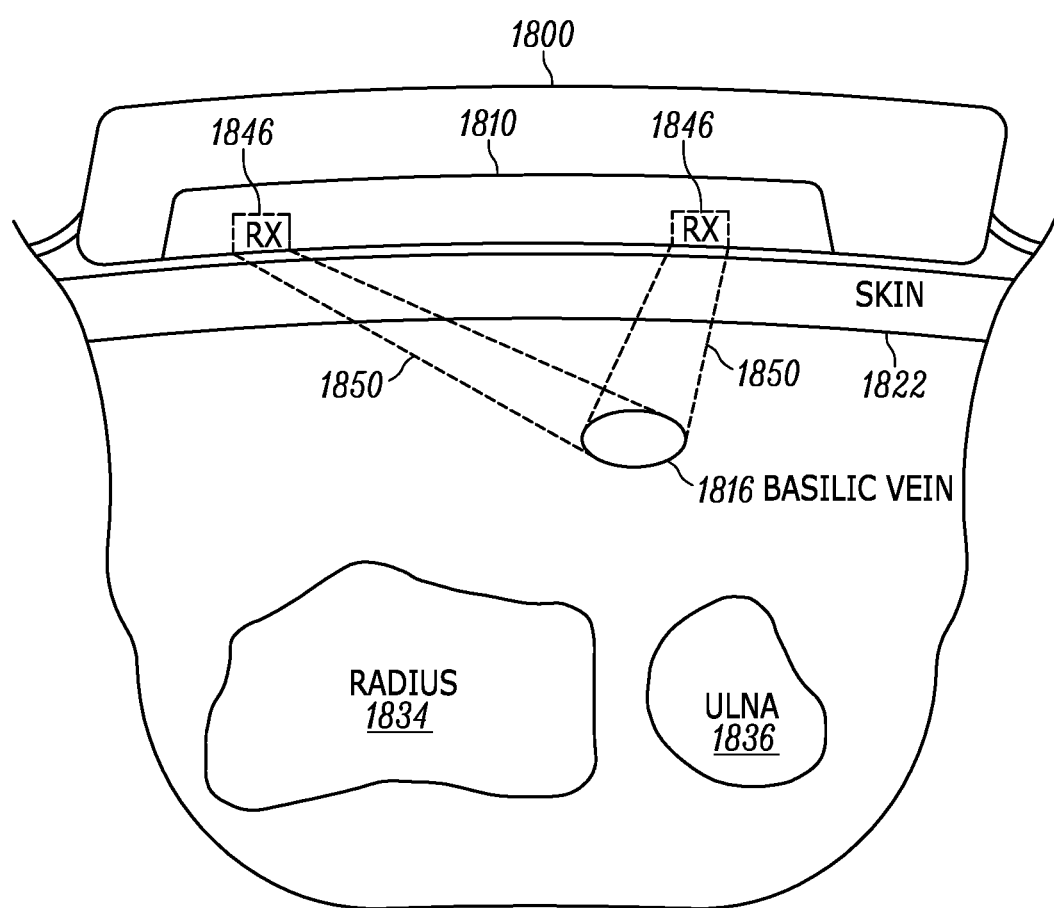
FIG. 18 depicts an expanded view of the anatomy of a wrist, similar to that described above with reference to FIGS. 2A-4D, relative to RX antennas of a sensor system that is integrated into a wearable device such as a smartwatch.

Beamforming is a signal processing technique used in sensor arrays for directional signal transmission and/or reception. Beamforming can be implemented by combining elements in a phased antenna array in such a way that signals at particular angles experience constructive interference while other signals experience destructive interference. Beamforming can be used in both transmit operations and receive operations in order to achieve spatial selectivity, e.g., to isolate some received signals from other received signals. In an embodiment, beamforming techniques are utilized to isolate signals that correspond to reflections from blood in a vein (such as the basilic vein) from signals that correspond to reflections from other undesired anatomical features (such as tissue and bones) and from signals that correspond to leakage from the TX antennas. An example of the concept of beamforming as applied to blood glucose monitoring using a wearable device such as a smartwatch is illustrated in FIG. 18. In particular, FIG. 18 depicts an expanded view of the anatomy of a wrist, similar to that described above with reference to FIGS. 2A-4D, relative to RX antennas 1846 of a sensor system 1810 that is integrated into a wearable device such as a smartwatch 1800. The anatomical features of the wrist that are illustrated in FIG. 18 include the skin 1822, a vein such as the basilic vein 1816, the radius bone 1834, and the ulna bone 1836. FIG. 18 also illustrates 2D representations of reception beams 1850 (although it should be understood that the beams occupy a 3D space/volume) that correspond to electromagnetic energy that is reflected from the blood in the basilic vein to the respective RX antenna.

In an embodiment, a beamforming technique involves near-field beamforming, where each RX antenna of the phased antenna array is steered independently to a different angle as opposed to far-field beamforming where all of the antennas in a phased antenna array are steered collectively to the same angle. For example, near-field beamforming is used when the target is less than about 4-10 wavelengths from the phased antenna array. In the case of a sensor system operating at 122-126 GHz, 4-10 wavelengths is approximately within about 10-25 mm from the phased antenna array. In the case of monitoring a health parameter related to blood, the blood vessels that are monitored (e.g., the basilic and/or cephalic veins) are likely to be less than 10-25 mm from the phase antenna array. Thus, in an embodiment, near-field beamforming techniques are used to isolate desired signals (e.g., signals that correspond to reflections from blood in a vein such as the basilic vein) from undesired signals (e.g., signals that correspond to reflections from other undesired anatomical features, such as tissue and bones, and from signals that correspond to leakage from the TX antennas). Beamforming can be accomplished in digital, in analog, or in a combination of digital and analog signal processing. In an embodiment, the ranging technique described above, which utilizes stepped frequencies, is used in combination with beamforming to isolate signals that correspond to the reflection of electromagnetic energy from the basilic vein.

The Doppler effect relates to the change in frequency or wavelength of a wave (e.g., an electromagnetic wave) in relation to an observer, which is moving relative to the source of the wave. The Doppler effect can be used to identify fluid flow by sensing the shift in wavelength of reflections from particles moving with the fluid flow. In accordance with an embodiment of the invention, signal processing based on the Doppler effect is applied to signals received by the sensor system to isolate signals that correspond to reflections from flowing blood from signals that correspond to reflections from objects that are stationary, at least with respect to the flowing blood. As described above, millimeter wave radio waves are transmitted below the skin to illuminate anatomical features below the skin. In the area of the body around the wrist, blood flowing through veins such as the basilic and cephalic veins is moving relative to the other anatomical features in the area. Thus, Doppler effect theory and corresponding signal processing is used to filter for those signals that correspond to movement (movement relative to other signals that correspond to stationary objects). In the health monitoring application as described herein, the signals that correspond to the flowing blood can be identified by applying the Doppler effect theory to the signal processing to isolate the signals that correspond to the flowing blood. The isolated signals can then be used to measure a health parameter such as blood glucose level.

Figure 19:
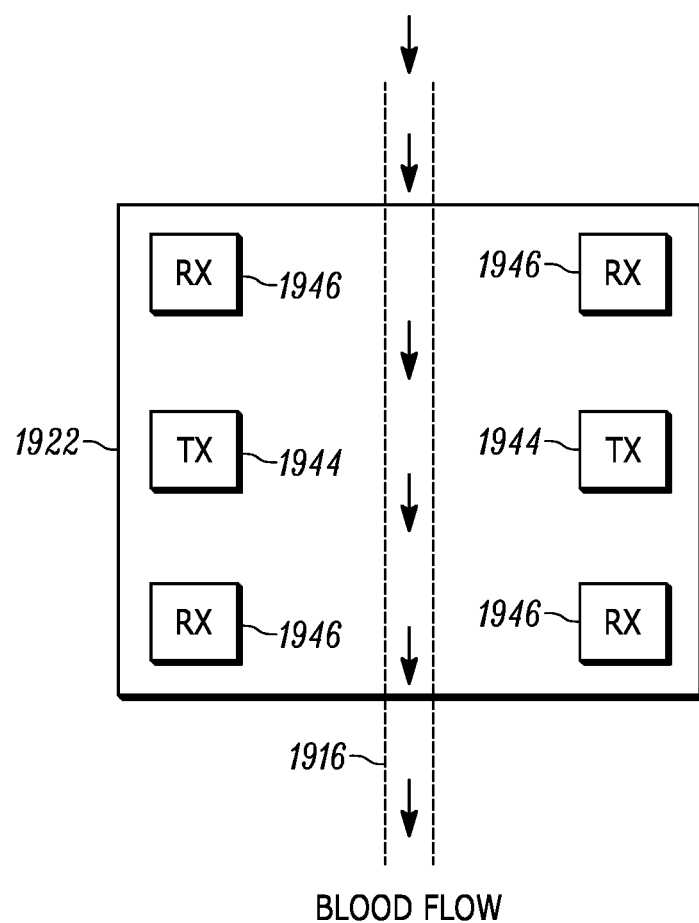
FIG. 19 illustrates an IC device similar to the IC device shown in FIG. 8A relative to a vein and blood flowing through the vein.

FIG. 19 illustrates an IC device 1922 similar to the IC device 822 shown in FIG. 8A relative to a vein 1916 such as the basilic or cephalic vein in the wrist area of a person. FIG. 19 also illustrates the flow of blood through the vein relative to the IC device. Because the blood is moving relative to the TX and RX antennas 1944 and 1946 of the sensor system, Doppler effect theory can be applied to signal processing of the received signals to isolate the signals that correspond to the flowing blood from the signals that correspond to objects that are stationary relative to the flowing blood. For example, received signals that correspond to flowing blood are isolated from received signals that correspond to stationary objects such as bone and fibrous tissue such as muscle and tendons. In an embodiment, Doppler processing involves performing a fast Fourier transform (FFT) on samples to separate the samples into component Doppler shift frequency bins. Frequency bins that represent no frequency shift can be ignored (as they correspond to reflections from stationary objects) and frequency bins that represent a frequency shift (which corresponds to reflections from a moving object) can be used to determine a health parameter. That is, Doppler effect processing can be used to isolate signals that represent no frequency shift (as they correspond to reflections from stationary objects) from frequency bins that represent a frequency shift (which correspond to reflections from a moving object). In an embodiment, Doppler effect signal processing may involve sampling over a relatively long period of time to achieve small enough velocity bins to decipher relative movement. Thus, Doppler effect theory and corresponding signal processing can be used to filter for only those signals that correspond to movement (movement relative to the other received signals). Such an approach allows signals that correspond to reflections from flowing blood, e.g., blood in a vein, to be isolated from other signals, e.g., signals that correspond to stationary object. In an embodiment, Doppler signal processing is performed digitally by a DSP and/or by a CPU.

With reference to FIG. 8A, during operation of the IC device 822, some electromagnetic energy that is emitted from the TX antennas 844 will be received directly by at least one of the RX antennas 846 without first passing through the skin of the person. Signals that correspond to such electromagnetic energy do not correspond to a health parameter that is to be monitored and are referred to herein as electromagnetic energy leakage or simply as "leakage." In an embodiment, various signal processing techniques may be implemented to mitigate the effects of leakage. For example, signals that correspond to leakage should be isolated from signals that correspond to reflections of radio waves from blood in a vein. In an embodiment, leakage is mitigated by applying signal processing to implement beamforming, Doppler effect processing, range discrimination or a combination thereof. Other techniques such as antenna design and antenna location can also be used to mitigate the effects of leakage.

Figure 20:
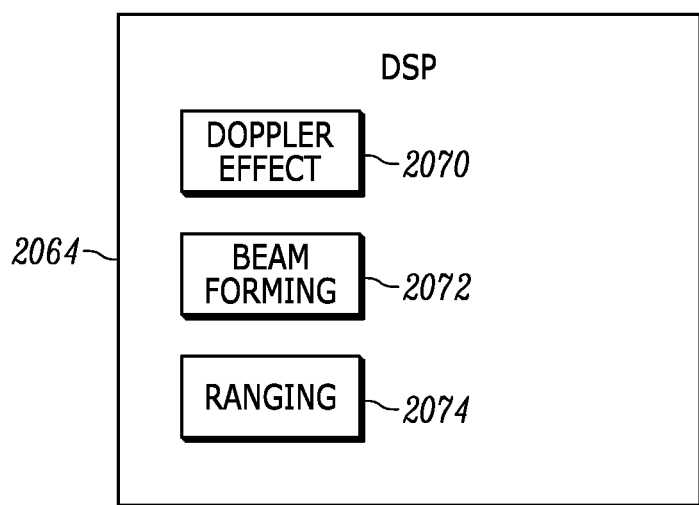
FIG. 20 is an embodiment of a DSP that includes a Doppler effect component, a beamforming component, and a ranging component.

In an embodiment, signal processing to isolate signals that correspond to reflections of radio waves from blood in a vein from signals that correspond to reflections of radio waves from other anatomical objects (such as bone and fibrous tissue such as muscle and tendons) and from signals that correspond to leakage can be implemented in part or in full digitally by a DSP. FIG. 20 is an embodiment of a DSP 2064 that includes a Doppler effect component 2070, a beamforming component 2072, and a ranging component 2074. In an embodiment, the Doppler effect component is configured to implement digital Doppler effect processing, the beamforming component is configured to implement digital beamforming, and the ranging component is configured to implement digital ranging. Although the DSP is shown as including the three components, the DSP may include fewer components and the DSP may include other digital signal processing capability. The DSP may include hardware, software, and/or firmware or a combination thereof that is configured to implement the digital signal processing that is described herein. In an embodiment, the DSP may be embodied as an ARM processor (Advanced RISC (reduced instruction set computing) Machine). In some embodiments, components of a DSP can be implemented in the same IC device as the RF front-end and the TX and RX antennas. In other embodiments, components of the DSP are implemented in a separate IC device or IC devices.

In an embodiment, the transmission of millimeter radio waves and the processing of signals that correspond to received radio waves is a dynamic process that operates to locate signals corresponding to the desired anatomy (e.g., signals that correspond to reflections of radio waves from a vein) and to improve the quality of the desired signals (e.g., to improve the SNR). For example, the process is dynamic in the sense that the process is an iterative and ongoing process as the location of the sensor system relative to a vein or veins changes.

Although the techniques described above are focused on monitoring the blood glucose level in a person, the disclosed techniques are also applicable to monitoring other parameters of a person's health such as, for example, blood pressure and heart rate. For example, the reflectively of blood in a vessel such as the basilic vein will change relative to a change in blood pressure. The change in reflectivity as monitored by the sensor system can be correlated to a change in blood pressure and ultimately to an absolute value of a person's blood pressure. Additionally, monitored changes in blood pressure can be correlated to heart beats and converted over time to a heart rate, e.g., in beats per minute. In other embodiments, the disclosed techniques can be used to monitor other parameters of a person's health that are affected by the chemistry of the blood. For example, the disclosed techniques may be able to detect changes in blood chemistry that correspond to the presence of foreign chemicals such as alcohol, narcotics, cannabis, etc. The above-described techniques may also be able to monitor other parameters related to a person, such as biometric parameters.

In an embodiment, health monitoring using the techniques described above, may involve a calibration process. For example, a calibration process may be used for a particular person and a particular monitoring device to enable desired monitoring quality.

The above-described techniques are used to monitor a health parameter (or parameters) related to blood in a blood vessel or in blood vessels of a person. The blood vessels may include, for example, arteries, veins, and/or capillaries. The health monitoring technique can target blood vessels other than the basilic and/or cephalic veins. For example, other near-surface blood vessels (e.g., blood vessels in the subcutaneous layer) such as arteries may be targeted. Additionally, locations other than the wrist area can be targeted for health monitoring. For example, locations in around the ear may be a desirable location for health monitoring, including, for example, the superficial temporal vein and/or artery and/or the anterior auricular vein or artery. In an embodiment, the sensor system may be integrated into a device such as a hearing aid or other wearable device that is attached to the ear or around or near the ear. In another embodiment, locations in and around the elbow joint of the arm may be a desirable location for health monitoring. For example, in or around the basilica vein or the cephalic vein at or near the elbow.

Although the techniques are described as using a frequency range of 122-126 GHz, some or all of the above-described techniques may be applicable to frequency ranges other than 122-126 GHz. For example, the techniques may be applicable to frequency ranges around 60 GHz. In another embodiment, the techniques described herein may be applicable to the 2-6 GHz frequency range. For example, a system similar to that described with reference to FIG. 6 may be used to implement health monitoring by transmitting and receiving RF energy in the 2-6 GHz range. In still another embodiment, multiple non-contiguous frequency ranges may be used to implement health monitoring. For example, health monitoring may be implemented using both the 2-6 GHz frequency range and the 122-126 GHz frequency range. For example, in an embodiment, stepped frequency scanning in implemented in the lower frequency range and then in the higher frequency range, or vice versa. Using multiple non-contiguous frequency ranges (e.g., both the 2-6 GHz frequency range and the 122-126 GHz frequency range) may provide improved accuracy of health monitoring.

In an embodiment, the sensor system may be embedded into a different location in a monitoring device. For example, in an embodiment, a sensor system (or a portion of the sensor system such as IC device as shown in FIG. 8A) is embedded into an attachment device such as the strap of a smartwatch so that the sensor system can target a different blood vessel in the person. For example, the sensor system may be embedded into the strap of a smartwatch so that a blood vessel at the side area of the wrist and/or at the anterior area of the wrist can be monitored. In such an embodiment, the strap may include conductive signal paths that communicate signals between the sensor IC device and the processor of the smartwatch.

Figure 21:
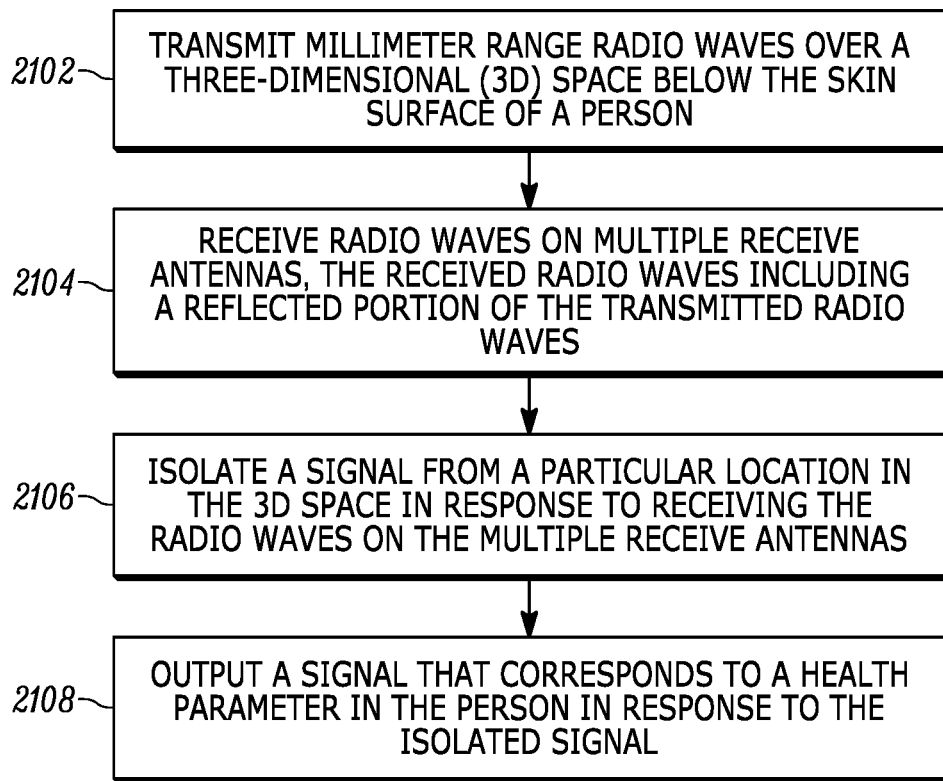
FIG. 21 is a process flow diagram of a method for monitoring a health parameter in a person.

FIG. 21 is a process flow diagram of a method for monitoring a health parameter in a person. At block 2102, millimeter range radio waves are transmitted over a three-dimensional (3D) space below the skin surface of a person. At block 2104, radio waves are received on multiple receive antennas, the received radio waves including a reflected portion of the transmitted radio waves. At block 2106, a signal is isolated from a particular location in the 3D space in response to receiving the radio waves on the multiple receive antennas. At block 2108, a signal that corresponds to a health parameter in the person is output in response to the isolated signal. In an embodiment, the health parameter is blood glucose level. In other embodiments, the health parameter may be blood pressure or heart rate.

In an embodiment, health monitoring information that is gathered using the above-described techniques can be shared. For example, the health monitoring information can be displayed on a display device and/or transmitted to another computing system via, for example, a wireless link.

Figure 22A:
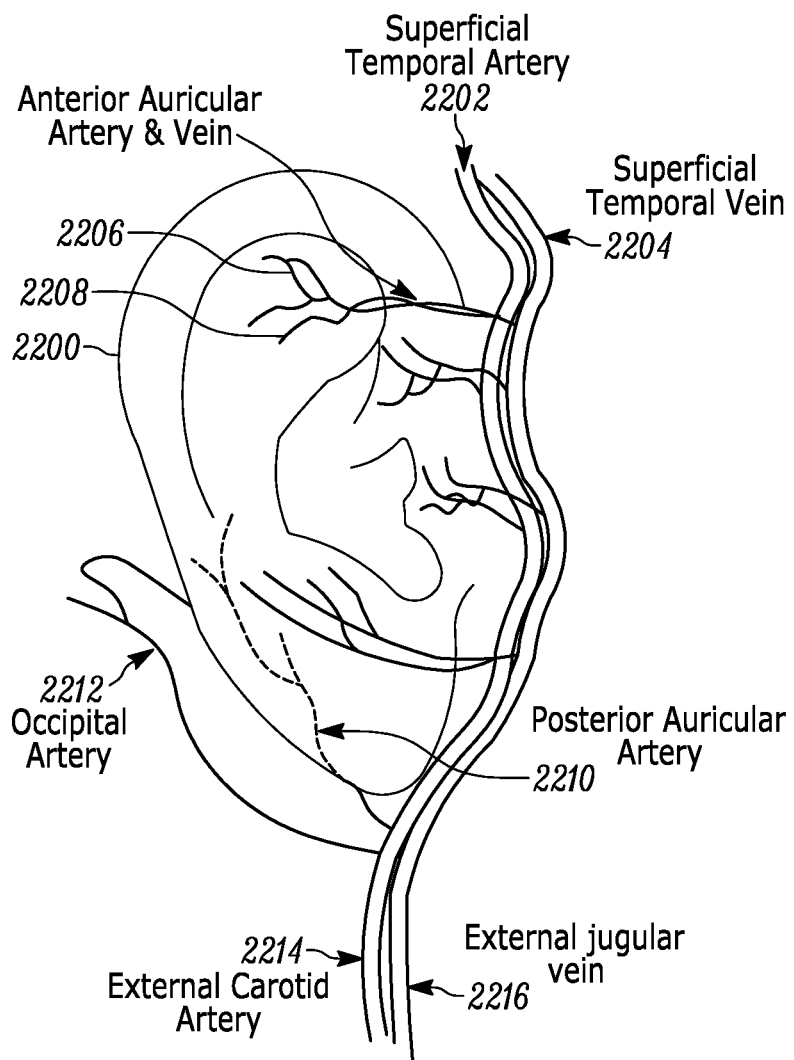
FIG. 22A depicts a side view of the area around a person's ear with the typical approximate locations of veins and arteries, including the superficial temporal artery, the superficial temporal vein, the anterior auricular artery and vein, the posterior auricular artery, the occipital artery, the external carotid artery, and the external jugular vein.
Figure 22B:
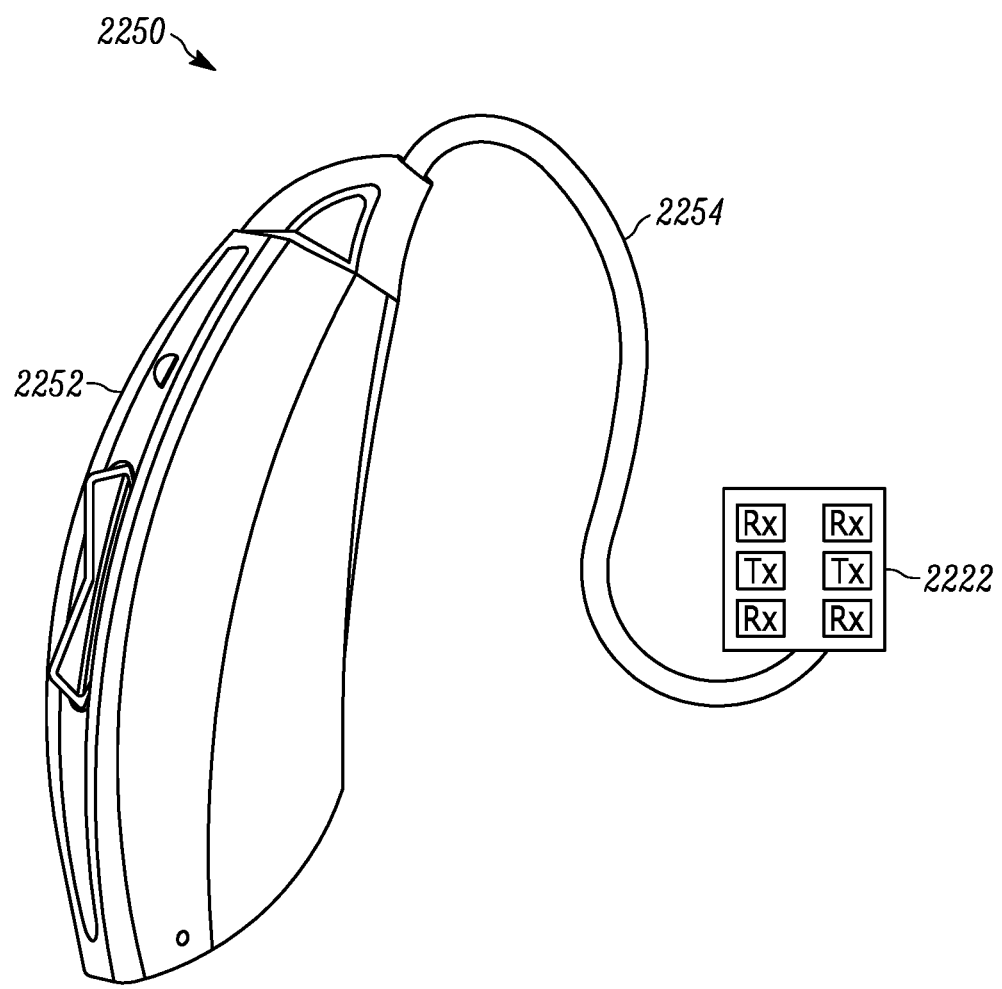
FIG. 22B depicts an embodiment of system in which at least elements of an RF front-end are located separate from a housing.
Figure 22C:
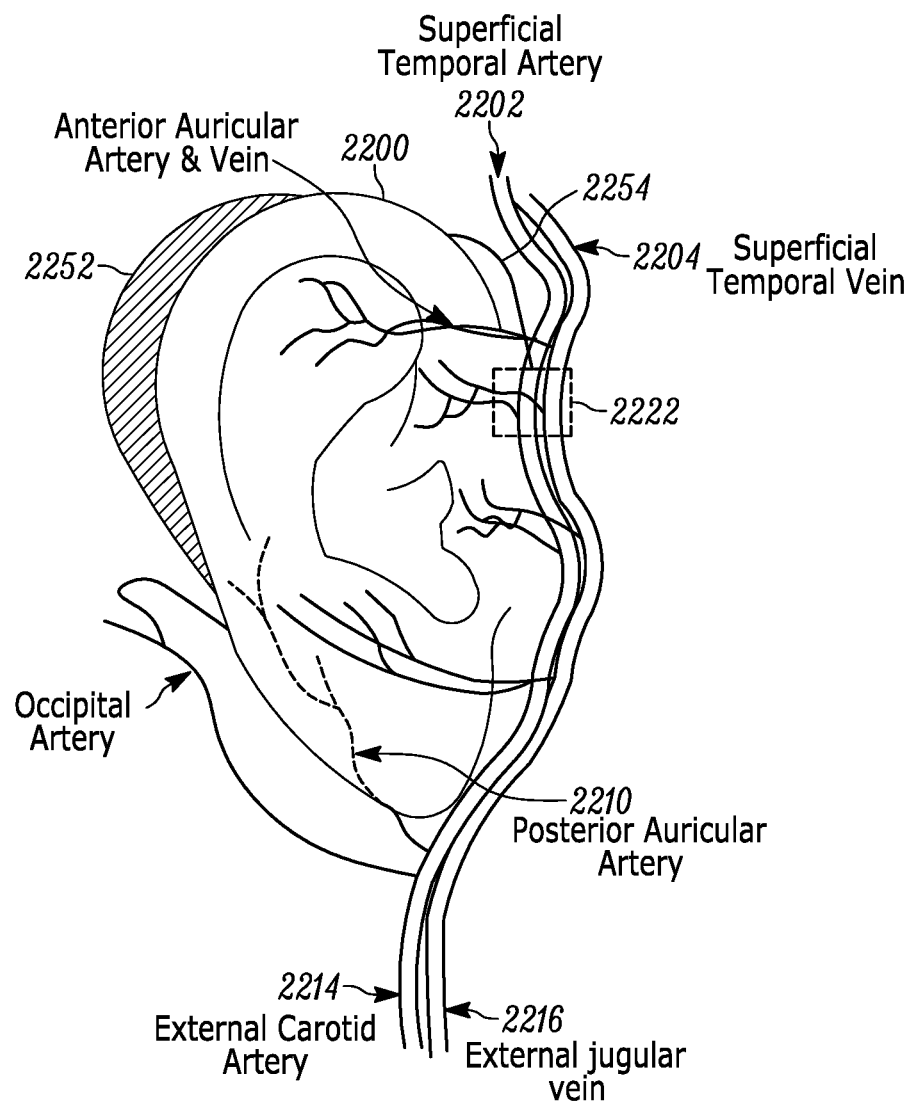
FIG. 22C illustrates how a device, such as the device depicted in FIG. 22B, may be worn near the ear of a person similar to how a conventional hearing aid is worn.

As mentioned above, locations in around the ear may be desirable for health monitoring, including, for example, the superficial temporal artery or vein, the anterior auricular artery or vein, and/or the posterior auricular artery. FIG. 22A depicts a side view of the area around a person's ear 2200 with the typical approximate locations of veins and arteries, including the superficial temporal artery 2202, the superficial temporal vein 2204, the anterior auricular artery 2206 and vein 2208, the posterior auricular artery 2210, the occipital artery 2212, the external carotid artery 2214, and the external jugular vein 2216. In an embodiment, a sensor system, such as the sensor system described herein, may be integrated into a device such as a hearing aid or another wearable device that is attached to the ear or around or near the ear. FIG. 22B depicts an embodiment of system 2250 in which at least elements of an RF front-end 2222 (including the transmit and receive antennas and corresponding transmit and receive components as shown in FIGS. 5-7) are located separate from a housing 2252 that includes, for example, a digital processor, wireless communications capability, and a source of electric power, all of which are enclosed within the housing. For example, components of the digital baseband system as shown in FIG. 5 may be enclosed within the housing and the housing is connected to the RF front-end by a communications medium 2254, such as a conductive wire or wires. In an embodiment, the housing 2252 is worn behind the ear 2200 similar to a conventional hearing aid and the RF front-end 2222 is located near a blood vessel that is around the ear. For example, the RF front-end may include adhesive material that enables the RF front-end to be adhered to the skin near a blood vessel such as, for example, the superficial temporal artery 2202 or vein 2204, the anterior auricular artery 2206 or vein 2208, and/or the posterior auricular artery 2210. FIG. 22C illustrates how a device, such as the device depicted in FIG. 22B, may be worn near the ear 2200 of a person similar to how a conventional hearing aid is worn. FIG. 22C also shows the RF front-end 2222 relative to the superficial temporal artery 2202 and the superficial temporal vein 2204 as shown in FIG. 22C. In an embodiment, the sensor system may be integrated with a conventional hearing aid to provide both hearing assistance and health monitoring. For example, the integrated system may include a housing, a speaker that is inserted into the ear, and an RF front-end that is attached to the skin around the ear and near to a blood vessel. In other embodiments, a sensor system may be integrated into ear buds or into some other type of device that is worn around or near the ear.

Although the magnitude of the reflected RF energy (also referred to as amplitude) that is received by the sensor system has been found to correspond to a health parameter, such as blood glucose level, it has further been found that the combination of the amplitude and the phase of the reflected RF energy can provide improved correspondence to a health parameter, such as a blood glucose level. Thus, in an embodiment, a value that corresponds to a health parameter of a person is generated in response to amplitude and phase data that is generated in response to received radio waves. For example, the value that corresponds to a health parameter may be a value that indicates a blood glucose level in mg/dL or some other indication of the blood glucose level, a value that indicates a person's heart rate (e.g., in beats per minute), and/or a value that indicates a person's blood pressure (e.g., in millimeters of mercury, mmHg). In an embodiment, a method for monitoring a health parameter (e.g., blood glucose level) in a person involves transmitting radio waves below the skin surface of a person and across a range of stepped frequencies, receiving radio waves on a two-dimensional array of receive antennas, the received radio waves including a reflected portion of the transmitted radio waves across the range of stepped frequencies, generating data that corresponds to the received radio waves, wherein the data includes amplitude and phase data across the range of stepped frequencies, and determining a value that is indicative of a health parameter in the person in response to the amplitude and phase data. In an embodiment, the phase data corresponds to detected shifts in sine waves that are received at the sensor system. In another embodiment, a value that is indicative of a health parameter in the person may be determined in response to phase data but not in response to amplitude data.

Additionally, it has been found that certain step sizes in stepped frequency scanning can provide good correspondence in health parameter monitoring. In an embodiment, the frequency range that is scanned using stepped frequency scanning is on the order of 100 MHz in the 122-126 GHz range and the step size is in the range of 100 kHz-1 MHz. For example, in an embodiment, the step size over the scanning range is around 100 kHz (±10%).

Although the amplitude and phase of the reflected RF energy that is received by the sensor system has been found to correspond to a health parameter, such as blood glucose level, it has further been found that the combination of the amplitude and phase of the reflected RF energy and some derived data, which is derived from the amplitude and/or phase data, can provide improved correspondence to a health parameter, such as blood glucose level. Thus, in an embodiment, some data is derived from the amplitude and/or phase data that is generated by the sensor system in response to the received RF energy and the derived data is used, often in conjunction with the amplitude and/or phase data, to determine a value that corresponds to a health parameter (e.g., the blood glucose level) of a person. For example, the data derived from the amplitude and/or phase data may include statistical data such as the standard deviation of the amplitude over a time window and/or the standard deviation of the phase over a time window. In an embodiment, data can be derived from the raw data on a per-receive antenna basis or aggregated amongst the set of receive antennas. In a particular example, it has been found that the amplitude, phase, and the standard deviation of amplitude over a time window (e.g., a time window of 1 second) corresponds well to blood glucose levels.

In an embodiment, a method for monitoring a health parameter (e.g., blood glucose level) in a person involves transmitting radio waves below the skin surface of the person and across a range of stepped frequencies, receiving radio waves on a two-dimensional array of receive antennas, the received radio waves including a reflected portion of the transmitted radio waves across the range of stepped frequencies, generating data that corresponds to the received radio waves, wherein the data includes amplitude and phase data, deriving data from at least one of the amplitude and phase data, and determining a value that is indicative of a health parameter in the person in response to the derived data. In an embodiment, the value is determined in response to not only the derived data but also in response to the amplitude data and the phase data. In an embodiment, the derived data is a statistic that is derived from amplitude and/or phase data that is generated over a time window. For example, the statistic is one of a standard deviation, a moving average, and a moving mean. In other embodiments, the derived data may include multiple statistics derived from the amplitude and/or phase data. In an embodiment, a value that is indicative of a health parameter is determined in response to a rich set of parameters associated with the stepped frequency scanning including the scanning frequency, the detected amplitudes and phases of the received RF energy, data derived from the detected amplitudes and phases, the state of the transmit components, and the state of the receive components.

Using a sensor system, such as the sensor system described above, there are various parameters to be considered in the stepped frequency scanning process. Some parameters are fixed during operation of the sensor system and other parameters may vary during operation of the sensor system. Of the parameters that may vary during operation of the sensor system, some may be controlled and others are simply detected. FIG. 23 is a table of parameters related to stepped frequency scanning in a system such as the above-described system. The table includes an identification of various parameters and an indication of whether the corresponding parameter is fixed during operation (e.g., fixed as a physical condition of the sensor system) or variable during operation and if the parameter is variable, whether the parameter is controlled, or controllable, during operation or simply detected during operation. In the table of FIG. 23, "Time" refers to an aspect of time such as an absolute moment in time relative to some reference (or may refer to a time increment, e.g., $\Delta t$). In an embodiment, the time corresponds to all of the other parameters in the table. That is, the state or value of all of the other parameters in the table is the state or value at that time in the stepped frequency scanning operation. "TX/RX frequency" refers to the transmit/receive frequency of the sensor system at the corresponding time as described above with reference to, for example, FIG. 6. The TX1 and TX2 state refers to the state of the corresponding transmitter (e.g., whether or not the corresponding power amplifiers (PAs) are on or off) at the corresponding time. In an embodiment, RF energy transmitted from the transmission antennas can be controlled by activating/deactivating the corresponding PAs. The RX1 and RX2 state refers to the state of the corresponding receive paths (e.g., whether or not components of the corresponding receive paths are active or inactive, which may involve powering on/off components in the receive path) at the corresponding time. In an embodiment, the receiving of RF energy on the receive paths can be controlled by activating/deactivating components of the corresponding receive paths. The RX detected amplitude refers to the amplitude of the received signals at the corresponding receive path and at the corresponding time and the RX detected phase refers to the phase (or phase shift) of the received signals at the corresponding receive path and at the corresponding time. The TX and RX antenna 2D position refers to information about the 2D position of the antennas in the sensor system (e.g., the positions of the antennas relative to each other or the positions of the antennas relative to a common location) and the antenna orientation refers to antenna characteristics that may be specific to a particular polarization orientation. For example, a first set of antennas may be configured for vertical polarization while a second set of antennas is configured for horizontal polarization in order to achieve polarization diversity. Other antenna orientations and/or configurations are possible. As indicated in the table, antenna position and antenna orientation are fixed during stepped frequency scanning.

Figure 25:
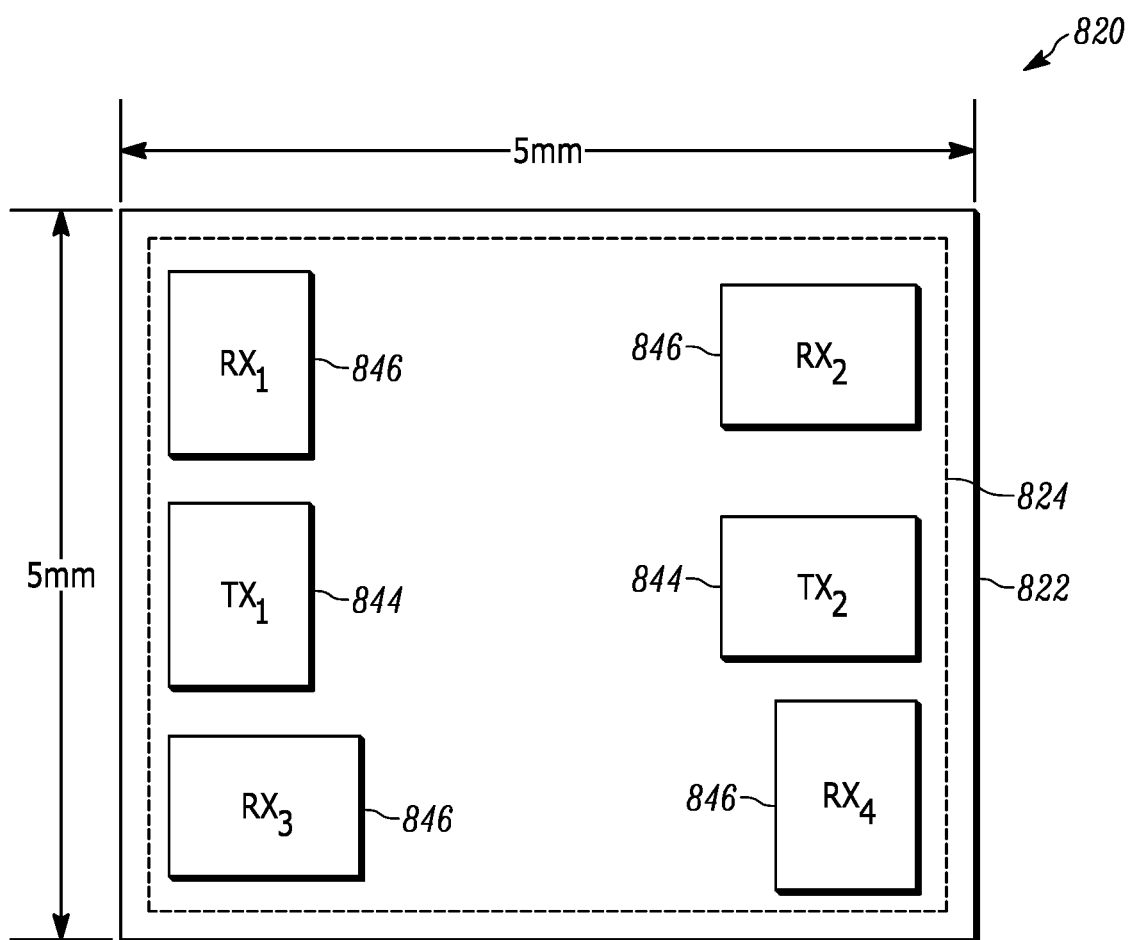
FIG. 25 depicts an embodiment of the IC device from FIG. 8A in which the antenna polarization orientation is illustrated by the orientation of the transmit and receive antennas.

FIG. 24 is a table of parameters similar to the table of FIG. 23 in which examples are associated with each parameter for a given step in a stepped frequency scanning operation in order to give some context to the table. As indicated in FIG. 24, the time is "t1" (e.g., some absolute time indication or a time increment) and the operating frequency is "X GHz," e.g., in the range of 2-6 GHz or 122-126 GHz. In the example of FIG. 24, TX1, RX1, and RX4 are active and TX2, RX2, and RX3 are inactive during this step in the stepped frequency scanning operation (e.g., at time 0). The detected amplitudes of RX1 and RX4 are indicated as "ampl1" and "ampl4" and the detected phases of RX1 and RX4 are indicated as "ph1" and "ph4." The detected amplitudes and phases of RX2 and RX3 are indicated as "n/a" since the receive paths are inactive. The positions of the transmit and receive antennas are indicated in the lower portion of the table and correspond to the configuration described above with reference to FIGS. 8A-8D and the antenna orientations are evenly distributed amongst vertical and horizontal orientations so as to enable polarization diversity. FIG. 25 depicts an embodiment of the IC device 820 from FIG. 8A in which the antenna polarization orientation is illustrated by the orientation of the transmit and receive antennas 844 and 846, respectively. In FIG. 25, rectangles with the long edges oriented vertically represent a vertical polarization orientation (e.g., antennas TX1, RX1, and RX4) and rectangles with the long edges oriented horizontally represent a horizontal polarization orientation (e.g., antennas TX2, RX2, and RX3). FIG. 24 reflects the same polarization orientations in which TX1 is configured to vertically polarize the transmitted RF energy and RX1 and RX4 are configured to receive vertically polarized RF energy and TX2 is configured to horizontally polarize the transmitted RF energy and RX2 and RX3 are configured to receive horizontally polarized RF energy. Although FIG. 24 is provided as an example, the parameter states of the variable parameters are expected to change during stepped frequency scanning and the fixed parameters may be different in different sensor system configurations.

In an embodiment, during a stepped frequency scanning operation, certain data, referred to herein as "raw data," is generated. For example, the raw data is generated as digital data that can be further processed by a digital data processor. FIG. 26 is a table of raw data (e.g., digital data) that is generated during stepped frequency scanning. The raw data depicted in FIG. 26 includes variable parameters of time, TX/RX frequency, RX1 amplitude/phase, RX2 amplitude/phase, RX3 amplitude/phase, and RX4 amplitude/phase. In the example of FIG. 26, the raw data corresponds to a set of data, referred to as a raw data record, which corresponds to one step in the stepped frequency scanning. For example, the raw data record corresponds to a particular frequency pulse as shown and described above with reference to FIG. 17. In an embodiment, a raw data record also includes some or all of the parameters identified in FIGS. 23 and 24. For example, the raw data record may include other variable and/or fixed parameters that correspond to the stepped frequency scanning operation. In an embodiment, multiple raw data records are accumulated and processed by a digital processor, which may include a DSP, an MCU, and/or a CPU as described above, for example, with reference to FIG. 5. Raw data (e.g., in the form of raw data records) may be used for machine learning.

As described above, it has been found that the combination of the amplitude and phase of reflected RF energy and some derived data, which is derived from amplitude and/or phase data (e.g., from the "raw data"), can provide improved correspondence to a health parameter, such as blood glucose level. Thus, in an embodiment, some data is derived from the amplitude and/or phase data that is generated by the sensor system in response to the received RF energy and the derived data is used, often in conjunction with the amplitude and/or phase data, to determine a value that corresponds to a health parameter (e.g., the blood glucose level) of a person. For example, the data is derived from the raw data records that include the data depicted in FIGS. 23, 24, and 26. For example, raw data records are accumulated over time and statistical data is derived from the accumulated raw data records. The statistical data, typically along with at least some portion of the raw data, is then used to determine a value of a health parameter of a person.

Although it has been found that derived data from the amplitude and/or phase data can provide improved correspondence to a health parameter, such as blood glucose level, the particular model that provides a desired level of correspondence (e.g., that meets a predetermined accuracy) may need to be learned in response to a specific set of operating conditions. Thus, in an embodiment, a learning process (e.g., machine learning) is implemented to identify and train a model that provides an acceptable correspondence to a health parameter such as blood glucose level.

Figure 27:
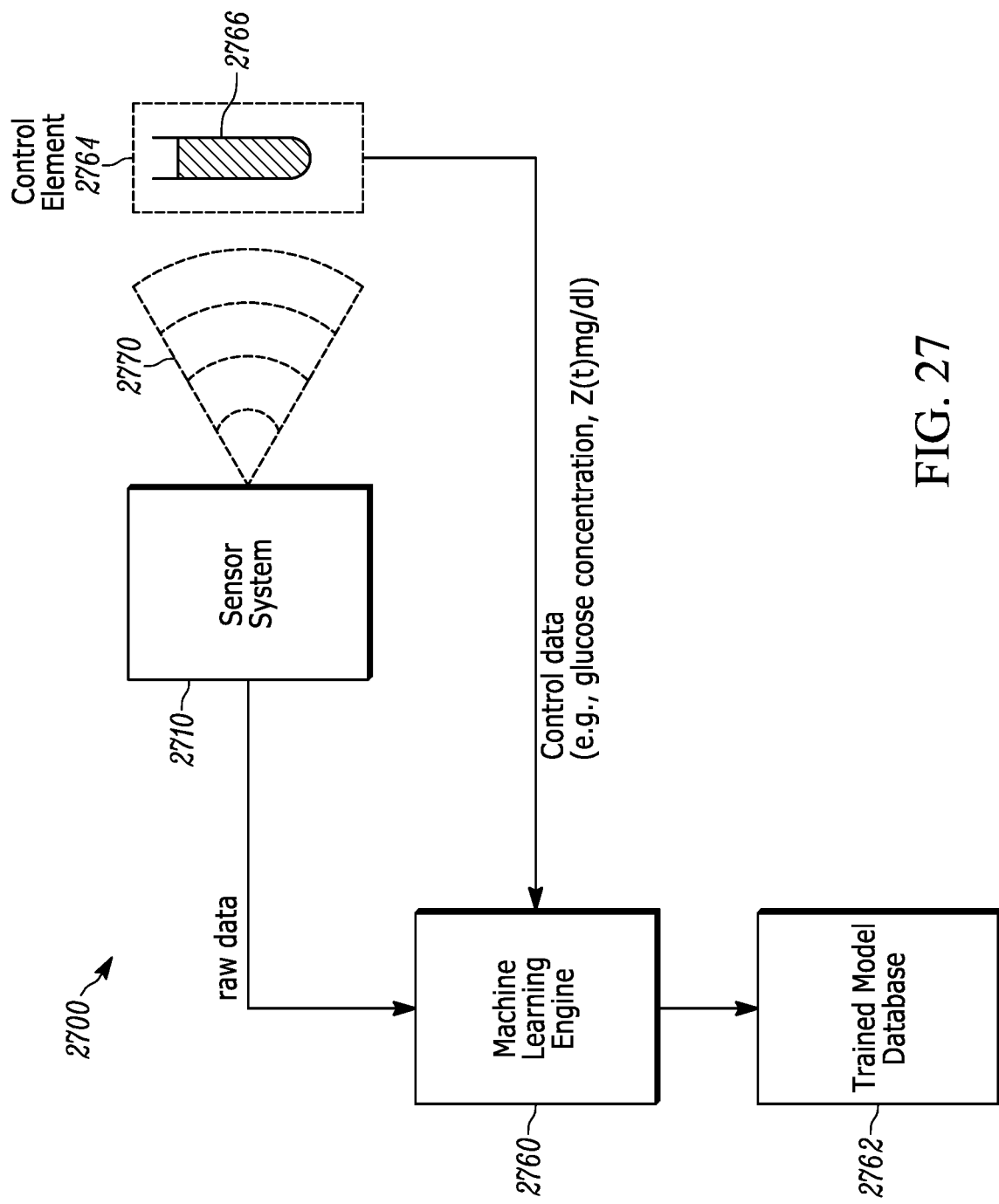
FIG. 27 illustrates a system and process for machine learning that can be used to identify and train a model that reflects correlations between raw data, derived data, and control data.

FIG. 27 illustrates a system 2700 and process for machine learning that can be used to identify and train a model that reflects correlations between raw data, derived data, and control data. For example, the machine learning process may be used to identify certain statistics (e.g., standard deviation of amplitude and/or phase over time) that can be used to improve the correspondence of determined values to actual health parameters (such as blood glucose levels) in a person. The machine learning process can also be used to train a model with training data so that the trained model can accurately and reliably determine values for health parameters such as blood glucose level, blood pressure, and/or heart rate in monitoring devices that are deployed in the field. With reference to FIG. 27, the system 2700 includes a sensor system 2710, a machine learning engine 2760, a trained model database 2762, and a control element 2764.

In an embodiment, the sensor system 2710 is similar to or the same as the sensor system described above. For example, the sensor system is configured to implement stepped frequency scanning in the 2-6 GHz and/or 122-126 GHz frequency range using two transmit antennas and four receive antennas. The sensor system generates and outputs raw data to the machine learning engine that can be accumulated and used as described below.

In an embodiment, the control element 2764 is configured to provide a control sample to the sensor system 2710. For example, the control element includes a sample material 2766 (e.g., a fluid) that has a known blood glucose level that is subjected to the sensor system. Additionally, in an embodiment, the control element is configured to provide control data to the machine learning engine that corresponds to the sample material. For example, the control element may include a sample material that has a known blood glucose level that changes as a function of time and the change in blood glucose level as a function of time (e.g., Z(t) mg/dL) is provided to the machine learning engine 2760 in a manner in which the raw data from the sensor system 2710 and the control data can be time matched (e.g., synchronized). In another embodiment, the control element 2764 includes a sample material that includes a static parameter, e.g., a static blood glucose level in mg/dL, and the static parameter is manually provided to the machine learning engine 2760 as the control data. For example, a particular sample is provided within range of RF energy 2770 that is transmitted from the sensor system (e.g., within a few millimeters), the concentration of the sample is provided to the machine learning engine (e.g., manually entered), and the sensor system accumulates digital data that corresponds to the received RF energy (including a reflected portion of the transmitted RF energy) and that is correlated to the sample. In one embodiment, the sample material is provided in a container such as a vial and in another embodiment, the control element includes a person that is simultaneously being monitored by the sensor system (e.g., for the purposes of machine learning) and by a second, trusted, control monitoring system. For example, the control element includes a person who's blood glucose level, blood pressure, and/or heart rate is being monitored by a known (e.g., clinically accepted) blood glucose level, blood pressure, and/or heart rate monitor while the person is simultaneously being monitored by the sensor system. The blood glucose level, blood pressure, and/or heart rate information from the known blood glucose level, blood pressure, and/or heart rate monitor is provided to the machine learning engine as control data.

In an embodiment, the machine learning engine 2760 is configured to process the raw data received from the sensor system 2710, e.g., as raw data records, and the control data received from the control element 2764 to learn a correlation, or correlations, that provides acceptable correspondence to a health parameter such as blood glucose levels. For example, the machine learning engine is configured to receive raw data from the sensor system, to derive data from the raw data such as statistical data, and to compare the derived data (and likely at least some portion of the corresponding raw data) to the control data to learn a correlation, or correlations, that provides acceptable correspondence between a determined value of a health parameter and a controlled, or known value, of the health parameter. In an embodiment, the machine learning engine is configured to derive statistics from the raw data such as a standard deviation, a moving average, and a moving mean. For example, the machine learning engine may derive the standard deviation of the amplitude and/or phase of the received RF energy and then correlate the derived statistic(s) and the raw data to the control data to find a correlation that provides an acceptable correspondence between the raw data, the derived data, and the actual value of the health parameter as provided in the control data. In an embodiment, correspondence between the raw data, the derived data, and the actual values of the health parameter in a control sample is expressed in terms of a correspondence threshold, which is indicative of, for example, the correspondence between values of a health parameter generated in response to the raw data, the derived data, and actual values of the health parameter in a control sample. For example, a correspondence is expressed as a percentage of correspondence to the actual value of the control sample such that a generated concentration value of a blood glucose level of 135 mg/dL and a value of a control sample at 140 mg/dL has a correspondence of 135/140=96.4%. In an embodiment, a correspondence threshold can be set to accept only those correlations that produce correspondence that meets a desired correspondence threshold. In an embodiment, a correspondence threshold of a generated value to the value of a control sample of within ±10% of the control sample is acceptable correspondence. In another embodiment, a correspondence threshold of within ±10% of the control sample in 95% of the measurements is acceptable correspondence.

Figure 28:
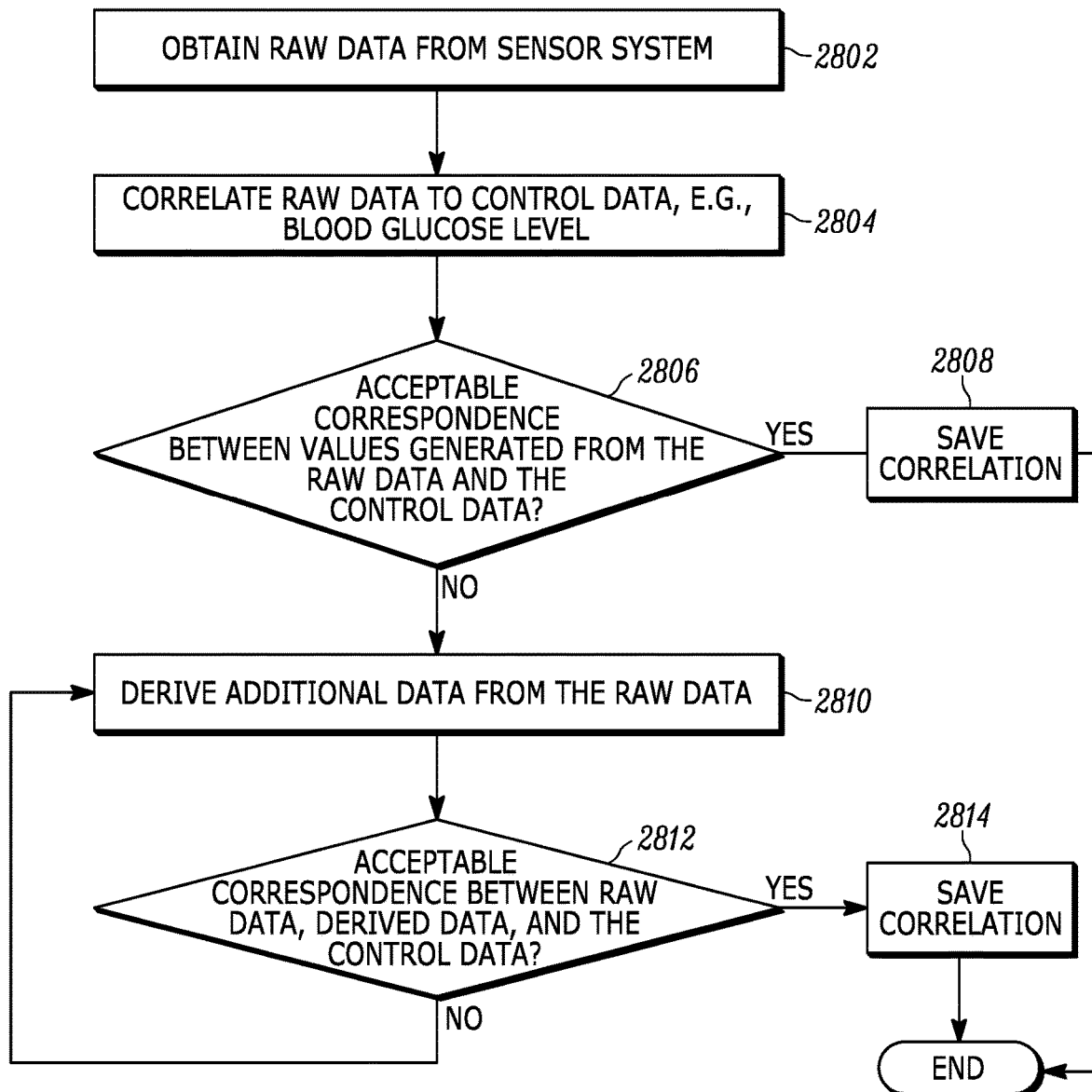
FIG. 28 is an example of a process flow diagram of a method for implementing machine learning.

FIG. 28 is an example of a process flow diagram of a method for implementing machine learning using, for example, the system described above with reference to FIG. 27 to select a correlation (e.g., a model or algorithm) that provides acceptable correspondence between values of a health parameter generated in response to the raw data, the derived data, and actual values of the health parameter in the control samples. At block 2802, raw data is obtained from the sensor system. At block 2804, the raw data is correlated to known control data, such as known blood glucose levels. At decision point 2806, it is determined whether a correlation between the raw data and the control data is acceptable, e.g., whether the correspondence is within an acceptable threshold. If it is determined that there is an acceptable correspondence, then the process proceeds to block 2808, where the correlation (e.g., a model or algorithm) is saved and then the initial learning process is ended. If at decision point 2806 it is determined that there is not an acceptable correspondence between the raw data and the control data (e.g., the correspondence is not within an acceptable threshold), then the process proceeds to block 2810. At block 2810, additional data is derived from the raw data. For example, the machine learning engine may derive a statistic or statistics from the raw data such as a standard deviation, a moving average, and a moving mean. For example, the machine learning engine may derive the standard deviation of the amplitude and/or phase of the received RF energy. At decision point 2812, it is determined whether a correlation between the raw data, the derived data, and the control data is acceptable (e.g., the correspondence is within an acceptable threshold). If it is determined that there is an acceptable correspondence between the raw data, the derived data, and the control data, then the process proceeds to block 2814, where the correlation (e.g., a model or algorithm) is saved and then the initial learning process is ended. If at decision point 2812 it is determined that there is not an acceptable correspondence between the raw data, the derived data, and the control data (e.g., the correspondence is not within an acceptable threshold), then the process returns to block 2810. At block 2810, additional data is derived from the raw data and/or from the derived data. For example, a different statistic, or statistics, is derived from the raw data and/or from the previously derived data. In an embodiment, the exploration of correlations between the raw data, the derived data, and the control data is an iterative process that converges on a correlation, or correlations, which provides acceptable correspondence between the raw data, the derived data, and the control data. In an embodiment, the machine learning process can be repeatedly used to continue to search for correlations that may improve the correspondence between the raw data, the derived data, and the control data to improve the accuracy of health parameter monitoring.

In an embodiment, the above-described process is used for algorithm selection and/or model building as is done in the field of machine learning. In an embodiment, algorithm selection and/or model building involves supervised learning to recognize patterns in the data (e.g., the raw data, the derived data, and/or the control data). In an embodiment, the algorithm selection process may involve utilizing regularized regression algorithms (e.g, Lasso Regression, Ridge Regression, Elastic-Net), decision tree algorithms, and/or tree ensembles (random forests, boosted trees).

In an embodiment, acceptable correlations that are learned by the machine learning engine are trained by the machine learning engine to produce a trained model, or trained models, that can be deployed in the field to monitor a health parameter of a person. Referring back to FIG. 27, a model that is trained by the machine learning engine 2760 is held in the trained model database 2762. In an embodiment, the trained model database may store multiple models that have been found to provide acceptable correspondence between generated values of a health parameter and the actual values of the health parameter as provided in the control data. Additionally, the trained model database 2762 may provide rules on how to apply the model in deployed sensor systems. For example, different models may apply to different deployment conditions, e.g., depending on the location of the RF front-end relative to a blood vessel, environmental conditions, etc.

In an embodiment, operation of the system 2700 shown in FIG. 27 to generate training data and to train a model using the training data involves providing a control sample in the control element 2764 and then operating the sensor system 2700 to implement stepped frequency scanning over a desired frequency range that is within, for example, the 2-6 GHz and/or 122-126 GHz frequency range. For example, control data corresponding to the control sample 2766 is provided to the machine learning engine 2760 and raw data generated from the sensor system 2710 is provided to the machine learning engine. The machine learning engine generates training data by combining the control data with the stepped frequency scanning data in a time synchronous manner. The machine learning engine processes the training data to train a model, or models, which provides an acceptable correspondence between generated values of a health parameter and the control data. The model, or models, is stored in the trained model database 2762, which can then be applied to a system 2700 that is deployed in the field to monitor a health parameter of a person. In an embodiment, the sensor system is exposed to multiple different samples under multiple different operating conditions to generate a rich set of training data.

In an embodiment, the goal of the training process is to produce a trained model that provides a high level of accuracy and reliability in monitoring a health parameter in a person over a wide set of parameter ranges and operational and/or environmental conditions. For example, the correspondence of a model during training can be expressed in terms of a correspondence threshold, which is indicative of, for example, the correspondence between values of a health parameter generated in response to the raw data, the derived data, and actual values of the health parameter in a control sample. For example, a correspondence is expressed as a percentage of correspondence to the actual value of the control sample such that a generated concentration value of a blood glucose level of 135 mg/dL and a value of a control sample at 140 mg/dL has a correspondence of 135/140=96.4%. In an embodiment, a correspondence threshold can be set for a trained model so that the trained model produces correspondence that meets a desired correspondence threshold. In an embodiment, a correspondence threshold of a generated value to the value of a control sample of within ±10% of the control sample is acceptable correspondence for a trained model. In another embodiment, a correspondence threshold of within ±10% of the control sample in 95% of the measurements is acceptable correspondence for a trained model.

In an embodiment, the correspondence between the raw and/or derived data and the control data may change in response to different factors including, for example, over different blood glucose levels, different monitoring locations, different environmental conditions, etc. Thus, in some embodiments, the trained model database 2762 may include multiple different trained models that are applicable to certain conditions. Additionally, the trained model database may evolve over time as more information is gathered and/or as different correlations are discovered.

As described above, the model training process utilizes raw data (e.g., in the form of raw data records) as inputs into the machine learning engine. FIG. 29 is an example of a table of a raw data record (e.g., digital data) generated during stepped frequency scanning that is used to generate the training data. The raw data record includes time t1, a known blood glucose level (e.g., a control sample with a known concentration of glucose in mg/dL, Z mg/dL) at the time t1, TX/RX frequency at the time t1, RX1 amplitude/phase, RX2 amplitude/phase, RX3 amplitude/phase, and RX4 amplitude/phase at the time t1. In the example of FIG. 29, the raw data record includes the glucose level of the control sample at the same time the amplitude and phase of the RF energy was received by the sensor system, thus, the control data is combined with the stepped frequency scanning data in a time synchronous manner. In addition, the raw data records that are used to generate the training data may include some or all of the parameters identified in FIGS. 23 and 24. For example, the raw data records and the corresponding training data may include other variable and/or fixed parameters that correspond to the stepped frequency scanning operation to provide a rich set of parameters from which to generate the training data.

In a stepped frequency scanning operation, multiple raw data records are generated as the sensor system scans across a frequency range. FIGS. 30A-30D are tables of at least portions of raw data records that are generated during a learning process that spans the time of t1-tn, where n corresponds to the number (e.g., an integer of 2 or greater) of time intervals, T, in the stepped frequency scanning. Each of the raw data records includes control data (e.g., known glucose level, Z mg/dL) that is combined with stepped frequency scanning data in a time synchronous manner.

With reference to FIG. 30A, at time, t1, the raw data record includes the time, t1, a known blood glucose level (e.g., Z1 in mg/dL) at time t1, a TX/RX frequency (e.g., X GHz) at time t1, RX1 amplitude/phase at time t1 (ampl1-t1/ph141), RX2 amplitude/phase at time t1 (ampl2-t1/ph2-t1), RX3 amplitude/phase at time t1 (ampl3-t1/ph3-t1), and RX4 amplitude/phase at time t1 (ampl4-t1/ph4-t1). In the stepped frequency scanning, at the next time, t2, the frequency is changed by one step size, e.g., incremented by Δf. In an embodiment, the stepped frequency scanning operation generates 200 raw data records per second, e.g., a sample rate of 200 samples/second. With reference to FIG. 30B, at time, t2, the raw data record includes the time, t2, a known blood glucose level (e.g., Z2 in mg/dL) at time t2, a TX/RX frequency (e.g., X+Δf GHz) at time t2, RX1 amplitude/phase at time t2 (ampl1-t2/ph1-t2), RX2 amplitude/phase at time t2 (ampl2-t2/ph2-t2), RX3 amplitude/phase at time t2 (ampl3-t2/ph3-t2), and RX4 amplitude/phase at time t2 (ampl4-t2/ph4-t2). With reference to FIG. 30C, at time, t3, the raw data record includes the time, t3, a known blood glucose level (e.g., Z3 in mg/dL) at time t3, a TX/RX frequency (e.g., X+2Δf GHz) at time t3, RX1 amplitude/phase at time t3 (ampl1-t3/ph1-t3), RX2 amplitude/phase at time t3 (ampl2-t3/ph2-t3), RX3 amplitude/phase at time t3 (ampl3-t3/ph3-t3), and RX4 amplitude/phase at time t3 (ampl4-t3/ph4-t3). With reference to FIG. 30D, at time, tn, the raw data record includes the time, tn, a known blood glucose level (e.g., Zn in mg/dL) at time tn, a TX/RX frequency (e.g., X+(n−1)Δf GHz) at time tn, RX1 amplitude/phase at time tn (ampl1-tn/ph1-tn), RX2 amplitude/phase at time tn (ampl2-tn/ph2-tn), RX3 amplitude/phase at time tn (ampl3-tn/ph3-tn), and RX4 amplitude/phase (ampl4-tn/ph4-tn) at time tn.

As illustrated above, raw data is collected on a per-antenna basis for the amplitude and/or phase of the received RF energy. Raw data collected on a per-antenna basis for amplitude and phase for the example of FIGS. 30A-30D may include:

ampl1: ampl1-t1, ampl1-t2, ampl1-t3, . . . , ampl1-tn;
ampl2: ampl2-t1, ampl2-t2, ampl2-t3, . . . , ampl2-tn;
ampl3: ampl3-t1, ampl3-t2, ampl3-t3, . . . , ampl3-tn;
ampl4: ampl4-t1, ampl4-t2, ampl4-t3, . . . , ampl4-tn;
ph1: ph1-t1, ph1-t2, ph1-t3, . . . , ph1-tn;
ph2: ph241, ph2-t2, ph2-t3, . . . , ph2-tn;
ph3: ph3-t1, ph3-t2, ph3-t3, . . . , ph3-tn); and
ph4: ph441, ph4-t2, ph4-t3, . . . , ph4-tn).

In the example of FIGS. 30A-30D, the standard deviation may be calculated on a per-antenna basis for the amplitude and phase and is a function of the following raw data elements:

$$\sigma(ampl1)=f(ampl1\text{-}t1+ampl1\text{-}t2+ampl1\text{-}t3+\ldots+ampl1\text{-}tn);$$

$$\sigma(ampl2)=f(ampl2\text{-}t1+ampl2\text{-}t2+ampl2\text{-}t3+\ldots+ampl2\text{-}tn);$$

$$\sigma(ampl3)=f(ampl3\text{-}t1+ampl3\text{-}t2+ampl3\text{-}t3+\ldots+ampl3\text{-}tn);$$

$$\sigma(ampl4)=f(ampl4\text{-}t1+ampl4\text{-}t2+ampl4\text{-}t3+\ldots+ampl4\text{-}tn);$$

$$\sigma(ph1)=f(ph1\text{-}t1+ph1\text{-}t2+ph1\text{-}t3+\ldots+ph1\text{-}tn);$$

$$\sigma(ph2)=f(ph2\text{-}t1+ph2\text{-}t2+ph2\text{-}t3+\ldots+ph2\text{-}tn);$$

$$\sigma(ph3)=f(ph3\text{-}t1+ph3\text{-}t2+ph3\text{-}t3+\ldots+ph3\text{-}tn);$$

$$\sigma(ph4)=f(ph4\text{-}t1+ph4\text{-}t2+ph4\text{-}t3+\ldots+ph4\text{-}tn);$$

In an embodiment, data is derived on a per-antenna basis. In other embodiments, data such as statistics can be derived from data corresponding to different combinations of antennas.

Raw data records collected over time can be used as described above to learn correlations (e.g., a model or algorithm) between the raw data, derived data, and the control data and to train a model. In an embodiment, a rich set of training data is collected and processed to train a model that can provide accurate and reliable measurements of a health parameter such as blood glucose level, blood pressure, and/or heart rate. In an embodiment, the raw data including amplitude and phase and the derived data including the standard deviation of the amplitude has been found to correspond well to the health parameter of blood glucose level.

Figure 31:
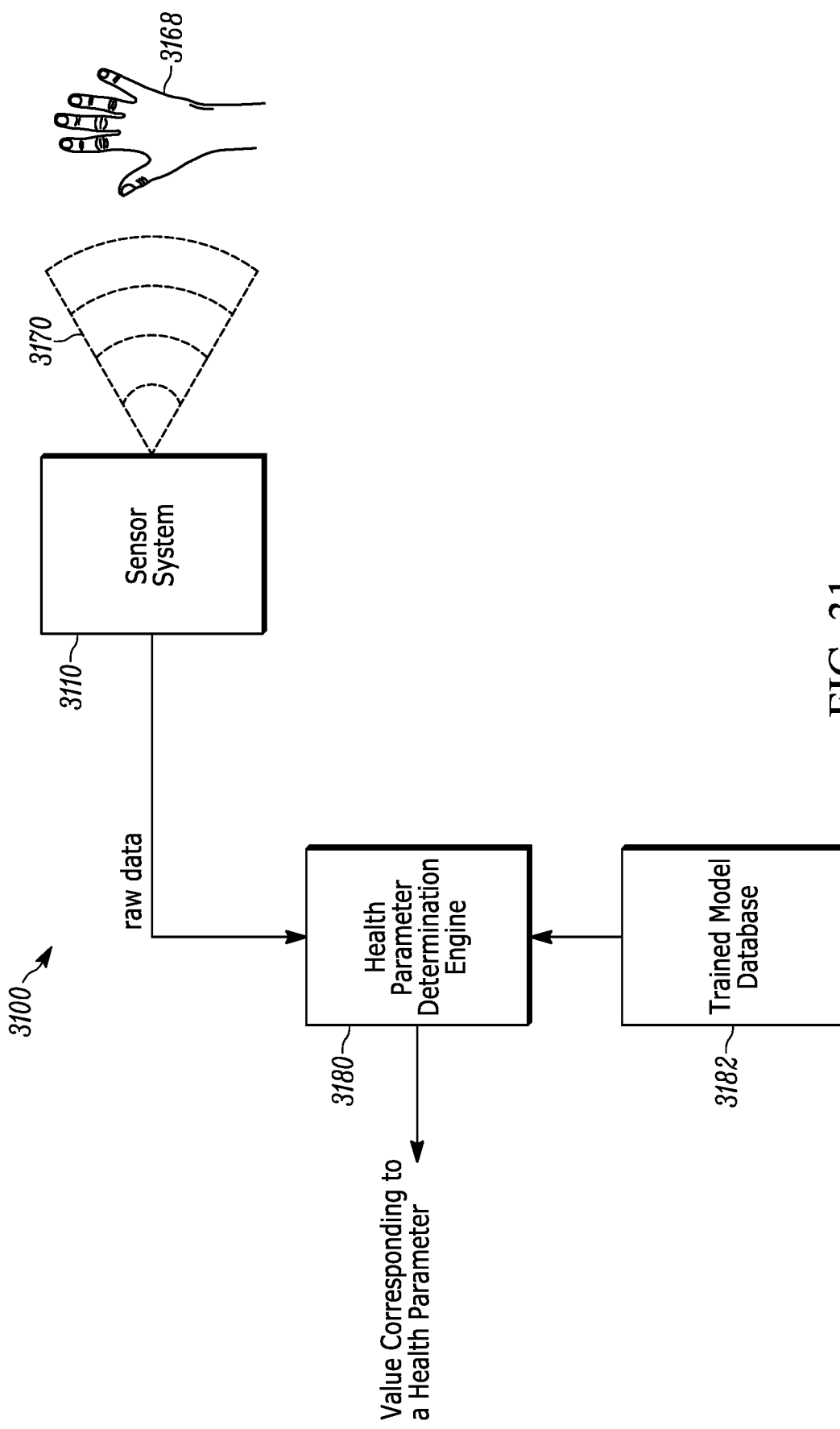
FIG. 31 illustrates a system for health parameter monitoring that utilizes a sensor system similar to or the same as the sensor system described with reference to FIGS. 5-7.

Once correlations between the raw data, the derived data, and the control data have been learned and a model has been trained, a sensor system can be deployed into the field for use in monitoring a health parameter of a person, such as the blood glucose level. FIG. 31 illustrates a system 3100 for health parameter monitoring that utilizes a sensor system similar to or the same as the sensor system described above. With reference to FIG. 31, the system includes a sensor system 3110, a health parameter determination engine 3180, and a trained model database 3182 relative to a hand 3168 of a person.

In an embodiment, the sensor system 3110 is similar to or the same as the sensor system described above. For example, the sensor system is configured to implement stepped frequency scanning in the 2-6 GHz and/or 122-126 GHz frequency range using two transmit antennas and four receive antennas. The sensor system generates and outputs raw data to the health parameter determination engine 3180 that can be accumulated and used to generate and output a value that corresponds to a health parameter.

A model (or models) that is trained by the machine learning engine as described above is held in the trained model database 3182. In an embodiment, the trained model database may store multiple models that have been trained to provide acceptable correspondence between a generated value of a health parameter and the actual value of the health parameter as provided in the control data. Additionally, the trained model database may provide rules on how to apply trained models in deployed sensor systems. In an embodiment, the trained model database includes memory for storing a trained model, or models. The memory may include, for example, RAM, SRAM, and/or SSD.

In an embodiment, the health parameter determination engine 3180 is configured to generate an output that corresponds to a health parameter in response to the raw data received from the sensor system 3110, derived data, and using a trained model that is stored in the trained model database 3182. For example, the health parameter determination engine 3180 outputs a value that indicates a blood glucose level in mg/dL or some other indication of the blood glucose level. In other embodiments, the health parameter determination engine may output a value that is an indication of a person's heart rate (e.g., in beats per minute) and/or an indication of a person's blood pressure (e.g., in millimeters of mercury, mmHg). In other embodiments, the "values" output by the health parameter determination engine may correspond to a health parameter in other ways. For example, the output value may indicate a value such as "high," "medium," "low" with respect to a health parameter (e.g., a high blood glucose level, a medium blood glucose level, or a low blood glucose level relative to a blood glucose scale), the output value may indicate a color, such as green, yellow, or red that indicates a health parameter, or the output value, may indicate a range of values, such as 130-140 mg/dL blood glucose, 70-80 beats per minute, or 110-120 mmHg blood pressure. In an embodiment, the health parameter determination engine recognizes patterns in the raw and/or derived data and applies the recognized patterns to the trained model to generate an output that corresponds to a health parameter in a person. The health parameter determination engine may be implemented by a digital processor, such as a CPU or MCU, in conjunction with computer readable instructions that executed by the digital processor.

In an embodiment, operation of the system 3100 shown in FIG. 31 involves bringing a portion of a person's anatomy 3186 (such as a wrist, arm, or ear area) into close proximity to the sensor system 3110 (or bringing the sensor system into close proximity to the portion of a person's anatomy) and operating the sensor system to implement stepped frequency scanning over a frequency range, e.g., in the range of 122-126 GHz such that transmitted RF energy 3170 penetrates below the surface of the person's skin. Raw data generated from implementing the stepped frequency scanning is output from the sensor system and received at the health parameter determination engine 3180. The health parameter determination engine processes the raw data in conjunction with at least one trained model from the trained model database 3182 to generate a value that corresponds to a health parameter of the person, e.g., a value that corresponds to the blood glucose level of the person. In an embodiment, the value that corresponds to the health parameter is output, for example, as a graphical indication of the blood glucose level. In an embodiment, the generated value may be stored in a health parameter database for subsequent access.

In an embodiment, the system 3100 depicted in FIG. 31 is implemented in a device such as a smartwatch or smartphone. In other embodiments, some portion of the system (e.g., the RF front-end) is implemented in a device, such as a dongle, a patch, a smartphone case, or some other device and the health parameter determination engine and the trained model correlations database is implemented in a nearby device such as a smartphone. For example, in one embodiment, the sensor system is embodied in a device that attaches near the ear of a person and raw data is communicated via a wireless connection to a device such as a smartphone that processes the raw data to generate a value that corresponds to the blood glucose level of the person.

Figure 32:
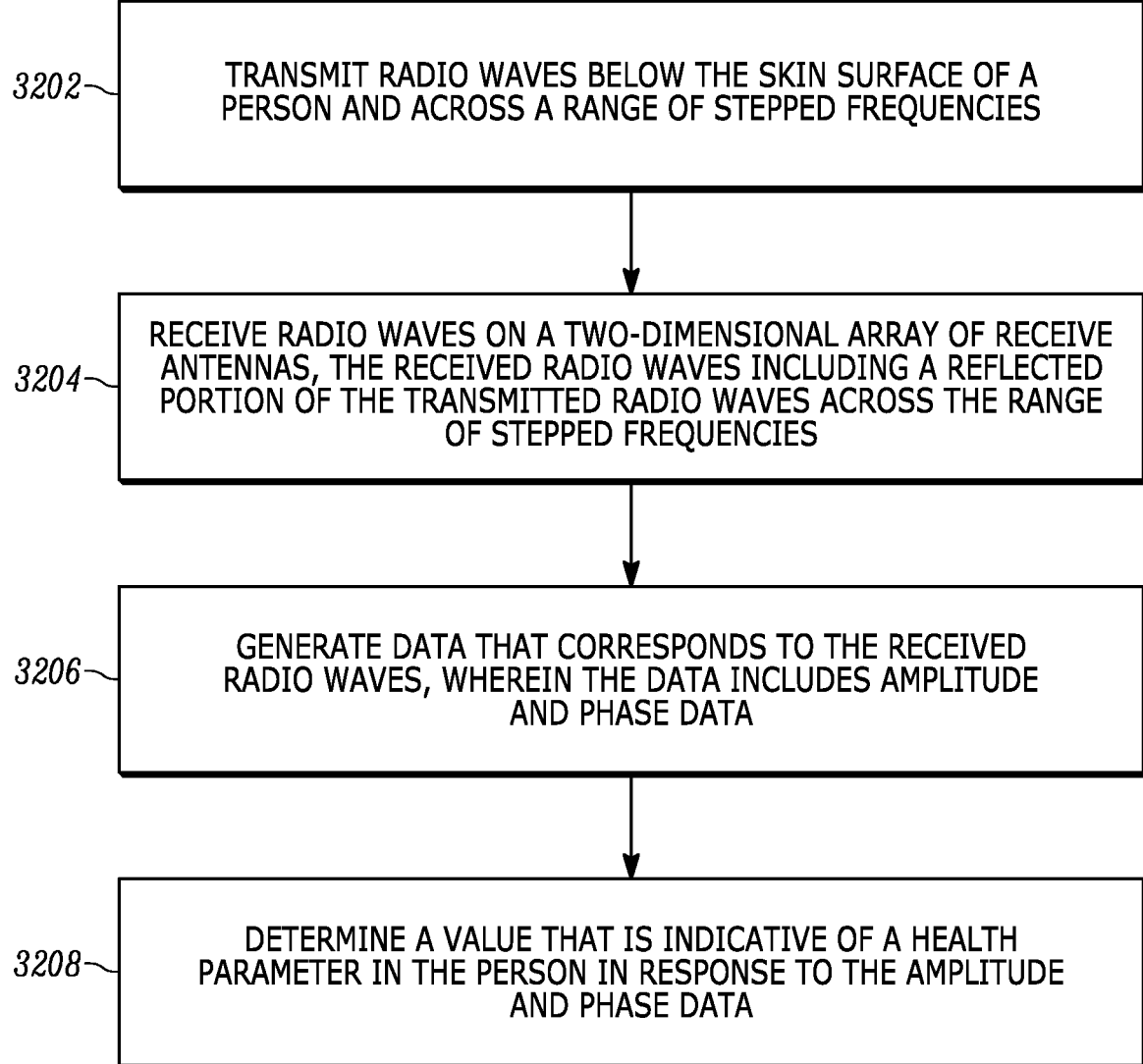
FIG. 32 is a process flow diagram of a method for monitoring a health parameter in a person.

FIG. 32 is a process flow diagram of a method for monitoring a health parameter in a person. At block 3202, radio waves are transmitted below the skin surface of a person and across a range of stepped frequencies. At block 3204, radio waves are received on a two-dimensional array of receive antennas, the received radio waves including a reflected portion of the transmitted radio waves across the range of stepped frequencies. At block 3206, data that corresponds to the received radio waves is generated, wherein the data includes amplitude and phase data. At block 3208, a value that is indicative of a health parameter in the person is determined in response to the amplitude and phase data.

Figure 33:
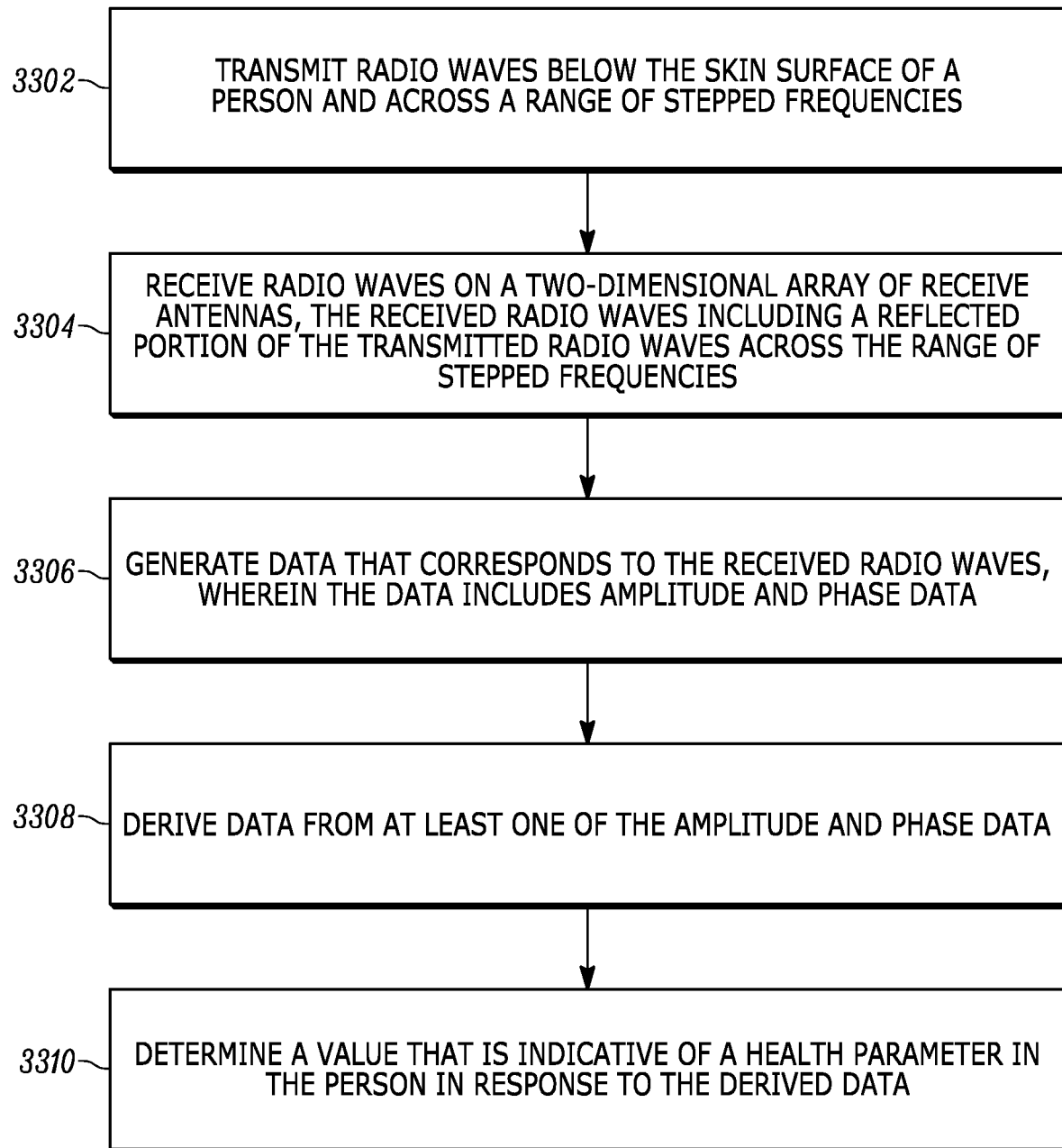
FIG. 33 is a process flow diagram of another method for monitoring a health parameter in a person.

FIG. 33 is a process flow diagram of another method for monitoring a health parameter in a person. At block 3302, radio waves are transmitted below the skin surface of a person and across a range of stepped frequencies. At block 3304, radio waves are received on a two-dimensional array of receive antennas, the received radio waves including a reflected portion of the transmitted radio waves across the range of stepped frequencies. At block 3306, data that corresponds to the received radio waves is generated, wherein the data includes amplitude and phase data. At block 3308, data is derived from at least one of the amplitude and phase data. At block 3310, a value that is indicative of a health parameter in the person is determined in response to the derived data.

Figure 34:
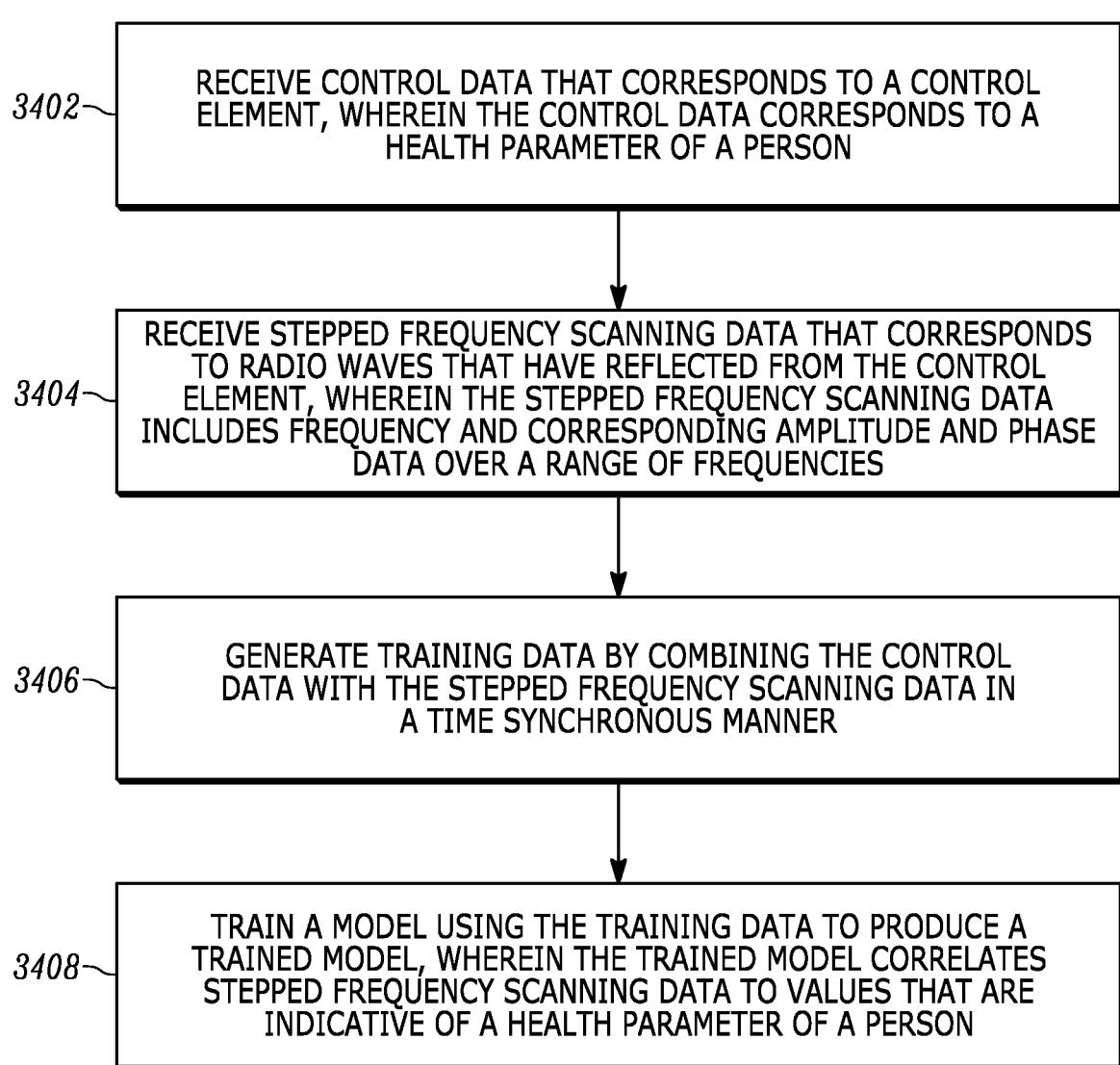
FIG. 34 is a process flow diagram of a method for training a model for use in monitoring a health parameter in a person.

FIG. 34 is a process flow diagram of a method for training a model for use in monitoring a health parameter in a person. At block 3402, control data that corresponds to a control element is received, wherein the control data corresponds to a health parameter of a person. At block 3404, stepped frequency scanning data that corresponds to radio waves that have reflected from the control element is received, wherein the stepped frequency scanning data includes frequency and corresponding amplitude and phase data over a range of frequencies. At block 3406, training data is generated by combining the control data with the stepped frequency scanning data in a time synchronous manner. At block 3408, a model is trained using the training data to produce a trained model, wherein the trained model correlates stepped frequency scanning data to values that are indicative of a health parameter of a person.

Figure 35A:
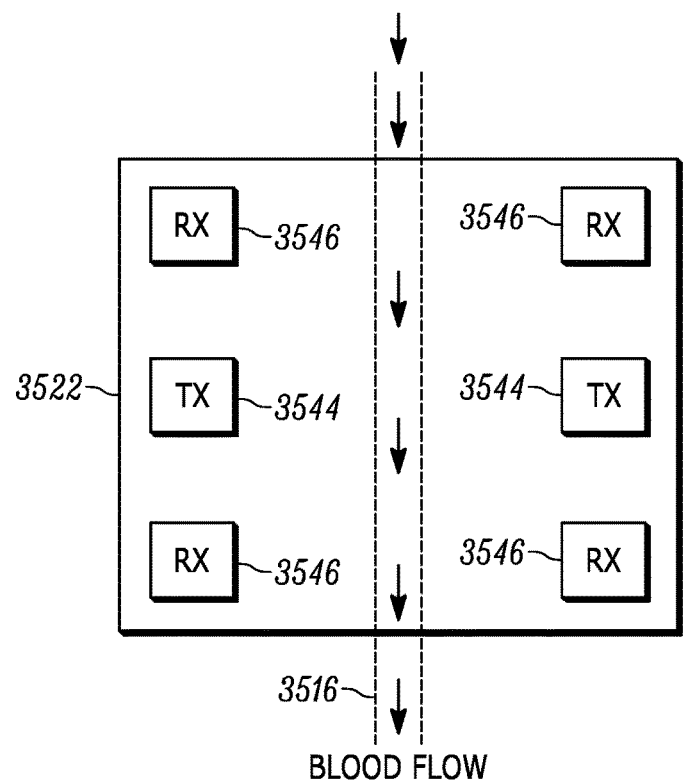
FIGS. 35A-35E illustrate the antennas of the sensor system as described above with reference to FIGS. 5-8D and a vein aligned between the TX and RX antennas of the sensor system.
Figure 35B:
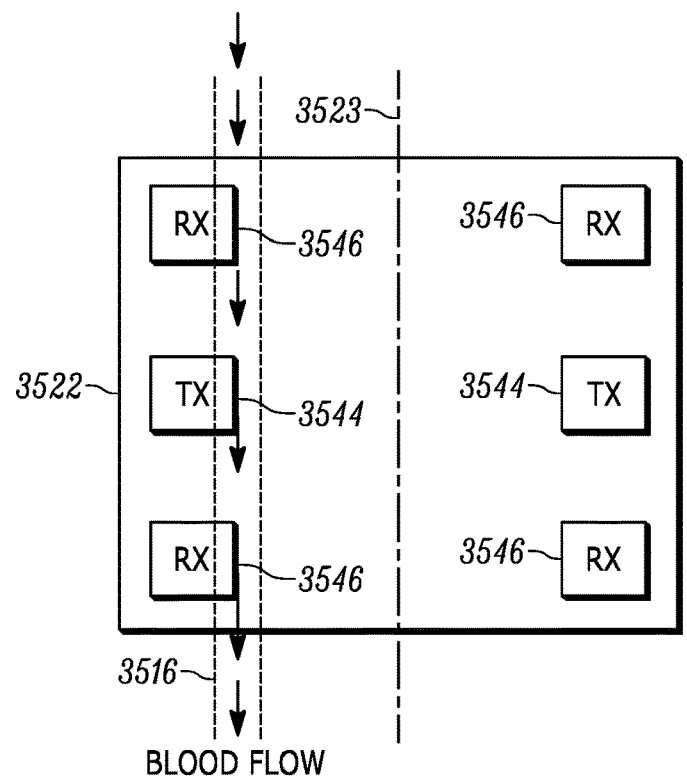
Figure 35C:
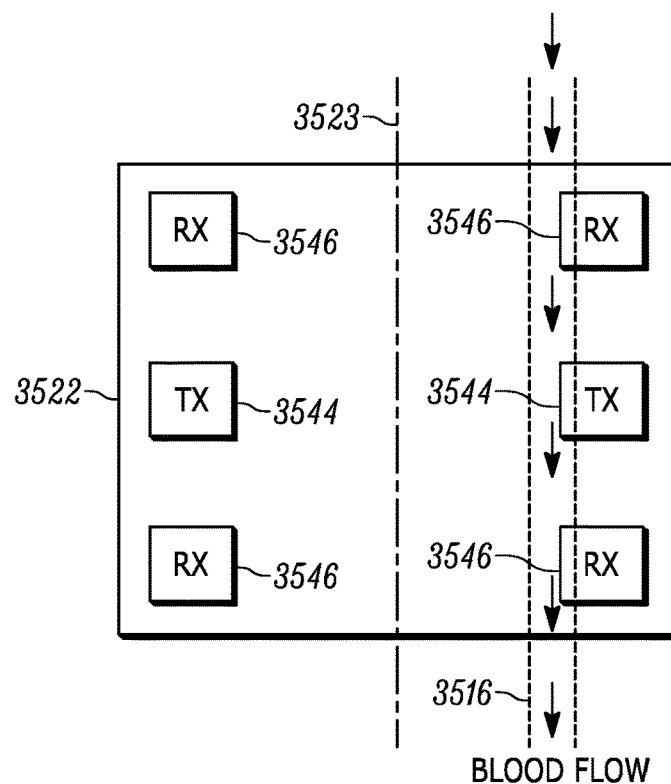
Figure 35D:
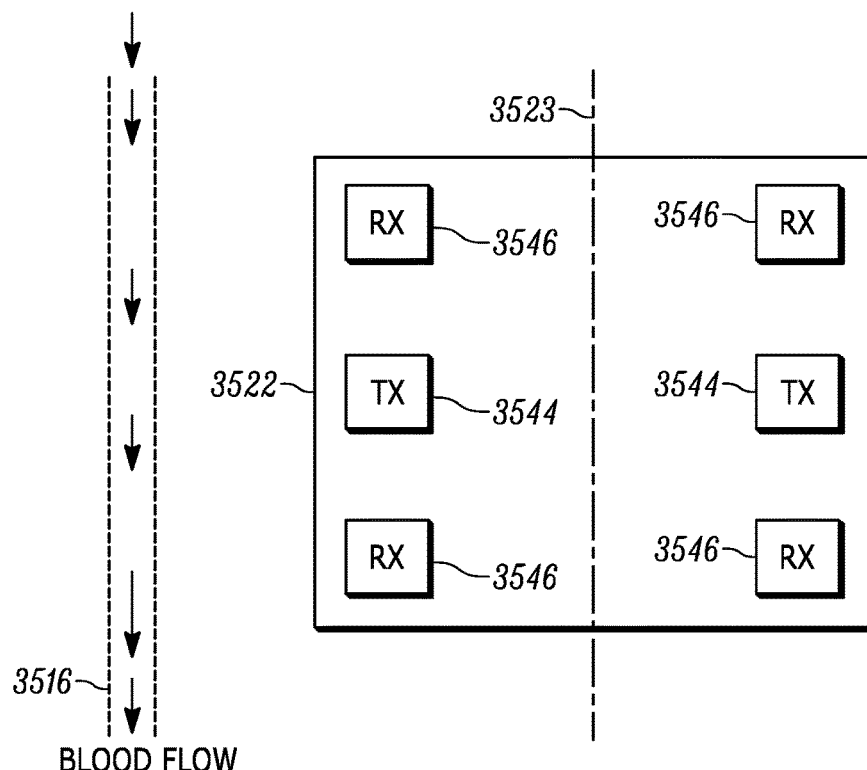
Figure 35E:
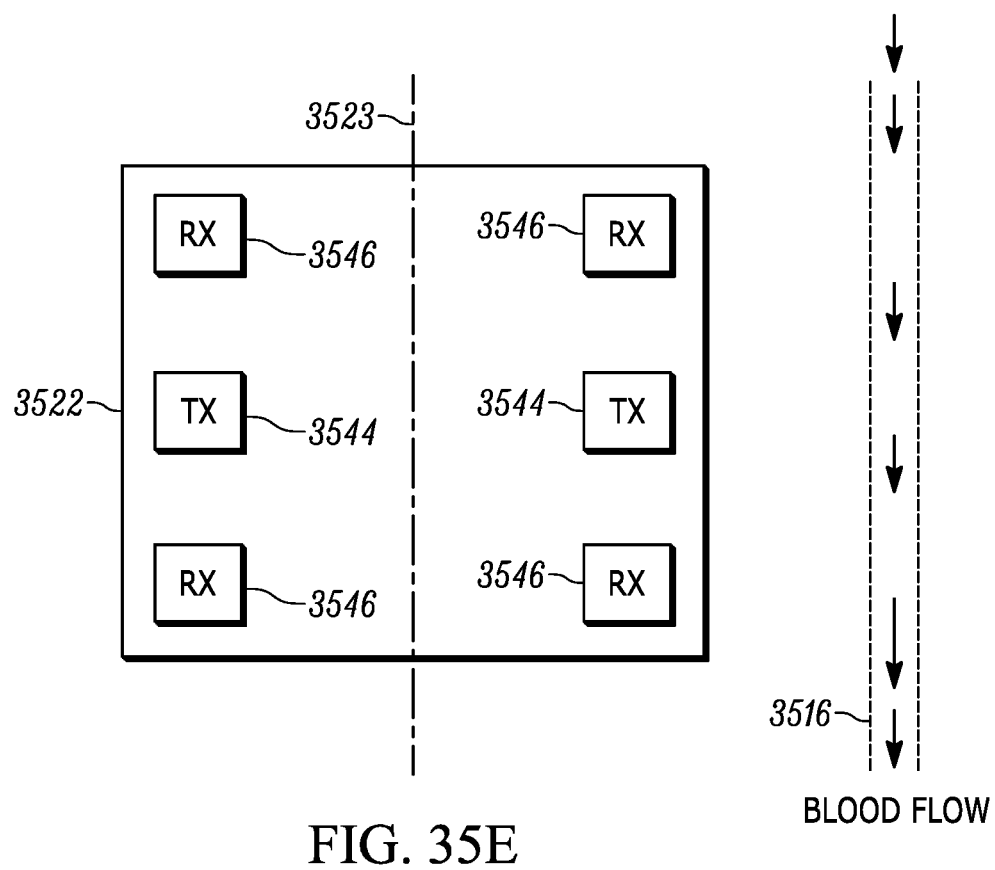

In order to achieve accurate and reliable correspondence between sensor measurements and actual values of the monitored health parameter using an RF-based sensor system, such as the above described RF-based sensor system, it is desirable to have the antenna array in contact with or close to the skin (e.g., within 5 mm) aligned with a vein that is to be sensed or monitored. For example, it is desirable to have the vein aligned with the two-dimensional array of antennas of the sensor system, e.g., laterally aligned with the two-dimensional array of receive antennas. FIG. 35A illustrates an antenna array of the sensor system 3522 as described above with reference to FIGS. 5-8D and a vein 3516 aligned between the TX antennas 3544 and RX antennas 3546 of the antenna array of the sensor system. Specifically, in the example of FIG. 35A, the antennas of the sensor system are positioned relative to the vein such that the vein is centered between the left side antennas (RX, TX, and RX) and the right side antennas (RX, TX, and RX). FIGS. 35B and 35C illustrate examples in which the antenna array of the sensor system is not aligned with the vein along a centerline 3523 between the antennas of the sensor system, but the alignment relative to the vein is either slightly left of the centerline between the antennas (FIG. 35B) or slightly right of the centerline between the antennas (FIG. 35C). In some embodiments, an alignment slightly off of the centerline may still provide acceptable accuracy and reliability of measurements. FIGS. 35D and 35E illustrate examples in which the antenna array of the sensor system is not aligned with the vein along the centerline of the sensor system. In particular, FIG. 35D illustrates a case in which the antenna array of the sensor system is fully outside of the footprint of, and to the left of, the sensor system and FIG. 35E illustrates a case in which the antenna array of the sensor system is fully outside of the footprint of, and to the right of, the sensor system.

As shown in FIGS. 35A-35E, the two-dimensional antenna array 3544 and 3546 of the sensor system 3522 can be in various different positions relative to the vein 3516 to be monitored, e.g., lateral positions relative to the plan views of FIGS. 35A-35E. In an embodiment, a measure of alignment between the antenna array and a vein to be monitored involves comparing an actual alignment of an antenna array to an ideal alignment of an antenna array, e.g., an ideal alignment in which the vein is aligned along the centerline 3523 between the antennas as shown in FIG. 35A. In an embodiment, a measure of alignment involves determining a distance (e.g., lateral distance relative to the plan views of FIGS. 35A-35E) of the vein from the centerline between the antennas. For example, the distance may be determined as a lateral distance of the vein from the centerline between the antennas at more than one location along the centerline, e.g., as viewed from a top plan view as shown in FIGS. 35A-35E. In an embodiment, the distance is measured as the average distance of the vein from the centerline between the antennas as determined at a point between the two upper receive antennas and at a point between the two lower antennas although other techniques for obtaining a measure of alignment are possible.

In an embodiment, an antenna array is considered aligned with a vein when the vein is within a predefined threshold distance from the centerline between the two-dimensional array of receive antennas. Examples of the predefined threshold may be for example within 10% of the linear distance between a particular receive antenna and the centerline between the two-dimensional array of receive antennas. In an embodiment, the location of an ideally aligned vein relative to an antenna array can be predefined by experimentation and or by geometric analysis. Additionally, alignment of a vein relative to an antenna array may vary depending on the spatial configuration of the antennas. In an embodiment, a desired alignment between a vein and an antenna array is an alignment that results in reflections of radio waves from the vein that have a higher amplitude than reflections of other alignments between the vein and the antenna array.

Although it is desirable to have the antenna array of the sensor system (e.g., including the two-dimensional array of receive antennas) aligned with a vein of the person that is to be monitored (e.g., in terms of both lateral alignment and separation distance between the antenna array and the skin of the person to be monitored), it has been found that aligning a sensor system (e.g., including the two-dimensional array of receive antennas) with a vein of a person that is to be monitored and maintaining the alignment during health parameter monitoring is not a trivial endeavor.

Various techniques for aligning a health monitoring device, in particular, an antenna array of an RF-based health monitoring device, with an object, which may include a vein of a person to be monitored and/or another alignment element, are described herein. Some of the techniques utilize digital data generated by an RF front-end to implement alignment while other techniques utilize a physical feature, or features, of a health monitoring device or a health monitoring system to implement alignment. Additionally, alignment features may be implemented in various different components of a health monitoring device or a health monitoring system depending on the configuration and/or form factor of the health monitoring device or the health monitoring system.

In at least some of the examples described below, the alignment technique is an RF-based alignment technique at least because alignment determinations are made in response to radio waves that are received by the sensor system. In an embodiment, alignment features are generated in response to a signal that is indicative of an alignment that is determined based on the received radio waves. For example, an alignment process may involve transmitting radio waves below the skin surface of a person, receiving radio waves on a two-dimensional array of receive antennas of an antenna array, the received radio waves including a reflected portion of the transmitted radio waves, determining an alignment of the antenna array relative to a vein in the person in response to the received radio waves, and outputting a signal that is indicative of the determined alignment of the antenna array relative to the vein. In an embodiment, the signal includes a visual indicator of alignment. In an embodiment, the process further involves displaying a visual indicator of alignment on a display of a health parameter monitoring system in response to the signal. In an embodiment, the visual indicator of alignment includes an alignment feature and a graphical representation of a detected vein. In an embodiment, the visual indicator of alignment includes an alignment feature on a display of a health parameter monitoring system. In an embodiment, the visual indicator of alignment includes an alignment feature that is stationary on a display and a visual representation of a detected vein that moves in response to movement of the antenna array relative to the detected vein. In an embodiment, the process involves emitting light from a light source of a health parameter monitoring system in response to the output signal as an indicator of alignment of the antenna array relative to the vein. In an embodiment, the process further involves generating an audio signal that is indicative of alignment of the antenna array relative to the vein in response to the output signal. In an embodiment, the process further involves generating a tactile signal that is indicative of alignment of the antenna array relative to the vein in response to the output signal. In an embodiment, the method further involves displaying a visual indicator of alignment of the antenna array relative to the vein on a display of a smartwatch in response to the output signal. In an embodiment, the process further involves displaying a visual indicator of alignment of the antenna array relative to the vein on a display of a smartphone in response to the output signal. In an embodiment, the process further involves generating a visual indicator of alignment of the antenna array relative to the vein in response to the output signal when it is determined that the antenna array is aligned with the vein. In an embodiment, the antenna array is aligned with the vein when an equal number of receive antennas are on either side of the vein. In an embodiment, the process further involves generating an audible indicator of alignment in response to the output signal when it is determined that the antenna array is aligned with the vein. In an embodiment, the method further involves generating a tactile indicator of alignment in response to the output signal when it is determined that the antenna array is aligned with the vein. In an embodiment, the transmitting and receiving are implemented in a removable smartphone case and the determining and outputting are implemented in a smartphone that is connected to the removable smartphone case. In an embodiment, the process further involves displaying a visual indicator of alignment on a display of the smartphone in response to the output signal. In an embodiment, the transmitting, the receiving, the determining, and the outputting are implemented in a removable smartphone case. In an embodiment, the process further involves generating a visual indicator of alignment on the removable smartphone case in response to the output signal.

Figure 36A:
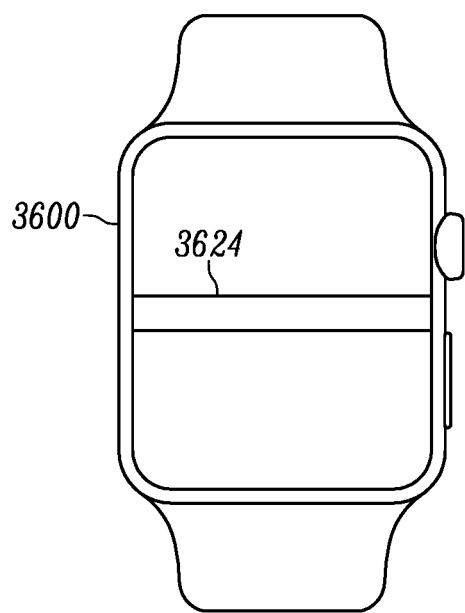
FIGS. 36A-36E illustrate an example of RF-based alignment of a sensor system to a vein on a graphical user interface of a smartwatch.

In an embodiment, the sensor system described above is implemented in a smartwatch and the smartwatch, including the sensor system is configured to implement RF-based alignment. An example of RF-based alignment is now described with reference to FIGS. 36A-36E. With reference to FIG. 36A, the smartwatch 3600 is configured to display an alignment feature 3620 on the display device (also referred to simply as the display) of the smartwatch. In the example of FIG. 36A, the alignment feature includes two horizontal lines that run parallel to each other across the display (e.g., from left side to the right side or vice versa) to form an "alignment channel." In an embodiment, the alignment channel is displayed as a graphical element on a graphical user interface of the smartwatch. In the example of FIG. 36A, the alignment channel is the only graphical element on the display although other information may be included on the display.

Figure 36B:
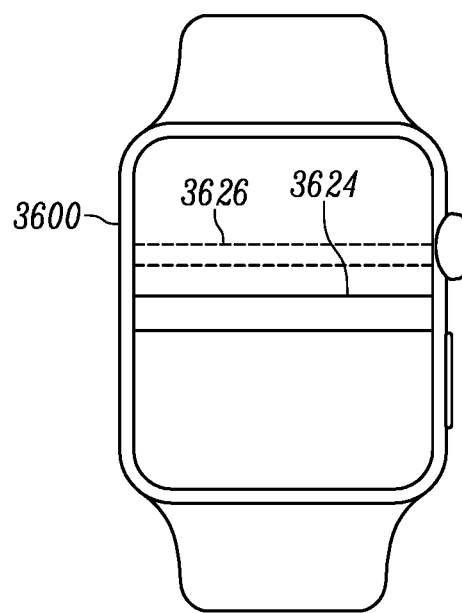
Figure 36C:
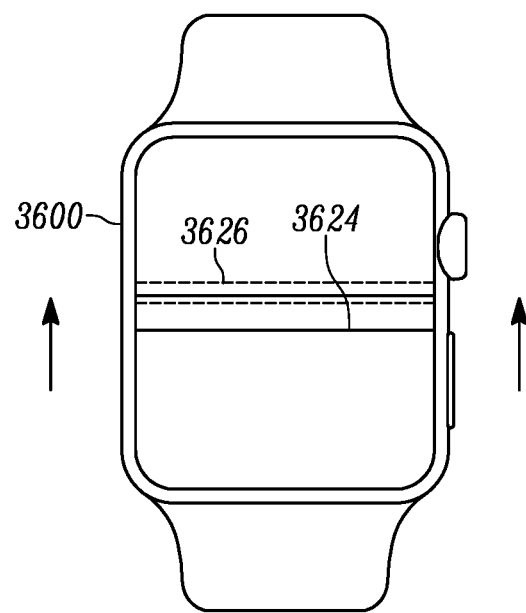

When the smartwatch 3600 is operational and worn on the wrist of a person, an alignment system of the smartwatch uses the RF-based sensor system to detect the location of a vein in the wrist relative to the antenna array of the sensor system. For example, the location of a vein in the wrist relative to the antenna array of the sensor system can be determined by a processor of the smartwatch using Doppler effect processing as described above with reference to FIG. 19. Other techniques may also be used to determine the location of a vein relative to the antenna array of the sensor system including, for example, beamforming techniques that involve isolating radio waves that are reflected from a specific location (e.g., onto a specific blood vessel) to provide a high-quality signal that can be used to determine the location of a vein relative to the antenna array (e.g., relative to the two-dimensional array of receive antennas). The location of the vein relative to the antenna array of the sensor system, also referred to in general as "the alignment," can be graphically represented by a visual indicator of alignment. In an embodiment, it is assumed that the separation distance between the smartwatch and the skin is known (e.g., no separation or a separation within a very narrow range, e.g., in the range of 0-10 mm, or in the range of 0-5 mm) and the alignment to be monitored and adjusted is primarily lateral alignment, e.g., laterally from a plan view as shown in FIGS. 35A-35E. FIG. 36B depicts an example of the alignment channel 3624 (as shown in FIG. 36A) and a graphical representation of the detected vein 3626 displayed relative to the alignment channel. As shown in FIG. 36B, the graphical representation of the vein is not aligned with the alignment channel, at least because no part of the visual representation of the vein falls within the alignment channel. Thus, FIG. 36B illustrates an example in which the antenna array of the sensor system and the monitored vein are not satisfactorily aligned with each other. In order to align the antenna array of the sensor system with the monitored vein, the display of the alignment channel relative to the graphical representation of the vein on the graphical user interface intuitively encourages a person (e.g., the person wearing the smartwatch) to manually move or adjust the position of the smartwatch on the wrist. For example, the wearer of the smartwatch is intuitively encouraged to move the smartwatch "upwards" to align the graphical representation of the vein with the alignment channel. FIG. 36C illustrates the upward movement of the smartwatch as indicated by the upward pointing arrows. FIG. 36C also illustrates that as the smartwatch is moved upwards, the graphical representation of the vein moves downward towards the alignment channel while the alignment feature remains stationary on the display. Although the graphical representation of the vein 3626 has moved closer to the alignment channel 3624, and indeed is partially within the bounds of the alignment channel, it is clear from the structure of the alignment channel and from the position of the graphical representation of the vein relative to the alignment channel, that a better alignment between the graphical representation of the vein and the alignment channel can be achieved. Thus, the wearer of the smartwatch is intuitively encouraged to continue to move and/or adjust the position of the smartwatch on the wrist.

Figure 36D:
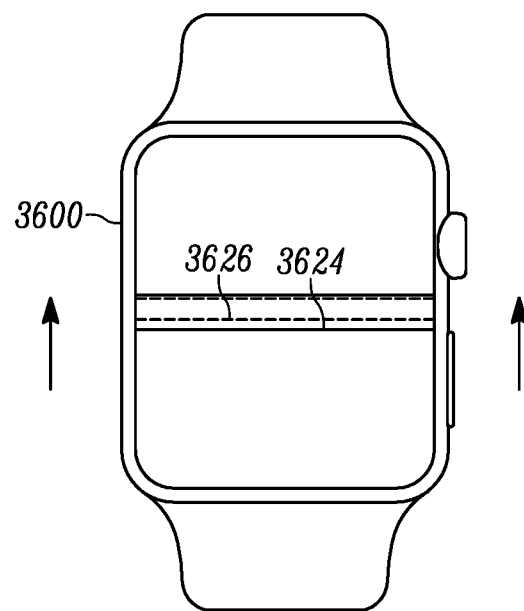
Figure 36E:
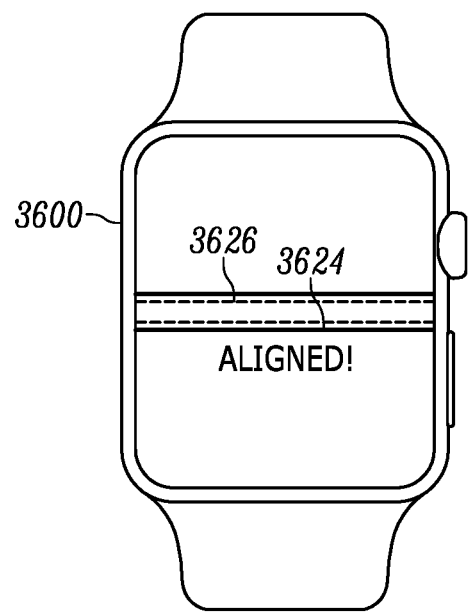

FIG. 36D illustrates further upward movement of the smartwatch 3600 as indicated by the upward pointing arrows. FIG. 36D also illustrates that as the smartwatch is moved upwards, the graphical representation of the vein 3626 moves further downwards and into alignment with the alignment channel 3624. As depicted in FIG. 36E, the graphical representation of the vein is now entirely within the bounds of the alignment channel, which graphically indicates alignment between the graphical representation of the vein and the alignment channel, which in turn correlates to alignment between the antenna array of the sensor system (e.g., the two-dimensional array of receive antennas) and the monitored vein.

As depicted in FIG. 36E, once alignment between the antenna array of the sensor system and the monitored vein is achieved, an output representative of the alignment can be displayed. For example, the boundaries of the alignment channel visibly change (e.g., thicken up, brighten up, and/or change color) and an alignment message (e.g., "Aligned!") is displayed.

Figure 37A:
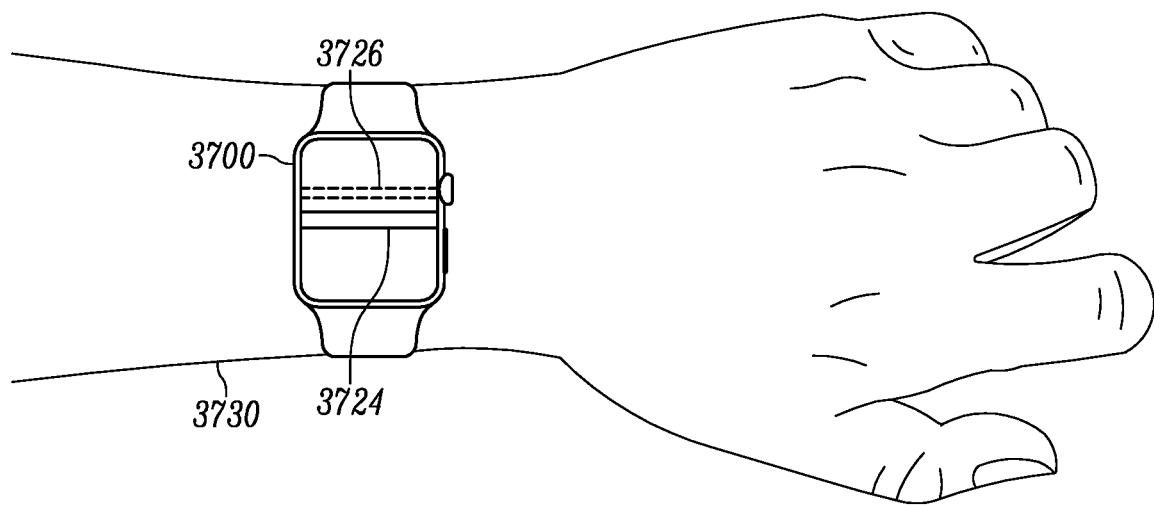
FIGS. 37A and 37B illustrate an example of the alignment process described with reference to FIGS. 36A-36E.
Figure 37B:
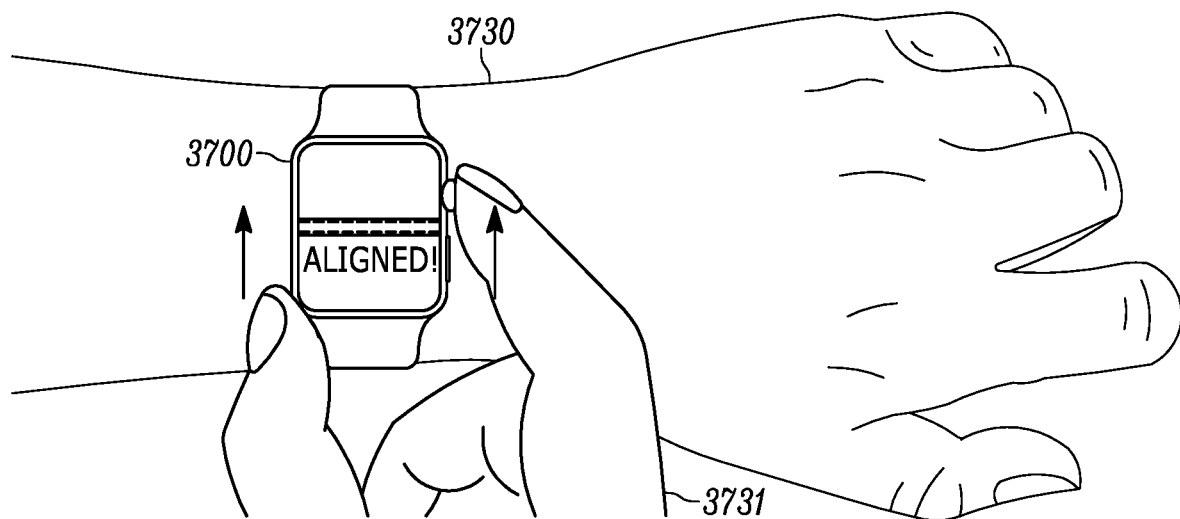

An example of the alignment process described with reference to FIGS. 36A-36E is further illustrated in FIGS. 37A and 37B. FIG. 37A depicts a smartwatch 3700 that is worn on the left wrist 3730 of a person. In the example of FIG. 37A, the graphical representation of the vein is not aligned with the alignment channel, which as described with reference to FIG. 36A, indicates that the antenna array of the sensor system is not aligned with the monitored vein in the wrist of the person wearing the smartwatch. For example, the antenna array is not laterally aligned with the vein, where lateral alignment is defined relative to a plan view as shown in FIGS. 35A-35E. FIG. 37B illustrates the position of the smartwatch being manually moved and/or adjusted by the right hand 3731 of the person wearing the smartwatch. As indicated by the upward pointing arrows, the smartwatch is moved upwards until the graphical representation of the vein is entirely within the bounds of the alignment channel. FIG. 37B also depicts the alignment message (e.g., "Aligned!") as depicted in FIG. 36E.

In the embodiments described with reference to FIGS. 36A-37B, the position of the vein relative to the alignment channel is determined in response to radio waves that are received by the sensor system. For example, the graphics of the graphical user interface are generated in response to digital data that is generated in response to reflected radio waves. For example, the graphics in the graphical user interface are driven by digital data from the RF sensor system and Doppler effect processing as described with reference to FIG. 19.

Figure 37C:
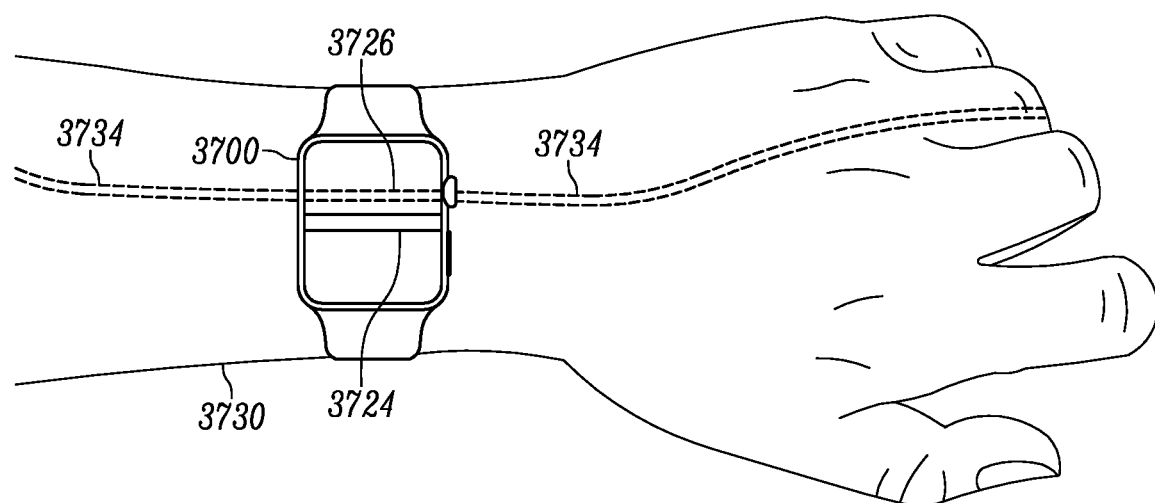
FIG. 37C illustrates an alignment indicator on a graphical user interface of a smartwatch relative to the actual location of a vein in the arm of a person.

In an embodiment, the alignment system is configured such that the alignment indicator (e.g., an alignment channel 3724) and the graphical representation of vein 3726 are oriented to correspond to the actual position of the monitored vein to make it appear as if the person can see the monitored vein. For example, FIG. 37C depicts the actual location of a vein 3734 running through a portion of the arm and hand and a graphical representation of the vein 3726 on the graphical user interface of the smartwatch in which the boundaries of the graphical representation of the vein match the boundaries of the actual vein at the location of the smartwatch. Such a configuration of the graphical representation of the vein helps to create an alignment feature that promotes intuitive alignment adjustments. In an embodiment, the alignment features can be adapted on-the-fly to the orientation of the antenna array relative to the vein. In an embodiment, the graphical representation of the vein may include other graphical features that, for example, represent blood flow, the direction of blood flow, the pulsing of the blood flow, and/or the color of the blood. In an embodiment, the color of the graphical representation of the vein or some other feature of the graphical representation of the vein (e.g., the texture) may be used to represent a value of a health parameter, such as a blood glucose level, a pulse rate, or blood pressure.

Figure 38A:
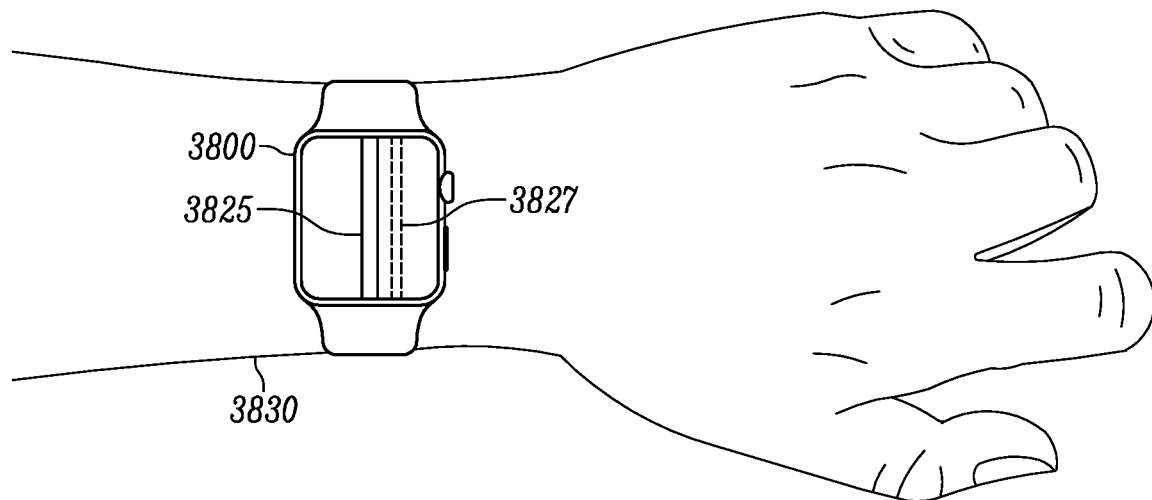
FIGS. 38A and 38B illustrate another example of an alignment process.
Figure 38B:
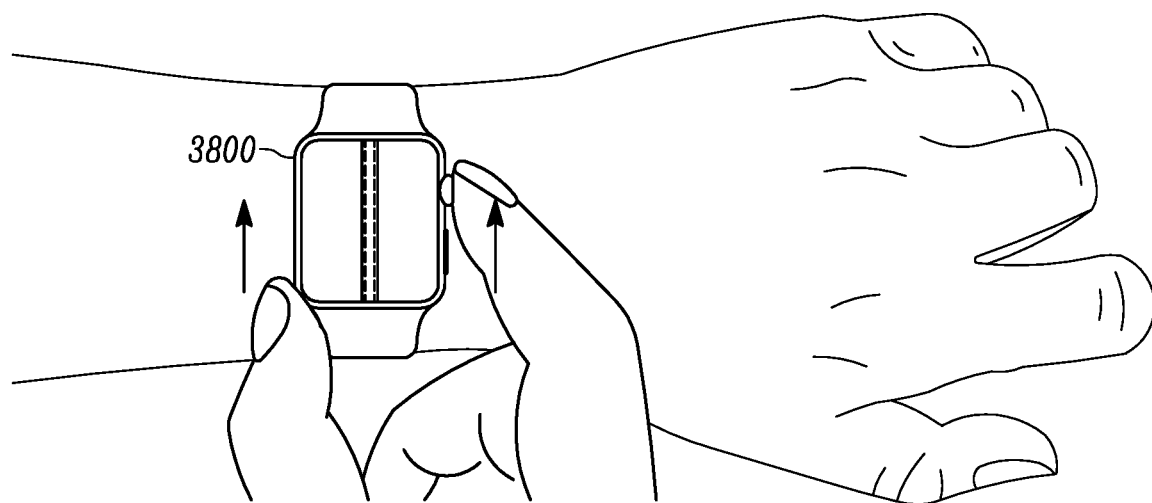

Other, less intuitive configurations of an alignment feature, or features are possible. FIGS. 38A and 38B, show an example of a less intuitive configuration of an alignment channel 3825 and a graphical representation of a vein 3827. In the example of FIGS. 38A and 38B, up and down movement of the smartwatch 3800 on the wrist 3830 causes left and right movement of the graphical representation of the vein, which may be less intuitive and may lead to confusion of the user. Thus, the configuration as described with reference to FIGS. 36A-36E and FIGS. 37A and 37B provides an intuitive user interface that may have advantages over other possible configurations.

Figure 39A:
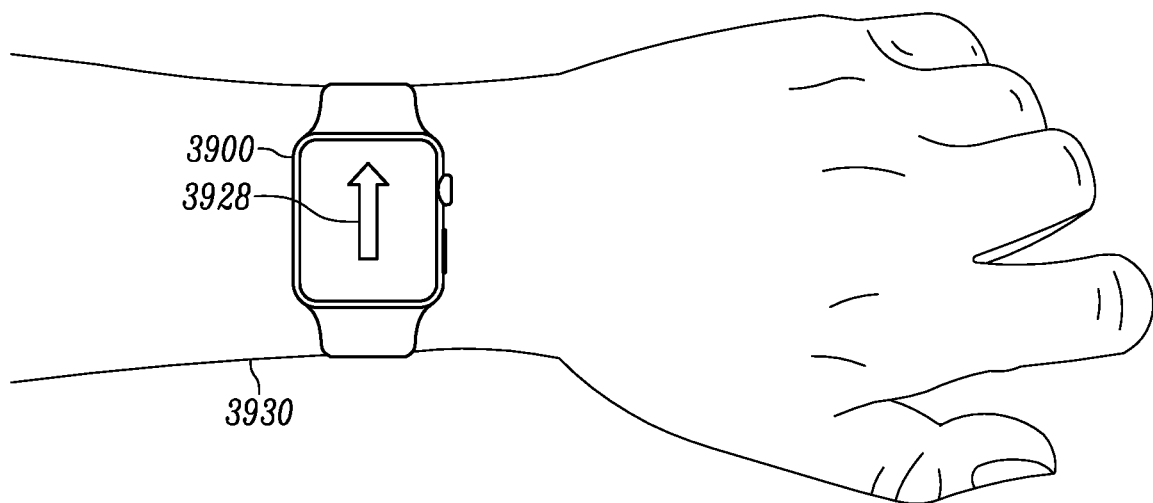
FIGS. 39A and 39B depict an example of another type of RF-based alignment feature that can be used to align an antenna array of a sensor system with a monitored vein.
Figure 39B:
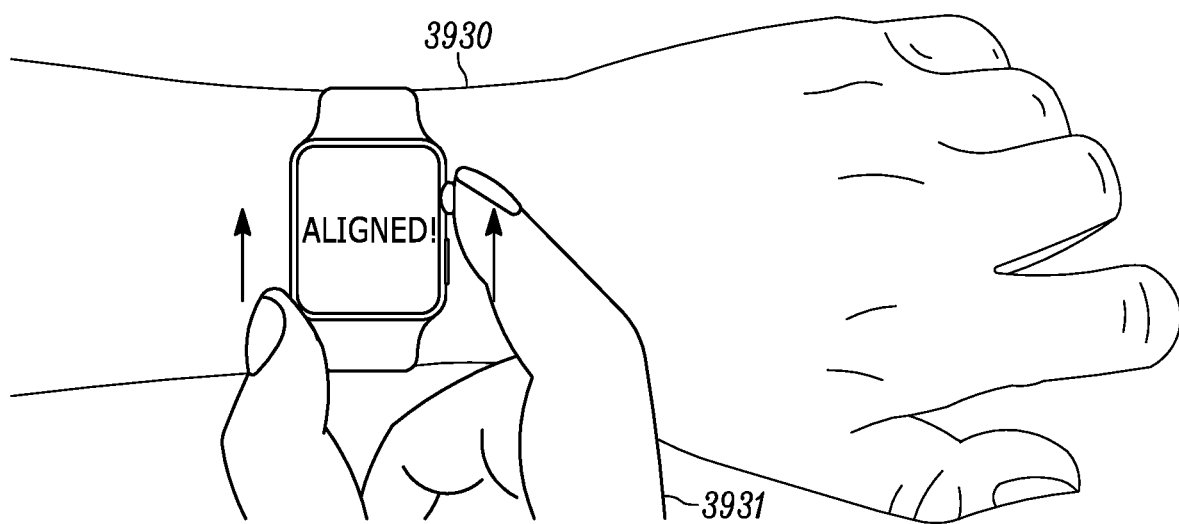

Although an example of an alignment feature and corresponding alignment technique is described with reference to FIGS. 36A-36E and FIGS. 37A and 37B, other RF-based alignment features can be implemented and displayed on the display of a health monitoring device such as a smartphone. FIGS. 39A and 39B depict an example of another type of RF-based alignment feature that can be used to align an antenna array of a sensor system with a monitored vein. With reference to FIG. 39A, the alignment feature is simply an arrow 3928 that encourages the user to move and/or adjust the position of the smartwatch 3900 on the wrist 3930 in the direction of the arrow. FIG. 39B illustrates the position of the smartwatch being manually moved and/or adjusted on the wrist in the direction of the arrow by the right hand 3931 of the person wearing the smartwatch. As indicated by the upward pointing arrows, the smartwatch is moved upwards until alignment is achieved and, for example, an alignment message (e.g., "Aligned!") is displayed.

Although some examples of RF-based alignment features are provided, other configurations of an RF-based alignment feature or features are possible. Additionally, in an embodiment, an output signal generated in response to the radio waves may be used to generate an indicator of alignment that is an audio signal (e.g., a sound that encourages alignment) or a tactile signal (e.g., a vibration that encourages alignment).

In the examples described above with reference to FIGS. 36A-39B, the sensor system is integrated into a smartwatch. In other embodiments, the sensor system can be integrated into other types of devices and/or systems, including, for example, a smartphone, a removable smartphone case, and a strap or band for a watch, a ring (e.g., to be worn on a finger), or another device.

Figure 40A:
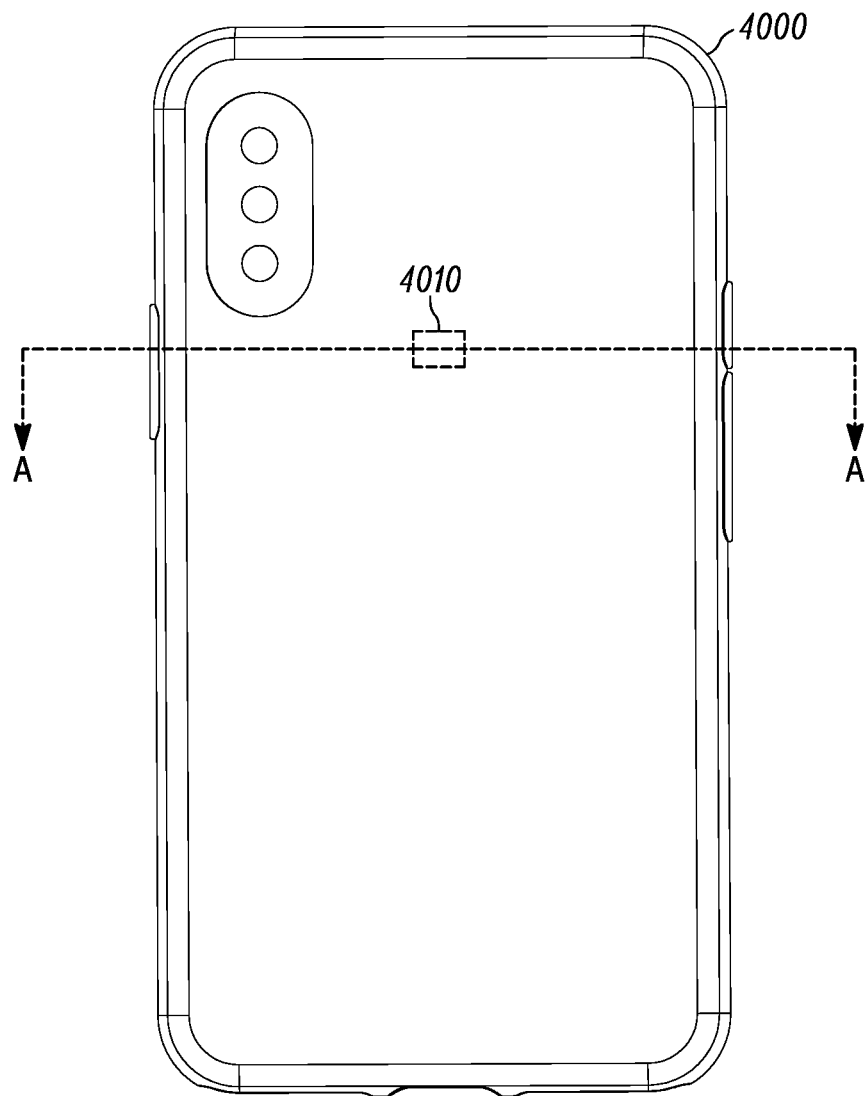
FIGS. 40A and 40B depict an embodiment of a smartphone that includes a sensor system integrated into the smartphone.
Figure 40B:
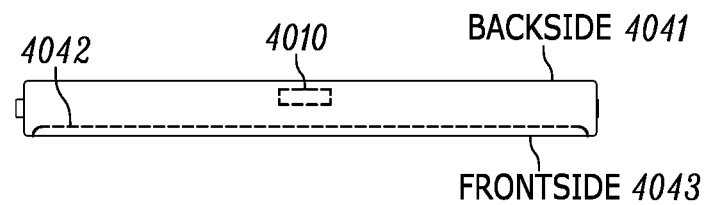

FIGS. 40A and 40B depict an embodiment of a smartphone 4000 that includes a sensor system as described above integrated into the smartphone. For example, the sensor system includes an RF IC device 4010 as described above with reference to FIGS. 5-8D integrated into the smartphone. In the embodiment depicted in FIG. 40B, the sensor system is integrated into the smartphone near the backside 4041 of the smartphone (opposite the display 4042 at the frontside 4043) so that a health parameter of a person can be monitored by bringing the backside of the smartphone into contact with (or close proximity to) the skin of the person that is to be monitored. In an embodiment, the antennas of the sensor system are at the surface of the smartphone so that the antennas can be brought into contact with the skin to improve radio wave transmission. In other embodiments, the antennas are very near to the backside external surface of the smartphone, e.g., within 0.25-3 mm. For example, the antennas may be covered by a thin layer of the material that forms the backside of the smartphone, e.g., a plastic material having a thickness in the range of 0.25-3 mm thick. In an embodiment in which the backside is made of a metal (e.g., aluminum), there may be openings in the aluminum at the locations of the antennas that are open to the antennas or filed with a material such as plastic through which radio waves can more easily pass. The sensor system may include all of the components of the sensor system as described with reference to FIG. 5 or only some of the components. For example, in an embodiment, the sensor system includes the RF front-end 548 and the digital baseband system 550 as shown in FIG. 5, but CPU functionality is provided by a CPU of the smartphone that performs many of the operations related to standard smartphone functionality.

Figure 41A:
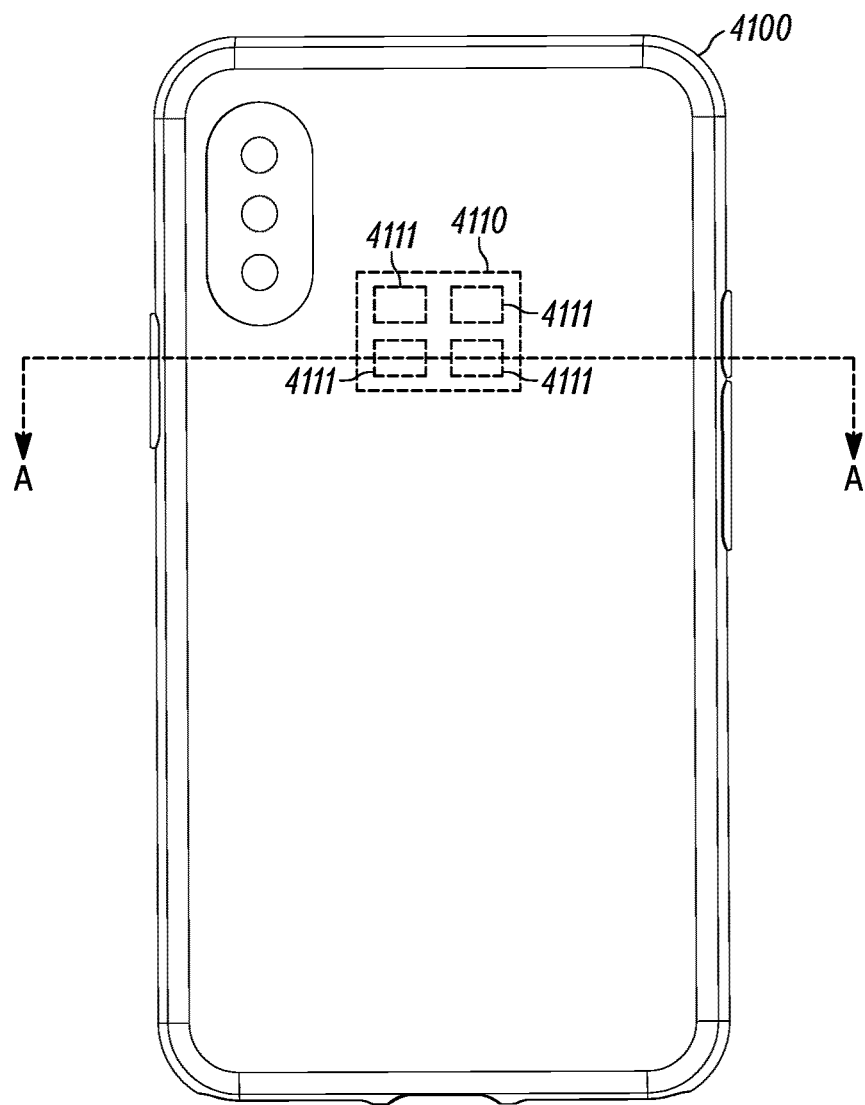
FIGS. 41A and 41B depict an embodiment of a smartphone that includes a sensor system with multiple RF front-ends integrated into the smartphone.
Figure 41B:
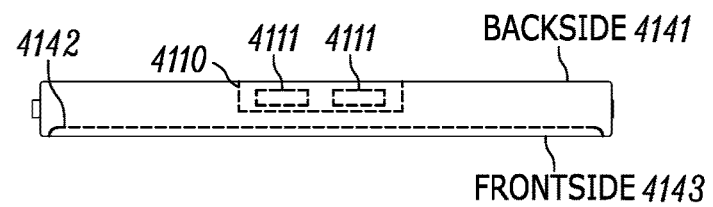

In another embodiment, multiple RF IC devices are included in a sensor system that is integrated into a smartphone. FIGS. 41A and 41B depict an embodiment of a smartphone 4100 that includes a sensor system 4110 with multiple RF front-ends (e.g., in the form of multiple different RF IC devices 4111 as described with reference to FIGS. 5-8D) integrated into the smartphone. For example, as depicted in FIG. 41A, the RF IC devices are configured in a two-dimensional array such that the sensor system includes in total, for example, 4×2=8 transmit antennas and 4×4=16 receive antennas. In the embodiment depicted in FIG. 41B, the sensor system having multiple different RF IC devices is integrated into the smartphone near the backside 4141 of the smartphone (opposite the display 4142 at the frontside 4143) so that a health parameter of a person can be monitored by bringing the backside of the smartphone into contact with (or close proximity to) the skin of the person that is to be monitored.

Figure 42B:
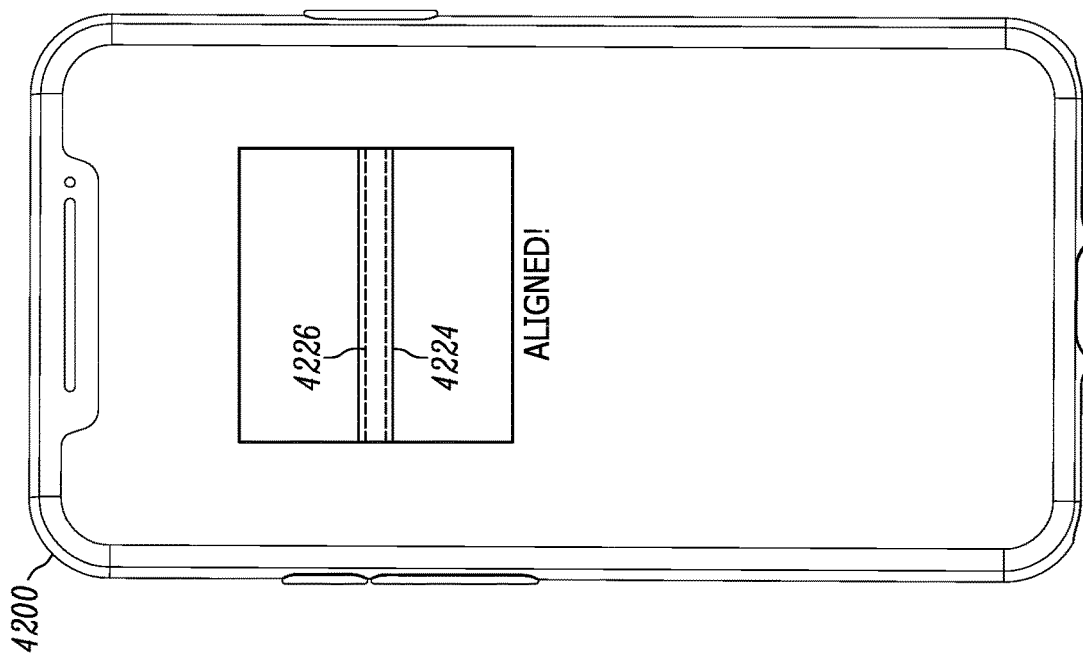
FIGS. 42A and 42B depict an embodiment of a smartphone that includes a sensor system as described with reference to FIGS. 5-8D that is configured to implement RF-based alignment of an antenna array of the sensor system to a vein of a person that is to be monitored.
Figure 42A:
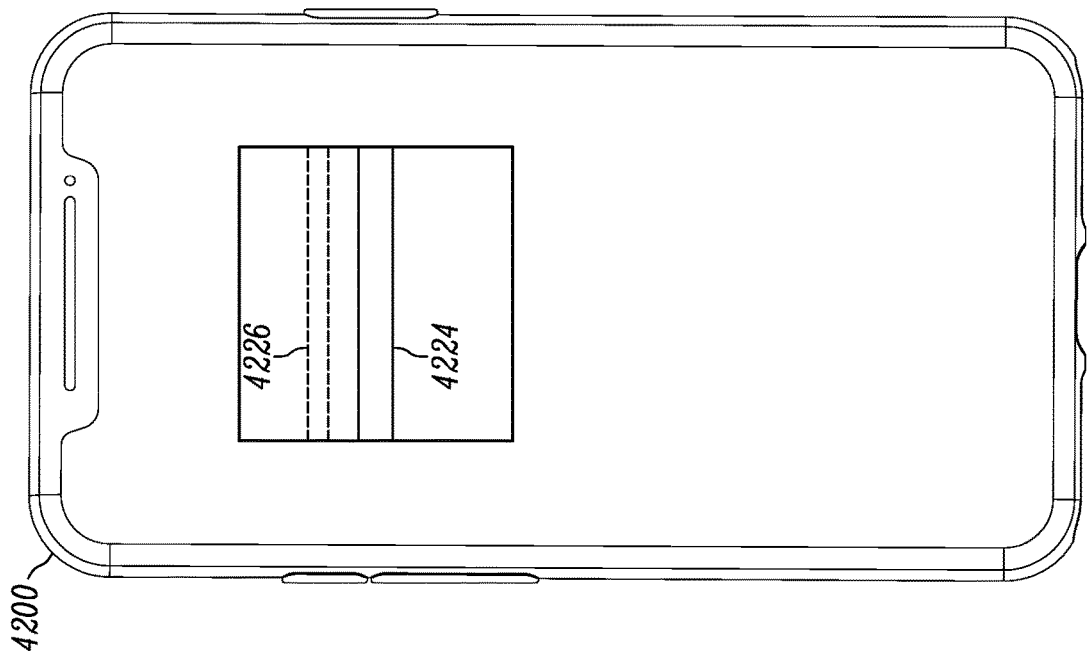

With an RF-based sensor system integrated into a smartphone, it is possible to implement RF-based alignment similar to that described above with reference to FIGS. 36A-36E, 37A, and 37B. For example, it is possible to generate digital alignment data from the RF-based sensor system and to use the digital alignment data to display a visual indicator of alignment in response to the digital alignment data. FIGS. 42A and 42B depict an embodiment of a smartphone that includes a sensor system (not shown), for example, as described with reference to FIGS. 5-8D that is configured to implement RF-based alignment of an antenna array of the sensor system to a vein of a person that is to be monitored. The alignment technique depicted in FIGS. 42A and 42B involves displaying an alignment feature (e.g., an alignment channel 4224) and a graphical representation of a vein 4226 as described above with reference to FIGS. 36A-36E, 37A, and 37B. When the smartphone is used to monitor a health parameter of a person, the smartphone is brought into contact with (or into close proximity to, e.g., less than 10 mm, or more preferred less than 2 mm) the skin of the person to be monitored and a graphical representation of a vein relative to an alignment channel is displayed on the display of the smartphone to encourage a user of the smartphone to move and/or adjust the position of the smartphone relative to the vein to align the antenna array of the sensor system with the monitored vein. In an embodiment, the smartphone is held in contact with the skin during health parameter monitoring to ensure that the separation distance is constant throughout the health monitoring operation.

In an embodiment, a vein in the upper forearm is monitored to monitor a health parameter of a person. In such an embodiment, a vein in the upper forearm is monitored by placing the antenna array of the smartphone on the forearm at the location of the vein that is intended to be monitored. An indicator in the form of an alignment channel and a graphical representation of the vein are then displayed on the display of the smartphone. Similar to the alignment technique described above with reference to FIGS. 36A-36E, FIG. 42A depicts a smartphone 4200 in which the graphical representation of the vein 4226 is out of alignment with the alignment feature 4224 and FIG. 42B depicts the smartphone in which the graphical representation of the vein is aligned with the alignment feature and in which an alignment message (e.g., "Aligned!") is displayed.

Figure 43A:
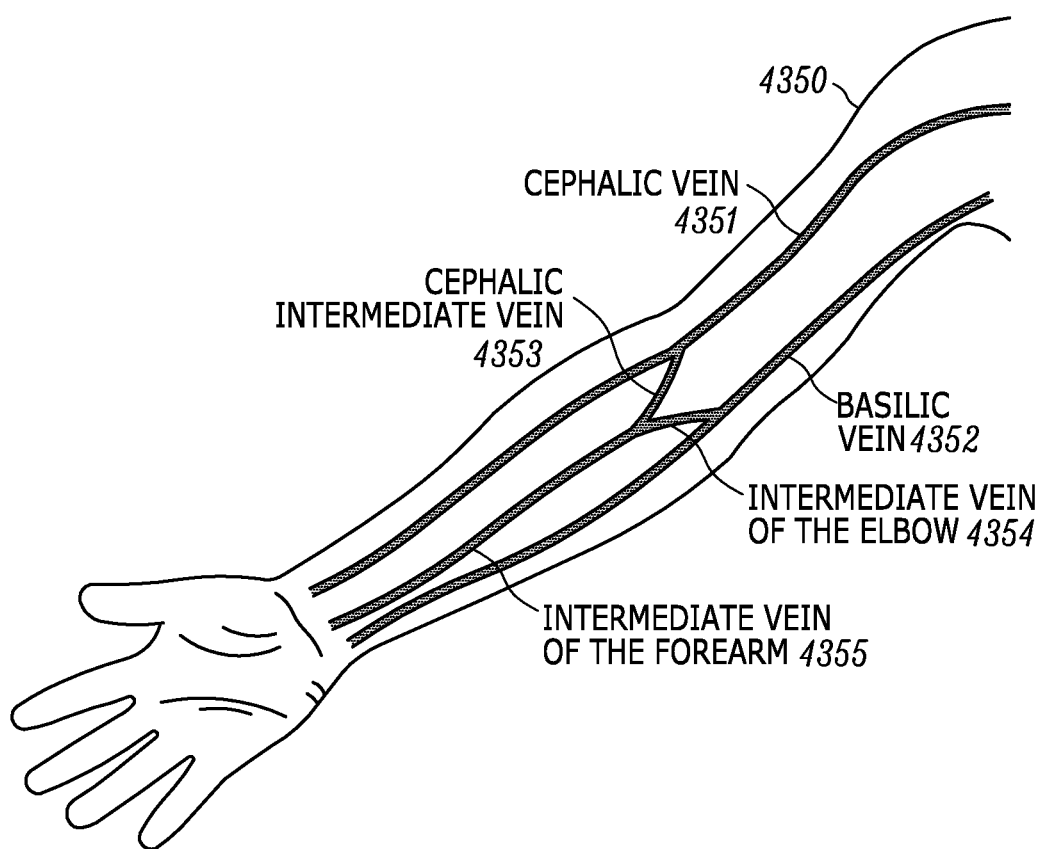
FIG. 43A depicts an example of the veins in the arm of a person.
Figure 43B:
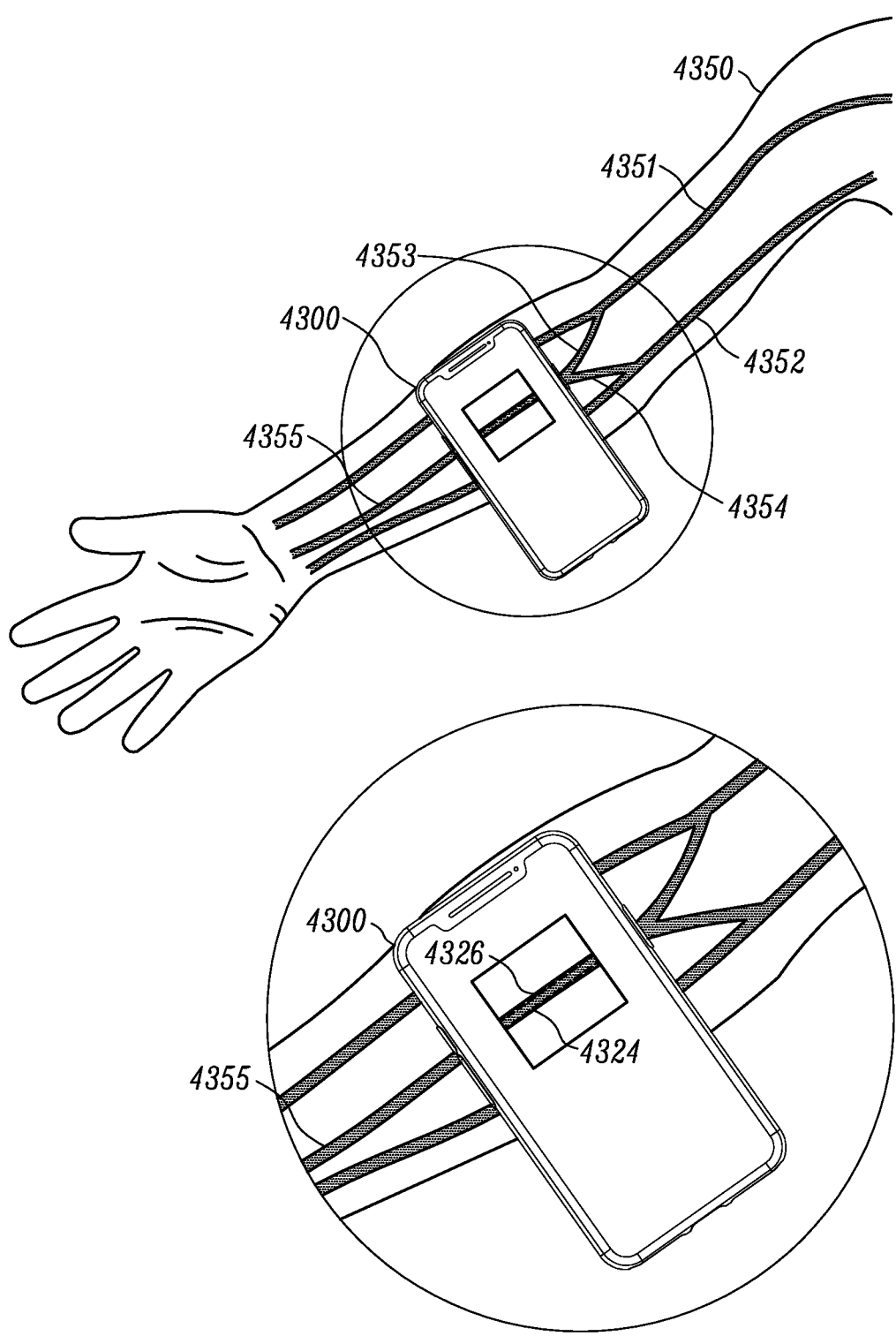
FIG. 43B depicts a smartphone, such as the smartphone described with reference to FIGS. 41A-42B placed on the skin at the location of (or in close proximity to) a vein such as the intermediate vein of the forearm.

As stated above, it may be desirable to monitor a vein in the forearm of a person. FIG. 43A depicts an example of the veins in the arm 4350 of a person. As shown in FIG. 43A, the veins include the cephalic vein 4351, the basilic vein 4352, the cephalic intermediate vein 4353, the intermediate vein of the elbow 4354, and the intermediate vein of the forearm 4355. FIG. 43B depicts a smartphone 4300, such as the smartphone described with reference to FIGS. 41A-42B placed on the skin at the location of (or in close proximity to) a vein such as the intermediate vein of the forearm 4355. As illustrated in FIG. 43B, the backside of the smartphone is placed on the forearm (or in close proximity to the forearm) and the frontside of the smartphone, including the display, is visible to a user of the smartphone. As shown in FIG. 43B, the alignment channel 4324 and the graphical representation of the vein 4326 are oriented to correspond to the orientation of the actual vein 4355 so that the alignment indicator can be intuitively interpreted and manipulated by the user. As described above, a person holding the smartphone on the skin can move and/or adjust the position of the smartphone relative to the vein as guided by the alignment channel and the graphical representation of the vein to adjust the position of the antenna array of the sensor system to a desired position relative to the vein. In an embodiment, the user adjusts the lateral position of the smartphone while holding the smartphone against the skin. Although an example of an RF-based alignment indicator is described with reference to FIG. 43B, other embodiments of an alignment indicator are possible.

As described above, in an embodiment, the alignment system of the health monitoring device is able to adapt the orientation of the displayed visual indicator on the display of the device (e.g., the smartphone) to correspond to the orientation of the vein relative to health monitoring device. Thus, if the smartphone is held in a different orientation relative to a vein, the displayed alignment features change accordingly. For example, with reference to FIG. 43B, the orientation of an alignment channel and a graphical representation of a vein may change to a vertical orientation when the smartphone is rotated ninety degrees relative to the vein.

Figure 44B:
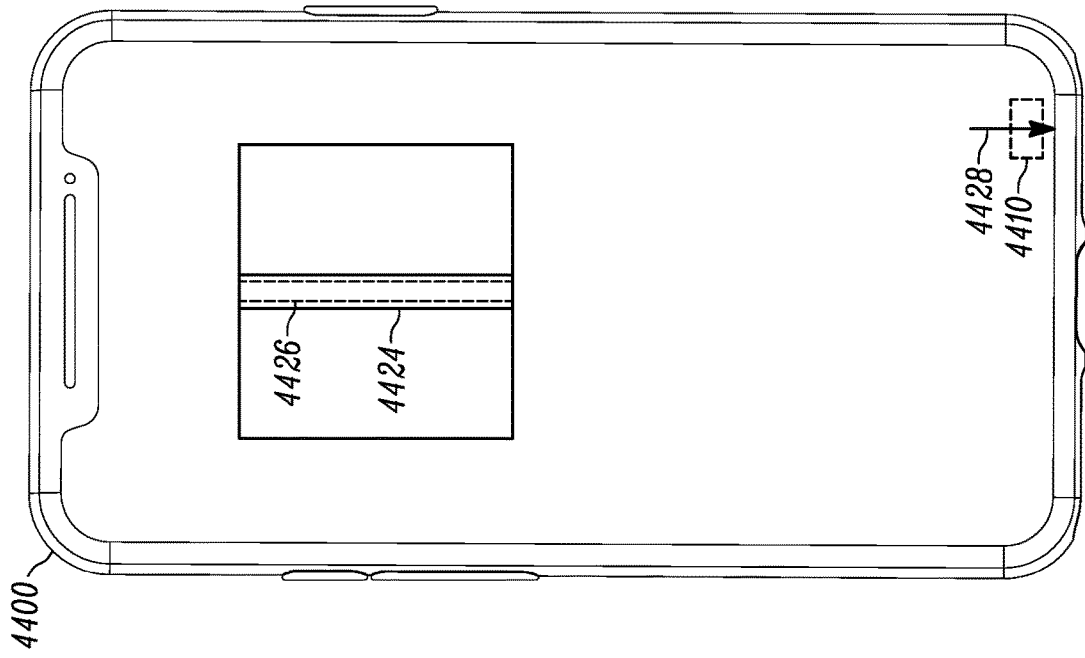
FIGS. 44A and 44B depict the backside and frontside of a smartphone in which a sensor system including the antenna array is located at a point near the bottom of the smartphone.
Figure 44A:
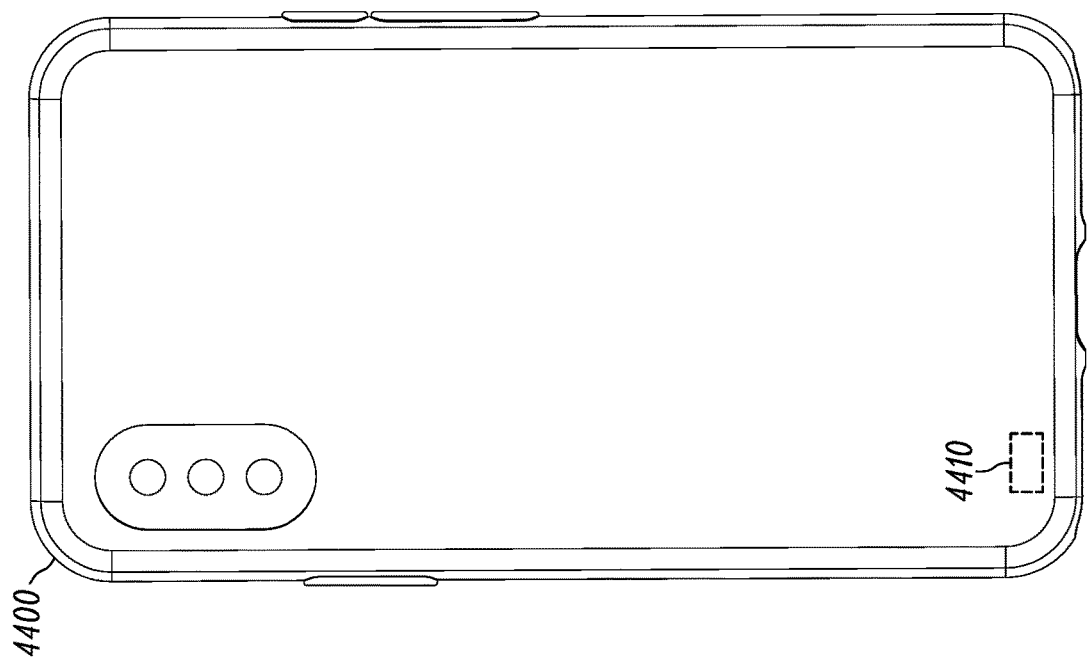

In an embodiment, the sensor system, including the antenna array, may be located in a different position within the smartphone to facilitate health monitoring. For example, in an embodiment, the sensor system, including the antenna array, is located at a point near the bottom of the smartphone. FIG. 44A depicts an example of the backside of a smartphone 4400 in which a sensor system 4410 including the antenna array is located at a point near the bottom of the smartphone. Additionally, in this example, the sensor system is located off of the centerline (e.g., to the left side) of the smartphone to, for example, avoid physically and/or electrically interfering with electronics that may be associated with a wired interface that is located at the centerline of the smartphone. With reference to FIG. 44B, which depicts the frontside of the smartphone 440, in an embodiment, the RF-based alignment technique involves generating and displaying a graphical indicator of alignment that graphically indicates to the user where to align the smartphone with a vein that is intended to be monitored. In the example of FIG. 44B, the graphical indicator is an arrow 4428 that is generated and displayed as a graphical element on the display of the smartphone. As shown in FIG. 44B, the graphical alignment indicator is collocated with the sensor system 4410 such that aligning the arrow with the vein to be monitored also aligns the sensor system (e.g., the antenna array of the sensor system) with the vein to be monitored. In an embodiment, the graphical alignment indicator and the sensor system (e.g., the antenna array of the sensor system) are collocated when graphical alignment indicator and the sensor system overlap with each other or are within a few millimeters from each other when viewed from a plan view as shown in FIG. 44B. In an embodiment, an alignment feature such as the arrow 4428 can be used alone to achieve alignment. In another embodiment and as shown in FIG. 44B, an additional alignment indicator may be provided to help achieve alignment between the sensor system and the monitored vein. As shown in FIG. 44B, the alignment indicator includes an alignment channel 4424 and a graphical representation of the vein 4426 as described above. In an embodiment, multiple RF-based alignment features can be used together to achieve alignment. Additionally, although an arrow is shown as an example of a visible alignment feature, other graphical elements on the graphical user interface, including lines, shapes, colors, and text can be used.

Figure 44C:
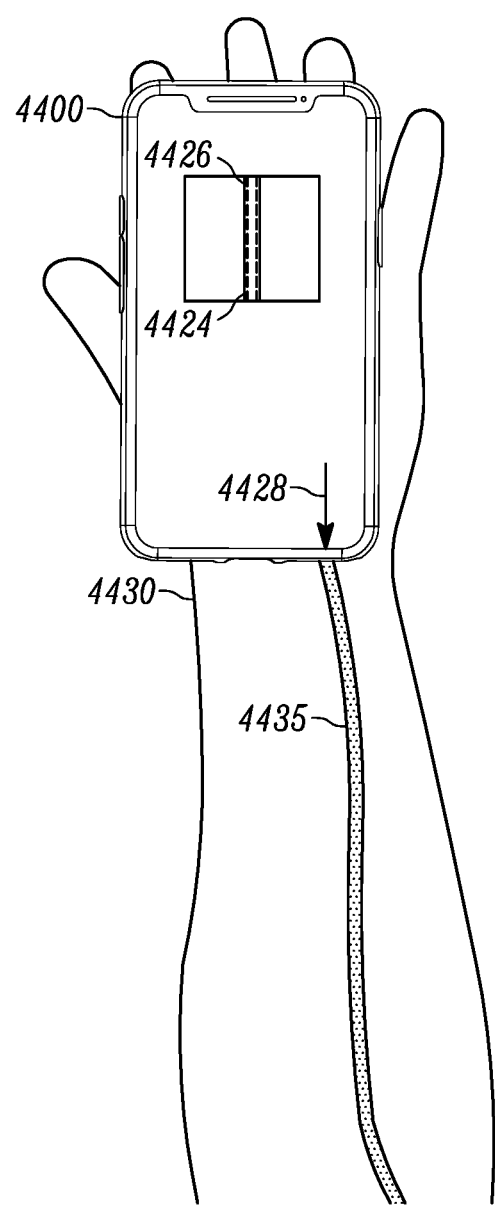
FIG. 44C illustrates a person holding the smartphone as described with reference to FIGS. 44A and 44B against the skin at the wrist and using the alignment feature on the graphical user interface to align the sensor system of the smartphone with the monitored vein.

FIG. 44C illustrates a person holding the smartphone 4400 as described with reference to FIGS. 44A and 44B against the skin at the wrist 4430 and using the alignment feature on the graphical user interface (e.g., the arrow 4428 as shown in FIG. 44B) to align the sensor system of the smartphone with the monitored vein 4435. FIG. 44C also shows an additional alignment feature (e.g., an alignment channel 4424 and a graphical representation of the vein 4426) on the display device as shown in FIG. 44B to further help facilitate alignment between the antenna array of the sensor system and the monitored vein. In an embodiment, the alignment arrow helps the user to achieve course alignment between the antenna array of the sensor system and the monitored vein and the alignment channel helps the user to achieve fine alignment between the antenna array of the sensor system and the monitored vein. Also note that the alignment channel is oriented to match the orientation of the vein relative to the graphical user interface of the smartphone in order to provide the user with an intuitive way to align the antenna array of the sensor system, which is embedded within the smartphone, with the monitored vein. For example, the orientation of the alignment channel matches the orientation of the vein in that the alignment channel, the graphical representation of the vein, and the actual vein run in parallel to each other (e.g., if not exactly in parallel, then roughly in parallel, e.g., to within about plus or minus 5 degrees).

Figure 45B:
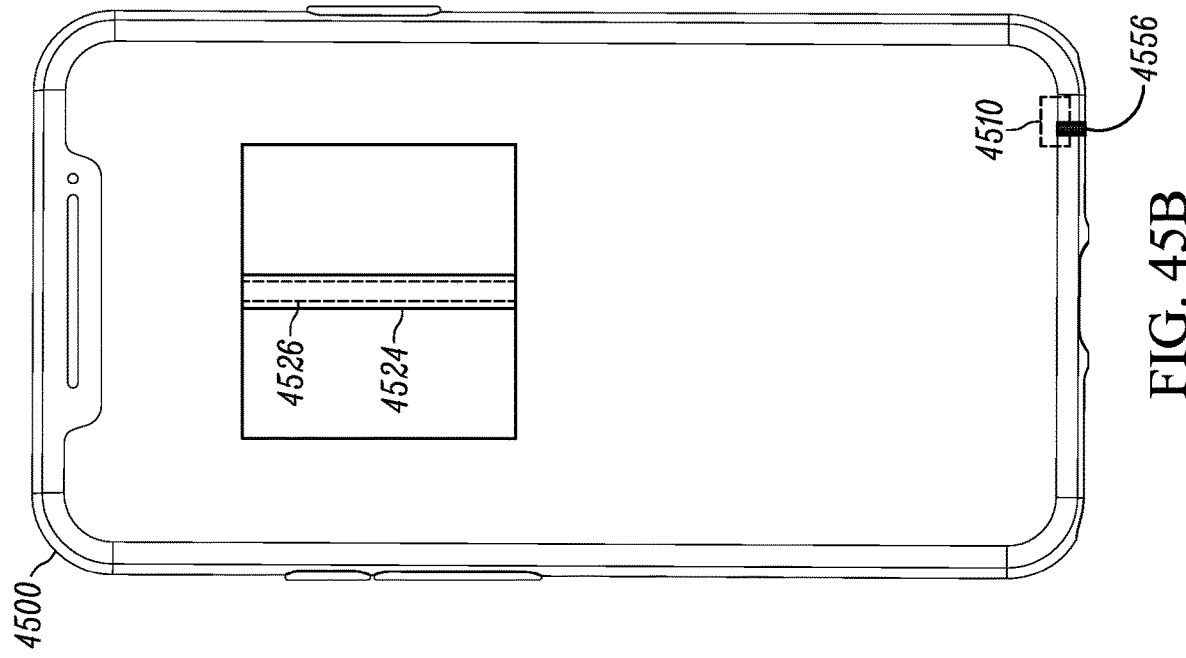
FIG. 45B depicts the frontside of the smartphone from FIG. 45A in which an alignment feature is provided as a marking on the body of the smartphone that is visible to a user of the smartphone.
Figure 45A:
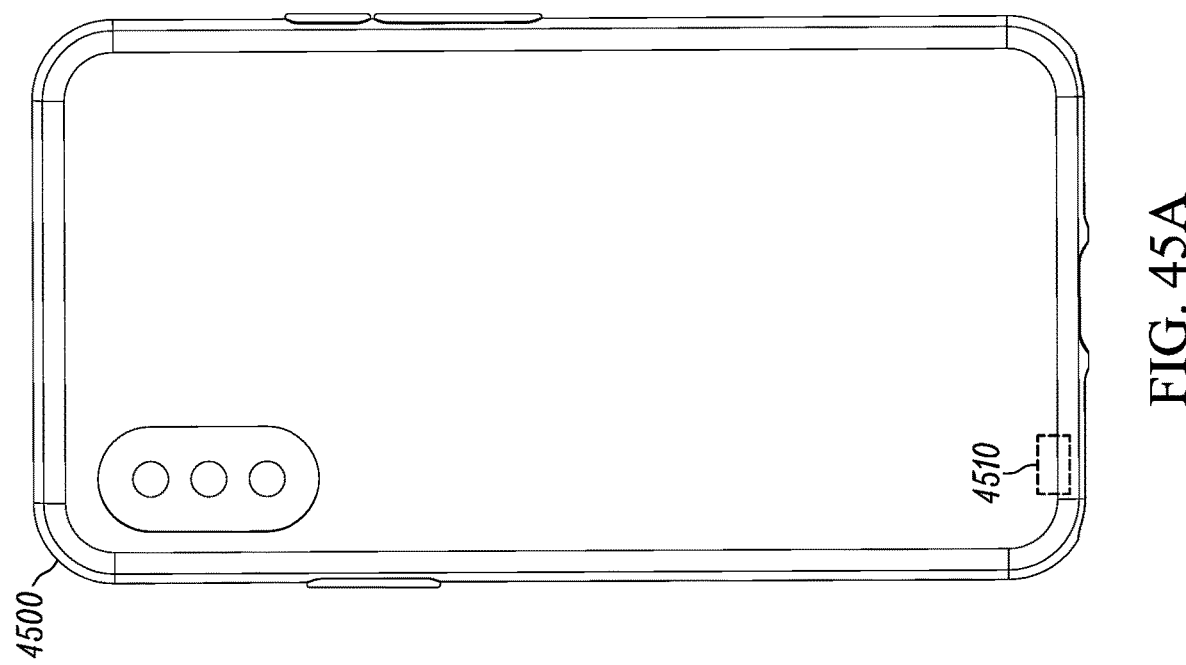
FIG. 45A depicts the backside of a smartphone in which the sensor system is located at a point near the bottom of the smartphone, similar to the example described with reference to FIG. 44A.

In the embodiment of FIGS. 44A-44C, the alignment arrow 4428 is generated in response to RF signals generated by the sensor system 4410 and is displayed on the display of the smartphone as a graphical element of a graphical user interface. In another embodiment, a visual alignment feature is a visible marking on the body of the smartphone that is used to align the sensor system of the smartphone with the vein that is to be monitored. FIG. 45A depicts the backside of a smartphone 4500 in which the sensor system 4510 is located at a point near the bottom of the smartphone, similar to the example described with reference to FIG. 44A. With reference to FIG. 45B, which depicts the frontside of the smartphone 4500, an alignment feature 4556 is provided as a marking on the body of the smartphone that is visible to a user of the smartphone. For example, the visible marking is a marking of a different color from the surrounding portion of the body or the visible marking is a groove or bump in the body that is visible to a user of the smartphone. Other visible markings on the body of the smartphone can also be used as a visual alignment indicator that can be seen by a user of the smartphone. In an embodiment, the alignment feature is referred to as a "physical" alignment feature because the alignment feature includes a physical element on the body of the smartphone (even if the physical element is simply a contrasting color or other visible marking). As shown in FIG. 45B, the visible marking is collocated with the sensor system 4510 such that aligning the visible marking 4556 with the vein to be monitored also aligns the sensor system (e.g., the antenna array of the sensor system) with the vein to be monitored. In operation, a user of the smartphone uses the visible marking to align the smartphone with a vein of a person as illustrated, for example, in FIG. 44C. In one embodiment, the visible alignment feature is the only alignment feature that exists for aligning the sensor system to a monitored vein. In another embodiment, another alignment feature may be utilized in conjunction with the visible marking. For example, FIG. 45B depicts a physical alignment feature on the body of the smartphone along with an alignment channel 4524 and a graphical representation of a vein 4426 displayed on a graphical user interface of the display.

Figure 46:
FIG. 46 is a perspective view of a removable smartphone case.

In an embodiment, some components of the sensor system, such as the sensor system described with reference to FIGS. 5-7 are integrated into a removable case for a smartphone and digital data generated by the sensor system (e.g., the digital baseband system 550 of FIG. 5) is communicated from the removable smartphone case to the smartphone via a communications interface for further processing to determine a value of a health parameter. FIG. 46 depicts a perspective view of an example of a removable case 4660 for a smartphone (also referred to as a "removable smartphone case," a "smartphone case," a "case," or a "cover"). As shown in FIG. 46, the removable smartphone case includes a body having a backwall and a sidewall that goes around the perimeter of the backwall, which together form a bed within which a smartphone can be secured. As is known in the field, the backwall typically includes an opening for a camera and the sidewall includes at least one opening that corresponds to buttons and/or interfaces on the side of the smartphone.

Figure 47B:
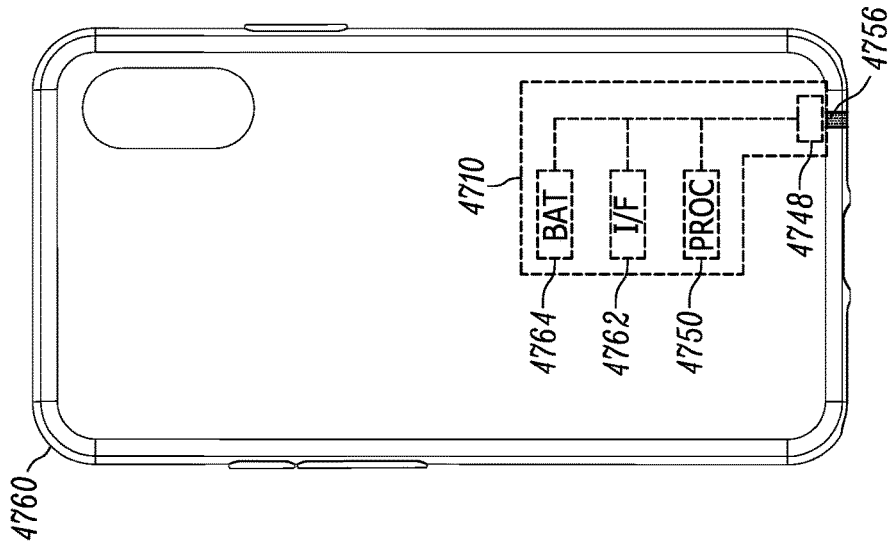
FIGS. 47A and 47B depict the backside and frontside, respectively, of an embodiment of a removable smartphone case that includes a sensor system having an RF front-end, a processor, a communications interface, and a battery integrated into the case.
Figure 47A:
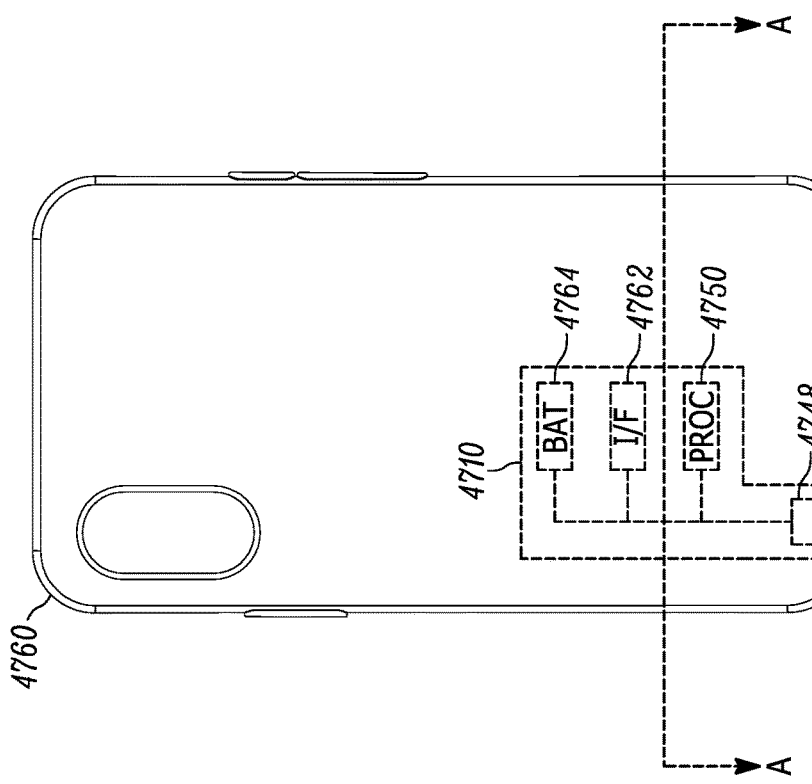
Figure 47C:
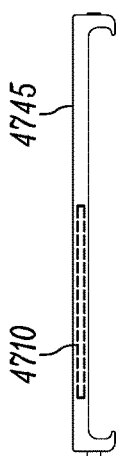
FIG. 47C depicts a side cutaway view of the removable smartphone case shown at cross section AA of FIG. 47A.

FIGS. 47A and 47B depict the backside and frontside, respectively, of an embodiment of a removable smartphone case 4760 that includes a sensor system 4710 having an RF front-end 4748, a processor 4750, a communications interface 4762, and a battery 4764 integrated into the case and an alignment feature 4756. In the example of FIGS. 47A and 47B, the RF front-end is similar to the RF front-end 548 described above with reference to FIG. 5 and the processor is similar to the digital baseband system 550 described with reference to FIG. 5. In the example of FIGS. 47A and 47B, the communications interface is a wireless interface, such as a BLUETOOTH low energy (BLE) wireless interface although other wireless or wired interfaces are possible. The battery may be, for example, a lithium-ion rechargeable battery that has a thin profile and that is rechargeable via wireless and or wired charging. FIG. 47C depicts a side cutaway view of the removable smartphone case shown at cross section AA of FIG. 47A. As shown in FIG. 47C, the sensor system 4710 is integrated into the body of the case. In an embodiment, the antennas of the sensor system are at the backside 4745 of the body of the removable smartphone case so that the antennas can be brought into contact with the skin to improve radio wave transmission. In other embodiments, the antennas are very near to the backside external surface of the smartphone case, e.g., within 0.25-3 mm. For example, the antennas may be covered by a thin layer of the material of the removable smartphone case, e.g., a plastic material having a thickness in the range of 0.25-3 mm thick. In an embodiment, some or all of the components of the sensor system are embedded into the case body and in other embodiments, some or all the components are attached to a surface of the case body. There are various ways in which the components of the sensor system can be connected to, attached to, and/or integrated with the case body. For example, the components of the sensor system may be embedded within a plastic material that is formed around the components and that forms at least part of the case body. In an embodiment, the antennas (e.g., the TX and RX antennas) are embedded close to the surface of the case body or at the surface of the case body such that they are close to the surrounding environment and/or directly exposed to the surrounding environment so that the antennas can be brought into contact with (or into close proximity to) the skin of the person that is to be monitored.

Figure 48B:
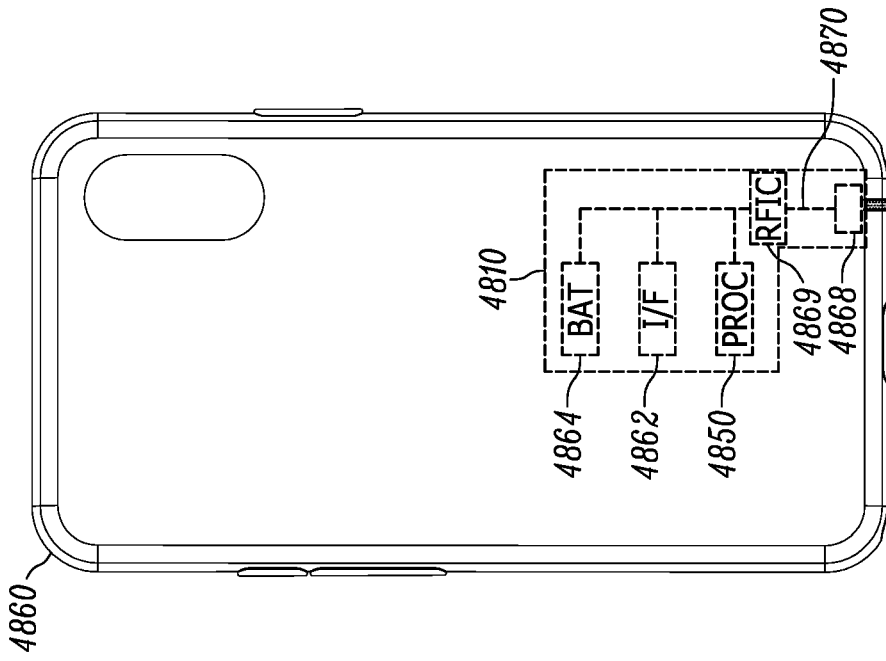
FIGS. 48A and 48B depict the frontside and backside, respectively, of an embodiment of a removable smartphone case that includes a sensor system in which the antenna array of the RF front-end is separated from the semiconductor substrate of the front RF front-end.
Figure 48A:
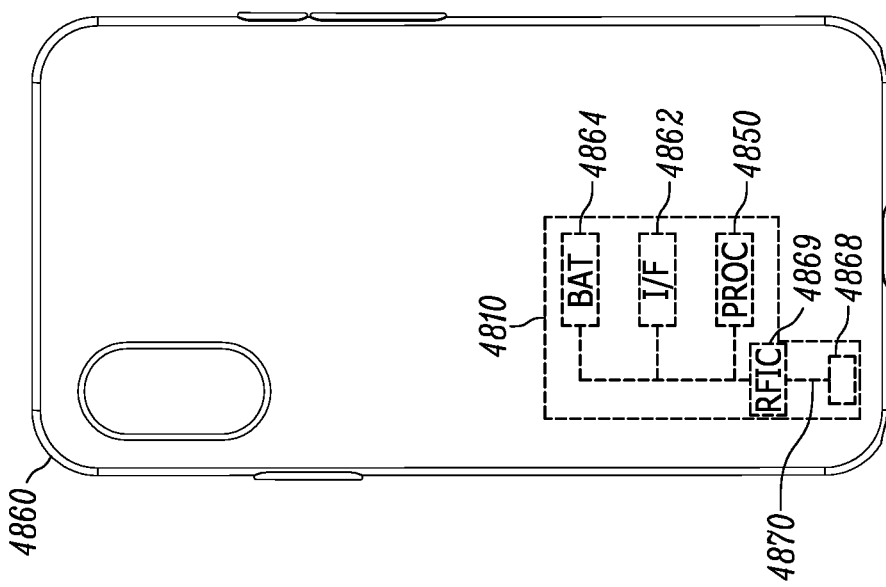

In the embodiment of FIGS. 47A-47C, the antennas of the RF front-end 4748 are closely integrated with a semiconductor substrate of the RF front-end (e.g., an RF IC) as is described, for example, with reference to FIGS. 8A-8D. This may be particularly important at high frequency ranges such as the 122-126 GHz frequency range. However, in other embodiments, the antennas (including the TX and/or RX antennas) may not be so closely integrated with the semiconductor substrate of the RF front-end. FIGS. 48A and 48B depict the frontside and backside, respectively, of an embodiment of a removable smartphone case 4860 that includes a sensor system 4810 having a processor 4850, an interface 4862, and a battery 4864 in which an antenna array 4868 of the RF front-end is separated from the semiconductor substrate (e.g., from the RF IC device 4869) of the front RF front-end. For example, the antennas of the antenna array may be electrically connected by conductive paths 4870 but physically separated from the RF IC device 4769 by 0.5-20 centimeters. In an embodiment, the antennas of the sensor system are at the surface of the body of the removable smartphone case so that the antennas can be brought into contact with the skin to improve radio wave transmission. In other embodiments, the antennas are very near to the backside external surface of the smartphone case, e.g., within 0.25-3 mm.

Figure 49B:
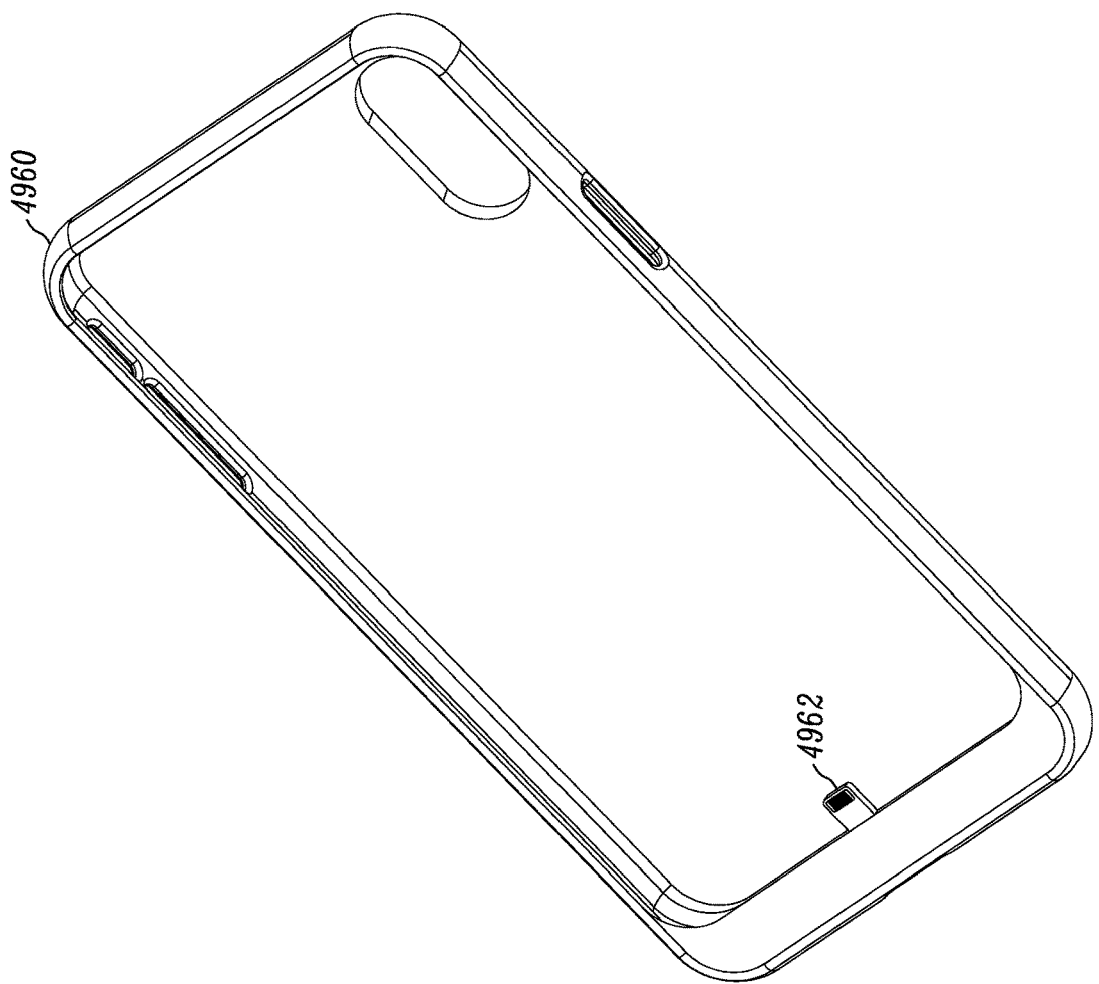
FIG. 49B depicts a perspective view of the removable smartphone case of FIG. 49A.
Figure 49A:
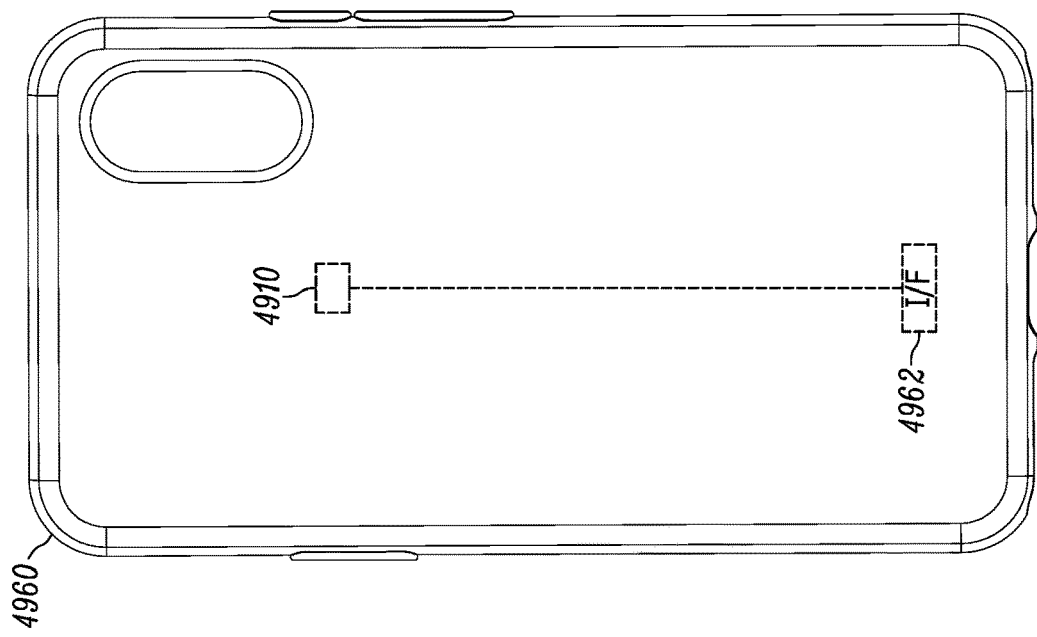
FIG. 49A depicts the backside of a removable smartphone case in which the sensor system is integrated into the case and the communications interface is a wired interface such as a male interface that is configured to connect to a female interface of a smartphone.

In an embodiment, the communications interface of the sensor system may be a wired communications interface. FIG. 49A depicts the backside of a removable smartphone case 4960 in which the sensor system 4910 is integrated into the case and the communications interface 4962 is a wired interface such as a male interface that is configured to connect to a female interface of a smartphone. FIG. 49B depicts a perspective view of the removable smartphone case 4960 of FIG. 49A that depicts the communications interface 4962 through which information can be communicated from the sensor system (e.g., an RF front-end and a digital baseband system) to a smartphone that is secured in the removable smartphone case. In an embodiment, the removable smartphone case may include additional components such as, for example, an alignment indicator device (e.g., an LED or a speaker) or a display device that can be used for health monitoring including alignment of the health monitoring device with a vein of a person.

Whether the removable smartphone case includes a wireless communications interface or a wired communications interface, the RF-based sensor system generates digital data in response to received radio waves. The digital data can be used for alignment of the sensor system and/or for health parameter monitoring. FIG. 50A illustrates alignment information (e.g., in the form of digital data generated by the sensor system 5010 in response to received radio waves) being communicated from the removable smartphone case 5060 to the smartphone 5000. In FIG. 50A, front views of the removable smartphone case and the smartphone are shown separate from each other to more clearly illustrate the communication of alignment information between the removable smartphone case and the smartphone although it should be understood that during normal operation, the smartphone would be held within the removable smartphone case and the communications interface of the smartphone case would communicate with the corresponding communications interface of the smartphone. As shown in FIG. 50A, the smartphone displays an RF-based alignment channel 5024 and a graphical representation of a vein 5026 in response to the received alignment information.

FIG. 50B illustrates health parameter information (e.g., in the form of digital data generated by the sensor system in response to receive radio waves) being communicated from the removable smartphone case 5060 to the smartphone 5000. As shown in FIG. 50B, the smartphone displays a value of a health parameter (e.g., a blood glucose level of 120 mg/dL) that is determined in response to the received health parameter information. In an embodiment, some of the processing used to determine the value of the health parameter (e.g., the blood glucose level) is implemented by a processor of the smartphone (e.g., a processor such as the APPLE A13 processor or the QUALCOMM Snapdragon processor). For example, the processor of the smartphone may be configured (e.g., through computer readable instructions and/or through specialized special-purpose hardware) to implement at least some portion of the machine learning engine, the health parameter determination engine, and/or the trained model database as described above with reference to FIGS. 27-31. In other embodiments, at least some portion of the machine learning engine, the health parameter determination engine, and/or the trained model database may be implemented in other processing devices such as a special-purpose processing device (e.g., a processing device of the smartphone and/or a processing device of the smartphone case). The communication of alignment information and/or health parameter information between a removable smartphone case and a smartphone may involve wired or wireless (e.g., BLE) communications depending on the configuration of the smartphone and/or the smartphone case. The examples of FIGS. 50A and 50B apply to both wired and wireless communications interfaces.

Various techniques for aligning an antenna array of a sensor system with an object, such as a vein of a person to be monitored, have been described above. Some of the techniques utilize digital data generated from received RF signals and other techniques utilize a visual marking on a smartphone or on a removable smartphone case. Additional alignment techniques that utilize alignment features integrated into the body of a device are described below. Such techniques utilize, for example, magnetic elements and/or out-of-plane physical features to promote alignment between an antenna array of a sensor system and an object, such as an alignment patch that is worn by the person to be monitored.

Figure 51B:
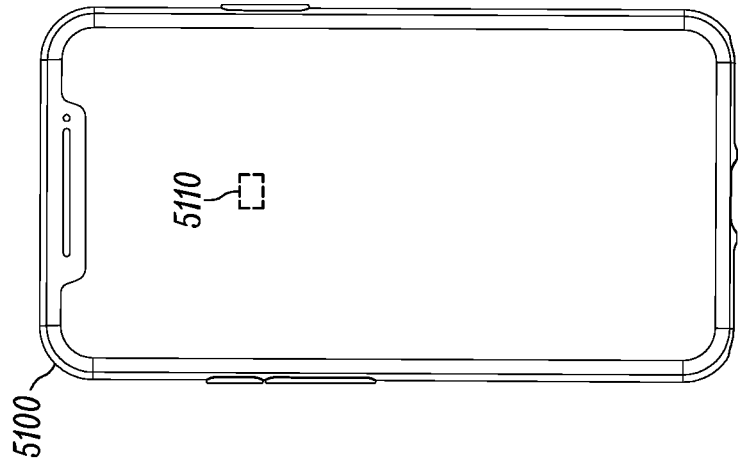
FIGS. 51A-51C depict an embodiment of a smartphone that includes magnetic alignment features integrated into the body of the smartphone.
Figure 51A:
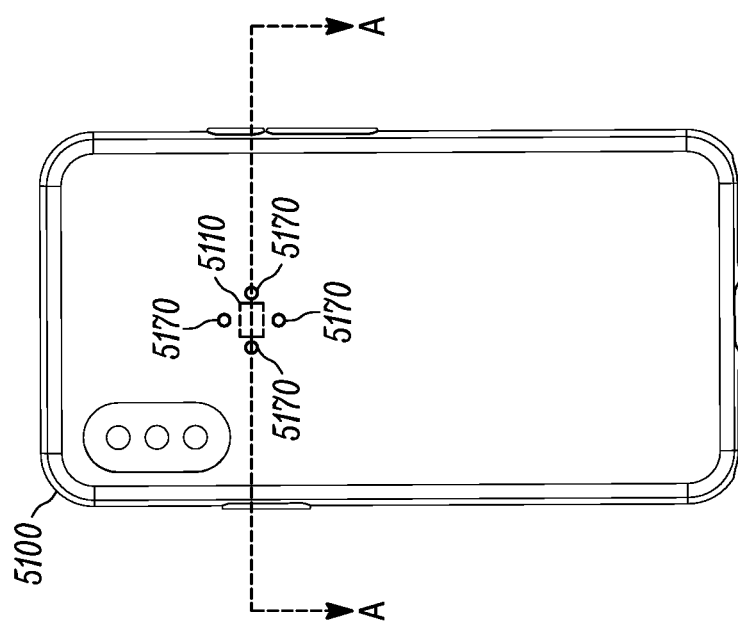
Figure 51C:
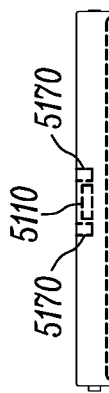

FIGS. 51A-51C depict an embodiment of a smartphone 5100 that includes magnetic alignment features 5170 integrated into the body of the smartphone. As is described below, the magnetic alignment features are configured to mate with alignment features of an alignment element (e.g., an alignment patch) that is worn by the person to be monitored. FIG. 51A is a view of the backside of a smartphone that includes a sensor system 5110 (including an antenna array) integrated into the smartphone and magnetic alignment elements 5170 integrated into the body of the smartphone. FIG. 51B depicts a view of the frontside of the smartphone with the location of the sensor system 5110 shown although the sensor system is not actually visible from the frontside of the smartphone. FIG. 51C depicts a side cutaway view of the smartphone at cross section AA of FIG. 51A, which shows the sensor system 5110 and the magnetic alignment elements 5170 integrated into the device body. In an embodiment, the magnetic alignment features are magnets such as small cylindrical neodymium magnets (e.g., 1-5 mm in diameter and 0.25-1 mm thick) that are secured into the case body. Although an example configuration of magnetic alignment elements is described with reference to FIGS. 51A-51C, other configurations of magnetic alignment elements are possible. Additionally, the sensor system and collocated alignment features could be located in other positions within the smartphone, such as, for example, the positions described with reference to FIGS. 44A, 44B, and 47A-47C.

Figure 52B:
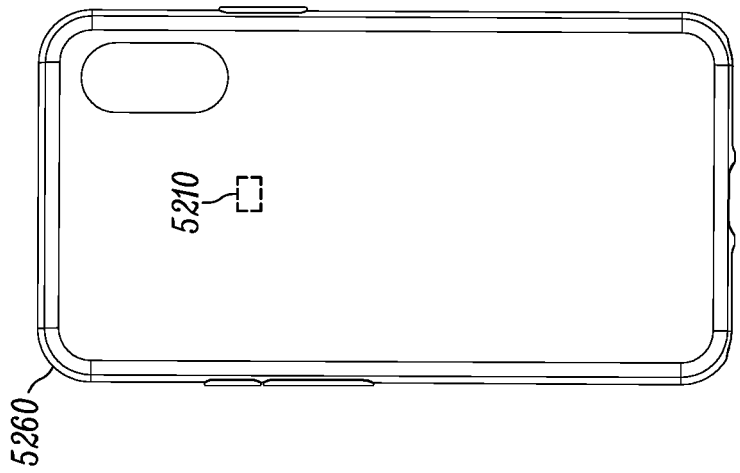
FIGS. 52A-52C depict an embodiment of a removable smartphone case that includes magnetic alignment elements integrated into the body of the removable smartphone case.
Figure 52A:
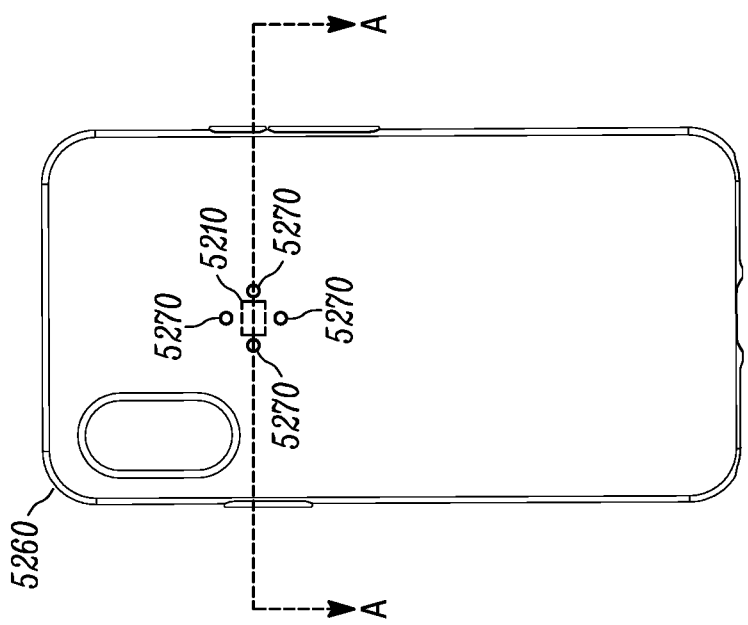
Figure 52C:
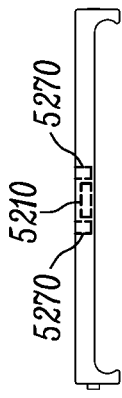

In the example of FIGS. 51A-51C, the alignment features are integrated into the body of a smartphone. In another embodiment, the alignment features are integrated into the body of a removable smartphone case. FIGS. 52A-52C depict an embodiment of a removable smartphone case 5260 that includes magnetic alignment elements 5270 integrated into the body of the removable smartphone case. As is described below, the magnetic alignment elements are configured to mate with alignment features of an alignment element (e.g., an alignment patch) that is worn by the person to be monitored. FIG. 52A is a view of the backside of a removable smartphone case that includes a sensor system 5210 (including an antenna array) and magnetic alignment elements 5270 integrated into the smartphone case. FIG. 52B depicts a view of the frontside of the smartphone case with the location of the sensor system 5210 shown although the sensor system may not actually be visible from the frontside of the smartphone case. FIG. 52C depicts a side cutaway view of the smartphone case at cross section AA of FIG. 52A, which shows the sensor system 5210 and the magnetic alignment elements 5270 integrated into the case body. In an embodiment, the magnetic alignment elements are small cylindrical neodymium magnets (e.g., 1-5 mm in diameter and 0.25-1 mm thick) that are secured into the case body. Although an example configuration of magnetic alignment features is described with reference to FIGS. 52A-52C, other configurations of magnetic alignment elements are possible. Additionally, the sensor system and collocated alignment features could be located in other positions within the removable smartphone case, such as, for example, the positions described with reference to FIGS. 44A, 44B, and 47A-47C.

Figure 53A:
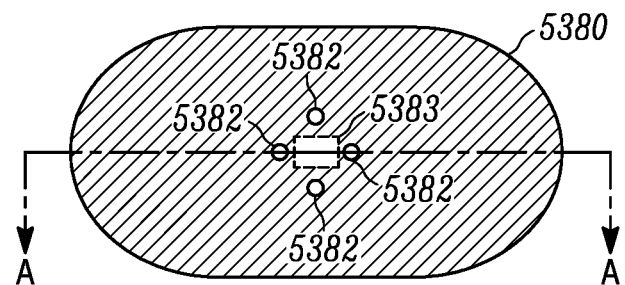
FIGS. 53A and 53B depict an embodiment of an alignment element in the form of an alignment patch that includes magnetic alignment features configured to mate with alignment features of the health monitoring device.
Figure 53B:
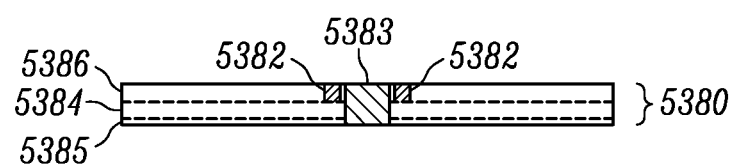

As stated above, the magnetic alignment features of the smartphone or smartphone case are configured to mate with alignment features of an alignment element, such as alignment patch, that is to be worn by a person. FIGS. 53A and 53B depict an embodiment of an alignment element 5380 in the form of an alignment patch that includes magnetic alignment features 5382 configured to mate with alignment features of the health monitoring device (e.g., a smartphone and/or a removable smartphone case). FIG. 53A is a top plan view of the alignment patch that includes four magnetic alignment elements located around an opening 5383 (referred to as an "alignment window") in the alignment patch. In an embodiment, the alignment window is provided so that a person can align the alignment patch with a vein to be monitored during application of the patch to the skin. For example, a person moves the alignment patch relative to the skin so that a targeted vein can be seen through the alignment window and then adheres the alignment patch to the skin such that the targeted vein is still visible through the alignment window after the alignment patch is adhered to the skin. In addition to providing visibility for alignment of the patch to a targeted vein, the alignment window also provides a pathway for radio waves to travel between the antenna array and the targeted vein that is free of interference from the patch material. For example, transmitted radio waves are able to pass from the transmit antenna(s) directly to the skin and targeted vein without passing through the patch material and at least some of the reflected radio waves are able to pass from the vein to the receive antennas free of interference from the patch material.

FIG. 53B is a side cutaway view of the alignment patch 5380 along section AA of FIG. 53A, which depicts a multilayer patch structure that includes a base layer 5384, an adhesive layer 5385, and a top layer 5386. In an embodiment, the base layer provides structural support for the adhesive layer and for the top layer. The adhesive layer is configured to adhere to a person's skin and may be covered by a removable cover material until the alignment patch is applied to the skin. The top layer may be configured to provide structural support for the magnetic alignment elements. The top layer may also be configured with functional and/or cosmetic characteristics that may help the alignment patch to be durable, comfortable, and/or cosmetically appealing while being worn by a person for an extended period of time (e.g., multiple days and/or weeks). With reference to FIG. 53A, the alignment patch may have a width dimension in the range of, for example, 1.27-7.62 cm and a height in the range of 1.27-7.62 cm, although other dimensions are possible. With reference to FIG. 53B, the thickness of the alignment patch may vary from, for example, 0.5-10 mm, although other thicknesses are possible. Although an example structure of an alignment patch is described with reference to FIGS. 53A and 53B, it should be understood that the configuration of an alignment element such as an alignment path can vary with for example, different material layers and different numbers, sizes, shapes, and orientations of the alignment features (e.g., the alignment magnets). For example, in the embodiment of FIGS. 53A and 53B, the alignment window is void of any patch material. In other embodiments, the alignment window may include a transparent material and/or a material that passes radio waves with less interference than the patch material that forms the borders of the alignment window. In still other embodiments, the entire patch (or a portion thereof) may be transparent and the alignment window may be formed by visible markings, such as a visible square that defines the alignment window.

Figure 54A:
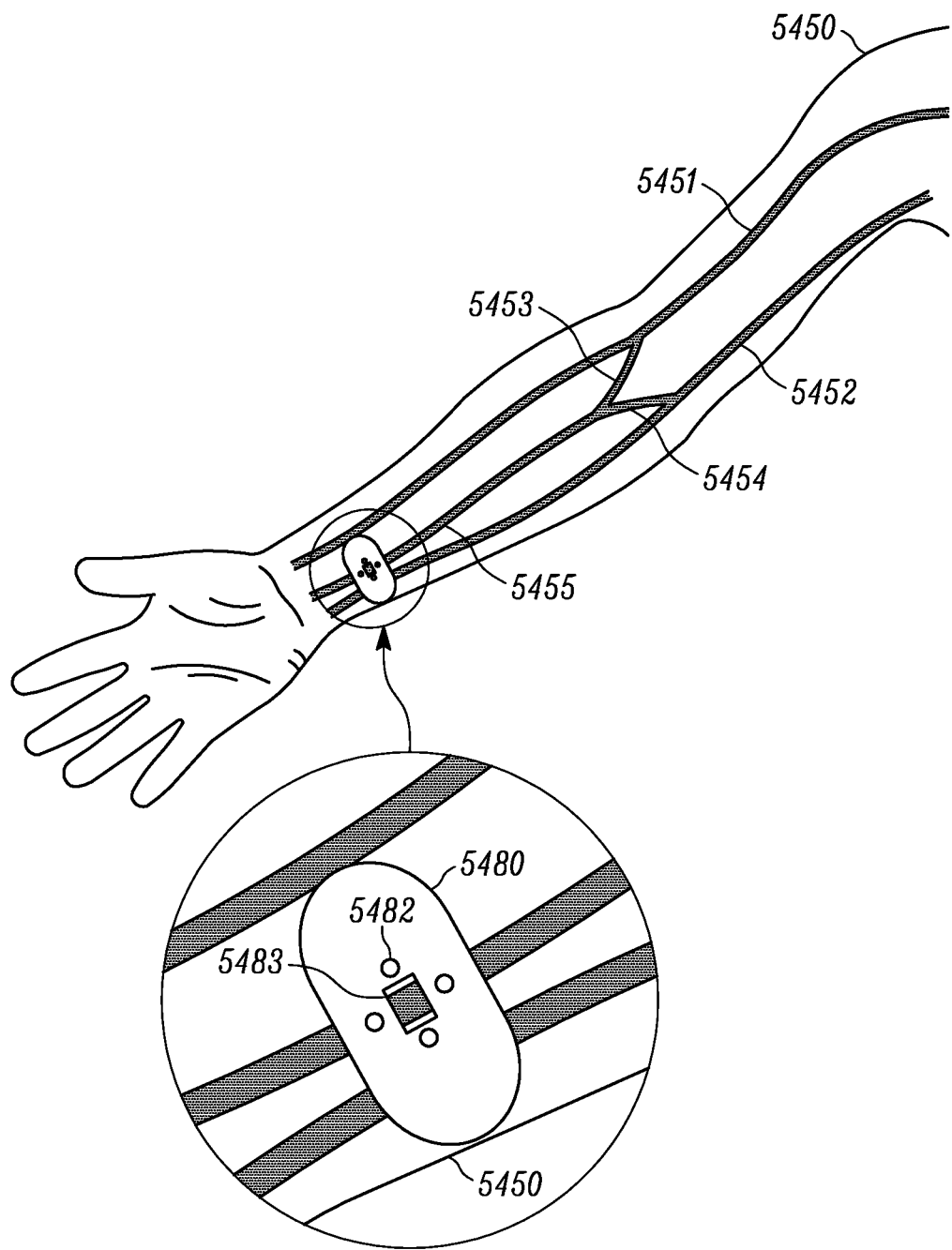
FIGS. 54A-54C illustrate an example alignment process between a health monitoring device and an alignment element in which the health monitoring device and the alignment element include matching configurations of magnetic alignment features.
Figure 54B:
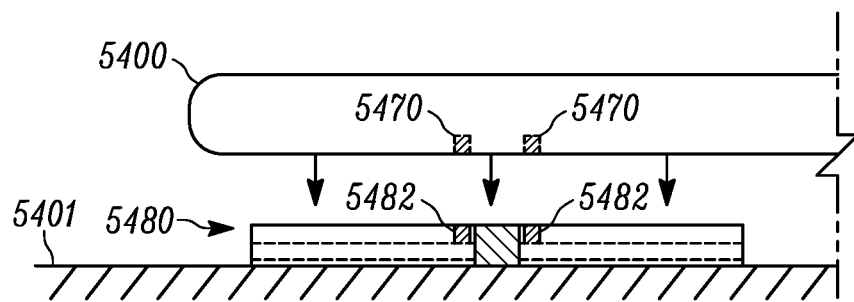
Figure 54C:
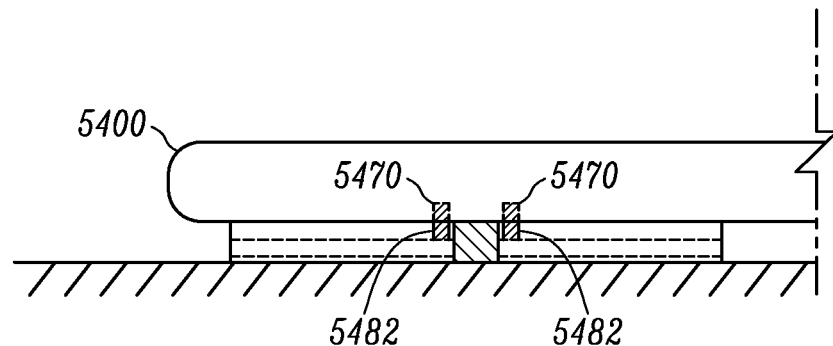

FIGS. 54A-54C illustrate an example alignment process between a health monitoring device (such as a smartphone or a smartphone and a removable smartphone case) and an alignment element (such as an alignment patch) in which the health monitoring device and the alignment element include matching configurations of magnetic alignment features. FIG. 54A depicts an example of the alignment patch 5480 of FIG. 53A being worn on the skin of a person to be monitored. In the example of FIG. 54A, the arm 5450 includes the cephalic vein 5451, the basilic vein 5452, the cephalic intermediate vein 5453, the intermediate vein of the elbow 5454, and the intermediate vein of the forearm 5455 and the alignment patch is attached to (e.g., adhered to) the skin at the right wrist of the person with the alignment window 5483 aligned with a vein in the wrist such that the vein is located within and/or visible within the alignment window. FIG. 54B illustrates the health monitoring device 5400 being moved towards the alignment patch 5380 that is worn on the skin of the person as shown in FIG. 54A. As illustrated, the magnetic alignment elements of the health monitoring device are brought into close proximity to the corresponding magnetic alignment elements of the alignment patch. When the magnetic alignment elements 5470 of the health monitoring device and the magnetic alignment elements 5482 of the alignment patch get close enough to each other, magnetic attraction between the mutually aligned magnets will become strong enough that the magnetic alignment elements of the health monitoring device magnetically attach to the magnetic alignment elements of the alignment patch. FIG. 54C illustrates the magnetic alignment elements of the health monitoring device magnetically attached to the corresponding magnetic alignment elements of the alignment patch. In the example of FIGS. 53A-54C, the magnetic attachment between the two sets of magnetic alignment elements causes the antenna array of the sensor system (not shown in FIGS. 54B and 54C but located between the magnetic alignment elements) to be aligned with the alignment window of the alignment patch. In an embodiment, the antenna array of the sensor system is aligned with the alignment window of the alignment patch when the antenna array is directly over the alignment window. Assuming the alignment window of the alignment patch is aligned with a vein to be monitored, the antenna array of the sensor system will also be aligned with the vein that is to be monitored. For example, the antenna array of the sensor system will be positioned directly over the vein that is to be monitored such that transmitted and reflected radio waves can pass between the antenna array and the vein through the alignment window. In an embodiment, the antenna array (including the transmit antenna(s) and the two-dimensional array of receive antennas) is aligned with the alignment window. In other embodiments, only the transmit antennas are aligned with the alignment window or only the two-dimensional array of receive antennas are aligned with the alignment window. Thus, the alignment window can serve a dual purpose of providing visibility for aligning the patch with a vein while also providing a low interference pathway through which radio waves can pass, e.g., a lower interference than a pathway that goes through the patch material.

In an embodiment, the health monitoring device 5400 is kept in the position as indicated in FIG. 54C while a health monitoring operation is conducted. For example, a health monitoring operation may take on the order of seconds to complete or a health monitoring operation may take on the order of a minute or a couple of minutes to complete. In the embodiment of FIGS. 54A-54C, the magnetic alignment elements 5470 and 5482 of both the health monitoring device and the alignment patch are magnetized to provide a strong magnetic attraction between the two sides. For example, as shown in FIG. 52A, the sensor system is collocated with the four alignment features, from a plan view perspective, a rectangle defined by the four alignment features overlaps with the position of the sensor system. However, in other embodiments, one side or the other may include magnetized alignment elements while the other side is simply a magnetic material. Although a particular configuration of alignment elements is described with reference to FIGS. 51A-54C, other configurations, including other materials, numbers of elements, sizes of elements, shapes of elements, orientations of elements, etc. are possible.

Figure 55B:
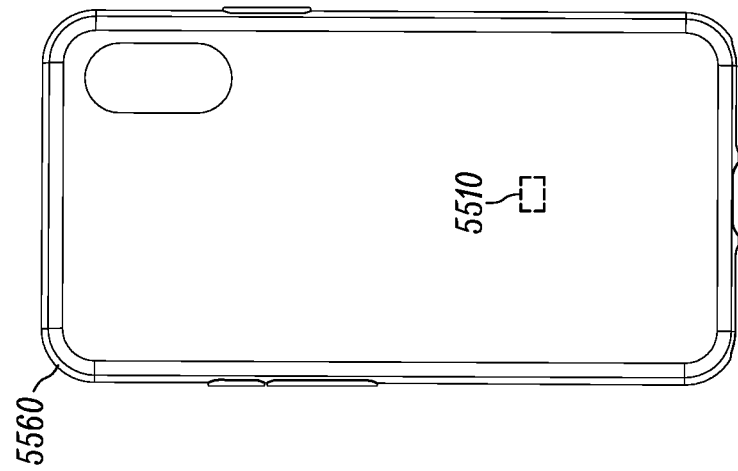
FIGS. 55A and 55B depict an example of a removable smartphone case in which the antenna array of the sensor system is not collocated with the alignment features.
Figure 55A:
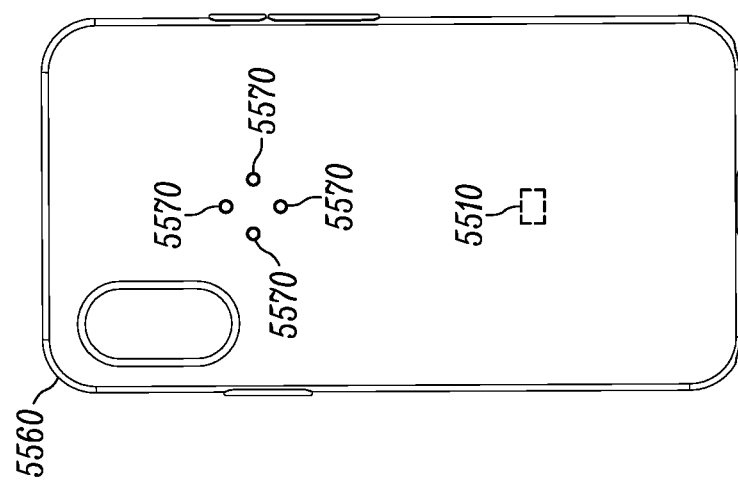

In the examples described above, the alignment features of the health monitoring device are collocated with the sensor system. For example, the magnetic alignment elements are located around the perimeter of the antenna array of the sensor system. In an embodiment, alignment features are "collocated" with an antenna array of the sensor system when, from a plan view perspective, the area defined by a perimeter that is formed by connecting the alignment features (or a line between alignment features) overlaps with at least a portion of the antenna array. However, in other embodiments, the alignment features may not be collocated with the antenna array of the sensor system. FIGS. 55A and 55B depict an example of a removable smartphone case in which the antenna array of the sensor system is not collocated with the alignment features. In particular, FIGS. 55A and 55B depict backside and frontside views, respectively, of a removable smartphone case 5560, similar to that described above with reference to FIGS. 52A-52C, in which the alignment features 5570 are located in an upper portion of the removable smartphone case while the sensor system 5510 (in this case including the antenna array) is located in a lower portion of the removable smart phone case. In such an embodiment, an alignment device that is worn on the skin of a person may be configured to align with the magnetic alignment features on the health monitoring device while also aligning the antenna array of the sensor system with a vein to be monitored. Embodiments in which the antenna array is not collocated with the alignment features include other health monitoring devices such as smartphones, smartwatches, etc. Additionally, embodiments in which the antenna array is not collocated with the alignment features may involve alignment features other than magnetic alignment features.

Figure 56B:
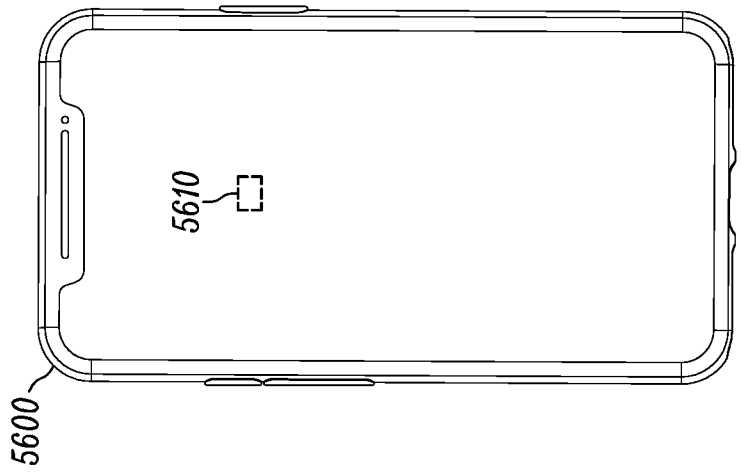
FIGS. 56A-56C depict an embodiment of a smartphone with out-of-plane physical elements that are integrated into the device body and configured to promote alignment between an antenna array of a sensor system and an object such as an alignment patch.
Figure 56A:
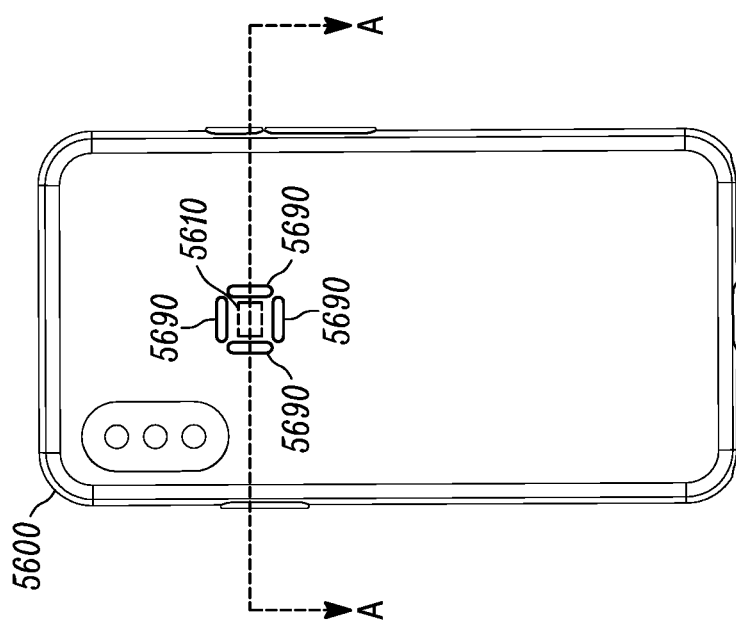
Figure 56C:
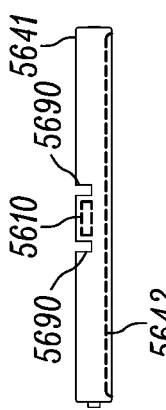

In the examples described above with reference to FIGS. 51A-55B, the alignment features integrated into the body of the health monitoring device are magnetic alignment features. In other embodiments, the alignment feature, or alignment features, may be physical elements such as physical elements that are "out-of-plane" with a major plane of the device body. For example, out-of-plane alignment features may include physical features such as bumps or grooves in the outer surface of the smartphone body that are configured to promote alignment between the smartphone and another device such as an alignment patch that includes corresponding physical alignment features. FIGS. 56A-56C depict an embodiment of a smartphone 5600 with out-of-plane physical elements 5690 that are integrated into the device body and configured to promote alignment between an antenna array of a sensor system and an object such as an alignment patch. As is described below, the out-of-plane alignment features are configured to mate with out-of-plane alignment features of an alignment element (e.g., an alignment patch) that is worn by the person to be monitored. FIG. 56A is a view of the backside of a smartphone that includes a sensor system 5610 (including an antenna array) integrated into the smartphone and out-of-plane alignment elements integrated into the body of the smartphone. FIG. 56B depicts a view of the frontside of the smartphone with the location of the sensor system 5610 shown although the sensor system is not actually visible from the frontside of the smartphone. FIG. 56C depicts a side cutaway view of the smartphone at cross section AA of FIG. 56A, which shows the sensor system 5610 and the out-of-plane alignment elements integrated into the backside 5641 of the device body. In particular, the side cutaway view shows that the out-of-plane alignment elements 5690 are seen as grooves or channels that are formed by sidewalls and a bottom wall that are not in the same plane as a plane that includes the major surface of the backside (opposite the display 5642) of the smartphone. For example, the sidewalls and bottom wall of the grooves or channels are not coplanar with the major plane of the device body. In the embodiment of FIGS. 56A-56C, the out-of-plane alignment features are grooves, channels, or cutouts that are formed by portions of the smartphone body that are not in the same plane as the major plane of the backside surface of the smartphone body. Although an example configuration of out-of-plane alignment features is described with reference to FIGS. 56A-56C, other configurations of out-of-plane alignment elements are possible. Additionally, other embodiments of physical alignment features may be used to ensure that an antenna array of an RF-based sensor system is aligned with an object such as an alignment patch and/or a vein that is to be monitored.

Figure 57B:
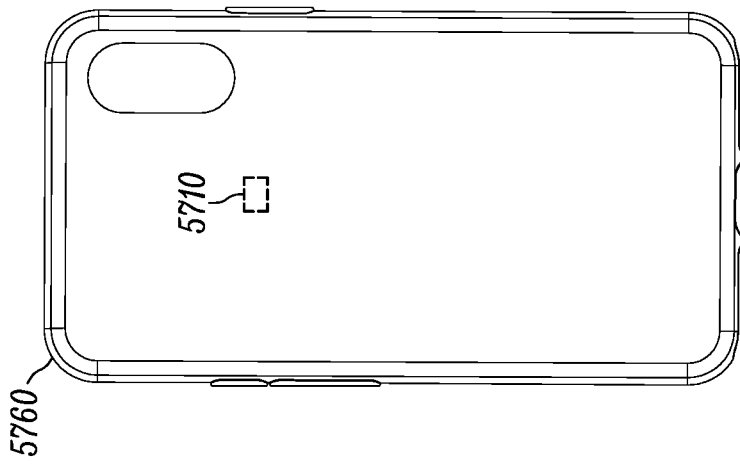
FIGS. 57A-57C depict an embodiment of the removable smartphone case that includes out-of-plane alignment elements integrated into the body of the removable smartphone case.
Figure 57A:
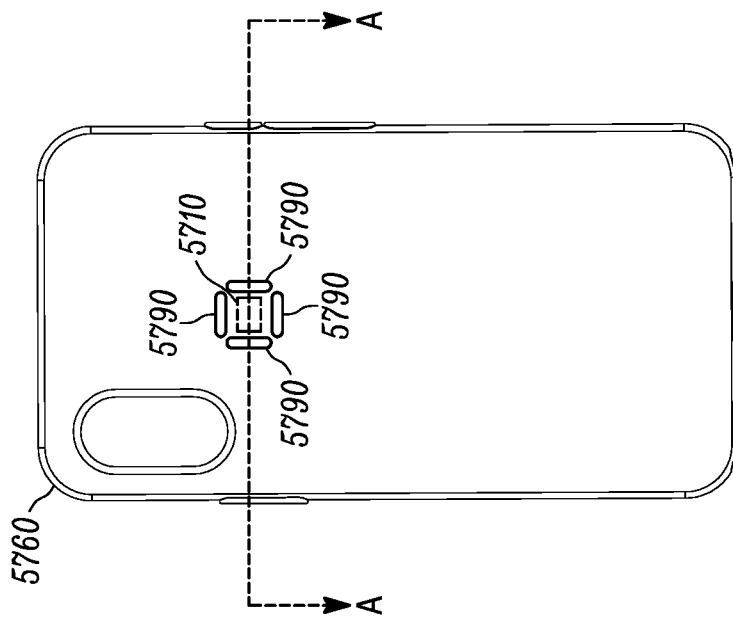
Figure 57C:
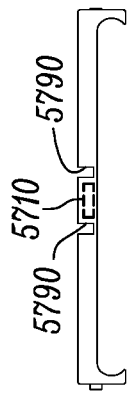

In the example of FIGS. 56A-56C, the out-of-plane alignment features 5690 are integrated into the body of a smartphone 5600. In another embodiment, the alignment features are integrated into the body of a removable smartphone case. FIGS. 57A-57C depict an embodiment of the removable smartphone case 5960 that includes out-of-plane alignment elements 5790 integrated into the body of the removable smartphone case. As is described below, the out-of-plane alignment features are configured to mate with out-of-plane alignment features of an alignment element (e.g., an alignment patch) that is worn by the person to be monitored. FIG. 57A is a view of the backside of a removable smartphone case that includes a sensor system 5710 (including an antenna array) and out-of-plane alignment elements 5790 integrated into the smartphone case. FIG. 57B depicts a view of the frontside of the smartphone case with the location of the sensor system 5710 shown although the sensor system may not actually be visible from the frontside of the smartphone case. FIG. 57C depicts a side cutaway view of the smartphone case at cross section AA of FIG. 57A, which shows the sensor system and the out-of-plane alignment elements 5790 integrated into the case body. In an embodiment, the out-of-plane alignment features are grooves, channels, or cutouts that are formed into the case body as described above with reference to FIGS. 56A-56C. For example, the out-of-plane features are formed by portions of the smartphone body that are not in the same plane as the major surface of the backside of the smartphone case. Although an example configuration of out-of-plane alignment features is described with reference to FIGS. 57A-57C, other configurations of out-of-plane alignment elements are possible.

Figure 58A:
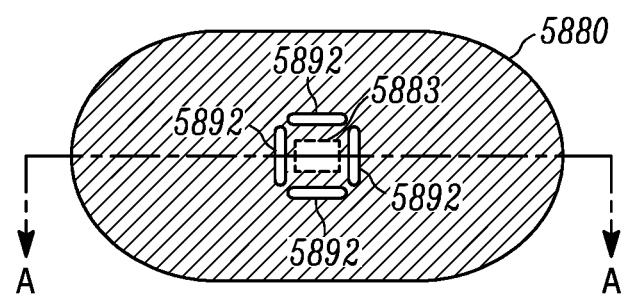
FIGS. 58A and 58B depict an embodiment of an alignment patch that includes out-of-plane alignment features configured to mate with out-of-plane alignment features of the health monitoring device.
Figure 58B:
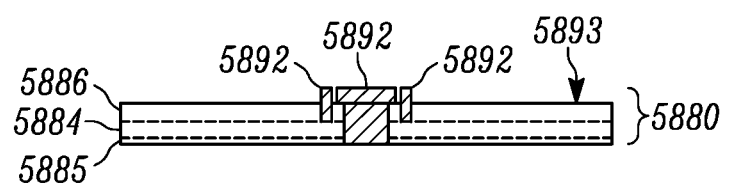

As stated above, the out-of-plane alignment features are configured to mate with out-of-plane alignment features of an alignment element, such as alignment patch, that is to be worn by a person to be monitored. FIGS. 58A and 58B depict an embodiment of an alignment patch 5880 that includes out-of-plane alignment features 5892 configured to mate with out-of-plane alignment features 5890 of the health monitoring device (e.g., a smartphone 5600 and/or a removable smartphone case 5760). FIG. 58A is a top plan view of the alignment patch that includes four raised structures 5892 located around an opening 5883 (referred to as an "alignment window") in the alignment patch. FIG. 58B is a side cutaway view of the alignment patch along section AA of FIG. 58A, which depicts a multilayer patch structure that includes a base layer 5884, an adhesive layer 5885, a top layer 5886, and the raised structures 5892 that are raised above and out-of-plane with a major surface of the alignment patch. For example, the alignment features are out-of-plane with a major surface 5893 of the top layer of the alignment patch. In an embodiment, the base layer provides structural support for the adhesive layer and for the top layer. The adhesive layer is configured to adhere to a person's skin and may be covered by a removable cover material until the alignment patch is applied to the skin. The top layer may be configured to provide structural support for the raised structures. The top layer may also be configured with functional and/or cosmetic characteristics that may help the alignment patch to be durable, comfortable, and/or cosmetically appealing while being worn by a person for an extended period of time (e.g., multiple days and/or weeks). With reference to FIG. 58A, the alignment patch may have a width dimension in the range of, for example, 1.27-7.62 cm and a height in the range of 1.27-7.62 cm although other dimensions are possible. With reference to FIG. 58B, the thickness of the alignment patch may vary from, for example, 0.5-10 mm, although other thicknesses are possible. Although an example structure of an alignment patch is described with reference to FIGS. 58A and 58B, it should be understood that the configuration of an alignment element such as an alignment patch can vary with, for example, different material layers and different numbers, sizes, shapes, and orientations of the alignment features (e.g., the out-of-plane alignment elements).

Figure 59A:
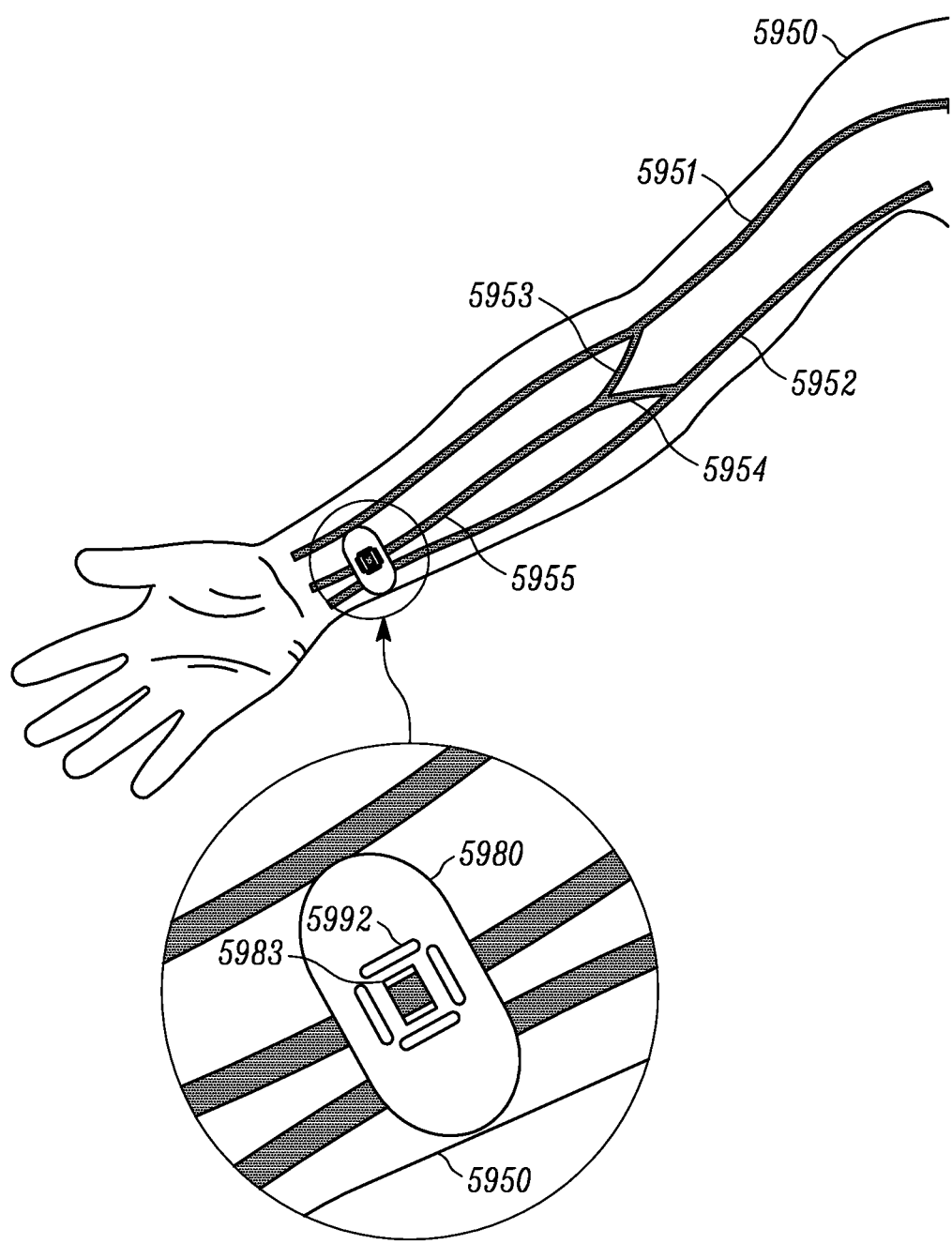
FIGS. 59A-59C illustrate an example alignment process between a health monitoring device and an alignment element in which the health monitoring device and the alignment element include matching or complimentary configurations of out-of-plane alignment features.
Figure 59B:
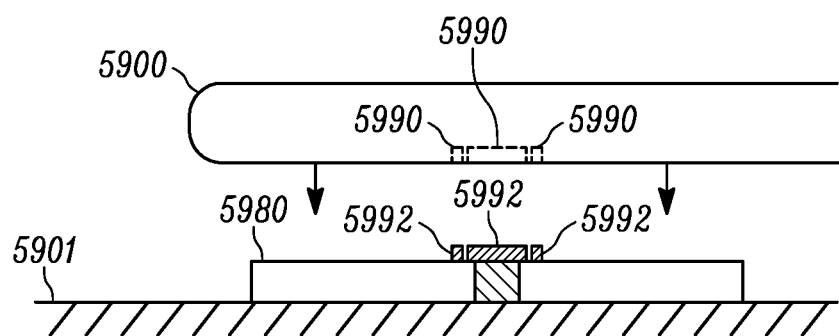
Figure 59C:
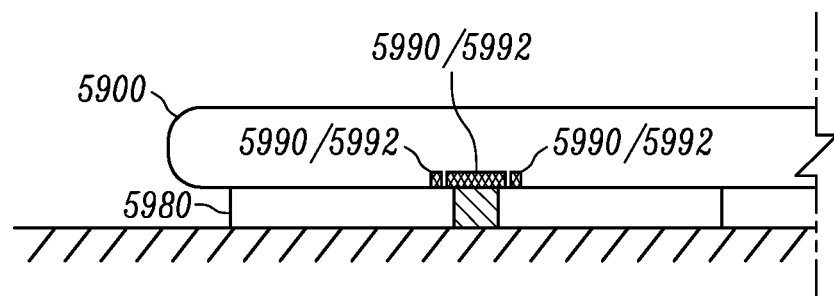

FIGS. 59A-59C illustrate an example alignment process between a health monitoring device 5900 (such as a smartphone or a smartphone held within a removable smartphone case) and an alignment element 5980 (such as an alignment patch) in which the health monitoring device and the alignment element include matching or complimentary configurations of out-of-plane alignment features. FIG. 59A depicts an example of an arm 5950 includes the cephalic vein 5951, the basilic vein 5952, the cephalic intermediate vein 5953, the intermediate vein of the elbow 5954, and the intermediate vein of the forearm 5955 and the alignment patch 5980 being worn on the skin of a person to be monitored. In the example of FIG. 59A, the alignment patch is attached (e.g., adhered to) the skin at the right wrist of a person with the alignment window 5983 aligned with a vein in the wrist such that the vein is located within and/or visible within the alignment window. FIG. 59B illustrates the health monitoring device 5900 being moved towards the alignment patch 5980 that is worn on the skin 5901 of the person as shown in FIG. 59A. As illustrated, the out-of-plane alignment elements 5990 of the health monitoring device are brought into close proximity to the corresponding out-of-plane alignment elements 5992 of the alignment patch 5980. When the out-of-plane alignment elements of the health monitoring device and the out-of-plane alignment elements of the alignment patch get close enough to each other, they engage and mutually align with each other. In particular, in this example, the out-of-plane alignment features of the patch, which include raised structures that extend above the major top plane of the patch, and the out-of-plane alignment features of the health monitoring device, which include grooves that extend below the major backside surface of the health monitoring device, fit together such that the raised structures fit snuggly within the grooves. When fit snuggly together, the complimentary shapes of the raised structures and the grooves reduce or eliminate lateral movement between the health monitoring device and the alignment patch, which in turn results in a stable alignment between the antenna array of the sensor system and the monitored vein. FIG. 59C illustrates the out-of-plane alignment elements 5990 of the health monitoring device seated on top of the out-of-plane alignment features 5992 of the alignment patch. In the example of FIGS. 59A-59C, engagement of the two sets of out-of-plane alignment elements causes the antenna array of the sensor system (sensor system not shown in FIGS. 59B and 59C but positioned as shown in FIGS. 57A-57C) to be aligned with the alignment window of the alignment patch. In an embodiment, the antenna array of the sensor system is aligned with the alignment window of the alignment patch when the antenna array is directly over the alignment window. Assuming the alignment window of the alignment patch is aligned with a vein to be monitored (e.g., a portion of the vein is located within and/or visible within the alignment window), the antenna array of the sensor system will also be aligned with the vein that is to be monitored. For example, the antenna array of the sensor system will be positioned directly over the vein that is to be monitored such that transmitted and reflected radio waves can pass between the antenna array and the vein through the alignment window. Thus, the alignment window can serve a dual purpose of providing visibility for aligning the patch with a vein while also providing a low interference pathway through which radio waves can pass, e.g., a lower interference than a pathway that goes through the patch material. In an embodiment, the antenna array (including the transmit antenna(s) and the two-dimensional array of receive antennas) is aligned with the alignment window. In other embodiments, only the transmit antenna or antennas are aligned with the alignment window or only the two-dimensional array of receive antennas is aligned with the alignment window. In an embodiment, the health monitoring device is kept in the position as indicated in FIG. 59C while a health monitoring operation is conducted. For example, a health monitoring operation may take on the order of seconds to complete or a health monitoring operation may take on the order of a minute or a couple of minutes to complete.

Figure 60A:
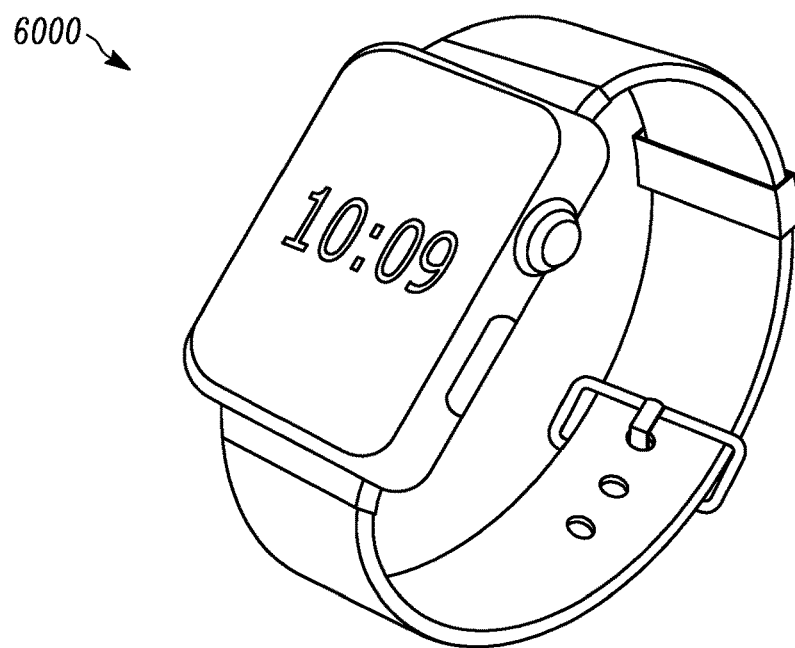
FIGS. 60A and 60B depict perspective views of a health monitoring device in the form of a smartwatch in which alignment features such as magnetic alignment elements are integrated into the backside of the smartwatch body.
Figure 60B:
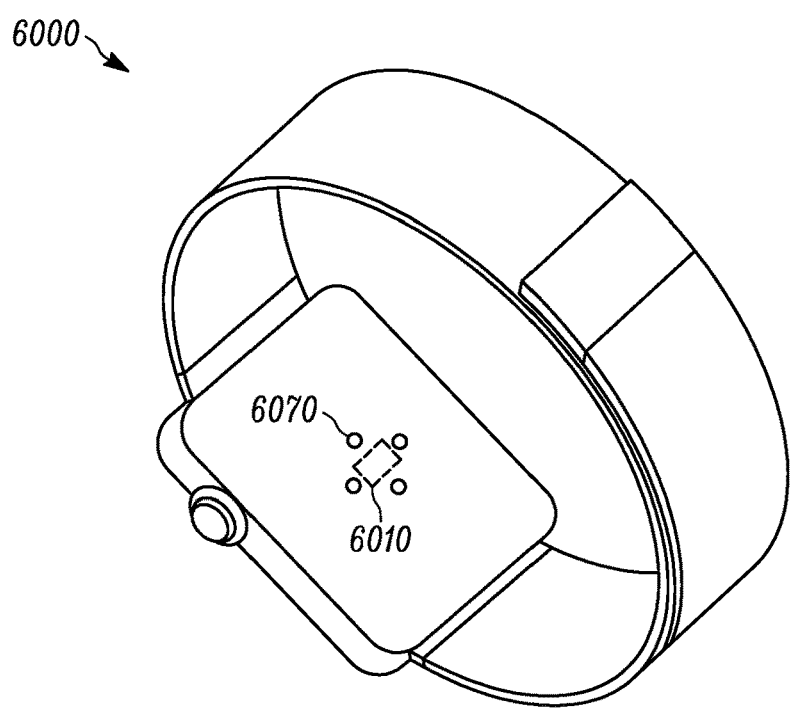
Figure 60C:
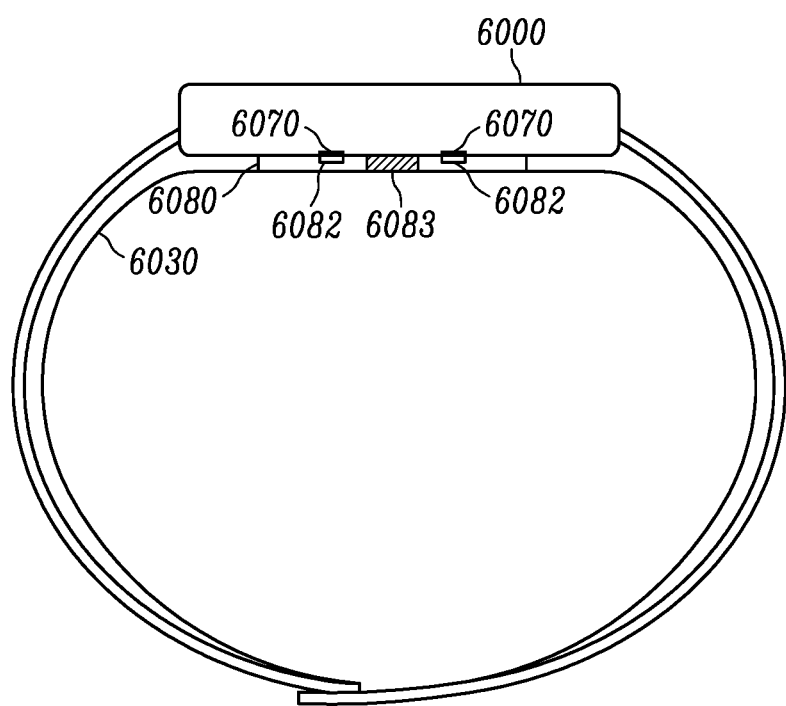
FIG. 60C is a side cutaway view of the smartwatch from FIGS. 60A and 60B attached around a wrist with the magnetic alignment features of the smartwatch magnetically engaged with complementary magnetic alignment features of an alignment patch that is attached to the skin of the wrist.

In the examples described above, the alignment features are integrated into the body of a smartphone and/or a removable smartphone case. In other embodiments, alignment features may be integrated into health monitoring devices that have other form factors. FIGS. 60A and 60B depict perspective views of a health monitoring device 6000 in the form of a smartwatch in which alignment features such as magnetic alignment elements 6070 are integrated into the backside of the smartwatch body. As shown in FIG. 60B, the magnetic alignment elements 6070 are collocated with a sensor system 6010 (which in this example includes an antenna array) in that the magnetic alignment elements are located around the perimeter of the antenna array. In an embodiment, the magnetic alignment elements are configured to mate with magnetic alignment elements integrated into an alignment element, such as an alignment patch, that is worn on the skin of a person. For example, an alignment patch such as the alignment patch described above with reference to FIGS. 53A and 53B is worn on the wrist and a smartwatch is worn on the wrist and over the patch such that the magnetic alignment elements of the smartwatch align with the magnetic alignment elements of the alignment patch. FIG. 60C is a side cutaway view of the smartwatch 6000 from FIGS. 60A and 60B attached around a wrist 6030 with the magnetic alignment features 6070 of the smartwatch magnetically engaged with complementary magnetic alignment features 6082 of an alignment patch 6080 that is attached to the skin of the wrist so that the alignment window 6083 is aligned with a vein.

Figure 61A:
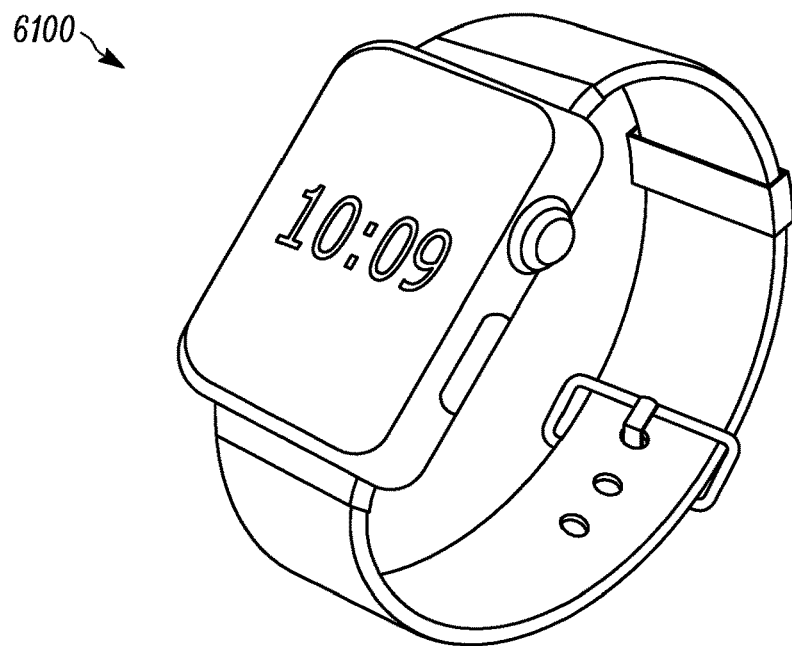
FIGS. 61A and 61B depict perspective views of a health monitoring device in the form of a smartwatch in which out-of-plane alignment features are integrated into the backside of the smartwatch body.
Figure 61B:
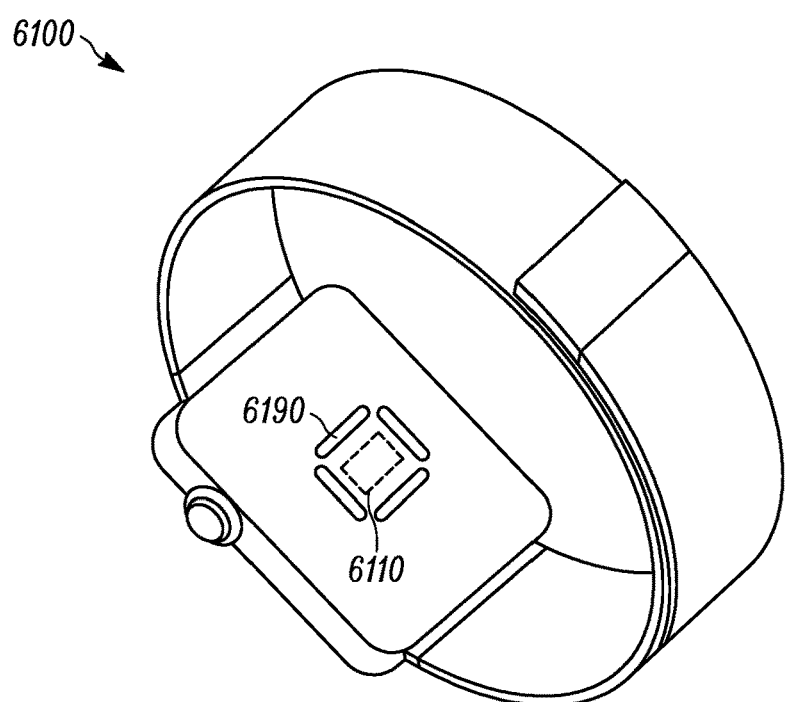
Figure 61C:
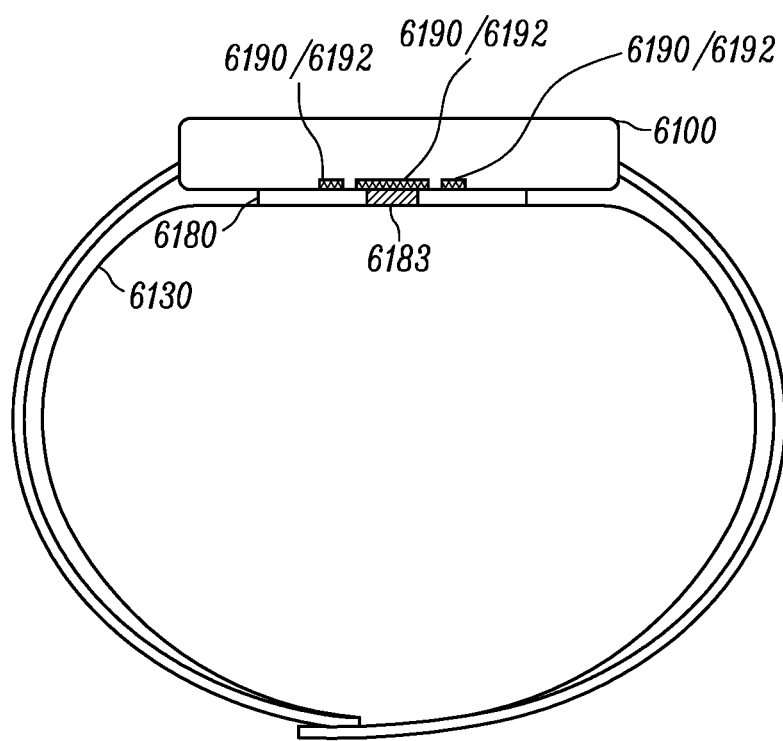
FIG. 61C is a side cutaway view of the smartwatch from FIG. 61B attached around a wrist with the out-of-plane alignment features of the smartwatch seated on top of complementary out-of-plane alignment features of an alignment patch that is attached to the skin of the wrist.

In the example of FIGS. 60A-60C, the smartwatch includes alignment features in the form of magnetic alignment elements. In other embodiments, a smartwatch may be configured with another type of alignment feature, such as out-of-plane alignment features. FIGS. 61A and 61B depict perspective views of a health monitoring device in the form of a smartwatch 6100 in which out-of-plane alignment features 6190 are integrated into the backside of the smartwatch body. In the embodiment of FIG. 61B, the out-of-plane alignment features are channels or grooves in the body of the smartwatch that extend below the major surface of the backside of the smartwatch body. Additionally, as shown in FIG. 61B, the out-of-plane alignment elements are collocated with a sensor system 6110 (which in this example includes an antenna array) in that the out-of-plane alignment elements are located around the perimeter of the antenna array. In an embodiment, the out-of-plane alignment elements are configured to mate with out-of-plane alignment elements integrated into an alignment element, such as an alignment patch, that is worn on the skin of a person as described above with reference to FIGS. 58A-59C. For example, an alignment patch as described above with reference to FIGS. 58A and 58B is worn on the wrist and a smartwatch is worn on the wrist and over the alignment patch such that the out-of-plane alignment elements of the smartwatch align with the out-of-plane alignment elements of the alignment patch. FIG. 61C is a side cutaway view of the smartwatch 6100 from FIG. 61B attached around a wrist 6130 with the out-of-plane alignment features 6190 of the smartwatch seated on top of complementary out-of-plane alignment features 6192 of an alignment patch 6180 that is attached to the skin of the wrist so that the alignment window 6183 is aligned with a vein.

Figure 62A:
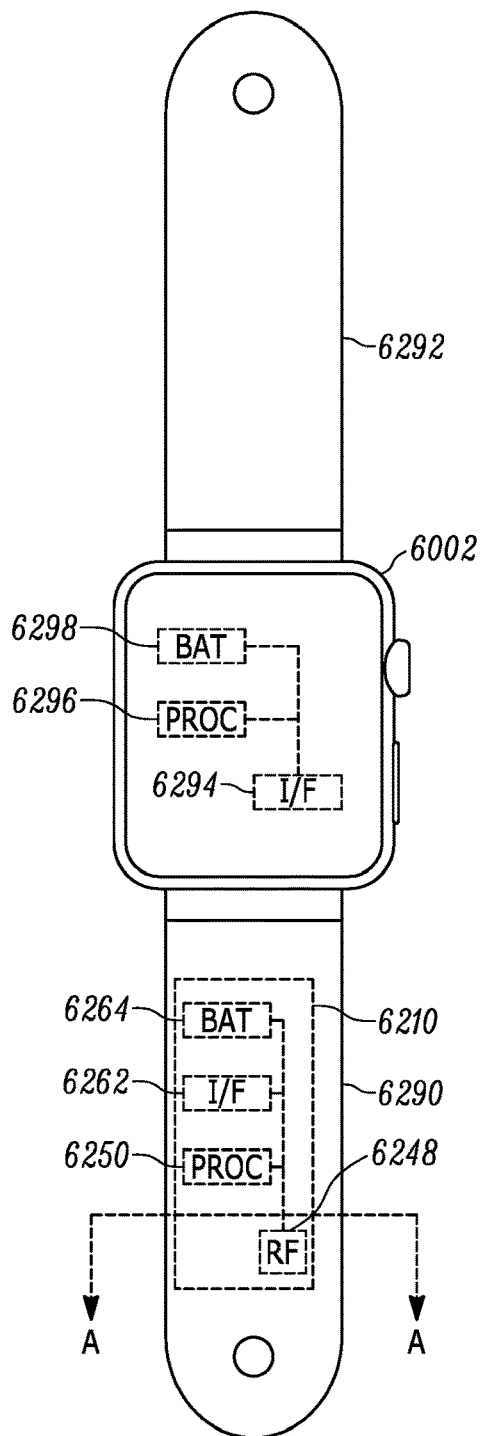
FIGS. 62A and 62B depict an embodiment in which an RF-based health monitoring system is integrated into a watch strap.
Figure 62B:
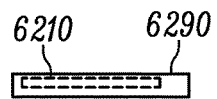

In another embodiment, a health monitoring system that includes an RF-based sensor system as described above may be integrated into a device such as a watch strap or watch band. FIGS. 62A and 62B depict an embodiment in which an RF-based health monitoring system 6210 is integrated into a watch strap 6290 and 6292. In the embodiment of FIGS. 62A and 62B, the health monitoring system 6210 is integrated into a first piece of 6290 of a two piece watch strap although the health monitoring system could be integrated into the second piece 6292. Alternatively, the watch strap may be a single piece. The particular configuration of the watch strap can vary depending on, for example, clasp design, whether there even is a clasp, single piece, multiple piece, etc. In the example shown in FIG. 62A, the RF-based health monitoring system includes an RF-based sensor system 6248 such as described above, a processor 6250, a communications interface 6262, and a battery 6264. In an embodiment, the elements are similar to elements as described above with reference to FIGS. 47A-47C, in which similar elements are integrated into a removable smartphone case. In the example of FIGS. 62A and 62B, the watch case 6002 is a smartwatch that includes a compatible communications interface 6294, a processor 6296, and a battery 6298.

In such an embodiment, the communications interface 6262 in the watch strap can communicate digital data (which is generated, for example, by the RF IC device 6248 in response to received radio waves) to the communications interface 6294 of the watch case 6002. In other embodiments, the watch case may be a conventional watch (e.g., with mechanical watch movement pieces and without a wireless communications interface, processor, or battery or a watch that does not include a communications interface that is compatible with the communications interface of the strap) and the communications interface 6262 of the watch strap 6290 can communicate with another compatible device such as a nearby smartphone or other computing device such as a laptop or desktop computer. In other embodiments, the communications interface 6262 of the watch strap may be able to communicate with both an attached smartwatch case 6002 and a nearby computing device such as a smartphone.

FIG. 62B depicts a side cutaway view of the first piece of the watch strap 6290 that shows the health monitoring system 6210 integrated within the watch strap. For example, the communications interface 6262, the processor 6250, and the RF IC device 6248 are fabricated on semiconductor substrates and the battery 6264 has a thin profile, e.g., 0.5-5 mm. In the example of FIGS. 62A and 62B, an RF-based sensor system is integrated into a watch strap. However, in other embodiments, the RF-based sensor system is integrated into a clasp or buckle for a watch strap. In still another embodiment, strap described above with reference to FIGS. 62A and 62B may be a strap that does not include the watch case. For example, the strap shown in FIGS. 62A and 62B is a continuous, e.g., single piece, strap that does not include the watch case. In such an embodiment, the communications interface in the strap can communicate with another computing device such as a smartwatch, a smartphone, or some other computing device. In an embodiment, alignment features may be integrated into the strap similar to the alignment features described above with reference to FIGS. 51A-61C.

Figure 63A:
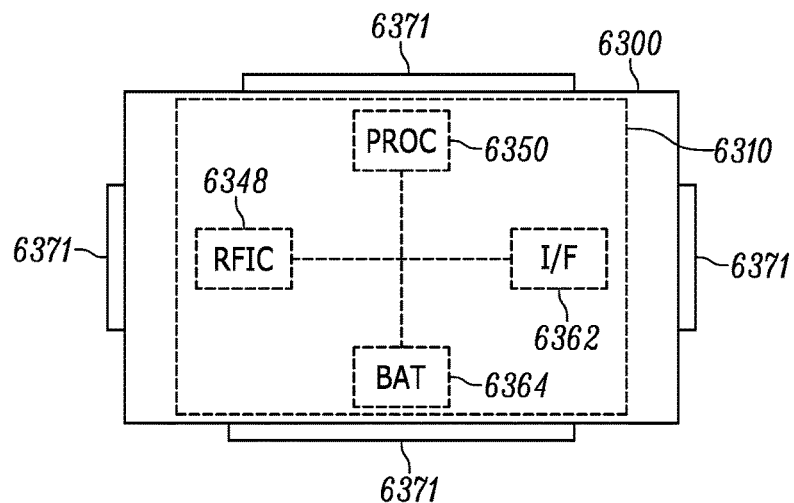
FIGS. 63A-63F depict an example of wearable health monitoring system that includes a health monitoring device and an alignment element, such as an alignment patch.
Figure 63B:
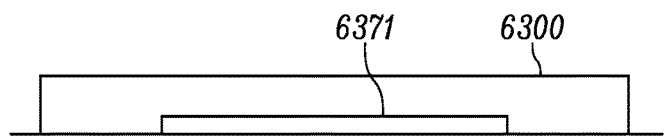
Figure 63C:
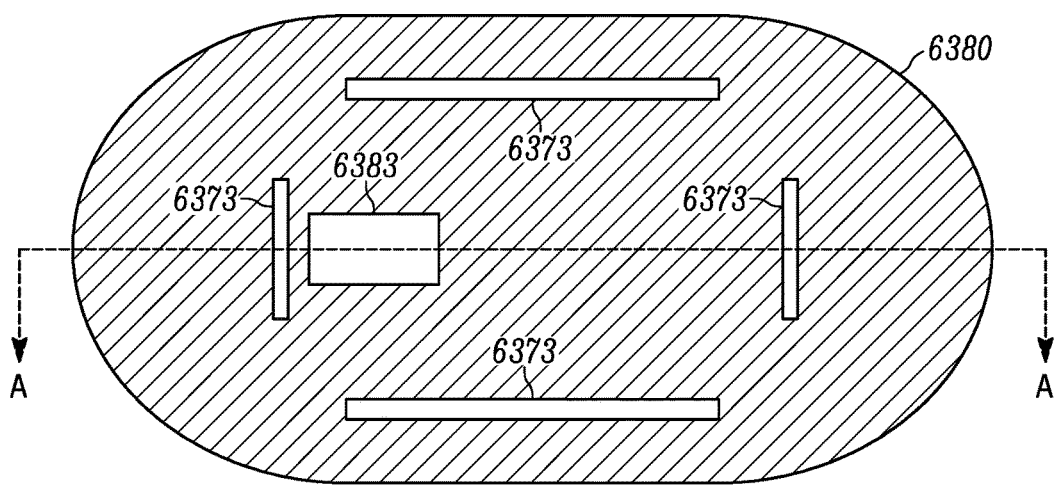
Figure 63D:
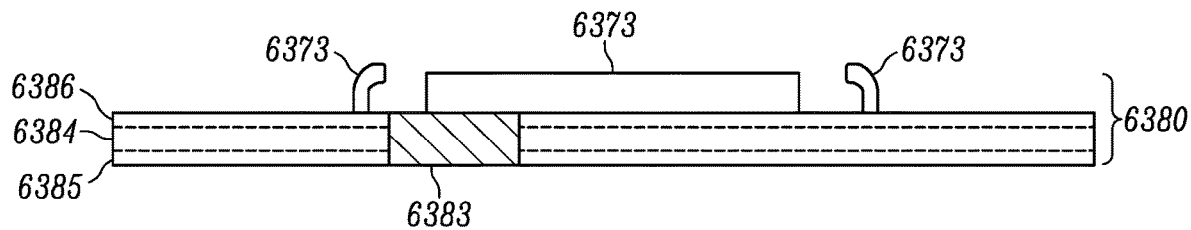

In another embodiment, the health monitoring device may be integrated into a wearable health monitoring system that is continuously worn on the body via, for example, an adhesive. FIGS. 63A-63F depict an example of wearable health monitoring system that includes a health monitoring device 6300 (FIGS. 63A and 63B) and an alignment element 6380 (FIGS. 63C and 63D), such as an alignment patch. In use, the alignment element is attached to the skin on of a person and the health monitoring device is attached to the alignment element. FIG. 63A is a top view of a health monitoring device 6300 that includes an RF-based sensor system 6310 (e.g., an RF IC device) that includes components similar to those described above with reference to FIGS. 47A-47C and FIGS. 5-8D. FIG. 63B is a side view of the health monitoring device of FIG. 63A. In the example of FIGS. 63A and 63B, the health monitoring device includes an RF front-end 6348 (e.g., embodied as an RF IC device), a processor 6350 (e.g., including a digital baseband system), a communications interface 6362, and battery 6364. The health monitoring device also includes attachment features 6371 that are configured to engage with attachment features of the alignment element 6380. FIGS. 63C and 63D depict a top view and side view, respectively, of the alignment element 6380 such as an alignment patch. With reference to FIG. 63C, the alignment patch includes four attachment features 6373 spaced to correspond to the perimeter of the health monitoring device shown in FIGS. 63A and 63B. The attachment features 6371 of the health monitoring device 6300 and the attachment features 6373 of the alignment patch 6380 are configured to engage with each other when the health monitoring device is brought into contact with the alignment patch. In an embodiment, the attachment features include angled and flexible components (e.g., clip structures) that allow the heath monitoring device to be "snapped" into position on the alignment patch and held securely. In an embodiment, the attachment features are also configured such that the health monitoring device can be removed on demand by a user by applying force to the health monitoring device. Various attachment features including, structural, magnetic, and/or adhesive may be incorporated into the health monitoring device and the alignment patch so that the health monitoring device can be securely attached to the alignment patch but also removed from the alignment patch when desired.

Figure 63E:
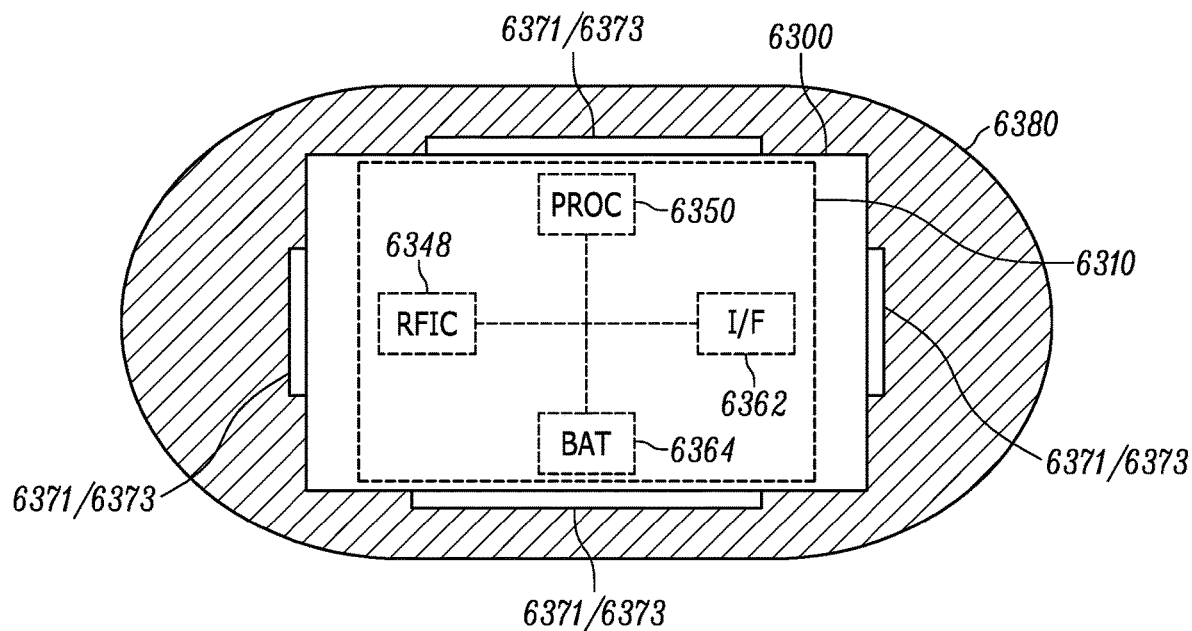
Figure 63F:
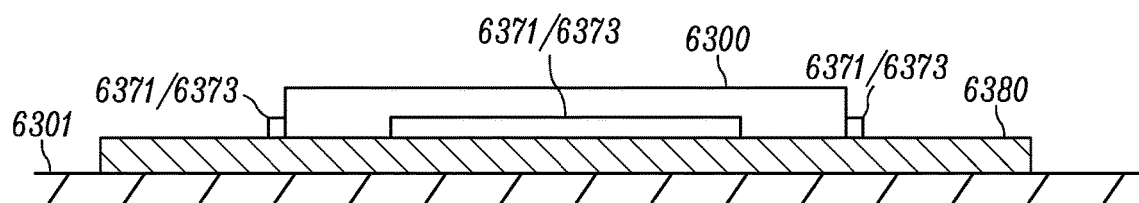

In an embodiment, an alignment window 6383 is provided within the alignment patch 6380 so that a person can align the alignment patch with a vein to be monitored during application of the patch to the skin. For example, a person moves the alignment patch relative to the skin so that a targeted vein can be seen through the alignment window and then adheres the alignment patch to the skin such that the targeted vein is still visible through the alignment window after the alignment patch is adhered to the skin. FIG. 63D is a side cutaway view of the alignment patch 6380 along section AA of FIG. 63C, which depicts a multilayer patch structure that includes a base layer 6384, an adhesive layer 6385, and a top layer 6386. In an embodiment, the base layer provides structural support for the adhesive layer and for the top layer. The adhesive layer is configured to adhere to a person's skin and may be covered by a removable cover material (not shown) until the alignment patch is applied to the skin. The top layer may be configured to provide structural support for the attachment features 6373. The top layer may also be configured with functional and/or cosmetic characteristics that may help the alignment patch to be durable, comfortable, and/or cosmetically appealing while being worn by a person for an extended period of time (e.g., multiple days and/or weeks). With reference to FIG. 63C, the alignment patch may have a width dimension in the range of, for example, 1-20 cm and a height in the range of 1-15 cm, although other dimensions are possible. With reference to FIG. 63D, the thickness of the alignment patch may vary from, for example, 0.5-10 mm, although other thicknesses are possible. Although an example structure of an alignment patch 6380 is described with reference to FIGS. 63C and 63D, it should be understood that the configuration of an alignment element such as an alignment path can vary with for example, different material layers and different numbers, sizes, shapes, and orientations of the attachment features. For example, in the embodiment of FIGS. 63C and 63D, the alignment window is void of any patch material. In other embodiments, the alignment window 6383 may include a transparent material. In still other embodiments, the entire patch (or a portion thereof) may be transparent and the alignment window may be formed by visible markings, such as a visible square that defines the alignment window. In the embodiment of FIGS. 63C and 63D, the alignment window is positioned to correspond to the location of the RF IC device (e.g., aligned with the antenna array) so that radio waves can pass between the skin of the person and the antenna array unimpeded by material of the alignment patch. That is, the wearable health monitoring system is configured so that the location of the alignment window 6383 matches the location of the antenna array of the RF-based sensor system (e.g., with the RF IC device 6348) when the health monitoring device is attached to the alignment patch. When the health monitoring device is attached to the alignment patch, the RF-based sensor system is directly above the alignment window. FIG. 63E is a top view of the health monitoring system that depicts the health monitoring device 6300 attached to the alignment element 6380 via the alignment features of both the health monitoring device and the alignment element 6371 and 6373, respectively. FIG. 63F depicts a side view of the wearable health monitoring system described with reference to FIGS. 63A-63E attached to the skin 6301 of a person. In the example of FIGS. 63A-63F, the attachment features 6373 of the health monitoring device 6300 and the attachment features 6373 of the alignment patch 6380 serve a dual purpose in that they enable attachment between the health monitoring device and the alignment patch and they cause the antenna array of the sensor system to be aligned with the alignment window 6383 of the alignment patch. Assuming the alignment window of the alignment patch is aligned with a vein to be monitored, the antenna array of the sensor system will also be aligned with the vein that is to be monitored. In an embodiment, the wearable health monitoring system is worn on the skin as indicated in FIG. 63F for an extended period of time, e.g., days or weeks, and health monitoring is performed on a continuous or periodic basis. In an embodiment, a particular health monitoring operation may take on the order of seconds to complete or a health monitoring operation may take on the order of a minute or a couple of minutes to complete. In an embodiment, the communications interface 6362 of the health monitoring system is configured to wirelessly communicate (e.g., via BLE) digital data generated from the RF-based health monitoring to a nearby computing device such as a smartphone or smartwatch.

Figure 64A:
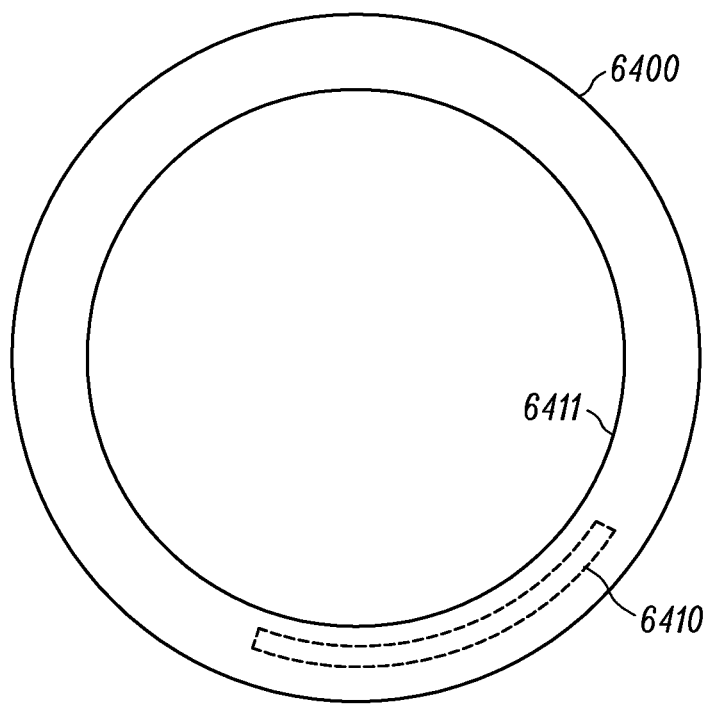
FIGS. 64A-64C depict an embodiment in which an RF-based health monitoring system is integrated into a ring that is to be worn on a finger or toe.
Figure 64B:
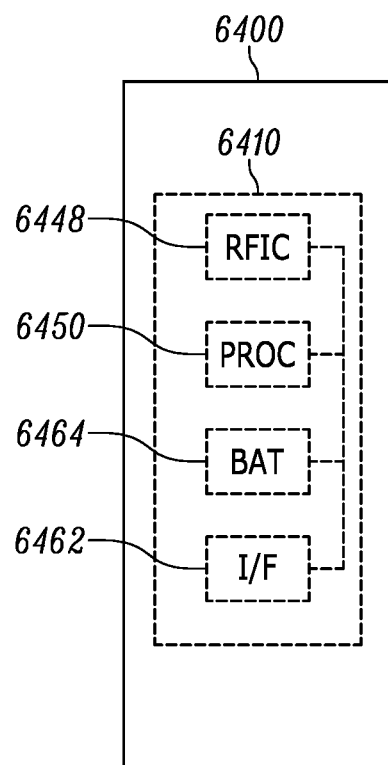
Figure 64C:
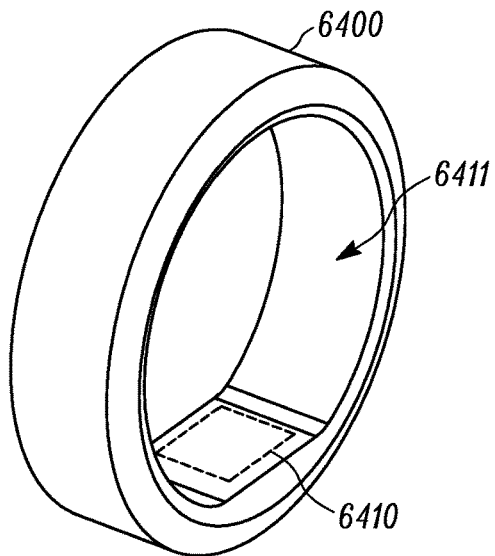

In another embodiment, a health monitoring system that includes an RF-based sensor system as described above may be integrated into a device such as a ring 6400 that is to be worn on a finger or toe. FIGS. 64A-64C depict an embodiment in which an RF-based health monitoring system 6410 is integrated into a ring that is to be worn on a finger or toe. In particular, FIG. 64A is a side view, FIG. 64B is front view, and FIG. 64C is a perspective view of the ring. In the example shown in FIGS. 64A and 64B, the RF-based health monitoring system 6410 includes an RF front-end 6448 such as described above (e.g., an RF IC device), a processor 6450, a communications interface 6462, and a battery 6464. In an embodiment, the elements are similar to elements as described above with reference to FIGS. 47A-47C and FIGS. 8A-8D. In the example of FIGS. 64A-64C, the communications interface 6462 is compatible with a computing device such as a smartwatch, a smartphone, or a desktop or laptop computer. In an embodiment, the antenna array of the RF front-end is located close to the inner surface 6411 of the ring so that the antenna array is close to the skin of the finger or toe on which the ring is worn. FIG. 64C depicts the RF front-end 6448 of the sensor system at the inner surface 6411 of the ring 6400.

Figure 65:
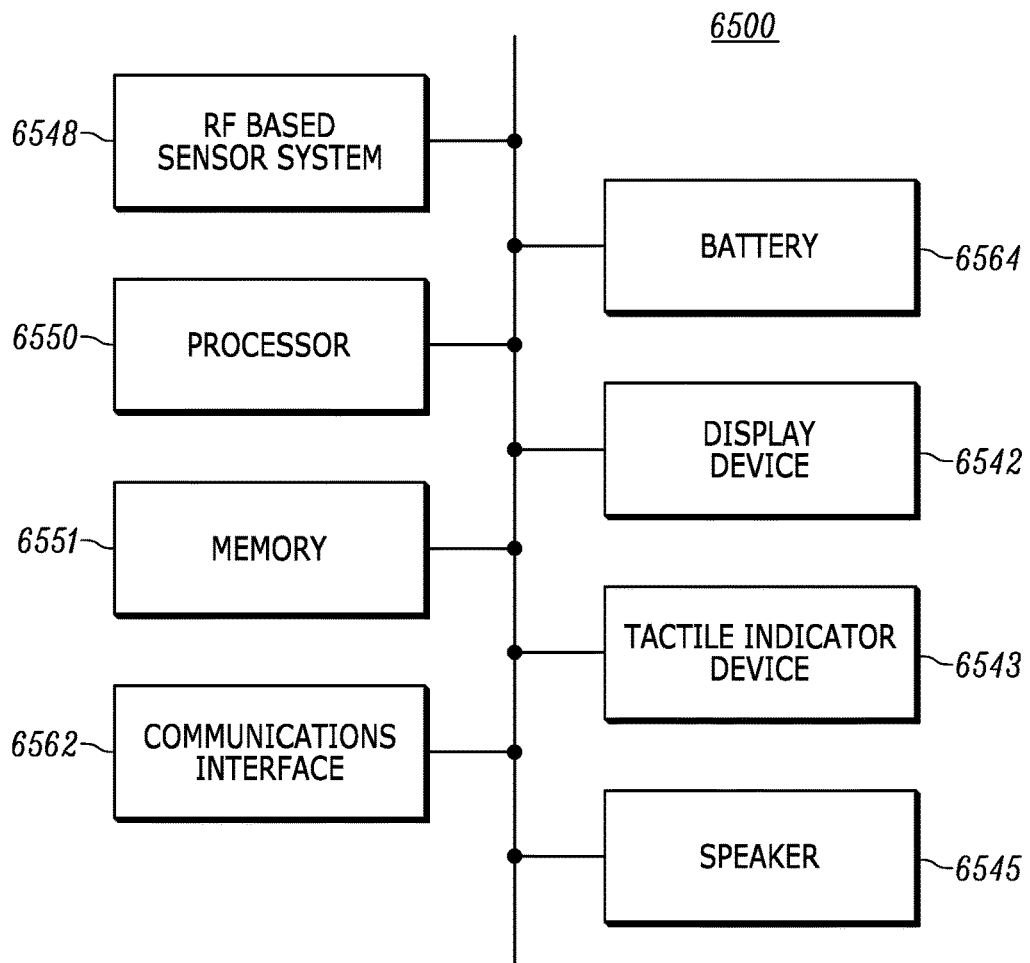
FIG. 65 is an example computing system that includes an RF-based sensor system, a processor, memory, a communications interface, a battery, a display device, a tactile indicator device, and a speaker.

FIG. 65 is an example computing system 6500 that includes an RF-based sensor system 6548, a processor 6550, memory 6551, a communications interface 6562, a battery 6564, a display device 6542, a tactile indicator device 6543, and a speaker 6545. The computing device may be embodied as any of the devices described herein, including, for example, a smartwatch, a smartphone, a removable smartphone case, a strap for a watch, a ring, or another health monitoring device. The computing device may include all of the components or some portion of the components. In an embodiment, the tactile indicator device may include a mechanism that generates tactile feedback (e.g., a vibration) in response to electrical control signal. The RF-based sensor system may comprise an RF-based sensor system as described herein, e.g., as described with reference to FIGS. 5-8D. The processor, memory, communications interface, battery, display device and speaker may be elements as are known in the field.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

It should also be noted that at least some of the operations for the methods described herein may be implemented using software instructions stored on a computer useable storage medium for execution by a computer. As an example, an embodiment of a computer program product includes a computer useable storage medium to store a computer readable program.

The computer-useable or computer-readable storage medium can be an electronic, magnetic, optical, electromagnetic, infrared, or semiconductor system (or apparatus or device). Examples of non-transitory computer-useable and computer-readable storage media include a semiconductor or solid state memory, magnetic tape, a removable computer diskette, a random access memory (RAM), a read-only memory (ROM), a rigid magnetic disk, and an optical disk. Current examples of optical disks include a compact disk with read only memory (CD-ROM), a compact disk with read/write (CD-R/W), and a digital video disk (DVD).

Alternatively, embodiments of the invention may be implemented entirely in hardware or in an implementation containing both hardware and software elements. In embodiments which use software, the software may include but is not limited to firmware, resident software, microcode, etc.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A device for monitoring a health parameter of a person, the device comprising:
   a device body;
   a radio frequency (RF) front-end connected to the device body and including a semiconductor substrate and an antenna array including at least one transmit antenna configured to transmit radio waves below the skin surface of a person and a two-dimensional array of receive antennas configured to receive radio waves, the received radio waves including a reflected portion of the transmitted radio waves, wherein the semiconductor substrate includes circuits configured to generate signals in response to the received radio waves; and
   an alignment feature integrated into the device body and configured to align the antenna array with an object, wherein the alignment feature comprises a plurality of magnetic elements connected to the device body and oriented on the device body next to the antenna array in a pattern around a perimeter of the antenna array, wherein the perimeter of the antenna array is from a plan view perspective of the antenna array.

2. The device of claim 1, wherein the device is a smartwatch.
3. The device of claim 1, wherein the device is a smartphone.
4. The device of claim 1, wherein the device is a removable case for a smartphone.
5. The device of claim 1, wherein the device is a health monitoring dongle.
6. The device of claim 1, wherein the device is a watch strap.
7. The device of claim 1, wherein the device is a smart ring.
8. The device of claim 1, wherein the alignment feature is collocated with the antenna array.
9. The device of claim 1, wherein the alignment feature is collocated with the two-dimensional array of receive antennas.
10. The device of claim 1, wherein the alignment feature comprises a visual marking on the device body that is collocated with the antenna array.
11. The device of claim 1, wherein the alignment feature comprises a visual marking on the device body that is collocated with the two-dimensional array of receive antennas.
12. The device of claim 1, wherein the alignment feature comprises at least one magnetic element connected to the device body.
13. The device of claim 1, wherein the pattern of magnetic elements matches a pattern of magnetic elements of an alignment element that is worn by a person.
14. The device of claim 1, wherein the alignment feature comprises a physical element that is out-of-plane with a major plane of the device body.
15. The device of claim 14, wherein the physical element is collocated with the antenna array.
16. The device of claim 1, wherein the alignment feature comprises a plurality of physical elements that are out-of-plane with a major plane of the device body.
17. The device of claim 16, wherein the plurality of physical elements is collocated with the antenna array.
18. The device of claim 17, wherein the plurality of physical elements matches a pattern of physical elements of an alignment element that is worn by a person.
19. The device of claim 17, wherein the plurality of physical elements matches a pattern of physical elements of an alignment patch that is worn by a person.
20. The device of claim 1, wherein the alignment feature comprises a plurality of physical elements that are out-of-plane with a major plane of the device body and oriented around a perimeter of the antenna array.
21. The device of claim 1, wherein the alignment feature comprises a plurality of physical elements that are out-of-plane with a major plane of the device body and oriented around a perimeter of the two-dimensional array of receive antennas.
22. The device of claim 1, wherein the plurality of magnetic elements and the antenna array are coplanar.
23. The device of claim 1, wherein the plurality of magnetic elements and the antenna array are coplanar on the device body.
24. A device for monitoring a health parameter of a person, the device comprising:
   a device body;
   a radio frequency (RF) front-end connected to the case body and including a semiconductor substrate and an antenna array including at least one transmit antenna configured to transmit radio waves below the skin surface of a person and a two-dimensional array of receive antennas configured to receive radio waves, the received radio waves including a reflected portion of the transmitted radio waves, wherein the semiconductor substrate includes circuits configured to generate signals in response to the received radio waves; and a processor configured to determine a health parameter of a person in response to the generated signals;

a display for outputting a signal that is indicative of the determined health parameter; and an alignment feature integrated into the device body and configured to align the antenna array with an object, wherein the alignment feature comprises a plurality of magnetic elements connected to the device body and oriented on the device body next to the antenna array in a pattern around a perimeter of the antenna array, wherein the perimeter of the antenna array is from a plan view perspective of the antenna array.

25. The device of claim 24, wherein the device is a smartwatch.

26. The device of claim 24, wherein the device is a smartphone.

27. The device of claim 24, wherein the device is a health monitoring dongle.

28. The device of claim 24, wherein the device is a watch strap.

29. The device of claim 24, wherein the device is a smart ring.

30. The device of claim 24, wherein the alignment feature is collocated with the antenna array.

31. The device of claim 24, wherein the alignment feature is collocated with the two-dimensional array of receive antennas.

32. The device of claim 24, wherein the alignment feature comprises a visual marking on the device body that is collocated with the antenna array.

33. The device of claim 24, wherein the alignment feature comprises a visual marking on the device body that is collocated with the two-dimensional array of receive antennas.

34. The device of claim 24, wherein the pattern of magnetic elements matches a pattern of magnetic elements of an alignment element that is worn by a person.

35. The device of claim 24, wherein the alignment feature comprises a physical element that is out-of-plane with a major plane of the device body.

36. The device of claim 24, wherein the physical element is collocated with the antenna array.

37. The device of claim 24, wherein the alignment feature comprises a plurality of physical elements that are out-of-plane with a major plane of the device body.

38. The device of claim 37, wherein the plurality of physical elements is collocated with the antenna array.

39. The device of claim 38, wherein the plurality of physical elements matches a pattern of physical elements of an alignment element that is worn by a person.

40. The device of claim 38, wherein the plurality of physical elements matches a pattern of physical elements of an alignment patch that is worn by a person.

41. The device of claim 24, wherein the alignment feature comprises a plurality of physical elements that are out-of-plane with a major plane of the device body and oriented around a perimeter of the antenna array.

42. The device of claim 24, wherein the alignment feature comprises a plurality of physical elements that are out-of-plane with a major plane of the device body and oriented around a perimeter of the two-dimensional array of receive antennas.

43. The device of claim 24, wherein the plurality of magnetic elements and the antenna array are coplanar.

44. The device of claim 24, wherein the plurality of magnetic elements and the antenna array are coplanar on the device body.

* * * * *